US007820379B2

(12) United States Patent
Bauer et al.

(10) Patent No.: US 7,820,379 B2
(45) Date of Patent: Oct. 26, 2010

(54) PROCESS FOR HIGH THROUGHPUT SCREENING OF CPG-BASED IMMUNO-AGONIST/ANTAGONIST

(75) Inventors: Stefan Bauer, Munich (DE); Grayson B. Lipford, Watertown, MA (US); Hermann Wagner, Eching (DE)

(73) Assignee: Coley Pharmaceutical GmbH, Dusseldorf (DE)

(*) Notice: Subject to any disclaimer, the term of this patent is extended or adjusted under 35 U.S.C. 154(b) by 473 days.

(21) Appl. No.: 11/084,777

(22) Filed: Mar. 18, 2005

(65) Prior Publication Data

US 2005/0181422 A1 Aug. 18, 2005

Related U.S. Application Data

(62) Division of application No. 09/954,987, filed on Sep. 17, 2001, now Pat. No. 6,943,240.

(60) Provisional application No. 60/300,210, filed on Jun. 22, 2001, provisional application No. 60/291,726, filed on May 17, 2001, provisional application No. 60/263,657, filed on Jan. 23, 2001, provisional application No. 60/233,035, filed on Sep. 15, 2000.

(51) Int. Cl.
*C12Q 1/68* (2006.01)
*G01N 33/53* (2006.01)
*C07K 14/00* (2006.01)
(52) U.S. Cl. .............................. 435/6; 435/7.8; 530/350
(58) Field of Classification Search ...................... 435/6, 435/7.8; 530/350
See application file for complete search history.

(56) References Cited

U.S. PATENT DOCUMENTS

| 5,567,604 | A | 10/1996 | Rando et al. |
| 5,663,153 | A | 9/1997 | Hutcherson et al. |
| 5,723,335 | A | 3/1998 | Hutcherson et al. |
| 6,013,639 | A | 1/2000 | Peyman et al. |
| 6,121,434 | A | 9/2000 | Peyman et al. |
| 6,194,388 | B1 | 2/2001 | Krieg et al. |
| 6,207,646 | B1 | 3/2001 | Krieg et al. |
| 6,214,806 | B1 | 4/2001 | Krieg et al. |
| 6,218,371 | B1 | 4/2001 | Krieg et al. |
| 6,221,882 | B1 | 4/2001 | Macfarlane |
| 6,239,116 | B1 | 5/2001 | Krieg et al. |
| 6,339,068 | B1 | 1/2002 | Krieg et al. |
| 6,339,630 | B1 | 6/2002 | Macfarlane |
| 6,406,705 | B1 | 6/2002 | Davis et al. |
| 6,429,199 | B1 | 8/2002 | Krieg et al. |
| 6,479,504 | B1 | 11/2002 | Macfarlane et al. |
| 6,521,637 | B2 | 2/2003 | Macfarlane |
| 6,653,292 | B1 | 11/2003 | Krieg et al. |
| 6,727,230 | B1 | 4/2004 | Hutcherson et al. |
| 6,821,957 | B2 | 11/2004 | Krieg et al. |
| 6,943,240 | B2 | 9/2005 | Bauer et al. |
| 6,949,520 | B1 | 9/2005 | Hartmann et al. |
| 2001/0044416 | A1 | 11/2001 | Davis et al. |
| 2002/0064515 | A1 | 5/2002 | Krieg et al. |
| 2002/0091097 | A1 | 7/2002 | Bratzler et al. |
| 2002/0164341 | A1 | 11/2002 | Davis et al. |
| 2002/0165178 | A1 | 11/2002 | Schetter et al. |
| 2003/0026801 | A1 | 2/2003 | Weiner et al. |
| 2003/0050261 | A1 | 3/2003 | Krieg et al. |
| 2003/0050263 | A1 | 3/2003 | Krieg et al. |
| 2003/0050268 | A1 | 3/2003 | Krieg et al. |
| 2003/0055014 | A1 | 3/2003 | Bratzler |
| 2003/0067902 | A1 | 4/2003 | Bratzler et al. |
| 2003/0091599 | A1 | 5/2003 | Davis et al. |
| 2003/0100527 | A1 | 5/2003 | Krieg et al. |
| 2003/0104523 | A1 | 6/2003 | Lipford et al. |
| 2003/0139364 | A1 | 7/2003 | Krieg et al. |
| 2003/0148316 | A1 | 8/2003 | Lipford et al. |
| 2003/0148976 | A1 | 8/2003 | Krieg et al. |

(Continued)

FOREIGN PATENT DOCUMENTS

EP 1142472 A1 10/2001

(Continued)

OTHER PUBLICATIONS

Beutler Nature 430:257-263; 2004.*

(Continued)

*Primary Examiner*—Fereydoun G Sajjadi
(74) *Attorney, Agent, or Firm*—Wolf, Greenfield & Sacks, P.C.; Gregg C. Benson

(57) ABSTRACT

The invention pertains to murine TLR9 and related TLR9s which include murine-specific amino acids, as well as nucleic acids which encode those polypeptides. The present invention also includes fragments and biologically functional variants of the murine TLR9. The invention further relates to methods of using such murine and non-murine TLR9 nucleic acids and polypeptides, especially in methods for screening for agonists and antagonists of immunostimulatory CpG nucleic acids. Also included are murine TLR9 inhibitors which inhibit murine TLR9 activity by inhibiting the expression or function of murine TLR9. In a further aspect the present invention pertains to murine TLR7 and murine TLR8, as well as related TLR7 and TLR8 molecules which include murine-specific amino acids, as well as nucleic acids which encode those polypeptides. The present invention also includes fragments and biologically functional variants of the murine TLR7 and TLR8. Methods are included for screening for ligands of TLR7 and TLR8, as well as for inhibitors and agonists and antagonists of signaling mediated by TLR7 and TLR8.

20 Claims, 20 Drawing Sheets

U.S. PATENT DOCUMENTS

| | | |
|---|---|---|
| 2003/0166001 A1 | 9/2003 | Lipford |
| 2003/0181406 A1 | 9/2003 | Schetter et al. |
| 2003/0191079 A1 | 10/2003 | Krieg et al. |
| 2003/0212026 A1 | 11/2003 | Krieg et al. |
| 2003/0224010 A1 | 12/2003 | Davis et al. |
| 2003/0232074 A1 | 12/2003 | Lipford et al. |
| 2003/0232856 A1 | 12/2003 | MacFarlane |
| 2004/0009949 A1 | 1/2004 | Krieg |
| 2004/0030118 A1 | 2/2004 | Wagner et al. |
| 2004/0053880 A1 | 3/2004 | Krieg |
| 2004/0067902 A9 | 4/2004 | Bratzler et al. |
| 2004/0067905 A1 | 4/2004 | Krieg |
| 2004/0087534 A1 | 5/2004 | Krieg et al. |
| 2004/0087538 A1 | 5/2004 | Krieg et al. |
| 2004/0092472 A1 | 5/2004 | Krieg |
| 2004/0106568 A1 | 6/2004 | Krieg et al. |
| 2004/0131628 A1 | 7/2004 | Bratzler et al. |
| 2004/0132685 A1 | 7/2004 | Krieg et al. |
| 2004/0142469 A1 | 7/2004 | Krieg et al. |
| 2004/0143112 A1 | 7/2004 | Krieg |
| 2004/0147468 A1 | 7/2004 | Krieg et al. |
| 2004/0152649 A1 | 8/2004 | Krieg |
| 2004/0152656 A1 | 8/2004 | Krieg et al. |
| 2004/0152657 A1 | 8/2004 | Krieg et al. |
| 2004/0162258 A1 | 8/2004 | Krieg et al. |
| 2004/0162262 A1 | 8/2004 | Krieg et al. |
| 2004/0167089 A1 | 8/2004 | Krieg et al. |
| 2004/0171150 A1 | 9/2004 | Krieg et al. |
| 2004/0171571 A1 | 9/2004 | Krieg et al. |
| 2004/0181045 A1 | 9/2004 | Krieg et al. |
| 2004/0198680 A1 | 10/2004 | Krieg |
| 2004/0198688 A1 | 10/2004 | Krieg et al. |
| 2004/0229835 A1 | 11/2004 | Krieg et al. |
| 2004/0234512 A1 | 11/2004 | Wagner et al. |
| 2004/0235770 A1 | 11/2004 | McCluskie et al. |
| 2004/0235774 A1 | 11/2004 | Bratzler et al. |
| 2004/0235777 A1 | 11/2004 | Wagner et al. |
| 2004/0235778 A1 | 11/2004 | Wagner et al. |
| 2004/0266719 A1 | 12/2004 | McCluskie et al. |
| 2005/0004061 A1 | 1/2005 | Krieg et al. |
| 2005/0004062 A1 | 1/2005 | Krieg et al. |
| 2005/0009774 A1 | 1/2005 | Krieg et al. |
| 2005/0032734 A1 | 2/2005 | Davis et al. |
| 2005/0032736 A1 | 2/2005 | Krieg et al. |
| 2005/0037403 A1 | 2/2005 | Krieg et al. |
| 2005/0037985 A1 | 2/2005 | Krieg et al. |
| 2005/0043529 A1 | 2/2005 | Davis et al. |
| 2005/0049215 A1 | 3/2005 | Krieg et al. |
| 2005/0049216 A1 | 3/2005 | Krieg et al. |
| 2005/0054601 A1 | 3/2005 | Wagner et al. |
| 2005/0054602 A1 | 3/2005 | Krieg et al. |
| 2005/0059619 A1 | 3/2005 | Krieg et al. |
| 2005/0059625 A1 | 3/2005 | Krieg et al. |
| 2005/0070491 A1 | 3/2005 | Krieg et al. |
| 2005/0075302 A1 | 4/2005 | Hutcherson et al. |
| 2005/0100983 A1 | 5/2005 | Bauer et al. |
| 2005/0101554 A1 | 5/2005 | Krieg et al. |
| 2005/0101557 A1 | 5/2005 | Krieg et al. |
| 2005/0119273 A1 | 6/2005 | Lipford et al. |
| 2005/0123523 A1 | 6/2005 | Krieg et al. |
| 2005/0130911 A1 | 6/2005 | Uhlmann et al. |
| 2005/0148537 A1 | 7/2005 | Krieg et al. |
| 2005/0169888 A1 | 8/2005 | Hartman et al. |
| 2005/0171047 A1 | 8/2005 | Krieg et al. |
| 2005/0181422 A1 | 8/2005 | Bauer et al. |
| 2005/0182017 A1 | 8/2005 | Krieg |
| 2005/0197314 A1 | 9/2005 | Krieg et al. |
| 2005/0215500 A1 | 9/2005 | Krieg et al. |
| 2005/0215501 A1 | 9/2005 | Lipford et al. |
| 2005/0233995 A1 | 10/2005 | Krieg et al. |
| 2005/0233999 A1 | 10/2005 | Krieg et al. |
| 2005/0239732 A1 | 10/2005 | Krieg et al. |
| 2005/0239733 A1 | 10/2005 | Jurk et al. |
| 2005/0239734 A1 | 10/2005 | Uhlmann et al. |
| 2005/0239736 A1 | 10/2005 | Krieg et al. |
| 2005/0244379 A1 | 11/2005 | Krieg et al. |
| 2005/0244380 A1 | 11/2005 | Krieg et al. |
| 2005/0245477 A1 | 11/2005 | Krieg et al. |
| 2005/0250726 A1 | 11/2005 | Krieg et al. |
| 2005/0256073 A1 | 11/2005 | Lipford et al. |
| 2005/0267057 A1 | 12/2005 | Krieg |
| 2005/0267064 A1 | 12/2005 | Krieg et al. |
| 2005/0277604 A1 | 12/2005 | Krieg et al. |
| 2005/0277609 A1 | 12/2005 | Krieg et al. |
| 2006/0003955 A1 | 1/2006 | Krieg et al. |
| 2006/0003962 A1 | 1/2006 | Ahluwalia et al. |
| 2006/0019916 A1 | 1/2006 | Krieg et al. |
| 2006/0019923 A1 | 1/2006 | Davis et al. |

FOREIGN PATENT DOCUMENTS

| | | |
|---|---|---|
| WO | WO94/29469 A2 | 12/1994 |
| WO | WO96/2555 A1 | 2/1996 |
| WO | WO96/24380 A1 | 8/1996 |
| WO | WO97/00957 A1 | 1/1997 |
| WO | WO98/18810 A1 | 5/1998 |
| WO | WO98/29430 A1 | 7/1998 |
| WO | WO98/32462 A1 | 7/1998 |
| WO | WO98/37919 A1 | 9/1998 |
| WO | WO98/40100 A1 | 9/1998 |
| WO | WO98/50547 A2 | 11/1998 |
| WO | WO98/52581 A1 | 11/1998 |
| WO | WO99/20756 A2 | 4/1999 |
| WO | WO99/51259 A2 | 10/1999 |
| WO | WO99/56755 A1 | 11/1999 |
| WO | WO99/58118 A2 | 11/1999 |
| WO | WO99/61056 A2 | 12/1999 |
| WO | WO00/06588 A1 | 2/2000 |
| WO | WO00/14217 A2 | 3/2000 |
| WO | WO00/67023 A1 | 11/2000 |
| WO | WO01/22972 A2 | 4/2001 |
| WO | WO01/22990 A2 | 4/2001 |
| WO | WO01/32877 A2 | 5/2001 |
| WO | WO01/55386 A1 | 8/2001 |
| WO | WO02/06936 A2 | 9/2002 |
| WO | WO03/03569 A2 | 1/2003 |
| WO | WO03/04357 A2 | 5/2003 |
| WO | WO 2004/007743 A2 | 1/2004 |
| WO | WO 2004/026888 A2 | 4/2004 |
| WO | WO 2004/094671 A2 | 11/2004 |

OTHER PUBLICATIONS

Sigma Catalog "Biochemicals, Organic Compounds, Diagnostic Reagents", 1990, pp. 776-778.

Aderem A et al., Toll-like receptors in the induction of the innate immune response. *Nature*. 2000 Aug. 17;406(6797):782-7.

Agrawal A et al., Transposition mediated by RAG1 and RAG2 and its implications for the evolution of the immune system. *Nature*. Aug. 20, 1998;394(6695):744-51.

Ahmad-Nejad P et al., Bacterial CpG-DNA and lipopolysaccharides activate Toll-like receptors at distinct cellular compartments. *Eur J Immunol*. Jul. 2002; 32(7):1958-68.

Bauer S et al., Human TLR9 confers responsiveness to bacterial DNA via species-specific CpG motif recognition. *Proc Natl Acad Sci USA*. Jul. 31, 2001;98(16):9237-42.

Chaudhary PM et al., Cloning and characterization of two Toll/Interleukin-1 receptor-like genes TIL3 and TIL4: evidence for a multi-gene receptor family in humans. *Human*. Jun. 1, 1998;91(11):4020-7.

Chuan T-H et al., Toll-like receptor 9 mediates CpG-DNA Signaling. *J. Leukoc Biol*. Mar. 2002;71(3):538-44.

Chuang TH et al., Cloning and characterization of a sub-family of human toll-like receptors: hTRL7, hTLR8 and hTLR9. *Eur Cytokine Netw*. Sep. 2000;11(3):372-8.

Demoulin JB et al., A single tyrosine of the interleukin-9 (IL-9) receptor is required for STAT activation, antiapoptotic activity, and growth regulation by IL-9. *Mol Cell Biol.* Sep. 1996;16(9):4710-6.

Du X et al., Three novel mammalian toll-like receptors: gene structure, expression, and evolution. *Eur Cytokine Netw.* Sep. 2000;11(3):362-71.

Eden CS et al., Host resistance to mucosal gram-negative infection. Susceptibility of lipopolysaccharide nonresponder mice. *J Immunol.* May 1, 1988;140(9):3180-5.

EMBL Accession No. AAY05867, Human Toll protein PRO286; Aug. 2, 1999.

Fearon DT et al., The instructive role of immunity in the acquired immune response. *Science.* Apr. 5, 1996;272(5258):50-3.

Fujita DT et al, Mechanism of transcriptional regulation by methyl-CpG binding Protein MBDI, *Mol Cell Biol* 20:5107-18 (2000).

Genbank Accession No. AF245704, Jun. 21, 2000.

Genbank Accession No. AF348140, Mus Musculus toll-like receptor 9 (Tlr9), mRNA, complete cds. Apr. 5, 2001.

Genbank Accession No. AL356815, May 25, 2000.

Genbank Accession No. AQ984126, Jan. 30, 2000.

Genbank Accession No. BE412777, Jul. 24, 2000.

Genbank Accession No. BE705670, Sep. 12, 2000.

Hacker H et al., Cell type-specific activation of mitogen-activated protein kinases by CpG-DNA controls interleukin-12 release from antigen-presenting cells. *EMBO J.* Dec. 15, 1999;18(24):6973-82.

Hacker H et al., CpG-DNA-specific activation of antigen-presenting cells requires stress kinase activity and is preceded by non-specific endocytosis and endosomal maturation. *EMBO J.* Nov. 2, 1998;17(21):6230-40.

Hacker H et al., Immune cell activation by bacterial CpG-DNA through myeloid differentiation marker 88 and tumor necrosis factor receptor-associated factor (TRAF)6. *J Exp Med.* Aug. 21, 2000;192(4):595-600.

Hemmi H et al., A Toll-like receptor recognizes bacterial DNA. *Nature.* Dec. 7, 2000;408(6813):740-5.

Hoffmann JA et al., Phylogenetic perspectives in innate immunity. *Science.* May 21, 1999;284(5418):1313-8.

Hoshino K et al., Cutting edge: Toll-like receptor 4 (TLR4)-deficient mice are hyporesponsive to lipopolysaccharide: evidence for TLR4 as the Lps gene product. *J Immunol.* Apr. 1, 1999;162(7):3749-52.

Janeway CA Jr., Approaching the asymptote? Evolution and revolution in immunology. *Cold Spring Harb Symp Quant Biol.* 1989;54 Pt 1:1-13.

Kirschning CJ et al., Human toll-like receptor 2 confers responsiveness to bacterial lipopolysaccharide. *J Exp Med.* Dec. 7, 1998;188(11):2091-7.

Kirschning CJ et al., Toll-like receptors: cellular signal transducers for exogenous molecular patterns causing immune responses. *Int J Med Microbiol.* Sep. 2001;291(4):251-60.

Kopp EB et al. The Toll-receptor family and control of innate immunity. *Curr Opin Immunol.* Feb. 1999;11(1):13-8.

Krieg AM et al., Causing a commotion in the blood: immunotherapy progresses from bacteria to bacterial DNA. *Immunol Today.* Oct. 2000;21(10):521-6.

Krieg AM et al., CpG motifs in bacterial DNA trigger direct B-cell activation. *Nature.* Apr. 6, 1995;374(6522):546-9.

Leifer CA et al., Role of Toll-like receptor 9 in CpG DNA-induced activation of human cells. (ABSTRACT #117). Activating Immunity with CpG Oligos, 2$^{nd}$ International Symposium, Amelia Island, Florida, Oct. 7-10, 2001.

Liang H et al., Activation of human B cells by phosphorothioate oligodeoxynucleotides. *J Clin Invest.* Sep. 1, 1996;98(5):1119-29.

Macfarlane DE et al., Antagonism of immunostimulatory CpG-oligodeoxynucleotides by quinacrine, chloroquine, and structurally related compounds. *J Immunol.* Feb. 1, 1998;160(3):1122-31.

Manzel L et al., Lack of immune stimulation by immobilized CpG-oligodeoxynucleotide. *Antisense Nucleic Acid Drug Dev.* Oct. 1999;9(5):459-64.

Means TK et al., Human toll-like receptors mediate cellular activation by Mycobacterium tuberculosis. *J Immunol.* Oct. 1, 1999;163(7):3920-7.

Medzhitov R et al., A human homologue of the Drosophilia Toll protein signals activation of adaptive immunity.*Nature.* Jul. 24, 1997;388(6640):394-7.

Medzhitov R et al., Innate immunity: the virtues of a nonclonal system of recognition. *Cell.* Oct. 31, 1997;91(3):295-8.

Muzio M et al., The human toll signaling pathway: divergence of nuclear factor kappaB and JNK/SAPK activation upstream of tumor necrosis factor receptor-associated factor 6 (TRAF6). *J Exp Med.* Jun. 15, 1998;187(12):2097-101.

Muzio M et al., Toll-like receptors. *Microbes Infect.* Mar. 2000;2(3):251-5.

Muzio M et al., Toll-like receptors: a growing family of immune receptors that are differentially expressed and regulated by different leukocytes. *J Leukoc Biol.* Apr. 2000;67(4):450-6.

Ohki I et al., Solution structure of the methyl-CpG-binding domain of the methylation-dependent transcriptional repressor MBDI. *EMBO J.* Dec. 1, 1999;18(23):6653-61.

Poltorak A et al., Defective LPS signaling in C3H/HeJ and C57BL/10ScCr mice: mutations in Tlr4 gene. *Science.* Dec. 11, 1998;282(5396):2085-8.

Qureshi ST et al., Endotoxin-tolerant mice have mutations in Toll-like receptor 4 (Tlr4) *J Exp Med.* Feb. 15, 1999;189(4):615-25.

Rock FL et al., A family of human receptors structurally related to Drosophila Toll. *Proc Natl Acad Sci USA.* Jan. 20, 1998;95(2):588-93.

Stratford-Perricaudet LD et al., Widespread long-term gene transfer to mouse skeletal muscles and heart. *J Clin Invest.* Aug. 1992;90(2):626-30.

Takeuchi O et al., Genetic approaches to the study of Toll-like receptor function. *Microbes Infect.* Jul. 2002;4(9):887-95.

Takeuchi O et al., TLR6: A novel member of an expanding toll-like receptor family. *Gene.* Apr. 29, 1999;231(1-2):59-65.

Wagner H, Bacterial CpG DNA activates immune cells to signal infectious danger. *Adv Immunol.* 1999;73:329-68.

Wagner H, Interactions between bacterial CpG-DNA and TLR9 bridge innate and adaptive immunity. *Curr Opin Microbiol.* Feb. 2002;5(1):62-9.

Yamamoto S et al., DNA from bacteria, but not from vertebrates, induces interferons, activates natural killer cells and inhibits tumor growth. *Microbiol Immunol.* 1992;36(9):983-97.

Yamamoto T et al., Lipofection of synthetic oligodeoxyribonucleotide having a palindromic sequence of AACGTT to murine splenocytes enhances interferon production and natural killer activity. *Microbiol Immunol.* 1994;38(10):831-6.

Yi AK et al., CpG motifs in bacterial DNA activate leukocytes through the pH-dependent generation of reactive oxygen species. *J Immunol.* May 15, 1998;160(10):4755-61.

\* cited by examiner

PROCESS FOR HIGH THROUGHPUT SCREENING OF CPG-BASED IMMUNO-AGONIST/ANTAGONIST

RELATED APPLICATIONS

This application is a divisional application of U.S. patent application Ser. No. 09/954,987, issued as U.S. Pat. No. 6,943,240, filed Sep. 17, 2001, which claims benefit of U.S. Provisional Application No. 60/300,210, filed Jun. 22, 2001, U.S. Provisional Application No. 60/291,726, filed May 17, 2001, U.S. Provisional Application No. 60/263,657, filed Jan. 23, 2001, and U.S. Provisional Application No. 60/233,035, filed Sep. 15, 2000.

FIELD OF THE INVENTION

The invention pertains to signal transduction by immunostimulatory nucleic acids.

BACKGROUND OF THE INVENTION

Bacterial DNA is a potent immunomodulatory substance. Yamamoto S et al., *Microbiol Immunol* 36:983-997 (1992). It has been hypothesized to be a pathogen-derived ligand recognized by an unidentified pathogen recognition receptor that initiates a host of innate and adaptive immune responses. Wagner H, *Adv Immunol* 73:329-368 (1999). CpG motif-containing oligodeoxynucleotides (CpG ODN) can mimic the biology of bacterial DNA. Krieg A M et al., *Nature* 374: 546-549 (1995). CpG ODN and DNA vectors have recently been shown to be of clinical value due to immunostimulatory, hematopoietic and adjuvant qualities.

The adaptive immune system appeared approximately 450 million years ago when a transposon that carried the forerunners of the recombinase activating genes, RAG-1 and RAG-2, was inserted into the germ line of early jawed vertebrates. Agarwal A. et al., *Nature* 394:744 (1998). The ability to mount an adaptive immune response allowed organisms to remember the pathogens that they had already encountered, and natural selection made the adaptive immune response a virtually universal characteristic of vertebrates. However, this did not lead to discarding the previous form of host defense, the innate immune system. Indeed, this earlier form of host defense has been coopted to serve a second function, stimulating and orienting the primary adaptive immune response by controlling the expression of costimulatory molecules.

It had been surmised for a decade that cells of the innate immune system bear receptors for conserved molecular patterns associated with microbial pathogens. According to this model, when the protein antigens derived from pathogens are processed and presented as peptides that serve as the stimulus for specific T cell receptors, pattern recognition receptors (PRRs) on the antigen-presenting cells also induce the synthesis of costimulatory molecules, cytokines, and chemokines. These activated antigen-presenting cells serve to attract and activate the antigen-specific T cells that are essential to all adaptive immune responses. Janeway C A J, *Cold Spring Harbor Symp Quant Biol* 54:1 (1989); Fearon D T et al., *Science* 272:50 (1996); and Medzhitov R et al., *Cell* 91:295 (1997). It was known that the substances that can induce costimulation include bacterial lipopolysaccharide (LPS), synthetic double-stranded RNA, glycans, and mannans. Furthermore, experimental evidence indicated that the processed antigen ligand for the T cell had to be on the same cell as the costimulatory molecule. This is obviously of crucial importance for maintaining self-tolerance; bystander presentation of costimulatory molecules would mean that tolerance would be lost whenever an infection occurred.

To validate this model, it was necessary to identify receptors for microbial patterns that, upon binding pathogen ligands, initiate signaling cascades leading to the production of costimulatory molecules and cytokines. Molecules such as mannose binding protein (MBP) do not qualify for this role, because they activate proteolytic cascades or promote phagocytosis but are not known to induce costimulation. The breakthrough came with the identification of a human homologue of *Drosophila* Toll initially cloned as a cDNA and later named hTLR4 (for human Toll-like receptor). Medzhitov R et al., *Nature* 388:394 (1997); Rock F L et al., *Proc Natl Acad Sci USA* 95:588 (1998); Chaudhary P M et al., *Blood* 91:4020-4027 (1998).

Toll-like receptors (TLRs) are a family of germline-encoded transmembrane proteins that facilitate pathogen recognition and activation of the innate immune system. Hoffmann J A et al., *Science* 284, 1313-1318 (1999); Rock F L et al., *Proc Natl Acad Sci USA* 95:588-593 (1998). TLRs engage conserved pathogen-derived ligands and subsequently activate the TLR/IL-1R signal transduction pathway to induce a variety of effector genes. Medzhitov R et al., *Mol Cell* 2:253-258 (1998); Muzio M et al., *J Exp Med* 187:2097-2101 (1998).

So far, ten different mammalian TLRs have been described. Rock F L et al., *Proc Natl Acad Sci USA* 95:588-593 (1998); Chaudhary P M et al., *Blood* 91:4020-4027 (1998); Takeuchi O et al., *Gene* 231:59-65 (1999); Aderem A. et al., *Nature* 406:782-7 (2000). So far, genetic data suggest that the TLRs have unique functions and are not redundant. Ligands for and the function of most of these TLRs, aside from TLR2 and TLR4, remain to be elucidated.

It turns out that an LPS-binding and signaling receptor complex is assembled when hTLR4 interacts with LPS bound to CD14, a peripheral membrane protein held to the cell surface by a glycosyl-phosphoinositol tail. The presence of LPS binding protein (LBP) further increases signaling. The hTLR4 protein has a leucine-rich repeat sequence in its extracellular domain that interacts with CD14 complexed with LPS. TLR4 then transduces the LPS signal across the membrane because destructive mutation of this gene lead to an LPS-unresponsive state in mice, which are also deficient in the clearance of Gram-negative bacteria. Poltorak A et al., *Science* 282:2085 (1998); Qureshi S T et al., *J Exp Med* 189:615-625 (1999); Eden C S et al., *J Immunol* 140:180 (1988). It has since become apparent that humans, like flies, have numerous Toll-like receptors (TLRs).

TLR4 and other TLRs have a cytoplasmic Toll/IL-1 receptor (TIR) homology domain. This domain communicates with a similar domain on an adapter protein (MyD88) that interacts with TLR4 by means of a like:like interaction of TIR domains. The next interaction is between the adapter and a kinase, through their respective "death domains." The kinase in turn interacts with tumor necrosis factor (TNF) receptor-associated factor-6 (TRAF6). Medzhitov R et al., *Mol Cell* 2:253 (1998); Kopp E B et al., *Curr Opin Immunol* 11:15 (1999). After TRAF6, two sequential kinase activation steps lead to phosphorylation of the inhibitory protein IκB and its dissociation from NF-κB. The first kinase is a mitogen-activated kinase kinase kinase (MAPKKK) known as NIK, for NF-κB-inducing kinase. The target of this kinase is another kinase made up of two chains, called IκB kinase α (IKKα) and IκB kinase β (IKKβ), that together form a heterodimer of IKKα:IKKβ, which phosphorylates IKβ. NF-κB translocates to the nucleus to activate genes with κB binding sites in their promoters and enhancers such as the genes encoding interleukin-1β (IL-1β), IL-6, IL-8, the p40 protein of IL-12, and the costimulatory molecules CD80 and CD86.

The types of cells that respond to CpG DNA—B cells, dendritic cells (DCs) and macrophages—are also stimulated by other pathogen-derived pattern-recognition factors, such as LPS. In general, the PRRs of the innate immune system are situated on the cell surface, where they are probably best able to detect microbes. Although cell-surface proteins that bind DNA are well described, and have been proposed to mediate immune activation by CpG motif (Liang H et al., *J Clin Invest* 98:1119-1129 (1998)), this binding is sequence-independent and does not bring about cell activation. Krieg A M et al., *Nature* 374:546-549 (1995); Yamamoto T et al., *Microbiol Immunol* 38:831-836 (1994); Häcker H et al., *EMBO J.* 17:6230-6240 (1998). Because CpG ODNs that have been immobilized to prevent cell uptake are nonstimulatory (Krieg A M et al., *Nature* 374:546-549 (1995); Manzel L et al., *Antisense Nucleic Acid Drug Dev* 9:459-464 (1999)), it appears that CpG ODN probably work by binding to an intracellular receptor. In support of this hypothesis, drugs such as chloroquine, which interfere with the endosomal acidification/processing of ODNs, specifically block the immune stimulatory effects of CpG DNA. Häcker H et al., *EMBO J.* 17:6230-6240 (1998); Macfarlane D E et al., *J Immunol* 160:1122-1131 (1998); Yi A K et al., *J Immunol* 160:4755-4761 (1998). It has been proposed that an endosomal step is required for the CpG-induced signal transduction pathways. Häcker H et al., *EMBO J.* 17:6230-6240 (1998); Yi A K et al., *J Immunol* 160:4755-4761 (1998). How the information contained in unmethylated CpG-motifs of bacterial DNA trigger changes in gene expression has not previously been discovered.

Since the receptor for bacterial DNA has been unknown, development of screening for optimal CpG motifs through direct binding analysis has been limited. An additional complication appears to be species-specific selectivity for CpG sequence, i.e., an optimal sequence for one species may not be optimal for another.

SUMMARY OF THE INVENTION

Nucleic acids encoding three Toll-like receptors, Toll-like receptor 7 (TLR7), TLR8, and TLR9 of the mouse have now been identified, isolated, cloned and sequenced by the inventors. The invention in general provides isolated nucleic acid molecules encoding TLRs and isolated fragments of those nucleic acid molecules; isolated TLR polypeptides and isolated fragments of those polypeptides; expression vectors containing the foregoing nucleic acid molecules; host cells having the foregoing expression vectors; fusion proteins including the TLR polypeptides and fragments thereof; and screening methods useful for identifying, comparing, and optimizing agents which interact with these TLRs, particularly agents that alter the expression of and signaling associated with these TLR molecules. In preferred embodiments the screening methods are high throughput screening methods.

The invention in some aspects arises from the surprising discovery that TLR9 is involved in immunostimulatory nucleic acid (ISNA)-induced immunostimulation. The invention also stems in part from the surprising discovery that TLR9 transduces immune activating signals in response to ISNA in a manner that is both sequence-specific and species-specific.

In a first aspect the invention provides isolated nucleic acid molecules which encode full-length murine TLR9. According to this aspect of the invention, isolated nucleic acid molecules are provided which are selected from the group consisting of (a) nucleic acid molecules which hybridize under stringent conditions to a nucleic acid molecule having a nucleotide sequence set forth as SEQ ID NO:1, and which code for a murine TLR9 having an amino acid sequence set forth as SEQ ID NO:3; (b) nucleic acid molecules that differ from the nucleic acid molecules of (a) in codon sequence due to degeneracy of the genetic code; and (c) complements of (a) or (b). In a certain embodiment, the isolated nucleic acid molecule codes for SEQ ID NO:3, where SEQ ID NO:3 represents the deduced amino acid sequence of full-length murine TLR9. In some embodiments the isolated nucleic acid molecule comprises the nucleotide sequence of SEQ ID NO:1 or SEQ ID NO:2, where these correspond to full-length cDNA and the open reading frame for murine TLR9, respectively.

The term "stringent conditions" as used herein refers to combined conditions based on parameters including salt, temperature, organic solvents, and optionally other factors with which the paractioner skilled in the art is familiar. Nucleic acid hybridization parameters may be found in references which compile such methods, e.g., *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. More specifically, stringent conditions, as used herein, refers, for example, to hybridization at 65° C. in hybridization buffer (3.5×SSC, 0.02% Ficoll, 0.02% polyvinyl pyrrolidone, 0.02% bovine serum albumin, 2.5 mM $NaH_2PO_4$ (pH7), 0.5% SDS, 2 mM EDTA). SSC is 0.15 M sodium chloride/0.15 M sodium citrate, pH7; SDS is sodium dodecyl sulfate; and EDTA is ethylenediaminetetraacetic acid. After hybridization, the membrane upon which the DNA is transferred is washed with 2×SSC at room temperature and then with 0.1-0.5×SSC/0.1×SDS at temperatures up to 68° C. There are other conditions, reagents, and so forth which can be used, which result in a similar degree of stringency. The skilled artisan will be familiar with such conditions, and thus they are not given here. It will be understood, however, that the skilled artisan will be able to manipulate the conditions in a manner to permit the clear identification of alleles of murine TLR nucleic acids of the invention. The skilled artisan also is familiar with the methodology for screening cells and libraries for expression of such molecules which then are routinely isolated, followed by isolation of the pertinent nucleic acid molecule and sequencing.

The invention in a second aspect provides isolated TLR9 polypeptides or fragments thereof. The isolated TLR9 polypeptides or fragments thereof include at least one amino acid of a murine TLR9 selected from the group consisting of amino acids 2, 3, 4, 6, 7, 18, 19, 22, 38, 44, 55, 58, 61, 62, 63, 65, 67, 71, 80, 84, 87, 88, 91, 101, 106, 109, 117, 122, 123, 134, 136, 140, 143, 146, 147, 157, 160, 161, 167, 168, 171, 185, 186, 188, 189, 191, 199, 213, 217, 220, 227, 231, 236, 245, 266, 269, 270, 271, 272, 273, 274, 278, 281, 285, 297, 298, 301, 305, 308, 311, 322, 323, 325, 326, 328, 332, 335, 346, 348, 353, 355, 358, 361, 362, 365, 367, 370, 372, 380, 381, 382, 386, 389, 392, 394, 397, 409, 412, 413, 415, 416, 419, 430, 432, 434, 435, 438, 439, 443, 444, 446, 447, 448, 450, 451, 452, 454, 455, 459, 460, 463, 465, 466, 468, 469, 470, 472, 473, 474, 475, 478, 488, 489, 494, 495, 498, 503, 508, 510, 523, 531, 539, 540, 543, 547, 549, 561, 563, 565, 576, 577, 579, 580, 587, 590, 591, 594, 595, 597, 599, 601, 603, 610, 611, 613, 616, 619, 632, 633, 640, 643, 645, 648, 650, 657, 658, 660, 667, 670, 672, 675, 679, 689, 697, 700, 703, 705, 706, 711, 715, 716, 718, 720, 723, 724, 726, 729, 731, 735, 737, 743, 749, 750, 751, 752, 754, 755, 759, 760, 772, 774, 780, 781, 786, 787, 788, 800, 814, 821, 829, 831, 832, 835, 844, 857, 858, 859, 862, 864, 865, 866, 879, 893, 894, 898, 902, 910, 917, and 927 of SEQ ID NO:3, wherein the TLR9 polypeptide or fragment thereof has an amino acid sequence which is identical to a human TLR9 polypeptide or fragment thereof except for the at least one amino acid of murine TLR9. The TLR9 polypeptide or fragment thereof in certain embodiments according to this aspect of the invention further includes at least one amino acid of murine TLR9 selected from the group consisting of amino acids 949, 972, 975, 976, 994, 997, 1000, 1003, 1004, 1010, 1011, 1018, 1023, and 1027 of SEQ ID NO:3. Thus specifically excluded from this aspect of the invention are TLR9 fragments restricted to the C-terminal 95 amino acids and fragments thereof.

In certain embodiments the TLR9 polypeptide and fragments thereof according to this aspect of the invention exclude those TLR9 polypeptides and fragments thereof which differ from human TLR9 and fragments thereof only by one or more conservative amino acid substitutions at particular sites noted above. As is well known in the art, a "conservative amino acid substitution" refers to an amino acid substitution which generally does not alter the relative charge or size characteristics of the polypeptide in which the amino acid substitution is made. Conservative substitutions of amino acids typically include substitutions made amongst amino acids within the following groups: methionine (M), isoleucine (I), leucine (L), valine (V); phenylalanine (F), tyrosine (Y), tryptophan (W); lysine (K), arginine (R), histidine (H); alanine (A), glycine (G); serine (S), threonine (T); glutamine (Q), asparagine (N); and glutamic acid (E), aspartic acid (D).

According to this and other aspects of the invention, with reference to TLR "polypeptides and fragments thereof," "fragments thereof" refers to polypeptide fragments having stretches of contiguous amino acid residues that are at least about 8 amino acids long. Generally the fragments are at least about 10 amino acids long; more generally at least 12 amino acids long; often at least about 14 amino acids long; more often at least about 16 amino acids long; typically at least 18 amino acids long; more typically at least 20 amino acids long; usually at least 22 amino acids long; and more usually at least 24 amino acids long. Certain preferred embodiments include larger fragments that are, for example, at least about 30 amino acids long, at least about 40 amino acids long, at least about 50 amino acids long, at least about 100 amino acids long, at least about 200 amino acids long, and so on, up to and including fragments that are a single amino acid shorter than full-length TLR polypeptide.

In certain embodiments, the human TLR9 has an amino acid sequence set forth as SEQ ID NO:6.

In preferred embodiments, the isolated TLR9 polypeptides or fragments thereof include an amino acid sequence selected from the group consisting of SEQ ID NO:3 and fragments of SEQ ID NO:3. In some embodiments according to this aspect of the invention, the isolated TLR9 polypeptides or fragments thereof include combinations of the foregoing human and murine TLR9 polypeptides.

In certain preferred embodiments the isolated TLR9 polypeptide or fragment thereof is an extracytoplasmic domain (also referred to herein as extracellular domain) of TLR9, or a portion thereof. As described in greater detail further herein, TLR7, TLR8, and TLR9 have certain structural and functional domains. Structural domains of these TLRs include but are not limited to an extracytoplasmic domain, a transmembrane domain, and a cytoplasmic domain. The extracytoplasmic domain extends into the lumen of endosomal/lysosomal vesicles. The cytoplasmic domain includes a Toll/interleukin-1 receptor-like domain (also referred to as Toll/IL-1R domain, TIR homology domain, or TIR domain). In murine TLR9 the extracytoplasmic, transmembrane, and cytoplasmic domains correspond to amino acids 1 to about 819, about 820 to about 837, and about 838 to about 1032, respectively.

As mentioned above, it has been discovered according to the invention that TLR9 is involved in immune activation induced by certain nucleic acid molecules referred to in the art as immunostimulatory nucleic acids (ISNAs), including CpG nucleic acids. It is believed by the inventors that binding of ISNA to TLR9 leads to signal transduction involving the TIR domain of TLR9. Thus in certain embodiments according to this aspect of the invention, the isolated TLR9 polypeptide or fragment thereof selectively binds to an ISNA, including an ISNA that is a CpG nucleic acid.

Also included according to this aspect of the invention are isolated TLR9 polypeptides or fragments thereof which are portions of the extracytoplasmic domain believed by the inventors to interact with immunostimulatory nucleic acids such as CpG nucleic acids. In certain embodiments such portions include an MBD motif set forth as any one of SEQ ID NOs: 126, 127, 210, and 211. In certain embodiments portions of the extracytoplasmic domain believed by the inventors to interact with immunostimulatory nucleic acids include a CXXC motif set forth as any one of SEQ ID NOs: 196, 197, and 198.

According to a third aspect of the invention, isolated nucleic acid molecules are provided which encode the foregoing isolated TLR9 polypeptides or fragments thereof. The isolated nucleic acid molecules according to this aspect of the invention specifically exclude certain expressed sequence tags (ESTs) identified by the following GenBank accession numbers: AA162495, AA197442, AA273731, AA794083, AA915125, AA968074, AI428529, AI451215, AI463056, AI893951, AV142833, AV326033, AV353853, AW048117, AW048548, AW215685, AW549817, BB179985, BB215203, BB283380, BB285606, BB312895, BB497196, BB622397, BF016670, BF150116, BF161011, BF300296, BF385702, BF539367, BF784415, BG863184, BG922959, BG967012, BG974917, BI105291, BI153921, BI651868, BI653892, and W76964.

In a fourth aspect the invention provides isolated nucleic acid molecules which encode full-length murine TLR7. According to this aspect of the invention, isolated nucleic acid molecules are provided which are selected from the group consisting of (a) nucleic acid molecules which hybridize under stringent conditions to a nucleic acid molecule having a nucleotide sequence set forth as SEQ ID NO:173, and which code for a murine TLR7 having an amino acid sequence set forth as SEQ ID NO:175; (b) nucleic acid molecules that differ from the nucleic acid molecules of (a) in codon sequence due to degeneracy of the genetic code; and (c) complements of (a) or (b). In a certain embodiment, the isolated nucleic acid molecule codes for SEQ ID NO:175, where SEQ ID NO:175 represents the deduced amino acid sequence of full-length murine TLR7. In some embodiments the isolated nucleic acid molecule comprises the nucleotide sequence of SEQ ID NO:173 or SEQ ID NO:174, where these correspond to full-length cDNA and the open reading frame for murine TLR7, respectively.

The invention in a fifth aspect provides isolated TLR7 polypeptides or fragments thereof. The isolated TLR7 polypeptides or fragments thereof include at least one amino acid of a murine TLR7 selected from the group consisting of amino acids 4, 8, 15, 16, 18, 21, 23, 24, 25, 27, 37, 39, 40, 41, 42, 44, 45, 61, 79, 83, 86, 89, 92, 96, 103, 109, 111, 113, 119, 121, 127, 128, 131, 145, 148, 151, 164, 172, 176, 190, 202, 203, 204, 205, 222, 225, 226, 228, 236, 238, 243, 250, 253, 266, 268, 271, 274, 282, 283, 287, 288, 308, 313, 314, 315, 325, 328, 331, 332, 341, 343, 344, 347, 351, 357, 360, 361, 362, 363, 364, 365, 366, 370, 371, 377, 378, 387, 388, 389, 392, 397, 398, 413, 415, 416, 419, 421, 422, 425, 437, 438, 440, 446, 449, 453, 454, 455, 456, 462, 470, 482, 486, 487, 488, 490, 491, 493, 494, 503, 505, 509, 511, 529, 531, 539, 540, 543, 559, 567, 568, 574, 583, 595, 597, 598, 600, 611, 613, 620, 624, 638, 645, 646, 651, 652, 655, 660, 664, 665, 668, 669, 672, 692, 694, 695, 698, 701, 704, 714, 720, 724, 727, 728, 733, 738, 745, 748, 755, 762, 777, 780, 789, 803, 846, 850, 851, 860, 864, 868, 873, 875, 884, 886, 888, 889, 890, 902, 903, 911, 960, 967, 970, 980, 996, 1010, 1018, 1035, and 1045 of SEQ ID NO:175, wherein the TLR7 polypeptide or fragment thereof has an amino acid sequence which is identical to a human TLR7 polypeptide or fragment thereof except for the at least one amino acid of murine TLR7.

In certain embodiments the TLR7 polypeptide and fragments thereof according to this aspect of the invention exclude those TLR7 polypeptides and fragments thereof which differ from human TLR7 and fragments thereof only by one or more conservative amino acid substitutions at particular sites noted above.

In certain embodiments, the human TLR7 has an amino acid sequence set forth as SEQ ID NO:170.

In preferred embodiments, the isolated TLR7 polypeptides or fragments thereof include an amino acid sequence selected from the group consisting of SEQ ID NO:175 and fragments of SEQ ID NO:175. In some embodiments according to this aspect of the invention, the isolated TLR7 polypeptides or fragments thereof include combinations of the foregoing human and murine TLR7 polypeptides.

In certain preferred embodiments the isolated TLR7 polypeptide or fragment thereof is an extracytoplasmic domain of TLR7, or a portion thereof. In certain embodiments according to this aspect of the invention, the isolated TLR7 polypeptide or fragment thereof selectively binds to an ISNA, including an ISNA that is a CpG nucleic acid. Also included according to this aspect of the invention are isolated TLR7 polypeptides or fragments thereof which are portions of the extracytoplasmic domain believed by the inventors to interact with immunostimulatory nucleic acids such as CpG nucleic acids. In certain embodiments such portions include an MBD motif set forth as any one of SEQ ID NOs: 203, 204, 212, and 213. In certain embodiments portions of the extracytoplasmic domain believed by the inventors to interact with immunostimulatory nucleic acids include a CXXC motif set forth as any one of SEQ ID NOs:196, 199, and 200.

According to a sixth aspect of the invention, isolated nucleic acid molecules are provided which encode the foregoing isolated TLR7 polypeptides or fragments thereof. The isolated nucleic acid molecules according to this aspect of the invention specifically exclude certain ESTs identified by the following GenBank accession numbers: AA176010, AA210352, AA241310, AA266000, AA266744, AA276879, AA288480, AA871870, AI119722, AI449297, AI466859, AI604175, AV322307, BB033376, BB116163, BB210788, BB464985, BB466708, BB636153, BF101884, BF124798, BF143871, BG067922, BG080980, BG082140, BG871070, BG964747, BG976560, BI150306, BI411471, and C87987.

In a seventh aspect the invention provides isolated nucleic acid molecules which encode full-length murine TLR8. According to this aspect of the invention, isolated nucleic acid molecules are provided which are selected from the group consisting of (a) nucleic acid molecules which hybridize under stringent conditions to a nucleic acid molecule having a nucleotide sequence set forth as SEQ ID NO:190, and which code for a murine TLR8 having an amino acid sequence set forth as SEQ ID NO:192; (b) nucleic acid molecules that differ from the nucleic acid molecules of (a) in codon sequence due to degeneracy of the genetic code; and (c) complements of (a) or (b). In a certain embodiment, the isolated nucleic acid molecule codes for SEQ ID NO:192, where SEQ ID NO:192 represents the deduced amino acid sequence of full-length murine TLR8. In some embodiments the isolated nucleic acid molecule comprises the nucleotide sequence of SEQ ID NO:190 or SEQ ID NO:191, where these correspond to full-length cDNA and the open reading frame for murine TLR8, respectively.

The invention in an eighth aspect provides isolated TLR8 polypeptides or fragments thereof. The isolated TLR8 polypeptides or fragments thereof include at least one amino acid of a murine TLR8 selected from the group consisting of amino acids 5, 6, 9, 10, 14, 15, 18, 21, 22, 23, 24, 25, 26, 27, 28, 30, 39, 40, 41, 43, 44, 50, 51, 53, 55, 61, 67, 68, 74, 80, 85, 93, 98, 99, 100, 104, 105, 106, 107, 110, 114, 117, 119, 121, 124, 125, 134, 135, 138, 145, 155, 156, 157, 160, 161, 162, 163, 164, 166, 169, 170, 174, 180, 182, 183, 186, 187, 191, 193, 194, 196, 197, 199, 200, 207, 209, 210, 227, 228, 230, 231, 233, 234, 241, 256, 263, 266, 267, 268, 269, 272, 274, 275, 276, 280, 285, 296, 298, 299, 300, 303, 305, 306, 307, 310, 312, 320, 330, 333, 335, 343, 344, 345, 346, 347, 349, 351, 356, 362, 365, 366, 375, 378, 379, 380, 381, 383, 384, 386, 387, 392, 402, 403, 408, 414, 416, 417, 422, 426, 427, 428, 429, 430, 431, 433, 437, 438, 439, 440, 441, 444, 445, 449, 456, 461, 463, 471, 483, 486, 489, 490, 494, 495, 496, 505, 507, 509, 512, 513, 519, 520, 523, 537, 538, 539, 541, 542, 543, 545, 554, 556, 560, 567, 569, 574, 575, 578, 586, 592, 593, 594, 595, 597, 599, 602, 613, 617, 618, 620, 621, 623, 628, 630, 633, 639, 641, 643, 644, 648, 655, 658, 661, 663, 664, 666, 668, 677, 680, 682, 687, 688, 690, 692, 695, 696, 697, 700, 702, 703, 706, 714, 715, 726, 727, 728, 730, 736, 738, 739, 741, 746, 748, 751, 752, 754, 757, 764, 766, 772, 776, 778, 781, 784, 785, 788, 791, 795, 796, 801, 802, 806, 809, 817, 820, 821, 825, 828, 829, 831, 839, 852, 853, 855, 858, 863, 864, 900, 903, 911, 918, 934, 977, 997, 1003, 1008, 1010, 1022, 1023, 1024, 1026, and 1030 of SEQ ID NO:192, wherein the TLR8 polypeptide or fragment thereof has an amino acid sequence which is identical to a human TLR8 polypeptide or fragment thereof except for the at least one amino acid of murine TLR8.

In certain embodiments the TLR8 polypeptide and fragments thereof according to this aspect of the invention exclude those TLR8 polypeptides and fragments thereof which differ from human TLR8 and fragments thereof only by one or more conservative amino acid substitutions at particular sites noted above.

In certain embodiments, the human TLR8 has an amino acid sequence set forth as SEQ ID NO:184.

In preferred embodiments, the isolated TLR8 polypeptides or fragments thereof include an amino acid sequence selected from the group consisting of SEQ ID NO:192 and fragments of SEQ ID NO:192. In some embodiments according to this aspect of the invention, the isolated TLR8 polypeptides or fragments thereof include combinations of the foregoing human and murine TLR8 polypeptides.

In certain preferred embodiments the isolated TLR8 polypeptide or fragment thereof is an extracytoplasmic domain of TLR8, or a portion thereof. In certain embodiments according to this aspect of the invention, the isolated TLR8 polypeptide or fragment thereof selectively binds to an ISNA, including an ISNA that is a CpG nucleic acid. Also included according to this aspect of the invention are isolated TLR8 polypeptides or fragments thereof which are portions of the extracytoplasmic domain believed by the inventors to interact with immunostimulatory nucleic acids such as CpG nucleic acids. In certain embodiments such portions include an MBD motif set forth as any one of SEQ ID NOs: 205, 206, 214, and 215. In certain embodiments portions of the extracytoplasmic domain believed by the inventors to interact with immunostimulatory nucleic acids include a CXXC motif set forth as any one of SEQ ID NOs: 196, 201, and 202.

According to a ninth aspect of the invention, isolated nucleic acid molecules are provided which encode the foregoing isolated TLR8 polypeptides or fragments thereof. The isolated nucleic acid molecules according to this aspect of the invention specifically exclude certain ESTs identified by the following GenBank accession numbers: AA116795, AA268605, AA920337, AI529457, AI849892, AV097766, AV 117427, AV164719, AV169968, AW551677, BB143750, BB214171, BB243478, BB244318, BB254686, BB256660, BB258368, BB278984, BB291470, BB292008, BB364655, BB373674, BB428800, BB439876, BB444812, BB445724, BB465766, BB470182, BB535086, BB573907, BB573981, BB607650, BF135656, BF722808, BG299237, BG918020, BG919592, and W39977.

In a further aspect, the invention provides TLR expression vectors comprising the foregoing isolated nucleic acid molecules operably linked to a promoter. Thus in certain embodiments pertaining to TLR9, the expression vector includes an isolated nucleic acid molecule according to the first aspect or the third aspect of the invention, operably linked to a promoter. In other embodiments, relating to TLR7, the expression vector includes an isolated nucleic acid molecule according to the fourth aspect or the sixth aspect of the invention, operably linked to a promoter. In yet other embodiments, relating to TLR8, the expression vector includes an isolated nucleic acid molecule according to the seventh aspect or the ninth aspect of the invention, operably linked to a promoter.

The expression vectors according to this aspect of the invention are designed and constructed so that when they are introduced into a cell, under proper conditions they direct expression of the gene product encoded by the incorporated isolated nucleic acid molecule. For example, the promoter can be constitutively active or it can be inducible or repressible upon interaction with a suitable inducer or repressor compound.

According to another aspect, host cells are provided that include a TLR expression vector of the invention. While any suitable method can be used, an expression vector typically is introduced into a cell by transfection or transformation. The host cells transformed or transfected with the TLR expression vectors are in some embodiments co-transformed or co-transfected with another expression vector useful for the expression of another polypeptide. Alternatively, a host cell can be tranformed or transfected with an expression vector capable of directing expression of a TLR polypeptide or fragment thereof of the invention and (i) at least one additional TLR polypeptide or fragment thereof, or (ii) at least one non-TLR polypeptide or fragment thereof. In certain preferred embodiments, the host cell includes separate expression vectors for any combination of TLR7, TLR8, and TLR9. In some embodiments, a co-transformed or co-transfected expression vector may be useful for detection or regulation of TLR expression or TLR-related signaling. Specifically, in certain preferred embodiments the host cell includes an expression vector providing a reporter construct capable of interacting with a TIR domain.

In another aspect, the invention provides agents which selectively bind the isolated TLR polypeptides and fragments thereof of the invention. In certain embodiments the agent does not bind a human TLR polypeptide or fragment thereof, wherein the human TLR is selected from human TLR7, TLR8, and TLR9. In certain embodiments the agent is a polypeptide, preferably one selected from the group consisting of monoclonal antibodies, polyclonal antibodies, Fab antibody fragments, F(ab')$_2$ antibody fragments, Fv antibody fragments, antibody fragments including a CDR3 region, and fusion proteins and other polypeptides including any such antibodies or antibody fragments.

Also provided are agents which selectively bind the foregoing isolated nucleic acid molecules, preferably antisense nucleic acid molecules which selectively bind to any of the foregoing isolated nucleic acid molecules encoding a TLR polypeptide or fragment thereof. In some embodiments the agent is an isolated nucleic acid molecule which hybridizes under stringent conditions to an isolated nucleic acid moleucle provided according to any of the first, third, fourth, fifth, sixth, and eighth aspects of the invention. In certain preferred embodiments the agent is an isolated nucleic acid molecule having a nucleotide sequence which is complementary to an isolated nucleic acid moleucle provided according to any of the first, third, fourth, fifth, sixth, and eighth aspects of the invention.

In still other aspects of the invention, methods for inhibiting TLR expression and TLR signaling in a cell are provided. The methods include contacting the cell with an amount of an agent effective to inhibit TLR expression and TLR signaling in the cell, wherein the TLR is selected from the group consisting of TLR7, TLR8, and TLR9. In some embodiments the agent brought into contact with the cell is selected from the group consisting of monoclonal antibodies, polyclonal antibodies, Fab antibody fragments, F(ab')$_2$ antibody fragments, Fv antibody fragments, antibody fragments including a CDR3 region, and fusion proteins and other polypeptides that include any such antibodies or antibody fragments. In some embodiments the cell is contacted with an antisense nucleic acid specific for the TLR, in an amount effective to inhibit TLR expression in the cell. In some embodiments the cell is contacted with an agent such as a cytokine or small molecule, in an amount effective to inhibit TLR expression in the cell.

In yet another aspect the invention provides a method for identifying nucleic acid molecules which interact with a TLR polypeptide or a fragment thereof. The method involves contacting a TLR polypeptide selected from the group consisting of TLR7, TLR8, TLR9, and nucleic acid-binding fragments thereof with a test nucleic acid molecule; and measuring an interaction of the test nucleic acid molecule with the TLR polypeptide or fragment thereof. Nucleic acid-binding fragments of TLRs preferably include the extracytoplasmic domain or subportions thereof, such as those which include at least an MBD motif, a CXXC motif, or both an MBD motif and a CXXC motif.

In this and other aspects of the invention involving methods of use of TLR polypeptides and fragments thereof, in some embodiments the TLR polypeptide or fragment thereof is TLR7. Likewise in this and other aspects of the invention involving methods of use of TLR polypeptides and fragments thereof, in some embodiments the TLR polypeptide or fragment thereof is TLR8. Also in this and other aspects of the invention involving methods of use of TLR polypeptides and fragments thereof, in some embodiments the TLR polypeptide or fragment thereof is TLR9.

In this and other aspects of the invention involving methods of use of TLR polypeptides and fragments thereof, in some embodiments the TLR polypeptide or fragment thereof is expressed in a cell. The cell expressing the TLR polypeptide or fragment thereof may naturally express the TLR polypeptide or fragment thereof, or it may be a host cell as provided by other aspects of the instant invention.

In this and other aspects of the invention involving methods of use of TLR polypeptides and fragments thereof, in some embodiments the TLR polypeptide or fragment thereof is an isolated TLR polypeptide or fragment thereof. In certain preferred embodiments the isolated TLR polypeptide or fragment thereof is immobilized on a solid support, for example a multiwell plate, a slide, a BIAcore chip, a bead, a column, and the like. The immobilization can be accomplished by any chemical or physical method suitable for the purpose of the assay to be performed according to the method of the invention.

In certain embodiments the TLR polypeptide or fragment thereof is fused with an Fc fragment of an antibody. The Fc fragment portion of such a fusion molecule may be useful, for example, for attaching the TLR polypeptide or fragment thereof to a substrate, or for providing a target for detecting the presence of the TLR polypeptide or fragment thereof. The Fc fragment can be selected from any suitable vertebrate species and will typically, but not necessarily, be derived from an antibody belonging to the IgG class of antibodies. For example, the Fc can be a human or a murine Fcγ. In certain embodiments the TLR polypeptide or fragment thereof is fused with an Fc fragment of an antibody with a specific cleavage site at or near the junction between the TLR polypeptide or fragment thereof and the Fc fragment. In one preferred embodiment the cleavage site is a thrombin protease recognition site. In a preferred embodiment the TLR polypeptide or fragment thereof fused with the Fc fragment includes a TLR extracytoplasmic domain.

In certain embodiments the interaction involving the TLR polyeptide or fragment thereof and the test nucleic acid molecule is binding between the TLR polypeptide or fragment thereof and the test nucleic acid molecule.

In certain embodiments according to this aspect of the invention, the measuring is accomplished by a method selected from the group consisting of enzyme-linked immunosorbent assay (ELISA), biomolecular interaction assay (BIA), electromobility shift assay (EMSA), radioimmunoassay (RIA), polyacrylamide gel electrophoresis (PAGE), and Western blotting.

In certain embodiments the measuring is accomplished by a method comprising measuring a response mediated by a TLR signal transduction pathway. For example, the response mediated by a TLR signal transduction pathway can be selected from the group consisting of induction of a gene under control of NF-κB promoter and secretion of a cytokine. In certain preferred embodiments the gene under control of NF-κB promoter is selected from the group consisting of IL-8, IL-12 p40, NF-κB-luc, IL-12 p40-luc, and TNF-luc. In certain preferred embodiments the secreted cytokine is selected from the group consisting of IL-8, TNF-α, and IL-12 p40.

In another embodiment the method according to this aspect of the invention can be used to determine if the test nucleic acid molecule is an immunostimulatory nucleic acid. The method involves the additional steps of comparing (a) the response mediated by a TLR signal transduction pathway as measured in the presence of the test nucleic acid molecule with (b) a response mediated by a TLR signal transduction pathway as measured in the absence of the test nucleic acid molecule; and determining the test nucleic acid molecule is an immunostimulatory nucleic acid when (a) exceeds (b).

In yet another embodiment the method according to this aspect of the invention can be used to determine if the response to the test nucleic acid molecule is stronger or weaker than a response to a reference nucleic acid molecule. The method involves the additional steps of comparing the response to a reference response when the TLR polypeptide is independently contacted with a reference nucleic acid molecule; and determining if the response is stronger or weaker than the reference response. In this embodiment the test nucleic acid molecule and the reference nucleic acid molecule are not able to compete or interact. For example, the reference response can be a parallel control or a historical control.

In another embodiment the method involves the additional steps of comparing the response to a reference response when the TLR polypeptide is concurrently contacted with a reference nucleic acid molecule; and determining if the response is stronger or weaker than the reference response. In this embodiment the test nucleic acid molecule and the reference nucleic acid molecule are potentially able to compete or interact since they are both present, for example, in a single reaction.

In another aspect the invention provides a screening method for identifying an immunostimulatory nucleic acid. The method according to this aspect involves contacting a functional TLR selected from the group consisting of TLR7, TLR8, and TLR9 with a test nucleic acid molecule; detecting presence or absence of a response mediated by a TLR signal transduction pathway in the presence of the test nucleic acid molecule arising as a result of an interaction between the functional TLR and the test nucleic acid molecule; and determining the test nucleic acid molecule is an ISNA when the presence of a response mediated by the TLR signal transduction pathway is detected. A functional TLR refers to a TLR polypeptide or fragment thereof that can bind with a ligand and as a consequence of the binding engage at least one step or additional polypeptide in a TLR signal transduction pathway.

In one embodiment the method according to this aspect of the invention includes the further step of comparing (a) the response mediated by the TLR signal transduction pathway arising as a result of an interaction between the functional TLR and the test nucleic acid molecule with (b) a response arising as a result of an interaction between the functional TLR and a reference ISNA. In this and other screening assays of the instant invention, in preferred embodiments the screening method is performed on a plurality of test nucleic acids. In certain preferred embodiments the response mediated by the TLR signal transduction pathway is measured quantitatively, and the response mediated by the TLR signal transduction pathway associated with each of the plurality of test nucleic acid molecules is compared with a response arising as a result of an interaction between the functional TLR and a reference ISNA.

In certain preferred embodiments a subset of the plurality of test nucleic acid molecules is selected based on the ability of the subset to produce a specific response mediated by the TLR signal transduction pathway. For example, the specific response can be induction of a specific cytokine or panel of cytokines, e.g., Th1 cytokines, or, alternatively, inhibition of a specific cytokine or panel of cytokines, e.g., Th2 cytokines. The specific response can be induction, or, alternatively, inhibition of a specific class or subclass of antibody or panel of classes or subclasses of antibodies, e.g., Th1-associated antibodies or Th2-associated antibodies. The specific response in some embodiments can be activation or inhibition of certain types of immune cells, e.g., B cells, dendritic cells (DCs), and natural killer (NK) cells. In some embodiments the specific response can be induction or inhibition of proliferation of certain types of immune cells, e.g., B cells, T cells, NK cells, dendritic cells, monocytes/macrophages. The subset of the plurality of test nucleic acids is therefore selected on the basis of the common association between the test nucleic acids of the subset and the particular type of response mediated by the TLR signal transduction pathway. The particular type of response mediated by the TLR signal transduction pathway is typically, but not necessarily, an immune cell response.

In certain embodiments the response mediated by a TLR signal transduction pathway is selected from the group consisting of induction of a gene under control of NF-κB promoter and secretion of a cytokine. In certain preferred embodiments the gene under control of NF-κB promoter is selected from the group consisting of IL-8, IL-12 p40, NF-κB-luc, IL-12 p40-luc, and TNF-luc. In certain preferred embodiments the cytokine is selected from the group consisting of IL-8, TNF-α, and IL-12 p40.

In certain preferred embodiments the reference ISNA is a CpG nucleic acid.

In certain preferred embodiments the test nucleic acid molecule is a CpG nucleic acid.

According to this and other aspects of the invention involving functional TLR in a screening assay, in some embodiments the functional TLR is expressed in a cell. In some embodiments the functional TLR is naturally expressed by the cell. In certain preferred embodiments the cell is an isolated mammalian cell that naturally expresses the functional TLR. Whether the cell expresses the TLR naturally or the cell expresses the TLR because an expression vector having an isolated nucleic acid molecule encoding the TLR operatively linked to a promoter has been introduced into the cell, in some embodiments the cell further includes an expression vector comprising an isolated nucleic acid which encodes a reporter construct selected from the group consisting of IL-8, IL-12 p40, NF-κB-luc, IL-12 p40-luc, and TNF-luc, operatively linked to a promoter.

Also according to this and other aspects of the invention involving functional TLR in a screening assay, in certain embodiments the functional TLR is part of a cell-free system.

Also according to this and other aspects of the invention involving functional TLR in a screening assay, in certain embodiments the functional TLR is part of a complex with another TLR. In certain preferred embodiments the complex is a complex of TLR9 and TLR7. In certain preferred embodiments the complex is a complex of TLR9 and TLR8.

Also according to this and other aspects of the invention involving functional TLR in a screening assay, in certain embodiments the functional TLR is part of a complex with a non-TLR protein selected from the group consisting of MyD88, IRAK, TRAF6, IκB, NF-κB, and functional homologues and derivatives thereof.

Further according to this and other aspects of the invention involving functional TLR in a screening assay, in certain embodiments the response mediated by a TLR signal transduction pathway is selected from the group consisting of induction of a gene under control of NF-κB promoter and secretion of a cytokine.

Also according to this and other aspects of the invention involving functional TLR in a screening assay, in certain embodiments the gene under control of NF-κB promoter is selected from the group consisting of IL-8, IL-12 p40, NF-κB-luc, IL-12 p40-luc, and TNF-luc.

Also according to this and other aspects of the invention involving functional TLR in a screening assay, in certain embodiments wherein the cytokine is selected from the group consisting of IL-8, TNF-α, and IL-12 p40.

In a further aspect, the invention provides a screening method for comparing TLR signaling activity of a test compound with an ISNA. The method entails contacting a functional TLR selected from the group consisting of TLR7, TLR8, and TLR9 with a reference ISNA and detecting a reference response mediated by a TLR signal transduction pathway; contacting a functional TLR selected from the group consisting of TLR7, TLR8, and TLR9 with a test compound and detecting a test response mediated by a TLR signal transduction pathway; and comparing the test response with the reference response to compare the TLR signaling activity of the test compound with the ISNA.

In certain embodiments according to this aspect of the invention, the reference ISNA is a CpG nucleic acid.

In certain embodiments according to this aspect of the invention, the test compound is a polypeptide. In certain embodiments the test compound is part of a combinatorial library of compounds.

In certain embodiments the functional TLR is contacted with the reference ISNA and the test compound independently. Accordingly, in certain embodiments the screening method is a method for identifying an ISNA mimic, and the test compound is determined to be an ISNA mimic when the test response is similar to the reference response obtained with the reference ISNA. A test response is similar to the reference response when the test and reference responses are qualitatively alike, even if not quantitatively alike. Thus, for example, the test and reference responses are considered alike when both responses include induction of a Th1-like immune response. The test response can be quantitatively less than, about the same as, or greater than the reference response.

In certain other embodiments the functional TLR is contacted with the reference ISNA and the test compound concurrently to produce a test-reference response mediated by a TLR signal transduction pathway, wherein the test-reference response may be compared to the reference response. In certain preferred embodiments the screening method is a method for identifying an ISNA agonist, wherein the test compound is an ISNA agonist when the test-reference response is greater than the reference response. In certain preferred embodiments the screening method is a method for identifying an ISNA antagonist, wherein the test compound is an ISNA antagonist when the test-reference response is less than the reference response.

In a further aspect the invention provides a screening method for identifying species specificity of an ISNA. The method according to this aspect of the invention involves contacting a functional TLR selected from the group consisting of TLR7, TLR8, and TLR9 of a first species with a test ISNA; contacting a functional TLR selected from the group consisting of TLR7, TLR8, and TLR9 of a second species with the test ISNA; measuring a response mediated by a TLR signal transduction pathway associated with the contacting the functional TLR of the first species with the test ISNA; measuring a response mediated by the TLR signal transduction pathway associated with the contacting the functional TLR of the second species with the test ISNA; and comparing (a) the response mediated by a TLR signal transduction pathway associated with the contacting the functional TLR of the first species with the test ISNA with (b) the response mediated by the TLR signal transduction pathway associated with the contacting the functional TLR of the second species with the test ISNA. In preferred embodiments the TLR of the first species corresponds to the TLR of the second species, e.g., the TLR of the first species is human TLR9 and the TLR of the second species is murine TLR9. In certain embodiments the functional TLR may be expressed in a cell, part of cell-free system, or part of a complex with another TLR or with a non-TLR protein, as previously described.

In yet another aspect the invention provides a method for identifying lead compounds for a pharmacological agent useful in the treatment of disease associated with TLR9 signaling activity. The method according to this aspect of the invention involves providing a cell comprising a TLR9 polypeptide or fragment thereof as provided in the second aspect of the invention; contacting the cell with a candidate pharmacological agent under conditions which, in the absence of the candidate pharmacological agent, cause a first amount of TLR9 signaling activity; and determining a second amount of TLR9 signaling activity as a measure of the effect of the pharmacological agent on the TLR9 signaling activity, wherein a second amount of TLR9 signaling activity which is less than the first amount indicates that the candidate pharmacological agent is a lead compound for a pharmacological agent which reduces TLR9 signaling activity and wherein a second amount of TLR9 signaling activity which is greater than the first amount indicates that the candidate pharmacological agent is a lead compound for a pharmacological agent which increases TLR9 signaling activity.

These and other aspects of the invention are described in greater detail below.

CXXCm to various stimuli at different concentrations. ODN are as follows: ODN 1668 (SEQ ID NO:84) and ODN 2006 (SEQ ID NO:112).

Figure 22:
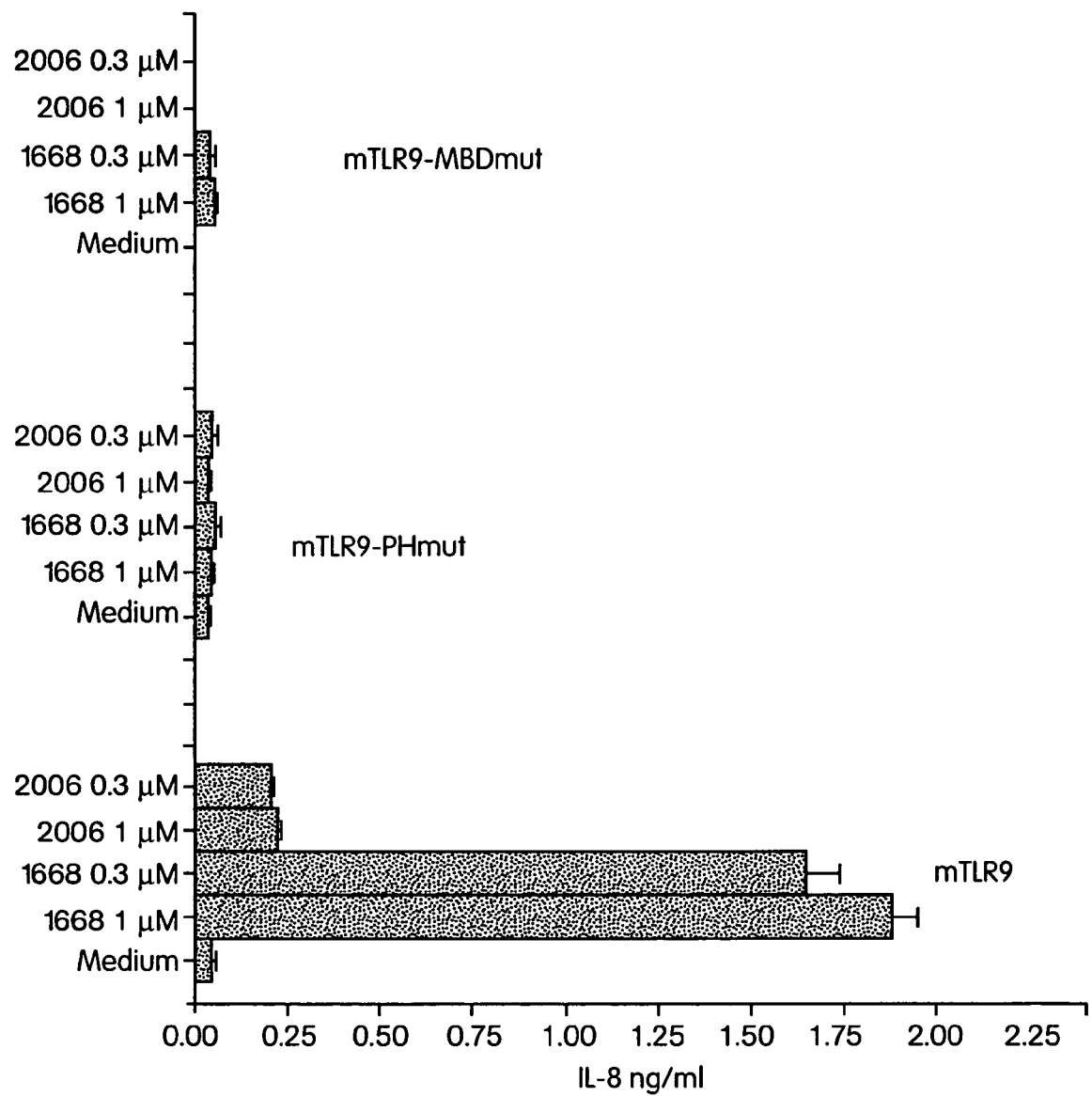

FIG. 22 is a bar graph showing the responsiveness of native form mTLR9, mTLR9 variant form mTLR9-Phmut, and mTLR9 variant form mTLR9-MBDmut to various stimuli at different concentrations. ODN are as follows: ODN 1668 (SEQ ID NO:84) and ODN 2006 (SEQ ID NO:112).

Figure 23:
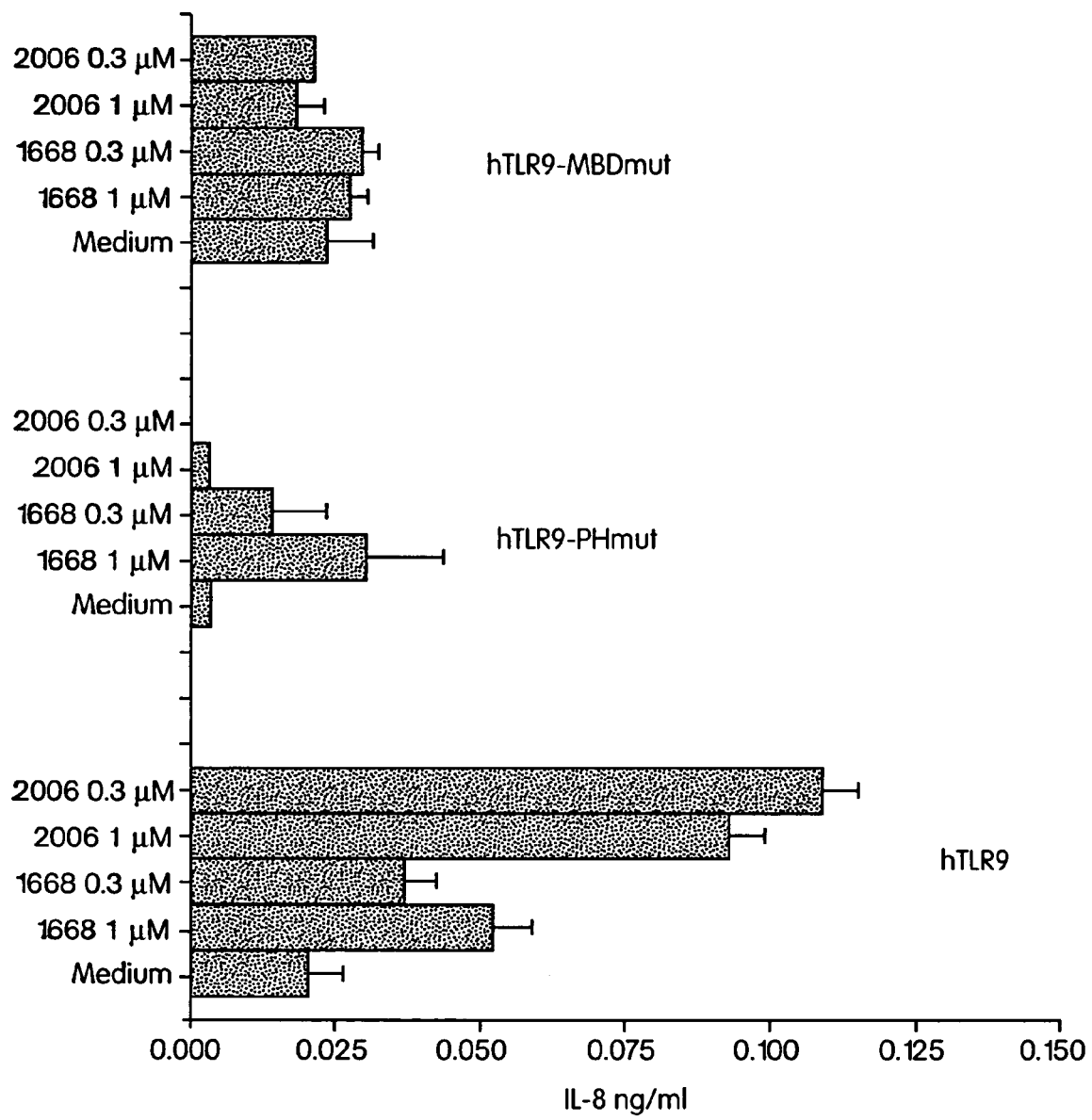

FIG. 23 is a bar graph showing the responsiveness of native form hTLR9, hTLR9 variant form hTLR9-PHmut, and hTLR9 variant form hTLR9-MBDmut to various stimuli at different concentrations. ODN are as follows: ODN 1668 (SEQ ID NO:84) and ODN 2006 (SEQ ID NO:112).

Figure 24:
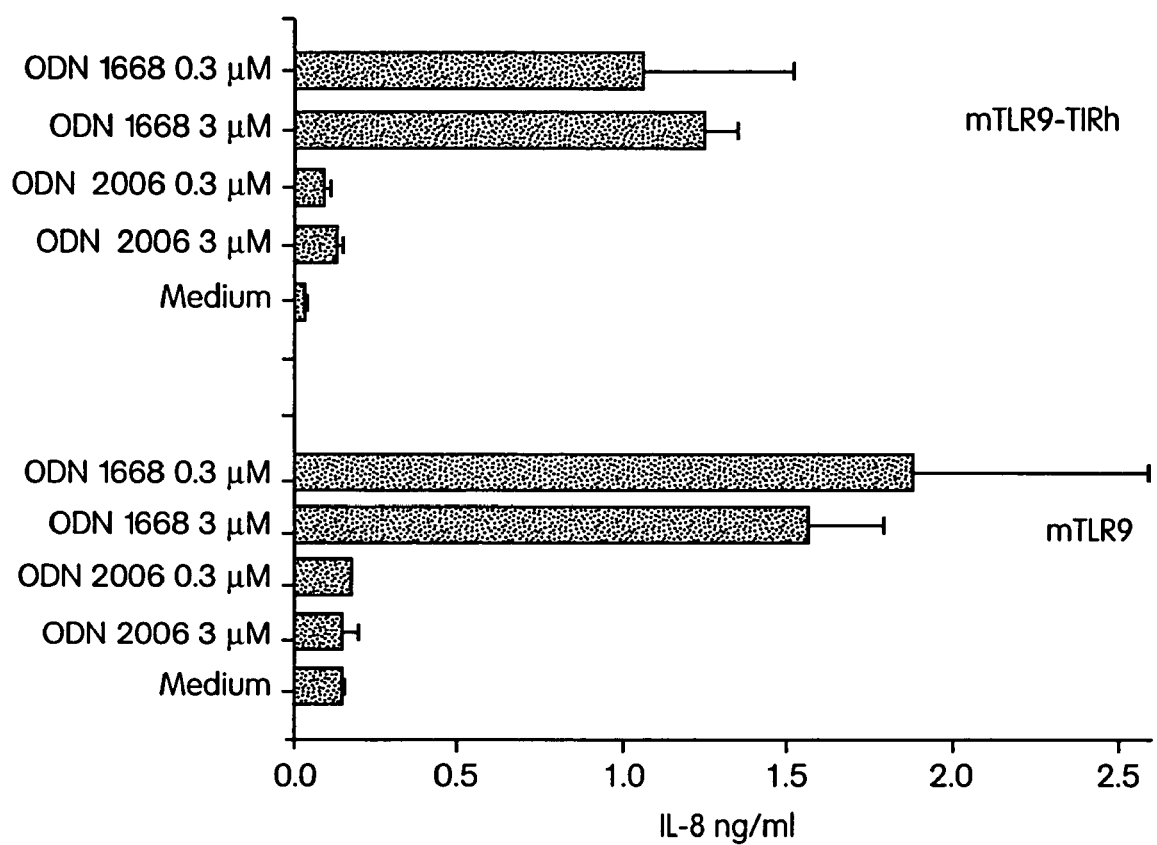

FIG. 24 is a bar graph showing the responsiveness of native form mTLR9 and mTLR9 variant form mTLR9-TIRh to various stimuli at different concentrations. ODN are as follows: ODN 1668 (SEQ ID NO:84) and ODN 2006 (SEQ ID NO:112).

Figure 25:
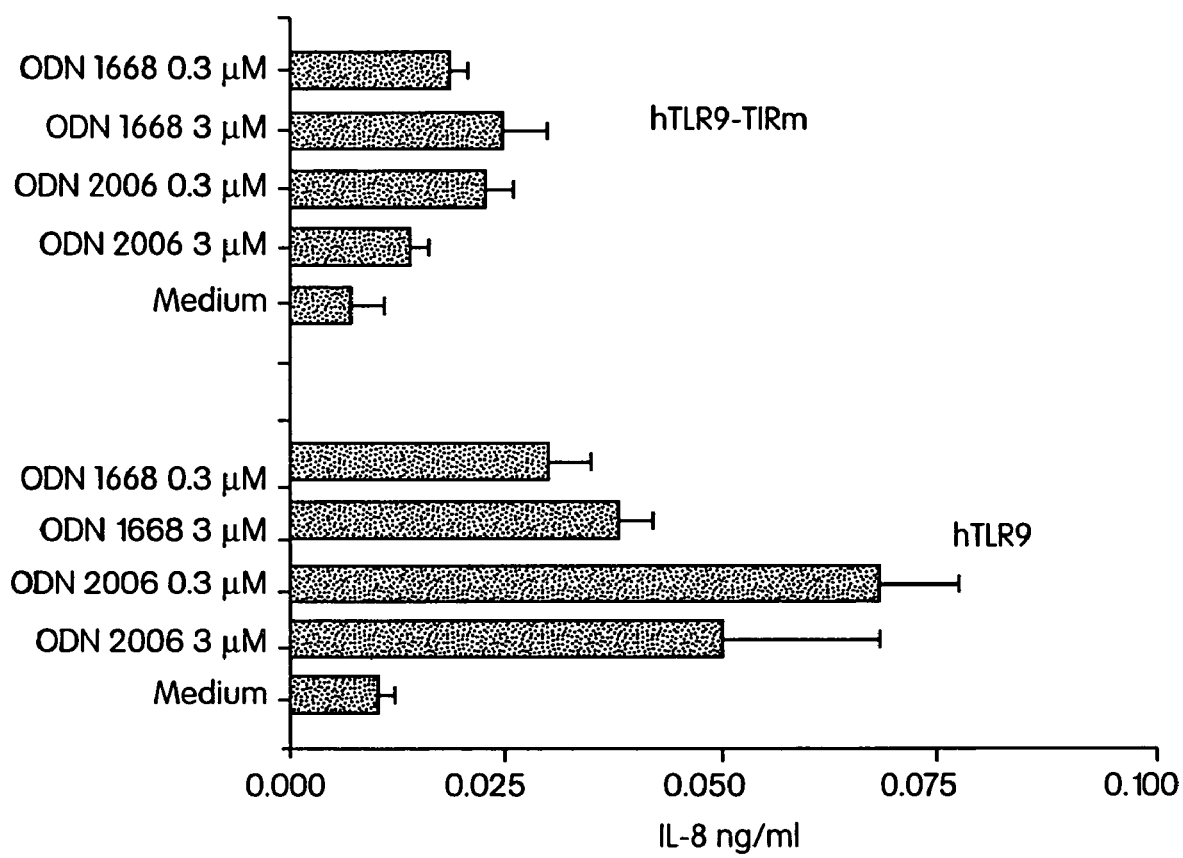

FIG. 25 is a bar graph showing the responsiveness of native form hTLR9 and hTLR9 variant form hTLR9-TIRm to various stimuli at different concentrations. ODN are as follows: ODN 1668 (SEQ ID NO:84) and ODN 2006 (SEQ ID NO:112).

Figure 26:
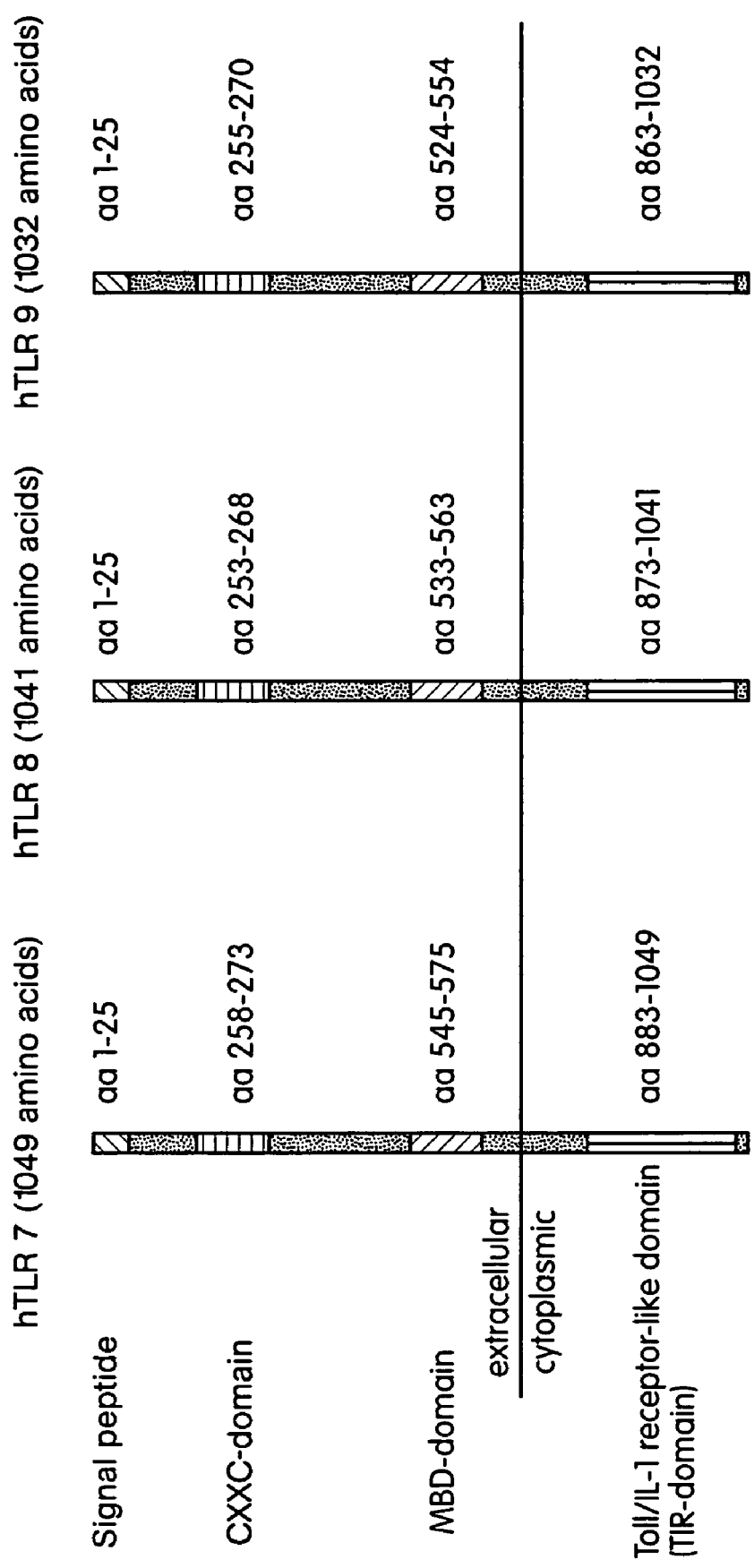

FIG. 26 is a series of linear maps representing various features of human TLR7, TLR8, and TLR9 polypeptides.

Figure 27:
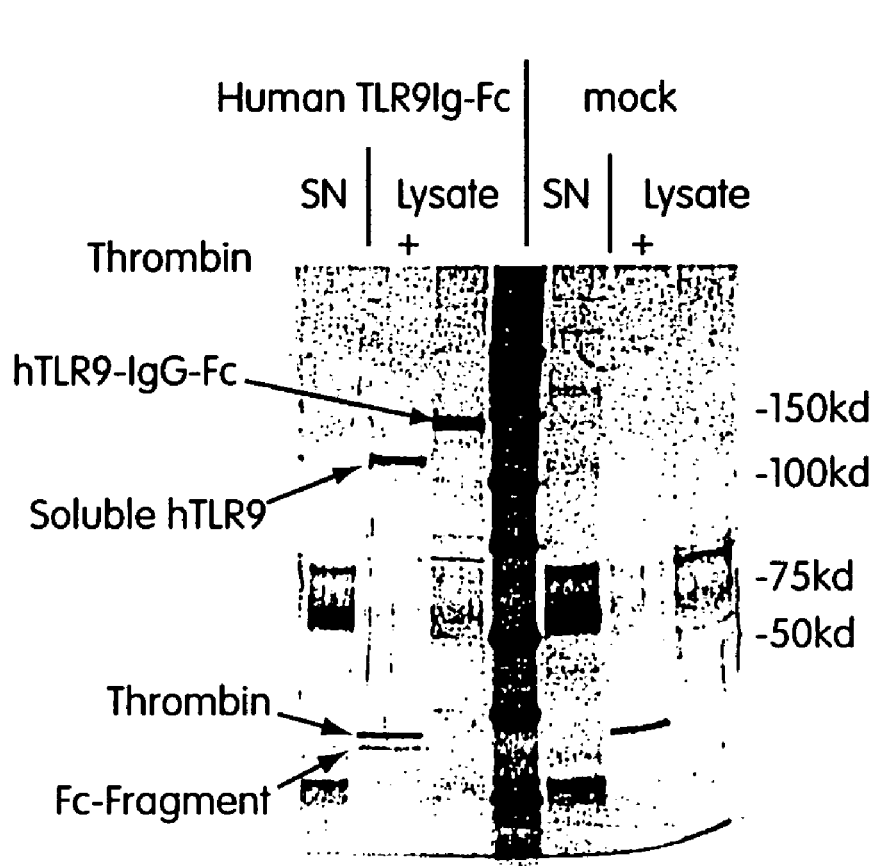
Figure 27:
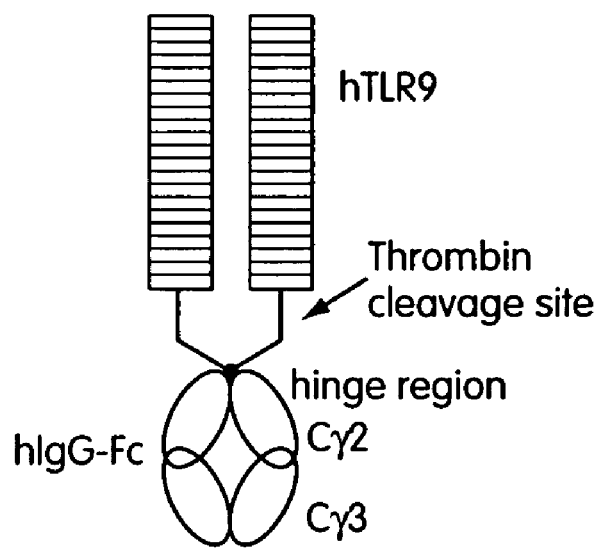

FIG. 27 is an image of a silver stained polyacrylamide gel and schematic representation of a fusion protein in which the extracellular domain of human TLR9 (hTLR9) is fused to a human IgG1 Fc domain (hIgG-Fc) with a thrombin protease recognition site interposed. From left to right, the gel was loaded with (1) supernatant of transfectants; (2) lysates of transfectants, treated with thrombin; (3) untreated lysates of transfectants; (4) molecular weight markers; (5) supernatant of mock transfectants; (6) lysates of mock transfectants, treated with thrombin; and (7) untreated lysates of mock transfectants. Soluble hTLR9 and Fc are the products released from intact hTLR9-IgG-Fc following thrombin treatment. Molecular weights are indicated along the right side of the silver stain gel image.

BRIEF DESCRIPTION OF SELECTED SEQUENCES

SEQ ID NO:1 is the nucleotide sequence encoding a cDNA for murine TLR9.

SEQ ID NO:2 is the nucleotide sequence encoding the coding region of murine TLR9.

SEQ ID NO:3 is the amino acid sequence of a murine TLR9 encoded by SEQ ID NO:1.

SEQ ID NO:173 is the nucleotide sequence encoding a cDNA for murine TLR7.

SEQ ID NO:174 is the nucleotide sequence encoding the coding region of murine TLR7.

SEQ ID NO:175 is the amino acid sequence of a murine TLR7 encoded by SEQ ID NO:173.

SEQ ID NO:190 is the nucleotide sequence encoding a cDNA for murine TLR8.

SEQ ID NO:191 is the nucleotide sequence encoding the coding region of murine TLR8.

SEQ ID NO:192 is the amino acid sequence of a murine TLR8 encoded by SEQ ID NO:190.

DETAILED DESCRIPTION OF THE INVENTION

The present invention in one aspect involves the identification of cDNAs encoding mouse TLR9, referred to herein as murine TLR9 and, equivalently, mTLR9. The nucleotide sequence of the cDNA for murine TLR9 is presented as SEQ ID NO:1, the coding region of the cDNA for murine TLR9 is presented as SEQ ID NO:2, and the amino acid sequence of the murine TLR9 is presented as SEQ ID NO:3. The closely related human TLR9 (equivalently, hTLR9) was deposited in GenBank under accession numbers AF245704 and NM_017742.

The nucleotide sequence of the cDNA for murine TLR9 presented as SEQ ID NO:1 is 3200 nucleotides long and includes the open reading frame (ORF, bases 40-3135) presented as SEQ ID NO:2 which spans 3096 nucleotides (excluding the stop codon). The amino acid sequence of the murine TLR9 presented as SEQ ID NO:3 is 1032 amino acids (aa) long, and it is believed to include an extracellular domain (aa 1-819), a transmembrane domain (aa 820-837), and an intracellular domain (aa 838-1032).

The amino acid sequence of human TLR9 (SEQ ID NO:6) and the amino acid sequence of the murine TLR9 (SEQ ID NO:3) are thus both 1032 amino acids long. Comparison of the aligned amino acid sequences for the murine and the human TLR9 molecules reveals a single base insertion at aa 435 of the murine TLR9 and a single base deletion at aa 860 of the human TLR9. (See Table 4 below.)

Whereas much of the polypeptide presented herein is identical to human TLR9, murine TLR9 has several single amino acid differences. These differences in amino acids are specifically amino acids 2, 3, 4, 6, 7, 18, 19, 22, 38, 44, 55, 58, 61, 62, 63, 65, 67, 71, 80, 84, 87, 88, 91, 101, 106, 109, 117, 122, 123, 134, 136, 140, 143, 146, 147, 157, 160, 161, 167, 168, 171, 185, 186, 188, 189, 191, 199, 213, 217, 220, 227, 231, 236, 245, 266, 269, 270, 271, 272, 273, 274, 278, 281, 285, 297, 298, 301, 305, 308, 311, 322, 323, 325, 326, 328, 332, 335, 346, 348, 353, 355, 358, 361, 362, 365, 367, 370, 372, 380, 381, 382, 386, 389, 392, 394, 397, 409, 412, 413, 415, 416, 419, 430, 432, 434, 435, 438, 439, 443, 444, 446, 447, 448, 450, 451, 452, 454, 455, 459, 460, 463, 465, 466, 468, 469, 470, 472, 473, 474, 475, 478, 488, 489, 494, 495, 498, 503, 508, 510, 523, 531, 539, 540, 543, 547, 549, 561, 563, 565, 576, 577, 579, 580, 587, 590, 591, 594, 595, 597, 599, 601, 603, 610, 611, 613, 616, 619, 632, 633, 640, 643, 645, 648, 650, 657, 658, 660, 667, 670, 672, 675, 679, 689, 697, 700, 703, 705, 706, 711, 715, 716, 718, 720, 723, 724, 726, 729, 731, 735, 737, 743, 749, 750, 751, 752, 754, 755, 759, 760, 772, 774, 780, 781, 786, 787, 788, 800, 814, 821, 829, 831, 832, 835, 844, 857, 858, 859, 862, 864, 865, 866, 879, 893, 894, 898, 902, 910, 917, 927, 949, 972, 975, 976, 994, 997, 1000, 1003, 1004, 1010, 1011, 1018, 1023, and 1027 of SEQ ID NO:3.

In some forms the mouse protein mTLR9 contains a signal sequence at the N-terminus (amino acids 1-26) which allows transport to the endoplasmic reticulum and subsequently to the cell surface or intracellular compartments. A transmembrane region (amino acids 820-837) anchors the protein to the cell membrane. The cytoplasmic tail contains a Toll/IL-1 receptor (TIR) homology domain which is believed to function in signaling upon ligand binding. Leucine-rich-repeats (LRR) can be found in the extracellular region (a common feature of TLRs) and may be involved in ligand binding or dimerization of the molecule.

Both mouse and human TLR9 have an N-terminal extension of approximately 180 amino acids compared to other TLRs. An insertion also occurs at amino acids 253-268, which is not found in TLRs 1-6 but is present in human TLR7 and human TLR8. (See FIG. 26.) This insert has two CXXC motifs which participate in forming a CXXC domain. The CXXC domain resembles a zinc finger motif and is found in DNA-binding proteins and in certain specific CpG binding proteins, e.g., methyl-CpG binding protein-1 (MBD-1). Fujita N et al., *Mol Cell Biol* 20:5107-5118 (2000). Both human and mouse TLR9 CXXC domains occur at aa 253-268:

```
CXXC motif:    GNCXXCXXXXXXCXXC    SEQ ID NO:196

Human TLR9:    GNCRRCDHAPNPCMEC    SEQ ID NO:197

Murine TLR9:   GNCRRCDHAPNPCMIC    SEQ ID NO:198
```

An additional motif involved in CpG binding is the MBD motif, also found in MBD-1, listed below as SEQ ID NO:125. Fujita, N et al., *Mol Cell Biol* 20:5107-18 (2000); Ohki I et al., *EMBO J.* 18:6653-6661 (1999). Amino acids 524-554 of hTLR9 and aa 525-555 of mTLR9 correspond to the MBD motif of MBD-1 as shown:

MBD motif:

```
                                             SEQ ID NO:125
MBD-1    R-XXXXXXX-R-X-D-X-Y-XXXXXXXXX-R-S-XXXXXX-Y

SEQ ID NO:126
hTLR9    Q-XXXXXXX-K-X-D-X-Y-XXXXXXXXX-R-L-XXXXXX-Y

SEQ ID NO:127
mTLR9    Q-XXXXXXX-K-X-D-X-Y-XXXXXXXXX-Q-L-XXXXXX-Y

SEQ ID NO:210
hTLR9    Q-VLDLSRN-K-L-D-L-Y-HEHSFTELP-R-L-EALDLS-Y

SEQ ID NO:211
mTLR9    Q-VLDLSHN-K-L-D-L-Y-HWKSFSELP-Q-L-QALDLS-Y
```

Although the signaling functions of MBD-1 and TLR9 are quite different, the core D-X-Y is involved in CpG binding and is conserved. The C-terminal octamer S-XXXXXX-Y of the MBD motif may not be involved in binding and the S is not conserved by TLR9. The other mismatches are highly conserved or moderately conserved; example R to K or R to Q. These changes could explain MBD-1 as a methyl-CpG binder and TLR9 as a non-methyl-CpG binder. The differences between mouse and human TLR9 may explain inter-species differences in CpG-motif sequence selectivity. See FIG. 14 for inter-species sequence selectivity.

As discussed in Example 11 below and shown in FIGS. 22 and 23, the D-X-Y core of this MBD motif occurs as D-L-Y in both mTLR9 (aa 535-537) and hTLR9 (aa 534-536). Substitution of A for D and A for Y in the D-X-Y core, resulting in A-L-A in place of D-L-Y, destroys receptor activity for mTLR9 and hTLR9 alike.

The invention involves in one aspect murine TLR9 nucleic acids and polypeptides, as well as therapeutics relating thereto. The invention also embraces isolated functionally equivalent variants, useful analogs and fragments of the foregoing nucleic acids and polypeptides; complements of the foregoing nucleic acids; and molecules which selectively bind the foregoing nucleic acids and polypeptides.

The murine TLR9 nucleic acids and polypeptides of the invention are isolated. As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which PCR primer sequences have been disclosed is considered isolated, but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art. An isolated nucleic acid as used herein is not a naturally occurring chromosome.

As used herein with respect to polypeptides, "isolated" means separated from its native environment and present in sufficient quantity to permit its identification or use. Isolated, when referring to a protein or polypeptide, means, for example: (i) selectively produced by expression cloning or (ii) purified as by chromatography or electrophoresis. Isolated proteins or polypeptides may be, but need not be, substantially pure. The term "substantially pure" means that the proteins or polypeptides are essentially free of other substances with which they may be found in nature or in vivo systems to an extent practical and appropriate for their intended use. Substantially pure polypeptides may be produced by techniques well known in the art. Because an isolated protein may be admixed with a pharmaceutically acceptable carrier in a pharmaceutical preparation, the protein may comprise only a small percentage by weight of the preparation. The protein is nonetheless isolated in that it has been separated from the substances with which it may be associated in living systems, i.e., isolated from other proteins.

As used herein a murine TLR9 nucleic acid refers to an isolated nucleic acid molecule which codes for a murine TLR9 polypeptide. Such nucleic acid molecules code for murine TLR9 polypeptides which include the sequence of SEQ ID NO:3 and fragments thereof. The nucleic acid molecules include the nucleotide sequences of SEQ ID NO:1, SEQ ID NO:2, and nucleotide sequences which differ from the sequences of SEQ ID NO:1 and SEQ ID NO:2 in codon sequence due to the degeneracy of the genetic code. The murine TLR9 nucleic acids of the invention also include alleles of the foregoing nucleic acids, as well as fragments of the foregoing nucleic acids. Such fragments can be used, for example, as probes in hybridization assays and as primers in a polymerase chain reaction. Preferred murine TLR9 nucleic acids include the nucleic acid sequence of SEQ ID NO:1 and SEQ ID NO:2. Complements of the foregoing nucleic acids also are embraced by the invention.

As used herein a murine TLR9 nucleic acid or murine TLR9 polypeptide also embraces homologues and alleles of murine TLR9. In general homologues and alleles typically will share at least 40% nucleotide identity and/or at least 50% amino acid identity to the sequences of specified nucleic acids and polypeptides, respectively. Thus homologues and alleles of murine TLR9 typically will share at least 40% nucleotide identity and/or at least 50% amino acid identity to the sequences of murine TLR9 nucleic acids and TLR9 polypeptides, respectively. In some instances homologues and alleles will share at least 50% nucleotide identity and/or at least 65% amino acid identity and in still other instances will share at least 60% nucleotide identity and/or at least 75% amino acid identity. Preferably the homologues and alleles will share at least 80% nucleotide identity and/or at least 90% amino acid identity, and more preferably will share at least 90% nucleotide identity and/or at least 95% amino acid identity. Most preferably the homologues and alleles will share at least 95% nucleotide identity and/or at least 99% amino acid identity. The homology can be calculated using various publicly available software tools developed by the National Center for Biotechnology Information (NCBI, Bethesda, Md.) that can be obtained through the internet. Exemplary tools include the BLAST system available from the NCBI, used with default settings. Pairwise and ClustalW alignments (BLOSUM30 matrix setting) as well as Kyte-Doolittle hydropathic analysis can be obtained, for example, using the MacVector sequence analysis software (Oxford Molecular Group). Watson-Crick complements of the foregoing nucleic acids also are embraced by the invention.

Alleles of the murine TLR9 nucleic acids of the invention can be identified by conventional techniques. For example, alleles of murine TLR9 can be isolated by hybridizing a probe which includes at least a fragment of SEQ ID NO:1 or SEQ ID NO:2 under stringent conditions with a cDNA library and selecting positive clones. Thus, an aspect of the invention is those nucleic acid sequences which code for murine TLR9 polypeptides and which hybridize to a nucleic acid molecule consisting of SEQ ID NO:1 or SEQ ID NO:2 under stringent conditions.

In screening for murine TLR nucleic acids, a Southern blot may be performed using the foregoing stringent conditions, together with a radioactive probe. After washing the membrane to which the DNA is finally transferred, the membrane can be placed against X-ray film to detect the radioactive signal. Corresponding non-radioactive methods are also well known in the art and can be used to similar effect.

The murine TLR nucleic acids of the invention also include degenerate nucleic acids which include alternative codons to those present in the native materials. For example, serine residues are encoded by the codons AGC, AGT, and TCA, TCC, TCG and TCT. Each of the six codons is equivalent for the purposes of encoding a serine residue. Thus, it will be apparent to one of ordinary skill in the art that any of the serine-encoding nucleotide triplets may be employed to direct the protein synthesis apparatus, in vitro or in vivo, to incorporate a serine residue into an elongating murine TLR polypeptide. Similarly, nucleotide sequence triplets which encode other amino acid residues include, but are not limited to: CCA, CCC, CCG and CCT (proline codons); CGA, CGC, CGG, CGT, AGA and AGG (arginine codons); ACA, ACC, ACG and ACT (threonine codons); AAC and AAT (asparagine codons); and ATA, ATC and ATT (isoleucine codons). As is well known by those of ordinary skill in the art, other specific amino acid residues may be encoded similarly by multiple nucleotide sequences. Thus, the invention embraces degenerate nucleic acids that differ from the biologically isolated nucleic acids in codon sequence due to the degeneracy of the genetic code. The above-noted codon degeneracy notwithstanding, it is well appreciated by those skilled in the art that there are certain codon usage preferences in specific host organisms, such that in practice it may be preferred to select or to avoid certain degenerate codons in a particular host.

The invention also provides modified nucleic acid molecules which include additions, substitutions and deletions of one or more nucleotides. The modified nucleic acid molecules according to this aspect of the invention exclude fully native human TLR9 nucleic acid molecules (GenBank Accession No. AF245704 (SEQ ID NO:4) or GenBank Accession No. NM_017442 (SEQ ID NO:5)). In preferred embodiments, these modified nucleic acid molecules and/or the polypeptides they encode retain at least one activity or function of the unmodified nucleic acid molecule and/or the polypeptides, such as signaling activity, etc. In certain embodiments, the modified nucleic acid molecules encode modified polypeptides, preferably polypeptides having conservative amino acid substitutions as are described elsewhere herein. The modified nucleic acid molecules are structurally related to the unmodified nucleic acid molecules and in preferred embodiments are sufficiently structurally related to the unmodified nucleic acid molecules so that the modified and unmodified nucleic acid molecules hybridize under stringent conditions known to one of skill in the art.

For example, modified nucleic acid molecules which encode polypeptides having single amino acid changes can be prepared. Each of these nucleic acid molecules can have one, two or three nucleotide substitutions exclusive of nucleotide changes corresponding to the degeneracy of the genetic code as described herein. Likewise, modified nucleic acid molecules which encode polypeptides having two amino acid changes can be prepared which have, e.g., 2-6 nucleotide changes. Numerous modified nucleic acid molecules like these will be readily envisioned by one of skill in the art, including for example, substitutions of nucleotides in codons encoding amino acids 2 and 3, 2 and 4, 2 and 5, 2 and 6, and so on. In the foregoing example, each combination of two amino acids is included in the set of modified nucleic acid molecules, as well as all nucleotide substitutions which code for the amino acid substitutions. Additional nucleic acid molecules that encode polypeptides having additional substitutions (i.e., 3 or more), additions or deletions (e.g., by introduction of a stop codon or a splice site(s)) also can be prepared and are embraced by the invention as readily envisioned by one of ordinary skill in the art. Any of the foregoing nucleic acids or polypeptides can be tested by routine experimentation for retention of structural relation or activity to the nucleic acids and/or polypeptides disclosed herein.

The invention also provides isolated fragments of SEQ ID NO:1 and SEQ ID NO:2. The fragments can be used as probes in Southern blot assays to identify such nucleic acids, or they can be used in amplification assays such as those employing PCR. Smaller fragments are those comprising 12, 13, 14, 15, 16, 17, 18, 20, 22, 25, 30, 40, 50, or 75 nucleotides, and every integer therebetween, and are useful, e.g., as primers for nucleic acid amplification procedures. As known to those skilled in the art, larger probes such as 200, 250, 300, 400 or more nucleotides are preferred for certain uses such as Southern blots, while smaller fragments will be preferred for uses such as PCR. Fragments also can be used to produce fusion proteins for generating antibodies or determining binding of the polypeptide fragments. Likewise, fragments can be employed to produce non-fused fragments of the murine TLR9 polypeptides, useful, for example, in the preparation of antibodies, in immunoassays, and the like. The foregoing nucleic acid fragments further can be used as antisense molecules to inhibit the expression of murine TLR9 nucleic acids and polypeptides, particularly for therapeutic purposes as described in greater detail below.

The invention also includes functionally equivalent variants of the murine TLR9, which include variant nucleic acids and polypeptides which retain one or more of the functional properties of the murine TLR9. Preferably such variants include the murine-specific N-terminal domain (e.g., amino acids 1-819 or amino acids 1-837 of SEQ ID NO:3). For example, variants include a fusion protein which includes the extracellular and transmembrane domains of the murine TLR9 (i.e., amino acids 1-837) which retains the ability to interact with extracellular molecules in a manner similar to intact murine TLR9. Alternative variants include, for example, a fusion protein which includes the cytoplasmic domain of murine TLR9 (i.e., amino acids 838-1032) which retains the ability to interact with intracellular molecules in a manner similar to intact murine TLR9. Still other functionally equivalent variants include truncations, deletions, point mutations, or additions of amino acids to the sequence of SEQ ID NO:3 which retain functions of SEQ ID NO:3. For example, the FLAG peptide sequence (DYKDDDDK) can be added at the N-terminal end, or green fluorescent protein (GFP) can be added at the C-terminal end. All such addition variant polypeptides are preferably made by translation of modified nucleic acids based on SEQ ID NO:1 or SEQ ID NO:2 with corresponding appropriate coding nucleic acid sequence appended thereto with maintenance of the proper reading frame.

Functionally equivalent variants also include a murine TLR9 which has had a portion (e.g., of the N-terminus) removed or replaced by a similar domain from another TLR (e.g., a "domain-swapping" variant). Examples of such domain-swapping variants include at least two types: those involving swapping a TLR9 domain from one species with a TLR9 domain from another species, and those involving swapping a TLR domain from TLR9 with a TLR domain from another TLR. In certain preferred embodiments the swapping involves corresponding domains between the different TLR molecules. It is believed that certain such domain-swapping variants are not functionally equivalent in a literal sense, insofar as they can function in a manner superior to either or both intact parent TLR molecules from which a particular domain-swapping variant derives. For example, the TLR/IL-1R signaling mediated by human TLR9 could be limited, not by the capacity of its extracellular domain to interact with CpG ODN, but rather by the capacity of its cytoplasmic domain to engage the TLR/IL-1R signaling pathway. In such a circumstance, it could be advantageous to substitute a more potent cytoplasmic domain from a TLR9 from another species. Such a domain-swapping variant, e.g., chimeric hTLR9/mTLR9, could be used in screening assays for CpG immunoagonist/antagonists to increase the sensitivity of the assay, without changing the species specificity.

Other functionally equivalent variants will be known to one of ordinary skill in the art, as will be methods for preparing such variants. The activity of a functionally equivalent variant can be determined using the methods provided herein, and in references that have described assays using other TLRs and TLRs of other species. Such variants are useful, inter alia, for evaluating bioavailability of drugs, in assays for identification of compounds which bind to and/or regulate the signaling function of the murine TLR9, and for determining the portions of the murine TLR9 which are required for signaling activity.

Variants which are non-functional also can be prepared as described above. Such variants are useful, for example, as negative controls in experiments testing TLR9 signaling activity. Examples of non-functional variants include those incorporating a mutation of proline at aa 915 to histidine (P915H) which renders both mTLR9 and hTLR9 nonfunctional with respect to signaling. Futher examples of non-functional variants include those incorporating a mutation of the D-X-Y core of the MBD motif to A-L-A, as discussed above, to render both mTLR9 and hTLR9 nonfunctional with respect to CpG DNA binding.

A murine TLR9 nucleic acid, in one embodiment, is operably linked to a gene expression sequence which can direct the expression of the murine TLR9 nucleic acid within a eukaryotic or prokaryotic cell. A "gene expression sequence" is any regulatory nucleotide sequence, such as a promoter sequence or promoter-enhancer combination, which facilitates the efficient transcription and translation of the nucleic acid to which it is operably linked. With respect to murine TLR9 nucleic acid, the "gene expression sequence" is any regulatory nucleotide sequence, such as a promoter sequence or promoter-enhancer combination, which facilitates the efficient transcription and translation of the murine TLR9 nucleic acid to which it is operably linked. The gene expression sequence may, for example, be a mammalian or viral promoter, such as a constitutive or inducible promoter. Constitutive mammalian promoters include, but are not limited to, the promoters for the following genes: hypoxanthine phosphoribosyl transferase (HPRT), adenosine deaminase, pyruvate kinase, β-actin promoter, and other constitutive promoters. Exemplary viral promoters which function constitutively in eukaryotic cells include, for example, promoters from the simian virus (e.g., SV40), papilloma virus, adenovirus, human immunodeficiency virus (HIV), Rous sarcoma virus (RSV), cytomegalovirus (CMV), the long terminal repeats (LTR) of Moloney murine leukemia virus and other retroviruses, and the thymidine kinase (TK) promoter of herpes simplex virus. Other constitutive promoters are known to those of ordinary skill in the art. The promoters useful as gene expression sequences of the invention also include inducible promoters. Inducible promoters are expressed in the presence of an inducing agent. For example, the metallothionein (MT) promoter is induced to promote transcription and translation in the presence of certain metal ions. Other inducible promoters are known to those of ordinary skill in the art.

In general, the gene expression sequence shall include, as necessary, 5' non-transcribing and 5' non-translating sequences involved with the initiation of transcription and translation, respectively, such as a TATA box, capping sequence, CAAT sequence, and the like. Especially, such 5' non-transcribing sequences will include a promoter region which includes a promoter sequence for transcriptional control of the operably joined murine TLR9 nucleic acid. The gene expression sequences optionally include enhancer sequences or upstream activator sequences as desired.

Generally a nucleic acid coding sequence and a gene expression sequence are said to be "operably linked" when they are covalently linked in such a way as to place the transcription and/or translation of the nucleic acid coding sequence under the influence or control of the gene expression sequence. Thus the murine TLR9 nucleic acid sequence and the gene expression sequence are said to be "operably linked" when they are covalently linked in such a way as to place the transcription and/or translation of the murine TLR9 coding sequence under the influence or control of the gene expression sequence. If it is desired that the murine TLR9 sequence be translated into a functional protein, two DNA sequences are said to be operably linked if induction of a promoter in the 5' gene expression sequence results in the transcription of the murine TLR9 sequence and if the nature of the linkage between the two DNA sequences does not (1) result in the introduction of a frame-shift mutation, (2) interfere with the ability of the promoter region to direct the transcription of the murine TLR9 sequence, or (3) interfere with the ability of the corresponding RNA transcript to be translated into a protein. Thus, a gene expression sequence would be operably linked to a murine TLR9 nucleic acid sequence if the gene expression sequence were capable of effecting transcription of that murine TLR9 nucleic acid sequence such that the resulting transcript might be translated into the desired protein or polypeptide.

The murine TLR9 nucleic acid molecules and the murine TLR9 polypeptides (including the murine TLR9 inhibitors described below) of the invention can be delivered to the eukaryotic or prokaryotic cell alone or in association with a vector. In its broadest sense, a "vector" is any vehicle capable of facilitating: (1) delivery of a nucleic acid or polypeptide to a target cell, (2) uptake of a nucleic acid or polypeptide by a target cell, or (3) expression of a nucleic acid molecule or polypeptide in a target cell. In this particular setting, a "vector" is any vehicle capable of facilitating: (1) delivery of a murine TLR9 nucleic acid or polypeptide to a target cell, (2) uptake of a murine TLR9 nucleic acid or polypeptide by a target cell, or (3) expression of a murine TLR9 nucleic acid molecule or polypeptide in a target cell. Preferably, the vectors transport the murine TLR9 nucleic acid or polypeptide into the target cell with reduced degradation relative to the extent of degradation that would result in the absence of the vector. Optionally, a "targeting ligand" can be attached to the vector to selectively deliver the vector to a cell which expresses on its surface the cognate receptor (e.g., a receptor, an antigen recognized by an antibody) for the targeting ligand. In this manner, the vector (containing a murine TLR9 nucleic acid or a murine TLR9 polypeptide) can be selectively delivered to a specific cell. In general, the vectors useful in the invention are divided into two classes: biological vectors and chemical/physical vectors. Biological vectors are more useful for delivery/uptake of murine TLR9 nucleic acids to/by a target cell. Chemical/physical vectors are more useful for delivery/uptake of murine TLR9 nucleic acids or murine TLR9 proteins to/by a target cell.

Biological vectors include, but are not limited to, plasmids, phagemids, viruses, other vehicles derived from viral or bacterial sources that have been manipulated by the insertion or incorporation of the nucleic acid sequences of the invention, and free nucleic acid fragments which can be linked to the nucleic acid sequences of the invention. Viral vectors are a preferred type of biological vector and include, but are not limited to, nucleic acid sequences from the following viruses: retroviruses, such as Moloney murine leukemia virus; Harvey murine sarcoma virus; murine mammary tumor virus; Rous sarcoma virus; adenovirus; adeno-associated virus; SV40-type viruses; polyoma viruses; poxviruses; Epstein-Barr viruses; papilloma viruses; herpes virus; vaccinia virus; and polio virus. One can readily employ other vectors not named but known in the art.

Preferred viral vectors are based on non-cytopathic eukaryotic viruses in which non-essential genes have been replaced with the gene of interest. Non-cytopathic viruses include retroviruses, the life cycle of which involves reverse transcription of genomic viral RNA into DNA with subsequent proviral integration into host cellular DNA. In general, the retroviruses are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell line with plasmid, production of recombinant retroviruses by the packaging cell line, collection of viral particles from tissue culture media, and infection of the target cells with viral particles) are provided in Kriegler, M., "*Gene Transfer and Expression, A Laboratory Manual*," W.H. Freeman Co., New York (1990) and Murray, E. J., ed., "*Methods in Molecular Biology*," vol. 7, Humana Press, Inc., Clifton, N.J. (1991).

Another preferred virus for certain applications is the adeno-associated virus (AAV), a double-stranded DNA virus. The AAV can be engineered to be replication-deficient and is capable of infecting a wide range of cell types and species. It further has advantages, such as heat and lipid solvent stability; high transduction frequencies in cells of diverse lineages; and lack of superinfection inhibition thus allowing multiple series of transductions. Reportedly, the AAV can integrate into human cellular DNA in a site-specific manner, thereby minimizing the possibility of insertional mutagenesis and variability of inserted gene expression. In addition, wild-type AAV infections have been followed in tissue culture for greater than 100 passages in the absence of selective pressure, implying that the AAV genomic integration is a relatively stable event. The AAV can also function in an extrachromosomal fashion.

Expression vectors containing all the necessary elements for expression are commercially available and known to those skilled in the art. See, e.g., *Molecular Cloning: A Laboratory Manual*, J. Sambrook, et al., eds., Second Edition, Cold Spring Harbor Laboratory Press, Cold Spring Harbor, N.Y., 1989. Cells are genetically engineered by the introduction into the cells of heterologous DNA (RNA) encoding a murine TLR9 polypeptide or fragment or variant thereof. That heterologous DNA (RNA) is placed under operable control of transcriptional elements to permit the expression of the heterologous DNA in the host cell.

Preferred systems for mRNA expression in mammalian cells are those such as pRc/CMV (available from Invitrogen, Carlsbad, Calif.) that contain a selectable marker such as a gene that confers G418 resistance (which facilitates the selection of stably transfected cell lines) and the human CMV enhancer-promoter sequences. Additionally, suitable for expression in primate or canine cell lines is the pCEP4 vector (Invitrogen), which contains an Epstein Barr virus (EBV) origin of replication, facilitating the maintenance of plasmid as a multicopy extrachromosomal element. Another expression vector is the pEF-BOS plasmid containing the promoter of polypeptide Elongation Factor 1α, which stimulates efficiently transcription in vitro. The plasmid is described by Mishizuma and Nagata (*Nucleic Acids Res* 18:5322 (1990)), and its use in transfection experiments is disclosed by, for example, Demoulin (*Mol Cell Biol* 16:4710-4716 (1996)). Still another preferred expression vector is an adenovirus, described by Stratford-Perricaudet, which is defective for E1 and E3 proteins (*J Clin Invest* 90:626-630 (1992)).

In addition to the biological vectors, chemical/physical vectors may be used to deliver a nucleic acid or polypeptide to a target cell and facilitate uptake thereby. As used herein, a "chemical/physical vector" refers to a natural or synthetic molecule, other than those derived from bacteriological or viral sources, capable of delivering an isolated nucleic acid or polypeptide to a cell. As used herein with respect to a murine TLR9 nucleic acid or polypeptide, a "chemical/physical vector" refers to a natural or synthetic molecule, other than those derived from bacteriological or viral sources, capable of delivering the isolated murine TLR9 nucleic acid or polypeptide to a cell.

A preferred chemical/physical vector of the invention is a colloidal dispersion system. Colloidal dispersion systems include lipid-based systems including oil-in-water emulsions, micelles, mixed micelles, and liposomes. A preferred colloidal system of the invention is a liposome. Liposomes are artificial membrane vesicles which are useful as a delivery vector in vivo or in vitro. It has been shown that large unilamellar vesicles (LUV), which range in size from 0.2-4.0 μm can encapsulate large macromolecules. RNA, DNA, and intact virions can be encapsulated within the aqueous interior and be delivered to cells in a biologically active form (Fraley et al., *Trends Biochem Sci* 6:77 (1981)). In order for a liposome to be an efficient nucleic acid transfer vector, one or more of the following characteristics should be present: (1) encapsulation of the nucleic acid of interest at high efficiency with retention of biological activity; (2) preferential and substantial binding to a target cell in comparison to non-target cells; (3) delivery of the aqueous contents of the vesicle to the target cell cytoplasm at high efficiency; and (4) accurate and effective expression of genetic information.

Liposomes may be targeted to a particular tissue by coupling the liposome to a specific ligand such as a monoclonal antibody, sugar, glycolipid, or protein. Ligands which may be useful for targeting a liposome to a particular cell will depend on the particular cell or tissue type. Additionally when the vector encapsulates a nucleic acid, the vector may be coupled to a nuclear targeting peptide, which will direct the murine TLR9 nucleic acid to the nucleus of the host cell.

Liposomes are commercially available from Gibco BRL, for example, as LIPOFECTIN™ and LIPOFECTACE™, which are formed of cationic lipids such as N-[1-(2,3 dioleyloxy)-propyl]-N,N,N-trimethylammonium chloride (DOTMA) and dimethyl dioctadecylammonium bromide (DDAB). Methods for making liposomes are well known in the art and have been described in many publications.

Other exemplary compositions that can be used to facilitate uptake by a target cell of nucleic acids in general, and nucleic acids encoding the murine TLR9 in particular, include calcium phosphate and other chemical mediators of intracellular transport, microinjection compositions, electroporation and homologous recombination compositions (e.g., for integrating a murine TLR9 nucleic acid into a preselected location within a target cell chromosome).

The invention also embraces so-called expression kits, which allow the artisan to prepare a desired expression vector or vectors. Such expression kits include at least separate portions of the previously discussed coding sequences. Other components may be added, as desired, as long as the previously mentioned sequences, which are required, are included.

It will also be recognized that the invention embraces the use of the murine TLR9 cDNA sequences in expression vectors to transfect host cells and cell lines, be these prokaryotic (e.g., $E.\ coli$), or eukaryotic (e.g., 293 fibroblast cells (ATCC, CRL-1573), MonoMac-6, THP-1, U927, CHO cells, COS cells, yeast expression systems and recombinant baculovirus expression in insect cells). Especially useful are mammalian cells such as human, pig, goat, primate, rodent, guinea pig, etc. They may be of a wide variety of tissue types, and include primary cells and cell lines. The expression vectors require that the pertinent sequence, i.e., those nucleic acids described supra, be operably linked to a promoter.

The invention also provides isolated murine TLR9 polypeptides which include the amino acid sequences of SEQ ID NO:3 and fragments thereof, encoded by the murine TLR9 nucleic acids described above. Murine TLR9 polypeptides also embrace alleles, functionally equivalent variants and analogs (those non-allelic polypeptides which vary in amino acid sequence from the disclosed murine TLR9 polypeptides by 1, 2, 3, 4, 5, or more amino acids) provided that such polypeptides retain TLR9 activity. Non-functional variants also are embraced by the invention; these are useful as antagonists of TLR9 signaling function, as negative controls in assays, and the like. Such alleles, variants, analogs and fragments are useful, for example, alone or as fusion proteins for a variety of purposes including as a component of assays.

Fragments of a polypeptide preferably are those fragments which retain a distinct functional capability of the intact polypeptide, in particular as a receptor of various molecules. Accordingly, fragments of a TLR9 polypeptide preferably are those fragments which retain a distinct functional capability of the TLR9 polypeptide, in particular as a receptor of various molecules. Of particular interest are fragments that bind to ISNAs, including, for example, fragments that bind CpG nucleic acids. Other functional capabilities which can be retained in a fragment of a polypeptide include signal transduction (e.g., TLR/IL-1R signaling by murine TLR9), interaction with antibodies and interaction with other polypeptides (such as would be found in a protein complex). Those skilled in the art are well versed in methods that can be applied for selecting fragments which retain a functional capability of the murine TLR9. Confirmation of the functional capability of the fragment can be carried out by synthesis of the fragment and testing of the capability according to standard methods. For example, to test the signaling activity of a murine TLR9 fragment, one inserts or expresses the fragment in a cell in which signaling can be measured. Such methods, which are standard in the art, are described further herein.

The invention embraces variants of the murine TLR9 polypeptides described above. As used herein, a "variant" of a polypeptide is a polypeptide which contains one or more modifications to the primary amino acid sequence of a polypeptide. Accordingly, a "variant" of a murine TLR9 polypeptide is a polypeptide which contains one or more modifications to the primary amino acid sequence of a murine TLR9 polypeptide. Modifications which create a murine TLR9 variant can be made to a murine TLR9 polypeptide for a variety of reasons, including 1) to reduce or eliminate an activity of a murine TLR9 polypeptide, such as signaling; 2) to enhance a property of a murine TLR9 polypeptide, such as signaling, binding affinity for nucleic acid ligand or other ligand molecule, protein stability in an expression system, or the stability of protein-protein binding; 3) to provide a novel activity or property to a murine TLR9 polypeptide, such as addition of an antigenic epitope or addition of a detectable moiety, e.g., luciferase, FLAG peptide, GFP; 4) to establish that an amino acid substitution does or does not affect molecular signaling activity; or 5) reduce immunogenicity of a murine TLR9 polypeptide. Modifications to a murine TLR9 polypeptide are typically made to the nucleic acid which encodes the murine TLR9 polypeptide, and can include deletions, point mutations, truncations, amino acid substitutions and additions of amino acids or non-amino acid moieties. Alternatively, modifications can be made directly to the polypeptide, such as by cleavage, addition of a linker molecule, addition of a detectable moiety (for example, biotin, fluorophore, radioisotope, enzyme, or peptide), addition of a fatty acid, and the like.

Modifications also embrace fusion proteins comprising all or part of the murine TLR9 amino acid sequence. One of skill in the art will be familiar with methods for predicting the effect on protein conformation of a change in protein sequence, and can thus "design" a variant murine TLR9 according to known methods. One example of such a method is described by Dahiyat and Mayo in $Science$ 278:82-87 (1997), whereby proteins can be designed de novo. The method can be applied to a known protein to vary a only a portion of the polypeptide sequence. By applying the computational methods of Dahiyat and Mayo, specific variants of a murine TLR9 polypeptide can be proposed and tested to determine whether the variant retains a desired conformation.

Variants include murine TLR9 polypeptides which are modified specifically to alter a feature of the polypeptide unrelated to its physiological activity. For example, cysteine residues can be substituted or deleted to prevent unwanted disulfide linkages. Similarly, certain amino acids can be changed to enhance expression of a murine TLR9 polypeptide by eliminating proteolysis by proteases in an expression system (e.g., dibasic amino acid residues in yeast expression systems in which KEX2 protease activity is present).

Mutations of a nucleic acid which encode a murine TLR9 polypeptide preferably preserve the amino acid reading frame of the coding sequence, and preferably do not create regions in the nucleic acid which are likely to hybridize to form secondary structures, such as hairpins or loops, which can be deleterious to expression of the variant polypeptide.

Mutations can be made by selecting an amino acid substitution, or by random mutagenesis of a selected site in a nucleic acid which encodes the polypeptide. Variant polypeptides are then expressed and tested for one or more activities to determine which mutation provides a variant polypeptide with a desired property. Further mutations can be made to variants (or to non-variant murine TLR9 polypeptides) which are silent as to the amino acid sequence of the polypeptide, but which provide preferred codons for translation in a particular host. The preferred codons for translation of a nucleic acid in, e.g., *E. coli*, are well known to those of ordinary skill in the art. Still other mutations can be made to the noncoding sequences of a murine TLR9 gene or cDNA clone to enhance expression of the polypeptide.

The activity of variants of murine TLR9 polypeptides can be tested by cloning the gene encoding the variant murine TLR9 polypeptide into a prokaryotic or eukaryotic (e.g., mammalian) expression vector, introducing the vector into an appropriate host cell, expressing the variant murine TLR9 polypeptide, and testing for a functional capability of the murine TLR9 polypeptides as disclosed herein. For example, the variant murine TLR9 polypeptide can be tested for ability to provide signaling, as set forth below in the examples. Preparation of other variant polypeptides may favor testing of other activities, as will be known to one of ordinary skill in the art.

The skilled artisan will also realize that conservative amino acid substitutions may be made in murine TLR9 polypeptides to provide functionally equivalent variants of the foregoing polypeptides, i.e., variants which retain the functional capabilities of the murine TLR9 polypeptides. As used herein, a "conservative amino acid substitution" refers to an amino acid substitution which does not alter the relative charge or size characteristics of the polypeptide in which the amino acid substitution is made. Variants can be prepared according to methods for altering polypeptide sequence known to one of ordinary skill in the art such as are found in references which compile such methods, e.g., *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. Exemplary functionally equivalent variants of the murine TLR9 polypeptides include conservative amino acid substitutions of SEQ ID NO:3. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Conservative amino acid substitutions in the amino acid sequence of murine TLR9 polypeptide to produce functionally equivalent variants of murine TLR9 typically are made by alteration of the nucleic acid sequence encoding murine TLR9 polypeptides (e.g., SEQ ID NO:1 and SEQ ID NO:2). Such substitutions can be made by a variety of methods known to one of ordinary skill in the art. For example, amino acid substitutions may be made by PCR-directed mutation, site-directed mutagenesis according to the method of Kunkel (Kunkel, *Proc Natl Acad Sci USA* 82:488-492 (1985)), or by chemical synthesis of a gene encoding a murine TLR9 polypeptide. The activity of functionally equivalent fragments of murine TLR9 polypeptides can be tested by cloning the gene encoding the altered murine TLR9 polypeptide into a bacterial or mammalian expression vector, introducing the vector into an appropriate host cell, expressing the altered murine TLR9 polypeptide, and testing for the ability of the murine TLR9 polypeptide to mediate a signaling event. Peptides which are chemically synthesized can be tested directly for function.

A variety of methodologies well known to the skilled practitioner can be utilized to obtain isolated murine TLR9 polypeptide molecules. The polypeptide may be purified from cells which naturally produce the polypeptide by chromatographic means or immunological recognition. Alternatively, an expression vector may be introduced into cells to cause production of the polypeptide. In another method, mRNA transcripts may be microinjected or otherwise introduced into cells to cause production of the encoded polypeptide. Translation of mRNA in cell-free extracts such as the reticulocyte lysate system also may be used to produce polypeptide. Those skilled in the art also can readily follow known methods for isolating murine TLR9 polypeptides. These include, but are not limited to, immunochromatography, HPLC, size-exclusion chromatography, ion-exchange chromatography and immune-affinity chromatography.

The invention as described herein has a number of uses, some of which are described elsewhere herein. For example, the invention permits isolation of the murine TLR9 polypeptide molecules by, e.g., expression of a recombinant nucleic acid to produce large quantities of polypeptide which may be isolated using standard protocols. As another example, the isolation of the murine TLR9 gene makes it possible for murine TLR9 to be used in methods for assaying molecular interactions involving TLR9.

As discussed further in the Examples below, it has been discovered according to one aspect of the invention that responsiveness to ISNA can be reconstituted in ISNA-unresponsive cells by introducing into ISNA-unresponsive cells an expression vector that directs the expression of murine TLR9 (and certain homologues and variants thereof). Cells so reconstituted also exhibit responses to substances other than phosphorothioate ISNA, e.g., *E. coli* DNA, phosphodiester CpG-ODN, and even methylated CpG-ODN.

Also as discussed further in the Examples below, it has been discovered according to certain aspects of the instant invention that TLR9 not only confers upon cells the ability to signal in response to binding ISNA, but also confers both sequence specificity and species specificity to such signaling responses. Thus murine TLR9 signaling in response to CpG-ODN 1668, reportedly an optimal murine ISNA, was found to be significantly stronger than the corresponding murine TLR9 signaling response to CpG-ODN 2006, reportedly an optimal human ISNA. The converse was also found to be true, i.e., human TLR9 signaling in response to CpG-ODN 2006 was found to be significantly stronger than the corresponding human TLR9 signaling response to CpG-ODN 1668. Furthermore, it has been discovered according to the instant invention that certain types of cells preferentially express TLR9. For example, TLR9 is strongly expressed in B cells and plasmacytoid dendritic cells (CD 123+DC), but only weakly by T cells, monocyte-derived dendritic cells (MDDC), and CD14+ monocytes. In contrast, TLR2 and TLR4 are strongly expressed by MDDC and CD14+ monocytes, but relatively weakly by B cells, CD123+ DC, and T cells.

The invention also embraces agents which bind selectively to the murine TLR9 nucleic acid molecules or polypeptides as well as agents which bind to variants and fragments of the polypeptides and nucleic acids as described herein. The agents include polypeptides which bind to murine TLR9, and antisense nucleic acids, both of which are described in greater detail below. The agents can inhibit or increase murine TLR9-mediated signaling activity (antagonists and agonists, respectively).

Some of the agents are inhibitors. A murine TLR9 inhibitor is an agent that inhibits murine TLR9-mediated signaling across a cell membrane.

As used herein "TLR9 signaling" refers to an ability of a TLR9 polypeptide to activate the TLR/IL-1R (TIR) signaling pathway, also referred to herein as the TLR signal transduction pathway. Without meaning to be held to any particular theory, it is believed that the TLR/IL-1R signaling pathway involves signaling via the molecules myeloid differentiation marker 88 (MyD88) and tumor necrosis factor (TNF) receptor-associated factor 6 (TRAF6), leading to activation of kinases of the IκB kinase complex and the c-jun $NH_2$-terminal kinases (e.g., JNK 1/2). Häcker H et al., *J Exp Med* 192:595-600 (2000). A molecule which inhibits TLR9 activity (an antagonist) is one which inhibits TLR9-mediated activation of the TLR/IL-1R signaling pathway, and a molecule which increases TLR9 signaling (an agonist) is one which increases TLR9-mediated activation of the TLR/IL-1R signaling pathway. Changes in TLR9 activity can be measured by assays such as those disclosed herein, including expression of genes under control of κB-sensitive promoters and enhancers. Such naturally occurring genes include the genes encoding IL-1, IL-6, IL-8, the p40 subunit of interleukin 12 (IL-12p40), and the costimulatory molecules CD80 and CD86. Other genes can be placed under the control of such regulatory elements (see below) and thus serve to report the level of TLR9 signaling. Additional nucleotide sequence can be added to SEQ ID NO:1 or SEQ ID NO:2, preferably to the 5' or the 3' end of SEQ ID NO:2, to yield a nucleotide sequence encoding a chimeric polypeptide that includes a detectable or reporter moiety, e.g., FLAG, luciferase (luc), green fluorescent protein (GFP) and others known by those skilled in the art. These are discussed in greater detail in the Examples below.

In one embodiment the murine TLR9 inhibitor is an antisense oligonucleotide that selectively binds to a murine TLR9 nucleic acid molecule, to reduce the expression of murine TLR9 (or TLR9 of another species) in a cell. This is desirable in virtually any medical condition wherein a reduction of TLR9 signaling activity is desirable.

As used herein, the term "antisense oligonucleotide" or "antisense" describes an oligonucleotide that is an oligoribonucleotide, oligodeoxyribonucleotide, modified oligoribonucleotide, or modified oligodeoxyribonucleotide which hybridizes under physiological conditions to DNA comprising a particular gene or to an mRNA transcript of that gene and, thereby, inhibits the transcription of that gene and/or the translation of that mRNA. The antisense molecules are designed so as to interfere with transcription or translation of a target gene upon hybridization with the target gene or transcript. Those skilled in the art will recognize that the exact length of the antisense oligonucleotide and its degree of complementarity with its target will depend upon the specific target selected, including the sequence of the target and the particular bases which comprise that sequence. It is preferred that the antisense oligonucleotide be constructed and arranged so as to bind selectively with the target under physiological conditions, i.e., to hybridize substantially more to the target sequence than to any other sequence in the target cell under physiological conditions.

Based upon SEQ ID NO:1 and SEQ ID NO:2, or upon allelic or homologous genomic and/or cDNA sequences, one of skill in the art can easily choose and synthesize any of a number of appropriate antisense molecules for use in accordance with the present invention. In order to be sufficiently selective and potent for inhibition, such antisense oligonucleotides should comprise at least 10 and, more preferably, at least 15 consecutive bases which are complementary to the target, although in certain cases modified oligonucleotides as short as 7 bases in length have been used successfully as antisense oligonucleotides. Wagner R W et al., *Nat Biotechnol* 14:840-844 (1996). Most preferably, the antisense oligonucleotides comprise a complementary sequence of 20-30 bases. Although oligonucleotides may be chosen which are antisense to any region of the gene or mRNA transcripts, in preferred embodiments the antisense oligonucleotides correspond to N-terminal or 5' upstream sites such as translation initiation, transcription initiation or promoter sites. In addition, 3'-untranslated regions may be targeted. Targeting to mRNA splicing sites has also been used in the art but may be less preferred if alternative mRNA splicing occurs. In addition, the antisense is targeted, preferably, to sites in which mRNA secondary structure is not expected (see, e.g., Sainio et al., *Cell Mol Neurobiol* 14 (5):439-457 (1994)) and at which polypeptides are not expected to bind. Thus, the present invention also provides for antisense oligonucleotides which are complementary to allelic or homologous cDNAs and genomic DNAs corresponding to murine TLR9 nucleic acid containing SEQ ID NO:1 or SEQ ID NO:2.

In one set of embodiments, the antisense oligonucleotides of the invention may be composed of "natural" deoxyribonucleotides, ribonucleotides, or any combination thereof. That is, the 5' end of one native nucleotide and the 3' end of another native nucleotide may be covalently linked, as in natural systems, via a phosphodiester internucleoside linkage. These oligonucleotides may be prepared by art-recognized methods which may be carried out manually or by an automated synthesizer. They also may be produced recombinantly by vectors.

In preferred embodiments, however, the antisense oligonucleotides of the invention also may include "modified" oligonucleotides. That is, the oligonucleotides may be modified in a number of ways which do not prevent them from hybridizing to their target but which enhance their stability or targeting or which otherwise enhance their therapeutic effectiveness.

The term "modified oligonucleotide" as used herein describes an oligonucleotide in which (1) at least two of its nucleotides are covalently linked via a synthetic internucleoside linkage (i.e., a linkage other than a phosphodiester linkage between the 5' end of one nucleotide and the 3' end of another nucleotide) and/or (2) a chemical group not normally associated with nucleic acids has been covalently attached to the oligonucleotide. Preferred synthetic internucleoside linkages are phosphorothioates, alkylphosphonates, phosphorodithioates, phosphate esters, alkylphosphonothioates, phosphoramidates, carbamates, carbonates, phosphate triesters, acetamidates, carboxymethyl esters and peptides.

The term "modified oligonucleotide" also encompasses oligonucleotides with a covalently modified base and/or sugar. For example, modified oligonucleotides include oligonucleotides having backbone sugars which are covalently attached to low molecular weight organic groups other than a hydroxyl group at the 3' position and other than a phosphate group at the 5' position. Thus modified oligonucleotides may include a 2'-O-alkylated ribose group. In addition, modified oligonucleotides may include sugars such as arabinose instead of ribose. The present invention, thus, contemplates pharmaceutical preparations containing modified antisense molecules that are complementary to and hybridizable with, under physiological conditions, nucleic acids encoding murine TLR9 polypeptides, together with pharmaceutically acceptable carriers.

Agents which bind murine TLR9 also include binding peptides and other molecules which bind to the murine TLR9 polypeptide and complexes containing the murine TLR9 polypeptide. When the binding molecules are inhibitors, the molecules bind to and inhibit the activity of murine TLR9. When the binding molecules are activators, the molecules bind to and increase the activity of murine TLR9. To determine whether a murine TLR9 binding agent binds to murine TLR9 any known binding assay may be employed. For example, the binding agent may be immobilized on a surface and then contacted with a labeled murine TLR9 polypeptide. The amount of murine TLR9 which interacts with the murine TLR9 binding agent or the amount which does not bind to the murine TLR9 binding agent may then be quantitated to determine whether the murine TLR9 binding agent binds to murine TLR9.

The murine TLR9 binding agents include molecules of numerous size and type that bind selectively or preferentially to murine TLR9 polypeptides, and complexes of both murine TLR9 polypeptides and their binding partners. These molecules may be derived from a variety of sources. For example, murine TLR9 binding agents can be provided by screening degenerate peptide libraries which can be readily prepared in solution, in immobilized form or as phage display libraries. Combinatorial libraries also can be synthesized of peptides containing one or more amino acids. Libraries further can be synthesized of peptoids and non-peptide synthetic moieties.

Phage display can be particularly effective in identifying binding peptides useful according to the invention. Briefly, one prepares a phage library (using, e.g., m13, fd, or lambda phage), displaying inserts from 4 to about 80 amino acid residues using conventional procedures. The inserts may represent, for example, a completely degenerate or biased array. One then can select phage-bearing inserts which bind to the murine TLR9 polypeptide. This process can be repeated through several cycles of reselection of phage that bind to the murine TLR9 polypeptide. Repeated rounds lead to enrichment of phage bearing particular sequences. DNA sequence analysis can be conducted to identify the sequences of the expressed polypeptides. The minimal linear portion of the sequence that binds to the murine TLR9 polypeptide can be determined. One can repeat the procedure using a biased library containing inserts containing part or all of the minimal linear portion plus one or more additional degenerate residues upstream or downstream thereof. Yeast two-hybrid screening methods also may be used to identify polypeptides that bind to the murine TLR9 polypeptides. Thus, the murine TLR9 polypeptides of the invention, or a fragment thereof, can be used to screen peptide libraries, including phage display libraries, to identify and select peptide binding partners of the murine TLR9 polypeptides of the invention. Such molecules can be used, as described, for screening assays, for purification protocols, for interfering directly with the functioning of murine TLR9 and for other purposes that will be apparent to those of ordinary skill in the art.

The invention also embraces agents which bind selectively to certain regulatory sequences associated with the murine TLR9 nucleic acid molecules described herein. The agents include polypeptides which bind to transcription and translation regulatory sequences of murine TLR9, and antisense nucleic acids, both of which are described in greater detail below. The agents can inhibit or increase murine TLR9 expression, as well as signaling activity (antagonists and agonists, respectively). Agents which bind selectively to regulatory sequences associated with the murine TLR9 nucleic acid molecules can be identified using methods familiar to those of skill in the art. For example, a promoter region including at least 100, 200, 300, 400, 500, or more nucleotides upstream (5') of the coding region of murine TLR9 can be identified by isolating, from appropriate genomic DNA, such nucleotide sequences using the sequences of SEQ ID NO:1 or SEQ ID NO:2 as primers or as probes, and then inserting the promoter region DNA into an appropriate expression vector so as to control the expression of TLR9 or some other reporter gene, introducing the TLR9 promoter vector into an appropriate host cell, and screening for TLR9 or reporter expression by those cells following their incubation in the presence and absence of various test agents. A reporter gene other than TLR9 can include, for example, an enzyme, a cytokine, a cell surface antigen, luciferase, chloramphenicol acetyl transferase (CAT), etc. An agent that inhibits expression of TLR9 or the reporter under the control of the TLR9 promoter is classified as a TLR9 expression inhibitor. Conversely, an agent that augments expression of TLR9 or reporter under the control of the TLR9 promoter is classified as a TLR9 expression enhancer. It was discovered according to the instant invention, for example, that the cytokine IL-4 inhibits the expression of TLR9. In this manner it is possible to identify agents that can be administered in conjunction with ISNA, for example by local administration, to enhance response to the ISNA. Such an enhancing effect might be desirable, for example, in the setting of immunization or vaccination. Conversely, it is possible to identify agents that can be administered in conjunction with a ISNA, for example by local administration, to inhibit response to the ISNA. Such an inhibiting response might be desirable, for example, in the setting of gene replacement therapy.

Therefore the invention generally provides efficient methods of identifying pharmacological agents or lead compounds for agents useful in the treatment of conditions associated with TLR9 activity and the compounds and agents so identified. Generally, the screening methods involve assaying for compounds which inhibit or enhance signaling through murine TLR9. Such methods are adaptable to automated, high throughput screening of compounds. Examples of such high throughput screening methods are described in U.S. Pat. Nos. 6,103,479; 6,051,380; 6,051,373; 5,998,152; 5,876,946; 5,708,158; 5,443,791; 5,429,921; and 5,143,854.

A variety of assays for pharmacological agents are provided, including labeled in vitro protein binding assays, signaling assays using detectable molecules, etc. For example, protein binding screens are used to rapidly examine the binding of candidate pharmacological agents to a murine TLR9. The candidate pharmacological agents can be derived from, for example, combinatorial peptide or nucleic acid libraries. Convenient reagents for such assays are known in the art. An exemplary cell-based assay of signaling involves contacting a cell having a murine TLR9 with a candidate pharmacological agent under conditions whereby the induction of a detectable molecule can occur. Specific conditions are well known in the art and are described, for example, in Häcker H et al., *J Exp Med* 192:595-600 (2000), and references cited therein. A reduced degree of induction of the detectable molecule in the presence of the candidate pharmacological agent indicates that the candidate pharmacological agent reduces the signaling activity of murine TLR9. An increased degree of induction of the detectable molecule in the presence of the candidate pharmacological agent indicates that the candidate pharmacological agent increases the signaling activity of murine TLR9.

Murine TLR9 used in the methods of the invention can be added to an assay mixture as an isolated polypeptide (where binding of a candidate pharmaceutical agent is to be measured) or as a cell or other membrane-encapsulated space which includes a murine TLR9 polypeptide. In the latter assay configuration, the cell or other membrane-encapsulated space can contain the murine TLR9 as a polypeptide or as a nucleic acid (e.g., a cell transfected with an expression vector containing a murine TLR9). In the assays described herein, the murine TLR9 polypeptide can be produced recombinantly, isolated from biological extracts, or synthesized in vitro. Murine TLR9 polypeptides encompass chimeric proteins comprising a fusion of a murine TLR9 polypeptide with another polypeptide, e.g., a polypeptide capable of providing or enhancing protein-protein binding, enhancing signaling capability, facilitating detection, or enhancing stability of the murine TLR9 polypeptide under assay conditions. A polypeptide fused to a murine TLR9 polypeptide or fragment thereof may also provide means of readily detecting the fusion protein, e.g., by immunological recognition or by fluorescent labeling.

The assay mixture also comprises a candidate pharmacological agent. Typically, a plurality of assay mixtures are run in parallel with different agent concentrations to obtain a different response to the various concentrations. Typically, one of these concentrations serves as a negative control, i.e., at zero concentration of agent or at a concentration of agent below the limits of assay detection. Candidate pharmaceutical agents encompass numerous chemical classes, although typically they are organic compounds. Preferably, the candidate pharmacological agents are small organic compounds, i.e., those having a molecular weight of more than 50 yet less than about 2500. Polymeric candidate agents can have higher molecular weights, e.g., oligonucleotides in the range of about 2500 to about 12,500. Candidate agents comprise functional chemical groups necessary for structural interactions with polypeptides, and may include at least an amine, carbonyl, hydroxyl or carboxyl group, preferably at least two of the functional chemical groups and more preferably at least three of the functional chemical groups. The candidate agents can comprise cyclic carbon or heterocyclic structure and/or aromatic or polyaromatic structures substituted with one or more of the above-identified functional groups. Candidate agents also can be biomolecules such as nucleic acids, peptides, saccharides, fatty acids, sterols, isoprenoids, purines, pyrimidines, derivatives or structural analogs of the above, or combinations thereof and the like. Where the agent is a nucleic acid, the agent typically is a DNA or RNA molecule, although modified nucleic acids having non-natural bonds or subunits are also contemplated.

Candidate agents are obtained from a wide variety of sources, including libraries of natural, synthetic, or semisynthetic compounds, or any combination thereof. For example, numerous means are available for random and directed synthesis of a wide variety of organic compounds and biomolecules, including expression of randomized oligonucleotides, synthetic organic combinatorial libraries, phage display libraries of random peptides, and the like. Alternatively, libraries of natural compounds in the form of bacterial, fungal, plant and animal extracts are available or readily produced. Additionally, natural and synthetically produced libraries and compounds can be readily modified through conventional chemical, physical, and biochemical means. Further, known pharmacological agents may be subjected to directed or random chemical modifications such as acylation, alkylation, esterification, amidification, etc., to produce structural analogs of the agents.

Therefore, a source of candidate agents are libraries of molecules based on known TLR9 ligands, e.g., CpG oligonucleotides shown herein to interact with TLR9, in which the structure of the ligand is changed at one or more positions of the molecule to contain more or fewer chemical moieties or different chemical moieties. The structural changes made to the molecules in creating the libraries of analog inhibitors can be directed, random, or a combination of both directed and random substitutions and/or additions. One of ordinary skill in the art in the preparation of combinatorial libraries can readily prepare such libraries based on existing TLR9 ligands.

A variety of other reagents also can be included in the mixture. These include reagents such as salts, buffers, neutral proteins (e.g., albumin), detergents, etc. which may be used to facilitate optimal protein-protein and/or protein-nucleic acid binding. Such a reagent may also reduce non-specific or background interactions of the reaction components. Other reagents that improve the efficiency of the assay such as protease inhibitors, nuclease inhibitors, antimicrobial agents, and the like may also be used.

The mixture of the foregoing assay materials is incubated under conditions whereby, but for the presence of the candidate pharmacological agent, the murine TLR9 mediates TLR/IL-1R signaling. For determining the binding of a candidate pharmaceutical agent to a murine TLR9, the mixture is incubated under conditions which permit binding. The order of addition of components, incubation temperature, time of incubation, and other parameters of the assay may be readily determined. Such experimentation merely involves optimization of the assay parameters, not the fundamental composition of the assay. Incubation temperatures typically are between 4° C. and 40° C. Incubation times preferably are minimized to facilitate rapid, high throughput screening, and typically are between 1 minute and 10 hours.

After incubation, the level of signaling or the level of specific binding between the murine TLR9 polypeptide and the candidate pharmaceutical agent is detected by any convenient method available to the user. For cell-free binding type assays, a separation step is often used to separate bound from unbound components. The separation step may be accomplished in a variety of ways. For example, separation can be accomplished in solution, or, conveniently, at least one of the components is immobilized on a solid substrate, from which the unbound components may be easily separated. The solid substrate can be made of a wide variety of materials and in a wide variety of shapes, e.g., microtiter plate, microbead, dipstick, resin particle, etc. The substrate preferably is chosen to maximize signal-to-noise ratios, primarily to minimize background binding, as well as for ease of separation and cost.

Separation may be effected for example, by removing a bead or dipstick from a reservoir, emptying or diluting a reservoir such as a microtiter plate well, rinsing a bead, particle, chromatographic column or filter with a wash solution or solvent. The separation step preferably includes multiple rinses or washes. For example, when the solid substrate is a microtiter plate, the wells may be washed several times with a washing solution, which typically includes those components of the incubation mixture that do not participate in specific bindings such as salts, buffer, detergent, non-specific protein, etc. Where the solid substrate is a magnetic bead, the beads may be washed one or more times with a washing solution and isolated using a magnet.

Detection may be effected in any convenient way for cell-based assays such as measurement of an induced polypeptide within, on the surface of, or secreted by the cell. Examples of detection methods useful in such cell-based assays include fluorescence-activated cell sorting (FACS) analysis, bioluminescence, fluorescence, enzyme-linked immunosorbent assay (ELISA), reverse transcriptase-polymerase chain reaction (RT-PCR), and the like.

A variety of methods may be used to detect the label, depending on the nature of the label and other assay components. For example, the label may be detected while bound to the solid substrate or subsequent to separation from the solid substrate. Labels may be directly detected through optical or electron density, radioactive emissions, nonradiative energy transfers, etc., or indirectly detected with antibody conjugates, streptavidin-biotin conjugates, etc. Methods for detecting the labels are well known in the art.

The murine TLR9 binding agent may also be an antibody or a functionally active antibody fragment. Antibodies are well known to those of ordinary skill in the science of immunology. As used herein, the term "antibody" means not only intact antibody molecules but also fragments of antibody molecules retaining specific target binding ability. Such fragments are also well known in the art and are regularly employed both in vitro and in vivo. In particular, as used herein, the term "antibody" means not only intact immunoglobulin molecules but also the well-known active fragments $F(ab')_2$ and Fab. $F(ab')_2$ and Fab fragments which lack the Fc fragment of intact antibody clear more rapidly from the circulation and may have less non-specific tissue binding than an intact antibody (Wahl R L et al., *J Nucl Med* 24:316-325 (1983)).

Monoclonal antibodies may be made by any of the methods known in the art utilizing murine TLR9, or a fragment thereof, as an immunogen. Alternatively the antibody may be a polyclonal antibody specific for murine TLR9 which inhibits murine TLR9 activity. The preparation and use of polyclonal antibodies are also known to one of ordinary skill in the art.

Significantly, as is well known in the art, only a small portion of an antibody molecule, the paratope, is involved in the binding of the antibody to its epitope (see, in general, Clark, W. R. (1986) *The Experimental Foundations of Modern Immunology*, Wiley & Sons, Inc., New York; Roitt, I. (1991) *Essential Immunology*, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an $F(ab')_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

The sequences of the antigen-binding Fab' portion of the anti-murine TLR9 monoclonal antibodies identified as being useful according to the invention in the assays provided above, as well as the relevant FR and CDR regions, can be determined using amino acid sequencing methods that are routine in the art. It is well established that non-CDR regions of a mammalian antibody may be replaced with corresponding regions of non-specific or hetero-specific antibodies while retaining the epitope specificity of the original antibody. This technique is useful for the development and use of "humanized" antibodies in which non-human CDRs are covalently joined to human FR and/or Fc/pFc' regions to produce a functional antibody. Techniques to humanize antibodies are particularly useful when non-human animal (e.g., murine) antibodies which inhibit murine TLR9 activity are identified. These non-human animal antibodies can be humanized for use in the treatment of a human subject in the methods according to the invention. Examples of methods for humanizing a murine antibody are provided in U.S. Pat. Nos. 4,816,567, 5,225,539, 5,585,089, 5,693,762 and 5,859,205. Other antibodies, including fragments of intact antibodies with antigen-binding ability, are often referred to as "chimeric" antibodies.

Thus, as will be apparent to one of ordinary skill in the art, the present invention also provides for $F(ab')_2$ and Fab fragments of an anti-murine TLR9 monoclonal antibody; chimeric antibodies in which the Fc and/or FR and/or CDR1 and/or CDR2 and/or light chain CDR3 regions of an anti-murine TLR9 antibody have been replaced by homologous human or non-human sequences; chimeric $F(ab')_2$ fragment antibodies in which the FR and/or CDR1 and/or CDR2 and/or light chain CDR3 regions of an anti-murine TLR9 antibody have been replaced by homologous human or non-human sequences; and chimeric Fab fragment antibodies in which the FR and/or CDR1 and/or CDR2 and/or light chain CDR3 regions have been replaced by homologous human or non-human sequences.

According to the invention murine TLR9 inhibitors also include "dominant negative" polypeptides derived from SEQ ID NO:3. A dominant negative polypeptide is an inactive variant of a polypeptide, which, by interacting with the cellular machinery, displaces an active polypeptide from its interaction with the cellular machinery or competes with the active polypeptide, thereby reducing the effect of the active polypeptide. For example, a dominant negative receptor which binds a ligand but does not transmit a signal in response to binding of the ligand can reduce the biological effect of expression of the receptor. As shown in the Examples below, TLR9 polypeptides which incorporate the substitution of histidine for proline at aa 915 (P915H mutation) are functionally inactive and are dominant negative with respect to the native TLR9 polypeptide.

The end result of the expression of a dominant negative murine TLR9 polypeptide of the invention in a cell is a reduction in TLR9 activity such as signaling through the TIR pathway. One of ordinary skill in the art can assess the potential for a dominant negative variant of a murine TLR9 polypeptide and, using standard mutagenesis techniques, create one or more dominant negative variant polypeptides. For example, given the teachings contained herein of a murine TLR9 polypeptide, one of ordinary skill in the art can modify the sequence of the murine TLR9 polypeptide by site-specific mutagenesis, scanning mutagenesis, partial gene deletion or truncation, and the like. See, e.g., U.S. Pat. No. 5,580,723 and

*Molecular Cloning: A Laboratory Manual*, J. Sambrook, et al., eds., Second Edition, Cold Spring Harbor Laboratory Press, Cold Spring Harbor, N.Y., 1989. The skilled artisan then can test the population of mutagenized polypeptides for diminution in murine TLR9 activity and/or for retention of such an activity. Other similar methods for creating and testing dominant negative variants of a murine TLR9 polypeptide will be apparent to one of ordinary skill in the art.

Each of the compositions according to this aspect of the invention is useful for a variety of therapeutic and non-therapeutic purposes. For example, the murine TLR9 nucleic acids of the invention are useful as oligonucleotide probes. Such oligonucleotide probes can be used herein to identify genomic or cDNA library clones possessing an identical or substantially similar nucleic acid sequence. A suitable oligonucleotide or set of oligonucleotides, which is capable of hybridizing under stringent hybridization conditions to the desired sequence, a variant or fragment thereof, or an antisense complement of such an oligonucleotide or set of oligonucleotides, can be synthesized by means well known in the art (see, for example, *Synthesis and Application of DNA and RNA*, S. A. Narang, ed., 1987, Academic Press, San Diego, Calif.) and employed as a probe to identify and isolate the desired sequence, variant or fragment thereof by techniques known in the art. Techniques of nucleic acid hybridization and clone identification are disclosed by Sambrook, et al., *Molecular Cloning. A Laboratory Manual*, J. Sambrook, et al., eds., Second Edition, Cold Spring Harbor Laboratory Press, Cold Spring Harbor, N.Y., 1989.

To facilitate the detection of a desired nucleic acid sequence, or variant or fragment thereof, whether for cloning purposes or for the mere detection of the presence of the sequence, the above-described probes may be labeled with a detectable group. Such a detectable group may be any material having a detectable physical or chemical property. Such materials have been well developed in the field of nucleic acid hybridization and, in general, many labels useful in such methods can be applied to the present invention. Particularly useful are radioactive labels. Any radioactive label may be employed which provides for an adequate signal and has a sufficient half-life. If single stranded, the oligonucleotide may be radioactively labeled using kinase reactions. Alternatively, oligonucleotides are also useful as nucleic acid hybridization probes when labeled with a non-radioactive marker such as biotin, an enzyme or a fluorescent group. See, for example, Leary J J et al., *Proc Natl Acad Sci USA* 80:4045 (1983); Renz M et al., *Nucleic Acids Res* 12:3435 (1984); and Renz M, *EMBO J.* 6:817 (1983).

Additionally, complements of the murine TLR9 nucleic acids can be useful as antisense oligonucleotides, e.g., by delivering the antisense oligonucleotide to an animal to induce a murine TLR9 "knockout" phenotype. The administration of antisense RNA probes to block gene expression is discussed in Lichtenstein C, *Nature* 333:801-802 (1988).

Alternatively, the murine TLR9 nucleic acid of the invention can be used to prepare a non-human transgenic animal. A "transgenic animal" is an animal having cells that contain DNA which has been artificially inserted into a cell, which DNA becomes part of the genome of the animal which develops from that cell. Preferred transgenic animals are primates, mice, rats, cows, pigs, horses, goats, sheep, dogs and cats. Animals suitable for transgenic experiments can be obtained from standard commercial sources such as Charles River (Wilmington, Mass.), Taconic (Germantown, N.Y.), Harlan (Indianapolis, Ind.), etc. Transgenic animals having a particular property associated with a particular disease can be used to study the effects of a variety of drugs and treatment methods on the disease, and thus serve as genetic models for the study of a number of human diseases. The invention, therefore, contemplates the use of murine TLR9 knockout and transgenic animals as models for the study of disorders involving TLR9-mediated signaling. A variety of methods known to one of ordinary skill in the art are available for the production of transgenic animals associated with this invention.

Inactivation or replacement of the endogenous TLR9 gene can be achieved by a homologous recombination system using embryonic stem cells. The resultant transgenic non-human mammals having a TLR9$^{-/-}$ knockout phenotype may be made transgenic for the murine TLR9 and used as a model for screening compounds as modulators (agonists or antagonists/inhibitors) of the murine TLR9. In this manner, such therapeutic drugs can be identified.

Additionally, a normal or mutant version of murine TLR9 can be inserted into the germ line to produce transgenic animals which constitutively or inducibly express the normal or mutant form of murine TLR9. These animals are useful in studies to define the role and function of murine TLR9 in cells.

Generally, doses of active compounds would be from about 0.01 mg/kg per day to 1000 mg/kg per day. It is expected that doses ranging from 50-500 mg/kg will be suitable and in one or several administrations per day. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compound, although fewer doses typically will be given when compounds are prepared as slow release or sustained release medications.

The antagonists, agonists, nucleic acids, and polypeptides of murine TLR9 useful according to the invention may be combined, optionally, with a pharmaceutically acceptable carrier. Thus the invention also provides pharmaceutical compositions and a method for preparing the pharmaceutical compositions which contain compositions of this aspect of the invention. The pharmaceutical compositions include any one or combination of the antagonists, agonists, nucleic acids and polypeptides of murine TLR9 useful according to the invention and, optionally, a pharmaceutically acceptable carrier. Each pharmaceutical composition is prepared by selecting an antagonist, agonist, nucleic acid or polypeptide of murine TLR9 useful according to the invention, as well as any combination thereof, and, optionally, combining it with a pharmaceutically acceptable carrier.

The term "pharmaceutically acceptable carrier" as used herein means one or more compatible solid or liquid fillers, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy.

The pharmaceutical compositions may contain suitable buffering agents, including, without limitation: acetic acid in a salt; citric acid in a salt; and phosphoric acid in a salt.

The pharmaceutical compositions also may contain, optionally, suitable preservatives, such as benzalkonium chloride, chlorobutanol, parabens, and thimerosal.

When administered, the pharmaceutical preparations of the invention are applied in pharmaceutically acceptable amounts and in pharmaceutically acceptable compositions. Such preparations may routinely contain salts, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically acceptable salts thereof and are not excluded from the scope of the invention. Such pharmacologically and pharmaceutically acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically acceptable salts can be prepared as alkaline metal or alkaline earth salts, such as sodium, potassium or calcium salts.

A variety of administration routes are available. The particular mode selected will depend, of course, upon the particular compound selected, the severity of the condition being treated, and the dosage required for therapeutic efficacy. The methods of the invention, generally speaking, may be practiced using any mode of administration that is medically acceptable, meaning any mode that produces effective levels of the active compounds without causing clinically unacceptable adverse effects. Such modes of administration include oral, rectal, topical, nasal, intradermal, or parenteral routes. The term "parenteral" includes, without limitation, subcutaneous, transdermal, intravenous, intra-arterial, intrathecal, intramuscular, intraperitoneal, mucosal (apart from gastrointestinal mucosa), pulmonary, intralesional, and infusion.

The pharmaceutical compositions may conveniently be presented in unit dosage form and may be prepared by any of the methods well-known in the art of pharmacy. All methods include the step of bringing the active agent into association with a carrier which constitutes one or more accessory ingredients. In general, the compositions are prepared by uniformly and intimately bringing the active compound into association with a liquid carrier, a finely divided solid carrier, or both, and then, if necessary, shaping the product.

Compositions suitable for oral administration may be presented as discrete units, such as capsules, tablets, lozenges, each containing a predetermined amount of the active compound. Other compositions include suspensions in aqueous liquids or non-aqueous liquids such as a syrup, elixir or an emulsion.

Compositions suitable for parenteral administration conveniently comprise a sterile aqueous preparation of the antagonists, agonists, nucleic acids, or polypeptides of murine TLR9, which is preferably isotonic with the blood of the recipient. This aqueous preparation may be formulated according to known methods using suitable dispersing or wetting agents and suspending agents. The sterile injectable preparation also may be a sterile injectable solution or suspension in a non-toxic parenterally acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables. Carrier formulation suitable for oral, subcutaneous, intravenous, intrathecal, intramuscular, etc. administrations can be found in Remington's Pharmaceutical Sciences, Mack Publishing Co., Easton, Pa.

Other delivery systems can include time-release, delayed release or sustained release delivery systems such as the biological/chemical vectors is discussed above. Such systems can avoid repeated administrations of the active compound, increasing convenience to the subject and the physician. Many types of release delivery systems are available and known to those of ordinary skill in the art. Use of a long-term sustained release implant may be desirable. Long-term release, are used herein, means that the implant is constructed and arranged to delivery therapeutic levels of the active ingredient for at least 30 days, and preferably 60 days. Long-term sustained release implants are well-known to those of ordinary skill in the art and include some of the release systems described above.

In another aspect the invention involves the identification of cDNAs encoding mouse TLR7 and mouse TLR8, referred to herein as murine TLR7 and murine TLR8 and, equivalently, mTLR7 and mTLR8, respectively. The nucleotide sequence of the cDNA for murine TLR7 is presented as SEQ ID NO:173, the coding region of the cDNA for murine TLR7 is presented as SEQ ID NO:174, and the amino acid sequence of the murine TLR7 is presented as SEQ ID NO:175. The closely related human TLR7 (equivalently, hTLR7) was previously deposited in GenBank under accession numbers AF245702 and AF240467. The nucleotide sequence of the cDNA for murine TLR7 presented as SEQ ID NO:173 is 3357 nucleotides long and includes the ORF spanning bases 117-3266, presented as SEQ ID NO:174, which spans 3150 nucleotides (excluding the stop codon). The amino acid sequence of the murine TLR7 presented as SEQ ID NO:175 is 1050 amino acids long.

The nucleotide sequence of the cDNA for murine TLR8 is presented as SEQ ID NO:190, the coding region of the cDNA for murine TLR8 is presented as SEQ ID NO:191, and the amino acid sequence of the murine TLR8 is presented as SEQ ID NO:192. The closely related human TLR8 (equivalently, hTLR8) was previously deposited in GenBank under accession numbers AF245703 and AF246971.

Like both human and murine TLR9, human TLR7 and human TLR8 each contains one CXXC motif and one MBD motif. The hTLR7 CXXC motif contains amino acids 258-273, and the hTLR8 CXXC motif contains amino acids 255-270.

| CXXC motif: | GNCXXCXXXXXXCXXC | SEQ ID NO:196 |
|---|---|---|
| hTLR9: | GNCRRCDHAPNPCMEC | SEQ ID NO:197 |
| mTLR9: | GNCRRCDHAPNPCMIC | SEQ ID NO:198 |
| hTLR7: | GNCPRCYNAPFPCAPC | SEQ ID NO:199 |
| mTLR7: | GNCPRCYNVPYPCTPC | SEQ ID NO:200 |
| hTLR8: | GNCPRCFNAPFPCVPC | SEQ ID NO:201 |
| mTLR8: | GNCPRCYNAPFPCTPC | SEQ ID NO:202 |

Also like human and murine TLR9, human TLR7 and TLR8 also have a single MBD motif. The hTLR7 MBD motif spans amino acids 545-575, and the hTLR8 MBD motif amino acids spans 533-563.

MBD Motif

|         |                                                    |              |
|---------|----------------------------------------------------|--------------|
| MBD-1   | R-XXXXXXX-R-X-D-X-Y-XXXXXXXXX-R-S-XXXXXX-Y         | SEQ ID NO:125 |
| hTLR9   | Q-XXXXXXX-K-X-D-X-Y-XXXXXXXXX-R-L-XXXXXX-Y         | SEQ ID NO:126 |
| mTLR9   | Q-XXXXXXX-K-X-D-X-Y-XXXXXXXXX-Q-L-XXXXXX-Y         | SEQ ID NO:127 |
| hTLR7   | R-XXXXXXX-R-X-D-X-L-XXXXXXXXX-K-L-XXXXXX-S         | SEQ ID NO:203 |
| mTLR7   | R-XXXXXXX-R-X-D-X-L-XXXXXXXXX-S-L-XXXXXX-S         | SEQ ID NO:204 |
| hTLR8   | K-XXXXXXX-R-X-D-X-D-XXXXXXXXX-D-L-XXXXXX-Y         | SEQ ID NO:205 |
| mTLR8   | K-XXXXXXX-R-X-D-X-D-XXXXXXXXX-D-L-XXXXXX-H         | SEQ ID NO:206 |
| hTLR7   | R-YLDFSNN-R-L-D-L-L-HSTAFEELH-K-L-EVLDIS-S         | SEQ ID NO:212 |
| mTLR7   | R-YLDFSNN-R-L-D-L-L-YSTAFEELQ-S-L-EVLDLS-S         | SEQ ID NO:213 |
| hTLR8   | K-YLDLTNN-R-L-D-F-D-NASALTELS-D-L-EVLDLS-Y         | SEQ ID NO:214 |
| mTLR8   | K-YLDLTNN-R-L-D-F-D-DNNAFSDLH-D-L-EVLDLS-H         | SEQ ID NO:215 |

The core D-X-Y in the MBD motif is involved in CpG binding of the MBD-1 protein and is conserved in TLR9 but only partially conserved in TLR8 and TLR7 (Y to D or L). The other mismatches are highly or moderately conserved; example R to K, Q, or D. These changes could explain MBD-1 as a methyl-CpG binder and TLR9 as a binder for CpG-DNA. The modification in the core sequence (D-X-Y) in hTLR7 (D-X-L) and TLR8 (D-X-D) is likely a structural basis for the recognition of different nucleic acid motifs. Combined with the presence of a CXXC domain TLR7 and TLR8 appear certainly to be nucleic acid binding receptors relevant to the innate immune system and thus clinical value.

The invention involves in one aspect murine TLR7 and murine TLR8 nucleic acids and polypeptides, as well as therapeutics relating thereto. The invention also embraces isolated functionally equivalent variants, useful analogs and fragments of the foregoing murine TLR7 and murine TLR8 nucleic acids and polypeptides; complements of the foregoing murine TLR7 and murine TLR8 nucleic acids; and molecules which selectively bind the foregoing murine TLR7 and murine TLR8 nucleic acids and polypeptides.

The murine TLR7 and murine TLR8 nucleic acids and polypeptides of the invention are isolated. The term "isolated," with respect to murine TLR7 and murine TLR8 nucleic acids and polypepetides, has the same meaning as used elsewhere herein.

As used herein a murine TLR7 nucleic acid refers to an isolated nucleic acid molecule which codes for a murine TLR7 polypeptide. Such nucleic acid molecules code for murine TLR7 polypeptides which include the sequence of SEQ ID NO:175 and fragments thereof. The nucleic acid molecules include the nucleotide sequences of SEQ ID NO:173, SEQ ID NO:174, and nucleotide sequences which differ from the sequences of SEQ ID NO:173 and SEQ ID NO:174 in codon sequence due to the degeneracy of the genetic code.

Also as used herein a murine TLR8 nucleic acid refers to an isolated nucleic acid molecule which codes for a murine TLR8 polypeptide. Such nucleic acid molecules code for murine TLR8 polypeptides which include the sequences of SEQ ID NO:193, and fragments thereof. The nucleic acid molecules include the nucleotide sequences of SEQ ID NO:190, SEQ ID NO:191, and nucleotide sequences which differ from the sequences of SEQ ID NO:190 and SEQ ID NO:191 in codon sequence due to the degeneracy of the genetic code.

The murine TLR7 and murine TLR8 nucleic acids of the invention also include alleles as well as fragments of the foregoing nucleic acids. Such fragments can be used, for example, as probes in hybridization assays and as primers in a polymerase chain reaction. Preferred murine TLR7 nucleic acids include the nucleic acid sequence of SEQ ID NO:173 and SEQ ID NO:174. Preferred murine TLR8 nucleic acids include the nucleic acid sequence of SEQ ID NO:190 and SEQ ID NO:191. Complements of the foregoing nucleic acids also are embraced by the invention.

As used herein a murine TLR7 nucleic acid or murine TLR7 polypeptide also embraces homologues and alleles of murine TLR7. Likewise, as used herein a murine TLR8 nucleic acid or murine TLR8 polypeptide also embraces homologues and alleles of murine TLR8. Homologues and alleles of murine TLR7 and murine TLR8 comply with the degrees of nucleotide and amino acid identity as previously set forth herein in reference to homologues and alleles of murine TLR9.

Alleles of the murine TLR7 and murine TLR8 nucleic acids of the invention can be identified by conventional techniques. For example, alleles of murine TLR7 can be isolated by hybridizing a probe which includes at least a fragment of SEQ ID NO:173 or SEQ ID NO:174 under stringent conditions with a cDNA library and selecting positive clones. Thus, an aspect of the invention is those nucleic acid sequences which code for murine TLR7 polypeptides and which hybridize to a nucleic acid molecule consisting of SEQ ID NO:173 or SEQ ID NO:174 under stringent conditions. Likewise, an aspect of the invention is those nucleic acid sequences which code for murine TLR8 polypeptides and which hybridize to a nucleic acid molecule consisting of SEQ ID NO:190 or SEQ ID NO:191 under stringent conditions. Stringent conditions in this context has the same meaning as described elsewhere herein, including the use of a suitable hybridization buffer and a temperature of about 65° C.

In screening for murine TLR7 or murine TLR8 nucleic acids, a Southern blot may be performed using the stringent conditions previously described herein, together with a radioactive probe. After washing the membrane to which the DNA is finally transferred, the membrane can be placed against X-ray film to detect the radioactive signal. Corresponding non-radioactive methods are also well known in the art and can be used to similar effect.

The murine TLR7 and murine TLR8 nucleic acids of the invention also include degenerate nucleic acids which include alternative codons to those present in the native materials, as previously described herein.

The invention also provides modified nucleic acid molecules which include additions, substitutions and deletions of one or more nucleotides. The modified nucleic acid molecules according to this aspect of the invention exclude fully native human TLR7 (SEQ ID NO:168, SEQ ID NO:169, GenBank Accession No. AF245702, and GenBank Accession No. AF240467) and fully native human TLR8 nucleic acid molecules (SEQ ID NO:182, SEQ ID NO:183, GenBank Accession No. AF245703, and GenBank Accession AF246971). In preferred embodiments, these modified nucleic acid molecules and/or the polypeptides they encode retain at least one activity or function of the unmodified nucleic acid molecule and/or the polypeptides, such as signaling activity, etc. In certain embodiments, the modified nucleic acid molecules encode modified polypeptides, preferably polypeptides having conservative amino acid substitutions as are described elsewhere herein. The modified nucleic acid molecules are structurally related to the unmodified nucleic acid molecules and in preferred embodiments are sufficiently structurally related to the unmodified nucleic acid molecules so that the modified and unmodified nucleic acid molecules hybridize under stringent conditions known to one of skill in the art.

The invention also provides isolated fragments of nucleotide sequences for murine TLR7 (SEQ ID NO:173 and SEQ ID NO:174) and for murine TLR8 (SEQ ID NO:190 and SEQ ID NO:191). The fragments can be used as probes in Southern blot assays to identify such nucleic acids, or can be used in amplification assays such as those employing PCR. Smaller fragments are those comprising 12, 13, 14, 15, 16, 17, 18, 20, 22, 25, 30, 40, 50, or 75 nucleotides, and every integer therebetween, and are useful, e.g., as primers for nucleic acid amplification procedures. As known to those skilled in the art, larger probes such as 200, 250, 300, 400 or more nucleotides are preferred for certain uses such as Southern blots, while smaller fragments will be preferred for uses such as PCR. Fragments also can be used to produce fusion proteins for generating antibodies or determining binding of the polypeptide fragments. Likewise, fragments can be employed to produce non-fused fragments of the murine TLR7 and murine TLR8 polypeptides, useful, for example, in the preparation of antibodies, in immunoassays, and the like. The foregoing nucleic acid fragments further can be used as antisense molecules to inhibit the expression of murine TLR7 and murine TLR8 nucleic acids and polypeptides.

The invention also includes functionally equivalent variants of the murine TLR7 and murine TLR8, which include variant nucleic acids and polypeptides which retain one or more of the functional properties of the murine TLR7 and murine TLR8. Preferably such variants include the murine-specific N-terminal domain.

Functionally equivalent variants also include a murine TLR7 or murine TLR8 which has had a portion (e.g., of the N-terminus) removed or replaced by a similar domain from another TLR (e.g., a "domain-swapping" variant). Examples of such domain-swapping variants include those involving swapping a TLR7 domain from another species and swapping a TLR domain from another TLR.

Other functionally equivalent variants will be known to one of ordinary skill in the art, as will be methods for preparing such variants. The activity of a functionally equivalent variant can be determined using the methods provided herein, and in references that have described assays using other TLRs and TLRs of other species. Such variants are useful, inter alia, for evaluating bioavailability of drugs, in assays for identification of compounds which bind to and/or regulate the signaling function of the murine TLR7 and murine TLR8, and for determining the portions of the murine TLR7 and murine TLR8 which are required for signaling activity.

Variants which are non-functional also can be prepared as described above. Such variants are useful, for example, as negative controls in experiments testing TLR7 and TLR8 signaling activity. Examples of non-functional variants include those incorporating a truncation or mutation of amino acids deemed critical to ligand binding or signaling activity.

In certain embodiments a murine TLR7 or murine TLR8 nucleic acid is operably linked to a gene expression sequence which can direct the expression of the murine TLR7 or murine TLR8 nucleic acid within a eukaryotic or prokaryotic cell. The terms "gene expression sequence" and "operably linked" are as previously described herein.

The murine TLR7 and murine TLR8 nucleic acid molecules and the murine TLR7 and murine TLR8 polypeptides of the invention can be delivered to a eukaryotic or prokaryotic cell alone or in association with a vector. As applied to murine TLR7 and murine TLR8 nucleic acid molecules, a "vector" is any vehicle capable of facilitating: (1) delivery of a murine TLR7 or murine TLR8 nucleic acid or polypeptide to a target cell, (2) uptake of a murine TLR7 or murine TLR8 nucleic acid or polypeptide by a target cell, or (3) expression of a murine TLR7 or murine TLR8 nucleic acid molecule or polypeptide in a target cell.

In addition to the biological vectors, chemical/physical vectors may be used to deliver a murine TLR7 or murine TLR8 nucleic acid or polypeptide to a target cell and facilitate uptake thereby. As used herein with respect to a murine TLR7 or murine TLR8 nucleic acid or polypeptide, a "chemical/physical vector" refers to a natural or synthetic molecule, other than those derived from bacteriological or viral sources, capable of delivering the isolated murine TLR7 or murine TLR8 nucleic acid or polypeptide to a cell.

Other exemplary compositions that can be used to facilitate uptake by a target cell of the murine TLR7 or murine TLR8 nucleic acids include calcium phosphate and other chemical mediators of intracellular transport, microinjection compositions, electroporation and homologous recombination compositions (e.g., for integrating a murine TLR7 or murine TLR8 nucleic acid into a preselected location within a target cell chromosome).

It will also be recognized that the invention embraces the use of the murine TLR7 and murine TLR8 cDNA sequences in expression vectors to transfect host cells and cell lines, be these prokaryotic (e.g., E. coli), or eukaryotic (e.g., 293 fibroblast cells (ATCC, CRL-1573), MonoMac-6, THP-1, U927, CHO cells, COS cells, yeast expression systems and recombinant baculovirus expression in insect cells). Especially useful are mammalian cells such as human, pig, goat, primate, rodent, guinea pig, etc. They may be of a wide variety of tissue types, and include primary cells and cell lines. The expression vectors require that the pertinent sequence, i.e., those nucleic acids described supra, be operably linked to a promoter.

The invention also provides isolated murine TLR7 and isolated murine TLR8 polypeptides which include the amino acid sequences of SEQ ID NO:175, SEQ ID NO:192, and fragments thereof, encoded by the murine TLR7 and murine TLR8 nucleic acids described above. Murine TLR7 and murine TLR8 polypeptides also embrace alleles, functionally equivalent variants and analogs (those non-allelic polypeptides which vary in amino acid sequence from the disclosed murine TLR7 and murine TLR8 polypeptides by 1, 2, 3, 4, 5, or more amino acids) provided that such polypeptides retain murine TLR7 or murine TLR8 activity. Non-functional variants also are embraced by the invention; these are useful as antagonists of TLR7 and TLR8 signaling function, as negative controls in assays, and the like. Such alleles, variants, analogs and fragments are useful, for example, alone or as fusion proteins for a variety of purposes including as a component of assays.

The invention also embraces variants of the murine TLR7 and murine TLR8 polypeptides described above. Modifications which create a murine TLR7 variant or murine TLR8 variant can be made to a murine TLR7 or murine TLR8 polypeptide for a variety of reasons, including 1) to reduce or eliminate an activity of a murine TLR7 or murine TLR8 polypeptide, such as signaling; 2) to enhance a property of a murine TLR7 or murine TLR8 polypeptide, such as signaling, binding affinity for nucleic acid ligand or other ligand molecule, protein stability in an expression system, or the stability of protein-protein binding; 3) to provide a novel activity or property to a murine TLR7 or murine TLR8 polypeptide, such as addition of an antigenic epitope or addition of a detectable moiety, e.g., luciferase, FLAG peptide, GFP; 4) to establish that an amino acid substitution does or does not affect molecular signaling activity; or 5) reduce immunogenicity. Modifications to a murine TLR7 or murine TLR8 polypeptide are typically made to the nucleic acid which encodes the murine TLR7 or murine TLR8 polypeptide, and can include deletions, point mutations, truncations, amino acid substitutions and additions of amino acids or non-amino acid moieties. Alternatively, modifications can be made directly to the polypeptide, such as by cleavage, addition of a linker molecule, addition of a detectable moiety (for example, biotin, fluorophore, radioisotope, enzyme, or peptide), addition of a fatty acid, and the like.

Modifications also embrace fusion proteins comprising all or part of the murine TLR7 or murine TLR8 amino acid sequence.

Variants include murine TLR7 and murine TLR8 polypeptides which are modified specifically to alter a feature of each polypeptide unrelated to its physiological activity. For example, cysteine residues can be substituted or deleted to prevent unwanted disulfide linkages. Similarly, certain amino acids can be changed to enhance expression of a murine TLR7 or murine TLR8 polypeptide by eliminating proteolysis by proteases in an expression system (e.g., dibasic amino acid residues in yeast expression systems in which KEX2 protease activity is present).

Mutations of a nucleic acid which encode a murine TLR7 or murine TLR8 polypeptide preferably preserve the amino acid reading frame of the coding sequence, and preferably do not create regions in the nucleic acid which are likely to hybridize to form secondary structures, such as hairpins or loops, which can be deleterious to expression of the variant polypeptide. Methods of making mutations of murine TLR7 or murine TLR8 are as described elsewhere herein with reference to making mutations of murine TLR9.

The activity of variants of murine TLR7 and murine TLR8 polypeptides can be tested by cloning the gene encoding the variant murine TLR7 or murine TLR8 polypeptide into a prokaryotic or eukaryotic (e.g., mammalian) expression vector, introducing the vector into an appropriate host cell, expressing the variant murine TLR7 or murine TLR8 polypeptide, and testing for a functional capability of the murine TLR7 or murine TLR8 polypeptides as disclosed herein.

The skilled artisan will also realize that conservative amino acid substitutions may be made in murine TLR7 and murine TLR8 polypeptides to provide functionally equivalent variants of the foregoing polypeptides, i.e., variants which retain the functional capabilities of the murine TLR7 and murine TLR8 polypeptides.

A variety of methodologies well known to the skilled practitioner can be utilized to obtain isolated murine TLR7 and murine TLR8 polypeptide molecules, as previously described in reference to murine TLR9 polypeptides.

The invention as described herein has a number of uses, some of which are described elsewhere herein. For example, the invention permits isolation of the murine TLR7 and the murine TLR8 polypeptide molecules by, e.g., expression of a recombinant nucleic acid to produce large quantities of polypeptide which may be isolated using standard protocols. As another example, the isolation of the murine TLR7 gene makes it possible for murine TLR7 to be used in methods for assaying molecular interactions involving TLR7.

The invention also embraces agents which bind selectively to the murine TLR7 or murine TLR8 nucleic acid molecules or polypeptides as well as agents which bind to variants and fragments of the polypeptides and nucleic acids as described herein. The agents include polypeptides which bind to murine TLR7 or murine TLR8, and antisense nucleic acids, both of which are described in greater detail below. Some agents can inhibit or increase murine TLR7-mediated signaling activity (antagonists and agonists, respectively), and some can inhibit or increase murine TLR8-mediated signaling activity.

In one embodiment the murine TLR7 inhibitor is an antisense oligonucleotide that selectively binds to a murine TLR7 nucleic acid molecule, to reduce the expression of murine TLR7 (or TLR7 of another species) in a cell. This is desirable in virtually any medical condition wherein a reduction of TLR7 signaling activity is desirable. Based upon SEQ ID NO:173 and SEQ ID NO:174, or upon allelic or homologous genomic and/or cDNA sequences, one of skill in the art can easily choose and synthesize any of a number of appropriate antisense molecules for use in accordance with the present invention.

In one embodiment the murine TLR8 inhibitor is an antisense oligonucleotide that selectively binds to a murine TLR8 nucleic acid molecule, to reduce the expression of murine TLR8 (or TLR8 of another species) in a cell. This is desirable in virtually any medical condition wherein a reduction of TLR8 signaling activity is desirable. Based upon SEQ ID NO:190 and SEQ ID NO:191, or upon allelic or homologous genomic and/or cDNA sequences, one of skill in the art can easily choose and synthesize any of a number of appropriate antisense molecules for use in accordance with the present invention.

Antisense oligonucleotides for murine TLR7 or murine TLR8 can include "natural" and "modified" oligonucleotides as previously described herein.

Agents which bind murine TLR7 or murine TLR8 also include binding peptides and other molecules which bind to the murine TLR7 or murine TLR8 polypeptide and complexes containing the murine TLR7 or murine TLR8 polypeptide, respectively. When the binding molecules are inhibitors, the molecules bind to and inhibit the activity of murine TLR7 or murine TLR8. When the binding molecules are activators, the molecules bind to and increase the activity of murine TLR7 or murine TLR8. To determine whether a murine TLR7 or murine TLR8 binding agent binds to murine TLR7 or murine TLR8, any known binding assay may be employed. For example, the binding agent may be immobilized on a surface and then contacted with a labeled murine TLR7 or murine TLR8 polypeptide. The amount of murine TLR7 or murine TLR8 which interacts with the murine TLR7 or murine TLR8 binding agent, or the amount which does not bind to the murine TLR7 or murine TLR8 binding agent, may then be quantitated to determine whether the murine TLR7 or murine TLR8 binding agent binds to murine TLR7 or murine TLR8.

The murine TLR7 or murine TLR8 binding agents include molecules of numerous size and type that bind selectively or preferentially to murine TLR7 or murine TLR8 polypeptides, and to complexes involving murine TLR7 or murine TLR8 polypeptides and their binding partners. These molecules may be derived from a variety of sources. For example, murine TLR7 or murine TLR8 binding agents can be provided by screening degenerate peptide libraries which can be readily prepared in solution, in immobilized form or as phage display libraries. Combinatorial libraries also can be synthesized of peptides containing one or more amino acids. Libraries further can be synthesized of peptoids and non-peptide synthetic moieties.

Exemplary methods useful for identifying murine TLR7 and murine TLR8 binding peptides are analogous to those described herein with reference to methods for identifying murine TLR9 binding peptides murine, and thus are not repeated here.

Therefore the invention generally provides efficient methods of identifying pharmacological agents or lead compounds for agents useful in the treatment of conditions associated with TLR7 and TLR8 activity, and the compounds and agents so identified. Generally, the screening methods involve assaying for compounds which inhibit or enhance the expression of or signaling through murine TLR7 or murine TLR8. Such methods are adaptable to automated, high throughput screening of compounds.

A variety of assays for pharmacological agents are provided, including labeled in vitro protein binding assays, signaling assays using detectable molecules, etc. For example, protein binding screens are used to rapidly examine the binding of candidate pharmacological agents to a murine TLR7 or murine TLR8. The candidate pharmacological agents can be derived from, for example, combinatorial peptide or nucleic acid libraries. Convenient reagents for such assays are known in the art. An exemplary cell-based assay of signaling involves contacting a cell having a murine TLR7 or murine TLR8 with a candidate pharmacological agent under conditions whereby the induction of a detectable molecule can occur. A reduced degree of induction of the detectable molecule in the presence of the candidate pharmacological agent indicates that the candidate pharmacological agent reduces the signaling activity of murine TLR7 or murine TLR8. An increased degree of induction of the detectable molecule in the presence of the candidate pharmacological agent indicates that the candidate pharmacological agent increases the signaling activity of murine TLR7 or murine TLR8.

Murine TLR7 and murine TLR8 used in the methods of the invention can be added to an assay mixture as an isolated polypeptide (where binding of a candidate pharmaceutical agent is to be measured) or as a cell or other membrane-encapsulated space which includes a murine TLR7 or murine TLR8 polypeptide. In the latter assay configuration, the cell or other membrane-encapsulated space can contain the murine TLR7 or murine TLR8 as a polypeptide or as a nucleic acid (e.g., a cell transfected with an expression vector containing a nucleic acid molecule encoding murine TLR7). In the assays described herein, the murine TLR7 or murine TLR8 polypeptide can be produced recombinantly, isolated from biological extracts, or synthesized in vitro. Murine TLR7 or murine TLR8 polypeptides encompass chimeric proteins comprising a fusion of a murine TLR7 or murine TLR8 polypeptide with another polypeptide, e.g., a polypeptide capable of providing or enhancing protein-protein binding, enhancing signaling capability, facilitating detection, or enhancing stability of the murine TLR7 or murine TLR8 polypeptide under assay conditions. A polypeptide fused to a murine TLR7 or murine TLR8 polypeptide or fragment thereof may also provide means of readily detecting the fusion protein, e.g., by immunological recognition or by fluorescent labeling.

The assay mixture also comprises a candidate pharmacological agent, as previously described in reference to murine TLR9. Candidate pharmacologic agents are obtained from a wide variety of sources, including libraries of natural, synthetic, or semisynthetic compounds, or any combination thereof. Presently, natural ligands of murine TLR7 and murine TLR8 are unknown, but they appear not to include CpG-ODN.

A variety of other reagents also can be included in the assay mixture. These include reagents such as salts, buffers, neutral proteins (e.g., albumin), detergents, etc. which may be used to facilitate optimal protein-protein and/or protein-nucleic acid binding. Such a reagent may also reduce non-specific or background interactions of the reaction components. Other reagents that improve the efficiency of the assay such as protease inhibitors, nuclease inhibitors, antimicrobial agents, and the like may also be used.

The mixture of the foregoing assay materials is incubated under conditions whereby, but for the presence of the candidate pharmacological agent, the murine TLR7 or murine TLR8 mediates TLR7-mediated or TLR8-mediated signaling, preferably TLR/IL-1R signaling. For determining the binding of a candidate pharmaceutical agent to a murine TLR7 or murine TLR8, the mixture is incubated under conditions which permit binding. The order of addition of components, incubation temperature, time of incubation, and other parameters of the assay may be readily determined. Such experimentation merely involves optimization of the assay parameters, not the fundamental composition of the assay. Incubation temperatures typically are between 4° C. and 40° C. Incubation times preferably are minimized to facilitate rapid, high throughput screening, and typically are between 1 minute and 10 hours.

After incubation, the level of signaling or the level of specific binding between the murine TLR7 or murine TLR8 polypeptide and the candidate pharmaceutical agent is detected by any convenient method available to the user, as described elsewhere herein.

The murine TLR7 or murine TLR8 binding agent may also be an antibody or a functionally active antibody fragment. Antibodies, including monoclonal antibodies and antibody fragments, are well known to those of ordinary skill in the science of immunology and are as described elsewhere herein. Monoclonal antibodies may be made by any of the methods known in the art utilizing murine TLR7 or murine TLR8, or a fragment thereof, as an immunogen. Alternatively the antibody may be a polyclonal antibody specific for murine TLR7 or murine TLR8 which inhibits murine TLR7 or murine TLR8 activity. The preparation and use of polyclonal antibodies are also known to one of ordinary skill in the art.

The sequences of the antigen-binding Fab' portion of the anti-murine TLR7 or anti-murine TLR8 monoclonal antibodies identified as being useful according to the invention in the assays provided above, as well as the relevant FR and CDR regions, can be determined using amino acid sequencing methods that are routine in the art. Such sequence information can be used to generate humanized and chimeric antibodies, as well as various fusion proteins and binding fragments, as described elsewhere herein.

Thus, as will be apparent to one of ordinary skill in the art, the present invention also provides for $F(ab')_2$ and Fab fragments of an anti-murine TLR7 or anti-murine TLR8 monoclonal antibody; chimeric antibodies in which the Fc and/or FR and/or CDR1 and/or CDR2 and/or light chain-CDR3 regions of an anti-murine TLR7 or anti-murine TLR8 antibody have been replaced by homologous human or non-human sequences; chimeric $F(ab')_2$ fragment antibodies in which the FR and/or CDR1 and/or CDR2 and/or light chain CDR3 regions of an anti-murine TLR7 or anti-murine TLR8 antibody have been replaced by homologous human or non-human sequences; and chimeric Fab fragment antibodies in which the FR and/or CDR1 and/or CDR2 and/or light chain CDR3 regions have been replaced by homologous human or non-human sequences.

According to the invention murine TLR7 and murine TLR8 inhibitors also include "dominant negative" polypeptides derived from SEQ ID NO:175 or SEQ ID NO:192, respectively. The end result of the expression of a dominant negative murine TLR7 or dominant negative murine TLR8 polypeptide of the invention in a cell is a reduction in TLR7 or murine TLR8 activity such as signaling through the TIR pathway. One of ordinary skill in the art can assess the potential for a dominant negative variant of a murine TLR7 or dominant negative murine TLR8 polypeptide and, using standard mutagenesis techniques, create one or more dominant negative variant polypeptides.

Each of the compositions according to this aspect of the invention is useful for a variety of therapeutic and non-therapeutic purposes. For example, the murine TLR7 and murine TLR8 nucleic acids of the invention are useful as oligonucleotide probes. Such oligonucleotide probes can be used herein to identify genomic or cDNA library clones possessing an identical or substantially similar nucleic acid sequence. Methods of hybridization, synthesis of probes, and detection are generally as described elsewhere herein.

Additionally, complements of the murine TLR7 and murine TLR8 nucleic acids can be useful as antisense oligonucleotides, e.g., by delivering the antisense oligonucleotide to an animal to induce a murine TLR7 or murine TLR8 "knockout" phenotype.

Alternatively, the murine TLR7 and murine TLR8 nucleic acids of the invention can be used to prepare a non-human transgenic animal. The invention, therefore, contemplates the use of murine TLR7 and murine TLR8 knockout and transgenic animals as models for the study of disorders involving TLR7- and murine TLR8-mediated signaling. A variety of methods known to one of ordinary skill in the art are available for the production of transgenic animals associated with this invention.

Inactivation or replacement of the endogenous TLR7 or TLR8 gene can be achieved by a homologous recombination system using embryonic stem cells. The resultant transgenic non-human mammals having a TLR7$^{-/-}$ or TLR8$^{-/-}$ knockout phenotype may be made transgenic for the murine TLR7 or murine TLR8 and used as a model for screening compounds as modulators (agonists or antagonists/inhibitors) of the murine TLR7 or murine TLR8. In this manner, such therapeutic drugs can be identified.

Additionally, a normal or mutant version of murine TLR7 or murine TLR8 can be inserted into the germ line to produce transgenic animals which constitutively or inducibly express the normal or mutant form of murine TLR7 or murine TLR8. These animals are useful in studies to define the role and function of murine TLR7 or murine TLR8 in cells.

The antagonists, agonists, nucleic acids, and polypeptides of murine TLR7 and murine TLR8 useful according to the invention may be combined, optionally, with a pharmaceutically acceptable carrier. Thus the invention also provides pharmaceutical compositions and a method for preparing the pharmaceutical compositions which contain compositions of this aspect of the invention. The pharmaceutical compositions include one or any combination of the antagonists, agonists, nucleic acids and polypeptides of murine TLR7 and murine TLR8 useful according to the invention and, optionally, a pharmaceutically acceptable carrier. Each pharmaceutical composition is prepared by selecting an antagonist, agonist, nucleic acid or polypeptide of murine TLR7 and murine TLR8 useful according to the invention, as well as any combination thereof, and, optionally, combining it with a pharmaceutically acceptable carrier.

A variety of administration routes are available, as described previously herein. The particular mode selected will depend, of course, upon the particular compound selected, the severity of the condition being treated, and the dosage required for therapeutic efficacy.

Likewise, a variety of formulations are contemplated, including, by analogy those discussed above in reference to murine TLR9, unit dose solids, liquids, extended release formulations, etc.

Screening Assays

In another aspect the invention provides methods for screening candidate compounds that act as ISNA mimics, agonists or antagonists in ISNA-induced immunomodulation via TLR7, TLR8, and TLR9. Preferably the screening method can be adapted to accommodate high throughput screening assays, as can be achieved, for example, through the use of multiwell arrays of samples in conjunction with robotic or automated array handling devices.

Immunostimulatory nucleic acids include but are not limited to CpG nucleic acids.

A "CpG nucleic acid" or a "CpG immunostimulatory nucleic acid" as used herein is a nucleic acid containing at least one unmethylated CpG dinucleotide (cytosine-guanine dinucleotide sequence, i.e. "CpG DNA" or DNA containing a 5' cytosine followed by 3' guanine and linked by a phosphate bond) and activates a component of the immune system. The entire CpG nucleic acid can be unmethylated or portions may be unmethylated but at least the C of the 5'CG 3' must be unmethylated.

In one embodiment a CpG nucleic acid is represented by at least the formula:

$$5'-N_1X_1CGX_2N_2-3'$$

wherein $X_1$ and $X_2$ are nucleotides, N is any nucleotide, and $N_1$ and $N_2$ are nucleic acid sequences composed of from about 0-25 N's each. In some embodiments $X_1$ is adenine, guanine, or thymine and/or $X_2$ is cytosine, adenine, or thymine. In other embodiments $X_1$ is cytosine and/or $X_2$ is guanine.

In other embodiments the CpG nucleic acid is represented by at least the formula:

$$5'-N_1X_1X_2CGX_3X_4N_2-3'$$

wherein $X_1$, $X_2$, $X_3$, and $X_4$ are nucleotides; N is any nucleotide; and $N_1$ and $N_2$ are nucleic acid sequences composed of from about 0-25 N's each. In some embodiments, $X_1X_2$ are nucleotides selected from the group consisting of: GpT, GpG, GpA, ApA, ApT, ApG, CpT, CpA, CpG, TpA, TpT, and TpG; and $X_3X_4$ are nucleotides selected from the group consisting of: TpT, CpT, ApT, TpG, ApG, CpG, TpC, ApC, CpC, TpA, ApA, and CpA. In some embodiments, $X_1X_2$ are GpA or GpT and $X_3X_4$ are TpT. In other embodiments $X_1$ or $X_2$ or both are purines and $X_3$ or $X_4$ or both are pyrimidines or $X_1X_2$ are GpA and $X_3$ or $X_4$ or both are pyrimidines.

In another embodiment the CpG nucleic acid is represented by at least the formula:

$$5'-TCN_1TX_1X_2CGX_3X_4-3'$$

wherein $X_1$, $X_2$, $X_3$, and $X_4$ are nucleotides; N is any nucleotide; and $N_1$ and $N_2$ are nucleic acid sequences composed of from about 0-25 N's each. In some embodiments, $X_1X_2$ are nucleotides selected from the group consisting of: GpT, GpG, GpA, ApA, ApT, ApG, CpT, CpA, CpG, TpA, TpT, and TpG; and $X_3X_4$ are nucleotides selected from the group consisting of: TpT, CpT, ApT, TpG, ApG, CpG, TpC, ApC, CpC, TpA, ApA, and CpA. In some embodiments, $X_1X_2$ are GpA or GpT and $X_3X_4$ are TpT. In other embodiments $X_1$ or $X_2$ or both are purines and $X_3$ or $X_4$ or both are pyrimidines or $X_1X_2$ are GpA and $X_3$ or $X_4$ or both are pyrimidines.

Examples of CpG nucleic acids according to the invention include but are not limited to those listed in Table 1, such as SEQ ID NOs:21-29, 31-42, 44, 46-50, 52-62, 64-75, 77-88, 90-117, 119-124.

TABLE 1

| Exemplary CpG nucleic acids | |
|---|---|
| AACGTTCT | SEQ ID NO:21 |
| AAGCGAAAATGAAATTGACT | SEQ ID NO:22 |
| ACCATGACGAACTGTTTCCCCTC | SEQ ID NO:23 |
| ACCATGACGACCTGTTTCCCCTC | SEQ ID NO:24 |
| ACCATGACGAGCTGTTTCCCCTC | SEQ ID NO:25 |
| ACCATGACGATCTGTTTCCCCTC | SEQ ID NO:26 |
| ACCATGACGGTCTGTTTCCCCTC | SEQ ID NO:27 |
| ACCATGACGTACTGTTTCCCCTC | SEQ ID NO:28 |
| ACCATGACGTTCTGTTTCCCCTC | SEQ ID NO:29 |
| AGATTTCTAGGAATTCAATC | SEQ ID NO:30 |
| AGCGGGGGCGAGCGGGGCG | SEQ ID NO:31 |
| AGCTATGACGTTCCAAGG | SEQ ID NO:32 |
| ATCGACTCTCGAGCGTTCTC | SEQ ID NO:33 |
| ATGACGTTCCTGACGTT | SEQ ID NO:34 |
| ATGGAAGGTCCAACGTTCTC | SEQ ID NO:35 |
| ATGGAAGGTCCAGCGTTCTC | SEQ ID NO:36 |
| ATGGACTCTCCAGCGTTCTC | SEQ ID NO:37 |
| ATGGAGGCTCCATCGTTCTC | SEQ ID NO:38 |
| CAACGTT | SEQ ID NO:39 |
| CACGTTGAGGGGCAT | SEQ ID NO:40 |
| CAGGCATAACGGTTGCGTAG | SEQ ID NO:41 |
| CCAACGTT | SEQ ID NO:42 |
| CTCCTAGTGGGGGTGTCCTAT | SEQ ID NO:43 |
| CTGATTTCCCCGAAATGATG | SEQ ID NO:44 |
| CTGCTGAGACTGGAG | SEQ ID NO:45 |
| GAGAACGATGGACCTTCCAT | SEQ ID NO:46 |
| GAGAACGCTCCAGCACTGAT | SEQ ID NO:47 |
| GAGAACGCTCGACCTTCCAT | SEQ ID NO:48 |
| GAGAACGCTGGACCTTCGAT | SEQ ID NO:49 |
| GAGAACGCTGGACCTTCCAT | SEQ ID NO:50 |
| GAGCAAGCTGGACCTTCCAT | SEQ ID NO:51 |
| GATTGCCTGACGTCAGAGAG | SEQ ID NO:52 |
| GCATGACGTTGAGCT | SEQ ID NO:53 |

TABLE 1-continued

| Exemplary CpG nucleic acids | |
|---|---|
| GCGGCGGGCGGCGCGCGCCC | SEQ ID NO:54 |
| GCGTGCGTTGTCGTTGTCGTT | SEQ ID NO:55 |
| GCTAGACGTTAGCGT | SEQ ID NO:56 |
| GCTAGACGTTAGTGT | SEQ ID NO:57 |
| GCTAGATGTTAGCGT | SEQ ID NO:58 |
| GCTTGATGACTCAGCCGGAA | SEQ ID NO:59 |
| GGAATGACGTTCCCTGTG | SEQ ID NO:60 |
| GGGGTCAACGTTGACGGGG | SEQ ID NO:61 |
| GGGGTCAGTCTTGAGGGGG | SEQ ID NO:62 |
| GTATTTCCCAGAAAAGGAAC | SEQ ID NO:63 |
| GTCCATTTCCCGTAAATCTT | SEQ ID NO:64 |
| GTCGCT | SEQ ID NO:65 |
| GTCGTT | SEQ ID NO:66 |
| TACCGCGTGCGACCCTCT | SEQ ID NO:67 |
| TATGCATATTGCTGTAAGTG | SEQ ID NO:68 |
| TCAACGTC | SEQ ID NO:69 |
| TCAACGTT | SEQ ID NO:70 |
| TCAAGCTT | SEQ ID NO:71 |
| TCAGCGCT | SEQ ID NO:72 |
| TCAGCGTGCGCC | SEQ ID NO:73 |
| TCATCGAT | SEQ ID NO:74 |
| TCCACGACGTTTTCGACGTT | SEQ ID NO:75 |
| TGCAGGACTTCTCTCAGGTT | SEQ ID NO:76 |
| TCCATAACGTTCCTGATGCT | SEQ ID NO:77 |
| TCCATAGCGTTCCTAGCGTT | SEQ ID NO:78 |
| TCCATCACGTGCCTGATGCT | SEQ ID NO:79 |
| TCCATGACGGTCCTGATGCT | SEQ ID NO:80 |
| TCCATGACGTCCCTGATGGT | SEQ ID NO:81 |
| TCCATGACGTGCCTGATGCT | SEQ ID NO:82 |
| TCCATGACGTTCCTGACGTT | SEQ ID NO:83 |
| TCCATGACGTTCCTGATGGT | SEQ ID NO:84 |
| TCCATGAGCTTCCTGATGCT | SEQ ID NO:85 |
| TCCATGCCGGTCCTGATGCT | SEQ ID NO:86 |
| TCCATGCGTGCGTGGGTTTT | SEQ ID NO:87 |
| TCCATGCGTTGCGTTGCGTT | SEQ ID NO:88 |
| TCCATGCTGGTCGTGATGCT | SEQ ID NO:89 |
| TCCATGGCGGTCCTGATGCT | SEQ ID NO:90 |
| TCCATGTCGATCCTGATGCT | SEQ ID NO:91 |

TABLE 1-continued

Exemplary CpG nucleic acids

| Sequence | ID |
|---|---|
| TCCATGTCGCTCCTGATGCT | SEQ ID NO:92 |
| TCCATGTCGGTCCTGATGCT | SEQ ID NO:93 |
| TCCATGTCGGTCCTGCTGAT | SEQ ID NO:94 |
| TCCATGTGGTCCCTGATGCT | SEQ ID NO:95 |
| TCCATGTCGTTCCTGATGCT | SEQ ID NO:96 |
| TCCATGTCGTTCCTGTCGTT | SEQ ID NO:97 |
| TCCATGTCGTTTTTGTCGTT | SEQ ID NO:98 |
| TCCTGACGTTCCTGACGTT | SEQ ID NO:99 |
| TCCTGTCGTTCCTGTCGTT | SEQ ID NO:100 |
| TCCTGTCGTTCCTTGTCGTT | SEQ ID NO:101 |
| TCCTGTCGTTTTTGTCGTT | SEQ ID NO:102 |
| TCCTTGTCGTTCCTGTCGTT | SEQ ID NO:103 |
| TCGATCGGGGCGGGGCGAGC | SEQ ID NO:104 |
| TCGTCGCTGTCTCCGCTTCTT | SEQ ID NO:105 |
| TCGTCGCTGTCTCCGCTTCTTCTTGCC | SEQ ID NO:106 |
| TCGTCGCTGTCTGCCCTTCTT | SEQ ID NO:107 |
| TCGTCGCTGTTGTCGTTTCTT | SEQ ID NO:108 |
| TCGTCGTCGTCGTT | SEQ ID NO:109 |
| TCGTCGTTGTCGTTGTCGTT | SEQ ID NO:110 |
| TCGTCGTTGTCGTTTTGTCGTT | SEQ ID NO:111 |
| TCGTCGTTTTGTCGTTTTGTCGTT | SEQ ID NO:112 |
| TCTCCCAGCGCGCGCCAT | SEQ ID NO:113 |
| TCTGCCAGCGGGCGCAT | SEQ ID NO:114 |
| TCTGCCAGCGTGCGCCAT | SEQ ID NO:115 |
| TCTTCGAA | SEQ ID NO:116 |
| TGCAGATTCGCAATCTGCA | SEQ ID NO:117 |
| TGCTGCTTTTGTGCTTTTGTGCTT | SEQ ID NO:118 |
| TGTCGCT | SEQ ID NO:119 |
| TGTCGTT | SEQ ID NO:120 |
| TGTCGTTGTCGTT | SEQ ID NO:121 |
| TGTCGTTGTCGTTGTCGTT | SEQ ID NO:122 |
| TGTCGTTGTCGTTGTCGTTGTCGTT | SEQ ID NO:123 |
| TGTCGTTTGTCGTTTGTCGTT | SEQ ID NO:124 |

Other ISNAs include but are not limited to T-rich nucleic acids, poly G nucleic acids, and nucleic acids having phosphate modified backbones, such as phosphorothioate backbones.

A "T rich nucleic acid" or "T rich immunostimulatory nucleic acid" is a nucleic acid which includes at least one poly T sequence and/or which has a nucleotide composition of greater than 25% T nucleotide residues and which activates a component of the immune system. A nucleic acid having a poly-T sequence includes at least four Ts in a row, such as 5'TTTT3'. Preferably the T rich nucleic acid includes more than one poly T sequence. In preferred embodiments the T rich nucleic acid may have 2, 3, 4, etc poly T sequences. One of the most highly immunostimulatory T rich oligonucleotides discovered according to the invention is a nucleic acid composed entirely of T nucleotide residues. Other T rich nucleic acids have a nucleotide composition of greater than 25% T nucleotide residues, but do not necessarily include a poly T sequence. In these T rich nucleic acids the T nucleotide resides may be separated from one another by other types of nucleotide residues, i.e., G, C, and A. In some embodiments the T rich nucleic acids have a nucleotide composition of greater than 30%, 40%, 50%, 60%, 70%, 80%, 90%, and 99%, T nucleotide residues and every integer % in between. Preferably the T rich nucleic acids have at least one poly T sequence and a nucleotide composition of greater than 25% T nucleotide residues.

In one embodiment the T rich nucleic acid is represented by at least the formula:

5' $X_1X_2$TTTT$X_3X_4$ 3' wherein $X_1$, $X_2$, $X_3$, and $X_4$ are nucleotides. In one embodiment $X_1X_2$ is TT and/or $X_3X_4$ is TT. In another embodiment $X_1X_2$ are any one of the following nucleotides TA, TG, TC, AT, AA, AG, AC, CT, CC, CA, CG, GT, GG, GA, and GC; and $X_3X_4$ are any one of the following nucleotides TA, TG, TC, AT, AA, AG, AC, CT, CC, CA, CG, GT, GG, GA, and GC.

In some embodiments it is preferred that the T-rich nucleic acid does not contain poly C (CCCC), poly A (AAAA), poly G (GGGG), CpG motifs, or multiple GGs. In other embodiments the T-rich nucleic acid includes these motifs. Thus in some embodiments of the invention the T rich nucleic acids include CpG dinucleotides and in other embodiments the T rich nucleic acids are free of CpG dinucleotides. The CpG dinucleotides may be methylated or unmethylated.

Poly G containing nucleic acids are also immunostimulatory. A variety of references, including Pisetsky and Reich, 1993 *Mol. Biol. Reports,* 18:217-221; Krieger and Herz, 1994, *Ann. Rev. Biochem.,* 63:601-637; Macaya et al., 1993, *PNAS,* 90:3745-3749; Wyatt et al., 1994, *PNAS,* 91:1356-1360; Rando and Hogan, 1998, In Applied Antisense Oligonucleotide Technology, ed. Krieg and Stein, p. 335-352; and Kimura et al., 1994, *J. Biochem.* 116, 991-994 also describe the immunostimulatory properties of poly G nucleic acids.

Poly G nucleic acids preferably are nucleic acids having the following formulas:

5' $X_1X_2$GGG$X_3X_4$ 3' wherein $X_1$, $X_2$, $X_3$, and $X_4$ are nucleotides. In preferred embodiments at least one of $X_3$ and $X_4$ are a G. In other embodiments both of $X_3$ and $X_4$ are a G. In yet other embodiments the preferred formula is 5' GGGNGGG 3', or 5' GGGNGGGNGGG 3' wherein N represents between 0 and 20 nucleotides. In other embodiments the Poly G nucleic acid is free of unmethylated CG dinucleotides. In other embodiments the poly G nucleic acid includes at least one unmethylated CG dinucleotide.

Nucleic acids having modified backbones, such as phosphorothioate backbones, also fall within the class of immunostimulatory nucleic acids. U.S. Pat. Nos. 5,723,335 and 5,663,153 issued to Hutcherson, et al. and related PCT publication WO95/26204 describe immune stimulation using phosphorothioate oligonucleotide analogues. These patents describe the ability of the phosphorothioate backbone to stimulate an immune response in a non-sequence specific manner.

The ISNAs may be double-stranded or single-stranded. Generally, double-stranded molecules may be more stable in vivo, while single-stranded molecules may have increased activity. The terms "nucleic acid" and "oligonucleotide" refer to multiple nucleotides (i.e. molecules comprising a sugar (e.g. ribose or deoxyribose) linked to a phosphate group and to an exchangeable organic base, which is either a substituted pyrimidine (e.g. cytosine (C), thymine (T) or uracil (U)) or a substituted purine (e.g., adenine (A) or guanine (G)) or a modified base. As used herein, the terms refer to oligoribonucleotides as well as oligodeoxyribonucleotides. The terms shall also include polynucleosides (i.e., a polynucleotide minus the phosphate) and any other organic base-containing polymer. The terms "nucleic acid" and "oligonucleotide" also encompass nucleic acids or oligonucleotides with a covalently modified base and/or sugar. For example, they include nucleic acids having backbone sugars which are covalently attached to low molecular weight organic groups other than a hydroxyl group at the 3' position and other than a phosphate group at the 5' position. Thus modified nucleic acids may include a 2'-O-alkylated ribose group. In addition, modified nucleic acids may include sugars such as arabinose instead of ribose. Thus the nucleic acids may be heterogeneous in backbone composition thereby containing any possible combination of polymer units linked together such as peptide-nucleic acids (which have amino acid backbone with nucleic acid bases). In some embodiments the nucleic acids are homogeneous in backbone composition.

The substituted purines and pyrimidines of the ISNAs include standard purines and pyrimidines such as cytosine as well as base analogs such as C-5 propyne substituted bases. Wagner R W et al., *Nat Biotechnol* 14:840-844 (1996). Purines and pyrimidines include but are not limited to adenine, cytosine, guanine, thymine, 5-methylcytosine, 2-aminopurine, 2-amino-6-chloropurine, 2,6-diaminopurine, hypoxanthine, and other naturally and non-naturally occurring nucleobases, substituted and unsubstituted aromatic moieties.

The ISNA is a linked polymer of bases or nucleotides. As used herein with respect to linked units of a nucleic acid, "linked" or "linkage" means two entities are bound to one another by any physicochemical means. Any linkage known to those of ordinary skill in the art, covalent or non-covalent, is embraced. Such linkages are well known to those of ordinary skill in the art. Natural linkages, which are those ordinarily found in nature connecting the individual units of a nucleic acid, are most common. The individual units of a nucleic acid may be linked, however, by synthetic or modified linkages.

Whenever a nucleic acid is represented by a sequence of letters it will be understood that the nucleotides are in 5' to 3' order from left to right and that "A" denotes adenine, "C" denotes cytosine, "G" denotes guanine, "T" denotes thymidine, and "U" denotes uracil unless otherwise noted.

Immunostimulatory nucleic acid molecules useful according to the invention can be obtained from natural nucleic acid sources (e.g., genomic nuclear or mitochondrial DNA or cDNA), or are synthetic (e.g., produced by oligonucleotide synthesis). Nucleic acids isolated from existing nucleic acid sources are referred to herein as native, natural, or isolated nucleic acids. The nucleic acids useful according to the invention may be isolated from any source, including eukaryotic sources, prokaryotic sources, nuclear DNA, mitochondrial DNA, etc. Thus, the term nucleic acid encompasses both synthetic and isolated nucleic acids.

The term "isolated" as used herein with reference to an ISNA means substantially free of or separated from components which it is normally associated with in nature, e.g., nucleic acids, proteins, lipids, carbohydrates or in vivo systems to an extent practical and appropriate for its intended use. In particular, the nucleic acids are sufficiently pure and are sufficiently free from other biological constituents of host cells so as to be useful in, for example, producing pharmaceutical preparations. Because an isolated nucleic acid of the invention may be admixed with a pharmaceutically-acceptable carrier in a pharmaceutical preparation, the nucleic acid may comprise only a small percentage by weight of the preparation. The nucleic acid is nonetheless substantially pure in that it has been substantially separated from the substances with which it may be associated in living systems.

The ISNAs can be produced on a large scale in plasmids, (see *Molecular Cloning: A Laboratory Manual*, J. Sambrook, et al., eds., Second Edition, Cold Spring Harbor Laboratory Press, Cold Spring Harbor, N.Y., 1989) and separated into smaller pieces or administered whole. After being administered to a subject the plasmid can be degraded into oligonucleotides. One skilled in the art can purify viral, bacterial, eukaryotic, etc. nucleic acids using standard techniques, such as those employing restriction enzymes, exonucleases or endonucleases.

For use in the instant invention, the ISNAs can be synthesized de novo using any of a number of procedures well known in the art. For example, the β-cyanoethyl phosphoramidite method (Beaucage S L and Caruthers M H, *Tetrahedron Let* 22:1859 (1981)); nucleoside H-phosphonate method (Garegg et al., *Tetrahedron Let* 27:4051-4054 (1986); Froehler et al., *Nucl Acid Res* 14:5399-5407 (1986); Garegg et al., *Tetrahedron Let* 27:4055-4058 (1986); Gaffney et al., *Tetrahedron Let* 29:2619-2622 (1988)). These chemistries can be performed by a variety of automated oligonucleotide synthesizers available in the market.

ISNAs having modified backbones, such as phosphorothioate backbones, also fall within the class of immunostimulatory nucleic acids. U.S. Pat. Nos. 5,723,335 and 5,663,153 issued to Hutcherson, et al. and related PCT publication WO95/26204 describe immune stimulation using phosphorothioate oligonucleotide analogues. These patents describe the ability of the phosphorothioate backbone to stimulate an immune response in a non-sequence specific manner.

The ISNA may be any size of at least 6 nucleotides but in some embodiments are in the range of between 6 and 100 or in some embodiments between 8 and 35 nucleotides in size. Immunostimulatory nucleic acids can be produced on a large scale in plasmids. These may be administered in plasmid form or alternatively they can be degraded into oligonucleotides before administration.

"Palindromic sequence" shall mean an inverted repeat (i.e., a sequence such as ABCDEE'D'C'B'A' in which A and A', B and B', etc., are bases capable of forming the usual Watson-Crick base pairs and which includes at least 6 nucleotides in the palindrome. In vivo, such sequences may form double-stranded structures. In one embodiment the nucleic acid contains a palindromic sequence. In some embodiments when the nucleic acid is a CpG nucleic acid, a palindromic sequence used in this context refers to a palindrome in which the CpG is part of the palindrome, and optionally is the center of the palindrome. In another embodiment the nucleic acid is free of a palindrome. A nucleic acid that is free of a palindrome does not have any regions of 6 nucleotides or greater in length which are palindromic. A nucleic acid that is free of a palindrome can include a region of less than 6 nucleotides which are palindromic.

A "stabilized ISNA" shall mean a nucleic acid molecule that is relatively resistant to in vivo degradation (e.g. via an exo- or endo-nuclease). Stabilization can be a function of length or secondary structure. Nucleic acids that are tens to hundreds of kbs long are relatively resistant to in vivo degradation. For shorter nucleic acids, secondary structure can stabilize and increase their effect. For example, if the 3' end of an oligonucleotide has self-complementarity to an upstream region, so that it can fold back and form a sort of stem loop structure, then the oligonucleotide becomes stabilized and therefore exhibits more activity.

Some stabilized ISNAs of the instant invention have a modified backbone. It has been demonstrated that modification of the oligonucleotide backbone provides enhanced activity of the ISNAs when administered in vivo. Nucleic acids, including at least two phosphorothioate linkages at the 5' end of the oligonucleotide and multiple phosphorothioate linkages at the 3' end, preferably 5, may provide maximal activity and protect the oligonucleotide from degradation by intracellular exo- and endo-nucleases. Other modified oligonucleotides include phosphodiester modified oligonucleotide, combinations of phosphodiester and phosphorothioate oligonucleotide, methylphosphonate, methylphosphorothioate, phosphorodithioate, and combinations thereof. Each of these combinations and their particular effects on immune cells is discussed in more detail in U.S. Pat. Nos. 6,194,388 and 6,207,646, the entire contents of which is hereby incorporated by reference. It is believed that these modified oligonucleotides may show more stimulatory activity due to enhanced nuclease resistance, increased cellular uptake, increased protein binding, and/or altered intracellular localization. Both phosphorothioate and phosphodiester nucleic acids are active in immune cells.

Other stabilized ISNAs include: nonionic DNA analogs, such as alkyl- and aryl-phosphates (in which the charged phosphonate oxygen is replaced by an alkyl or aryl group), phosphodiester and alkylphosphotriesters, in which the charged oxygen moiety is alkylated. Oligonucleotides which contain diol, such as tetraethyleneglycol or hexaethyleneglycol, at either or both termini have also been shown to be substantially resistant to nuclease degradation.

For use in vivo, ISNAs are preferably relatively resistant to degradation (e.g., via endo- and exo-nucleases). Secondary structures, such as stem loops, can stabilize nucleic acids against degradation. Alternatively, nucleic acid stabilization can be accomplished via phosphate backbone modifications. One type of stabilized nucleic acid has at least a partial phosphorothioate modified backbone. Phosphorothioates may be synthesized using automated techniques employing either phosphoramidate or H-phosphonate chemistries. Aryl- and alkyl-phosphonates can be made, e.g., as described in U.S. Pat. No. 4,469,863; and alkylphosphotriesters (in which the charged oxygen moiety is alkylated as described in U.S. Pat. No. 5,023,243 and European Patent No. 092,574) can be prepared by automated solid phase synthesis using commercially available reagents. Methods for making other DNA backbone modifications and substitutions have been described. Uhlmann E and Peyman A, *Chem Rev* 90:544 (1990); Goodchild J, *Bioconjugate Chem* 1:165 (1990).

Other sources of immunostimulatory nucleic acids useful according to the invention include standard viral and bacterial vectors, many of which are commercially available. In its broadest sense, a "vector" is any nucleic acid material which is ordinarily used to deliver and facilitate the transfer of nucleic acids to cells. The vector as used herein may be an empty vector or a vector carrying a gene which can be expressed. In the case when the vector is carrying a gene the vector generally transports the gene to the target cells with reduced degradation relative to the extent of degradation that would result in the absence of the vector. In this case the vector optionally includes gene expression sequences to enhance expression of the gene in target cells such as immune cells, but it is not required that the gene be expressed in the cell.

A basis for certain of the screening assays is the presence of a functional TLR 7, TLR 8, or TLR9 in a cell. The functional TLR in some instances is naturally expressed by the cell. In other instances, expression of the functional TLR can involve introduction or reconstitution of a species-specific TLR9 into a cell or cell line that otherwise lacks the TLR or lacks responsiveness to ISNA, resulting in a cell or cell line capable of activating the TLR/IL-1R signaling pathway in response to contact with an ISNA. Examples of cell lines lacking TLR9 or ISNA responsiveness include, but are not limited to, 293 fibroblasts (ATCC CRL-1573), MonoMac-6, THP-1, U937, CHO, and any TLR9 knock-out. The introduction of the species-specific TLR into the cell or cell line is preferably accomplished by transient or stable transfection of the cell or cell line with a TLR-encoding nucleic acid sequence operatively linked to a gene expression sequence (as described above).

The species-specific TLR, including TLR7, TLR8, and TLR9, is not limited to a murine TLR, but rather can include a TLR derived from murine or non-murine sources. Examples of non-murine sources include, but are not limited to, human, bovine, canine, feline, ovine, porcine, and equine. Other species include chicken and fish, e.g., aquaculture species.

The species-specific TLR, including TLR7, TLR8, and TLR9, also is not limited to native TLR polypeptides. In certain embodiments the TLR can be, e.g., a chimeric TLR in which the extracellular domain and the cytoplasmic domains are derived from TLR polypeptides from different species. Such chimeric TLR polypeptides, as described above, can include, for example, a human TLR extracellular domain and a murine TLR cytoplasmic domain, each domain derived from the corresponding TLR7, TLR8, or TLR9 of each species. In alternative embodiments, such chimeric TLR polypeptides can include chimeras created with different TLR splice variants or allotypes. Other chimeric TLR polypeptides useful for the purposes of screening ISNA mimics, agonists and antagonists can include chimeric polypeptides created with a TLR of a first type, e.g., TLR9, and another TLR, e.g., TLR7 or TLR8, of the same or another species as the TLR of the first type. Also contemplated are chimeric polypeptides which incorporate sequences derived from more than two polypeptides, e.g., an extracellular domain, a transmembrane domain, and a cytoplasmic domain all derived from different polypeptide sources, provided at least one such domain derives from a TLR7, TLR8, or TLR9 polypeptide. As a further example, also contemplated are constructs such as include an extracellular domain of one TLR9, an intracellular domain of another TLR9, and a non-TLR reporter such as luciferase, GFP, etc. Those of skill in the art will recognize how to design and generate DNA sequences coding for such chimeric TLR polypeptides.

The screening assays can have any of a number of possible readout systems based upon either TLR/IL-1R signaling pathway or other assays useful for assaying response to ISNAs. It has been reported that immune cell activation by CpG immunostimulatory sequences is dependent in some way on endosomal processing. It is not yet known whether TLR9 is directly involved in this endosomal pathway, or if there is some intermediary between TLR9 and the endosome.

In preferred embodiments, the readout for the screening assay is based on the use of native genes or, alternatively, cotransfected or otherwise co-introduced reporter gene constructs which are responsive to the TLR/IL-1R signal transduction pathway involving MyD88, TRAF6, p38, and/or ERK. Häcker H et al., *EMBO J.* 18:6973-6982 (1999). These pathways activate kinases including κB kinase complex and c-Jun N-terminal kinases. Thus reporter genes and reporter gene constructs particularly useful for the assays can include a reporter gene operatively linked to a promoter sensitive to NF-κB. Examples of such promoters include, without limitation, those for NF-κB, IL-1, IL-6, IL-8, IL-12 p40, CD80, CD86, and TNF-α. The reporter gene operatively linked to the TLR7-, TLR8-, or TLR9-sensitive promoter can include, without limitation, an enzyme (e.g., luciferase, alkaline phosphatase, β-galactosidase, chloramphenicol acetyltransferase (CAT), etc.), a bioluminescence marker (e.g., green-fluorescent protein (GFP, U.S. Pat. No. 5,491,084), etc.), a surface-expressed molecule (e.g., CD25), and a secreted molecule (e.g., IL-8, IL-12 p40, TNF-α). In preferred embodiments the reporter is selected from IL-8, TNF-α, NF-κB-luciferase (NF-κB-luc; Häcker H et al., *EMBO J.* 18:6973-6982 (1999)), IL-12 p40-luc (Murphy T L et al., *Mol Cell Biol* 15:5258-5267 (1995)), and TNF-luc (Häcker H et al., *EMBO J.* 18:6973-6982 (1999)). In assays relying on enzyme activity readout, substrate can be supplied as part of the assay, and detection can involve measurement of chemiluminescence, fluorescence, color development, incorporation of radioactive label, drug resistance, or other marker of enzyme activity. For assays relying on surface expression of a molecule, detection can be accomplished using FACS analysis or functional assays. Secreted molecules can be assayed using enzyme-linked immunosorbent assay (ELISA) or bioassays. Many such readout systems are well known in the art and are commercially available.

In another aspect the invention provides a screening method for identifying an immunostimulatory nucleic acid molecule (ISNA). The method entails contacting a functional TLR selected from the group consisting of TLR7, TLR8, and TLR9 with a test nucleic acid molecule; detecting the presence or absence of a response mediated by a TLR signal transduction pathway in the presence of the test nucleic acid molecule arising as a result of an interaction between the functional TLR and the test nucleic acid molecule; and determining the test nucleic acid molecule is an ISNA when the presence of a response mediated by the TLR signal transduction pathway is detected. "Functional TLR" and a "cell expressing functional TLR" are as described elsewhere herein. A response mediated by a TLR signal transduction pathway includes induction of a gene under control of a promoter responsive to the TLR/IL-1R signaling pathway, including but not limited to promoters responsive to NF-κB. The biological response thus can include, e.g., secretion of IL-8 and luciferase activity in a cell transfected with NF-κB-luc, IL-12 p40-luc, or TNF-luc. A test nucleic acid molecule can include a DNA, RNA, or modified nucleic acid molecule as described herein. In some embodiments the test nucleic acid molecule is a CpG nucleic acid.

Preferably, the test nucleic acid molecule is a sequence variant of a reference ISNA, containing at least one alternative base, at least one alternative internucleotide backbone linkage, or at least one alternative sugar moiety as compared to the particular reference ISNA. In a preferred embodiment the test nucleic acid molecule is a member of a library of such test nucleic acid molecules.

According to one embodiment of this method, comparison can be made to a reference ISNA. The reference ISNA may be any ISNA, including a CpG nucleic acid. In preferred embodiments the screening method is performed using a plurality of test nucleic acids. Preferably comparison of test and reference responses is based on comparison of quantitative measurements of responses in each instance.

The method can be used to select a subset of test nucleic acid molecules based on their ability to induce a similar specific response mediated by the TLR signal transduction pathway. For instance, the method can be used to classify test CpG nucleic acids as predominantly B-cell activating CpG nucleic acids, or as predominantly IFN-α inducing CpG nucleic acids. Other new classes of ISNAs may be identified and characterized using the method.

Application of this method permits the identification of ISNAs, delineation of sequence specificity of a given TLR, and also optimization of ISNA sequences. Identification of ISNAs involves screening candidate ISNAs as above and selecting any ISNA that induces a response as defined. Delineation of sequence specificity involves screening candidate ISNAs as above with reference to a particular TLR9, selecting any ISNAs that induce a response as defined, and categorizing ISNAs that do and do not induce a response on the basis of their sequence. Optimization of ISNA sequences involves an iterative application of the method as described, further including the steps of selecting the best sequence at any given stage or round in the screening and substituting it as a benchmark or reference in a subsequent round of screening. This latter process can further include selection of parameters to modify in choosing and generating candidate ISNAs to screen.

In another aspect the invention provides screening method for identifying species specificity of an ISNA. The method involves contacting a functional TLR selected from the group consisting of TLR7, TLR8, and TLR9 of a first species with a test ISNA; contacting a functional TLR selected from the group consisting of TLR7, TLR8, and TLR9 of a second species with the test ISNA; measuring a response mediated by a TLR signal transduction pathway associated with the contacting the functional TLR of the first species with the test ISNA; measuring a response mediated by the TLR signal transduction pathway associated with the contacting the functional TLR of the second species with the test ISNA; and comparing (a) the response mediated by a TLR signal transduction pathway associated with the contacting the functional TLR of the first species with the test ISNA with (b) the response mediated by the TLR signal transduction pathway associated with the contacting the functional TLR of the second species with the test ISNA. The functional TLR may be expressed by a cell or it may be part of a cell-free system. The functional TLR may be part of a complex, with either another TLR or with another protein, e.g., MyD88, IRAK, TRAF6, IκB, NF-κB, or functional homologues and derivatives thereof. Thus for example a given ODN can be tested against a panel of 293 fibroblast cells transfected with TLR7, TLR8, or TLR9 from various species and optionally cotransfected with a reporter construct (e.g., NF-κB-luc) sensitive to TLR/IL-1R activation pathways. Thus in another aspect, the invention provides a method for screening species selectivity with respect to a given nucleic acid sequence.

As mentioned above, the invention in one aspect provides a screening method for comparing TLR signaling activity or a test compound against corresponding TLR signaling activity of a reference ISNA. The methods generally involve contacting a functional TLR selected from the group consisting of TLR7, TLR8, and TLR9 with a reference ISNA and detecting a reference response mediated by a TLR signal transduction pathway; contacting a functional TLR selected from the group consisting of TLR7, TLR8, and TLR9 with a test compound and detecting a test response mediated by a TLR signal transduction pathway; and comparing the test response with the reference response to compare the TLR signaling activity of the test compound with the ISNA. Assays in which the test compound and the reference ISNA contact the TLR independently may be used to identify test compounds that are ISNA mimics. Assays in which the test compound and the reference ISNA contact the TLR concurrently may be used to identify test compounds that are ISNA agonists and ISNA antagonists.

An ISNA mimic as used herein is a compound which causes a response mediated by a TLR signal transduction pathway. As used herein the term "response mediated by a TLR signal transduction pathway" refers to a response which is characteristic of an ISNA-TLR interaction. As demonstrated herein responses which are characteristic of ISNA-TLR interactions include the induction of a gene under control of an ISNA-specific promoter such as a NF-κB promoter, increases in Th1 cytokine levels, etc. The gene under the control of the NF-κB promoter may be a gene which naturally includes an NF-κB promoter or it may be a gene in a construct in which an NF-κB promoter has been inserted. Genes which naturally include the NF-κB promoter include but are not limited to IL-8, IL-12 p40, NF-κB-luc, IL-12 p40-luc, and TNF-luc. Increases in Th1 cytokine levels is another measure characteristic of an ISNA-TLR interaction. Increases in Th1 cytokine levels may result from increased production or increased stability or increased secretion of the Th1 cytokines in response to the ISNA-TLR interaction. Th1 cytokines include but are not limited to IL-2, IFN-γ, and IL-12. Other responses which are characteristic of an ISNA-TLR interaction include but are not limited to a reduction in Th2 cytokine levels. Th2 cytokines include but are not limited to IL-4, IL-5, and IL-10.

The response which is characteristic of an ISNA-TLR interaction may be a direct response or an indirect response. A direct response is a response that arises directly as a result of the ISNA-TLR interaction. An indirect response is a response which involves the modulation of other parameters prior to its occurrence.

An ISNA agonist as used herein is a compound which causes an enhanced response to an ISNA mediated by a TLR signal transduction pathway. Thus an ISNA agonist as used herein is a compound which causes an increase in at least one aspect of an immune response that is ordinarily induced by the reference ISNA. For example, an immune response that is ordinarily induced by an ISNA can specifically include TLR7-, TLR8-, or TLR9-mediated signal transduction in response to immunostimulatory CpG nucleic acid. An ISNA agonist will in some embodiments compete with ISNA for binding to TLR7, TLR8, or TLR9. In other embodiments an ISNA agonist will bind to a site on TLR7, TLR8, or TLR9 that is distinct from the site for binding ISNA. In yet other embodiments an ISNA agonist will act via another molecule or pathway distinct from TLR7, TLR8, or TLR9.

An ISNA antagonist as used herein is a compound which causes a decreased response to an ISNA mediated by a TLR signal transduction pathway. Thus an ISNA antagonist as used herein is a compound which causes a decrease in at least one aspect of an immune response that is ordinarily induced by the reference ISNA. For example, an immune response that is ordinarily induced by an ISNA can specifically include TLR7-, TLR8-, or TLR9-mediated signal transduction in response to immunostimulatory CpG nucleic acid. An ISNA antagonist will in some embodiments compete with ISNA for binding to TLR7, TLR8, or TLR9. In other embodiments an ISNA antagonist will bind to a site on TLR7, TLR8, or TLR9 that is distinct from the site for binding ISNA. In yet other embodiments an ISNA antagonist will act via another molecule or pathway distinct from TLR7, TLR8, or TLR9.

The screening methods for comparing TLR signaling activity of a test compound with signaling activity of an ISNA involve contacting at least one test compound with a functional TLR selected from TLR7, TLR8, and TLR9 under conditions which, in the absence of a test compound, permit a reference ISNA to induce at least one aspect of an immune response. The functional TLR may be expressed by a cell or it may be part of a cell-free system. A cell expressing a functional TLR is a cell that either naturally expresses the TLR, or is a cell into which has been introduced a TLR expression vector, or is a cell manipulated to express TLR in a manner that allows the TLR to be expressed by the cell and to transduce a signal under conditions which normally permit signal transduction by the signal transducing portion of the TLR. The TLR can be a native TLR or it can be a fragment or variant thereof, as described above. According to these methods, the test compound is contacted with a functional TLR or TLR-expressing cell before, after, or simultaneously with contacting a reference ISNA with the functional TLR or TLR-expressing cell. A response of the functional TLR or TLR-expressing cell is measured and compared with the corresponding response that results or would result under the same conditions in the absence of the test compound. Where it is appropriate, the response in the absence of the test compound can be determined as a concurrent or historical control. Examples of such responses include, without limitation, a response mediated through the TLR signal transduction pathway, secretion of a cytokine, cell proliferation, and cell activation. In a preferred embodiment, the measurement of a response involves the detection of IL-8 secretion (e.g., by ELISA). In another preferred embodiment, the measurement of the response involves the detection of luciferase activity (e.g., NF-κB-luc, IL-12 p40-luc, or TNF-luc).

Examples of reference ISNAs include, without limitation, those listed in Table 1 (above). In some preferred embodiments the reference ISNA is a CpG nucleic acid.

Test compounds can include but are not limited to peptide nucleic acids (PNAs), antibodies, polypeptides, carbohydrates, lipids, hormones, and small molecules. Test compounds can further include variants of a reference ISNA incorporating any one or combination of the substitutions described above. Test compounds can be generated as members of a combinatorial library of compounds.

In preferred embodiments, the methods for screening test compounds, test nucleic acid molecules, test ISNAs, and candidate pharmacological agents can be performed on a large scale and with high throughput by incorporating, e.g., an array-based assay system and at least one automated or semi-automated step. For example, the assays can be set up using multiple-well plates in which cells are dispensed in individual wells and reagents are added in a systematic manner using a multiwell delivery device suited to the geometry of the multiwell plate. Manual and robotic multiwell delivery devices suitable for use in a high throughput screening assay are well known by those skilled in the art. Each well or array element can be mapped in a one-to-one manner to a particular test condition, such as the test compound. Readouts can also be performed in this multiwell array, preferably using a multiwell plate reader device or the like. Examples of such devices are well known in the art and are available through commercial sources. Sample and reagent handling can be automated to further enhance the throughput capacity of the screening assay, such that dozens, hundreds, thousands, or even millions of parallel assays can be performed in a day or in a week. Fully robotic systems are known in the art for applications such as generation and analysis of combinatorial libraries of synthetic compounds. See, for example, U.S. Pat. Nos. 5,443, 791 and 5,708,158.

The invention will be more fully understood by reference to the following examples. These examples, however, are merely intended to illustrate the embodiments of the invention and are not to be construed to limit the scope of the invention.

EXAMPLES

Example 1

Method of Cloning the Mouse TLR9

Alignment of human TLR9 protein sequence with mouse EST database using tfasta yielded 7 hits with mouse EST sequences aa197442, ai451215, aa162495, aw048117, ai463056, aw048548, and aa273731. Two primers were designed that bind to aa197442 EST sequence for use in a RACE-PCR to amplify 5' and 3' ends of the mouse TLR9 cDNA. The library used for the RACE PCR was a mouse spleen marathon-ready cDNA commercially available from Clonetech. A 5' fragment with a length of 1800 bp obtained by this method was cloned into Promega pGEM-T Easy vector. After sequencing of the 5' end, additional primers were designed for amplification of the complete mouse TLR9 cDNA. The primer for the 5' end was obtained from the sequence of the 5' RACE product whereas the primer for the 3' end was selected from the mouse EST sequence aa273731.

Three independent PCR reactions were set up using a murine macrophage RAW264.7 (ATCC TIB-71) cDNA as a template, and the resulting amplification products were cloned into the pGEM-T Easy vector. The inserts were fully sequenced, translated into protein and aligned to the human protein sequence. One out of three clones was error-free based on alignment comparison (clone mtlr932e.pep). The cDNA sequence for mTLR9 is SEQ ID NO:1, is presented in Table 2. The ATG start codon occurs at base 40, and a TAG termination codon occurs at base 3136. SEQ ID NO:2 (Table 3), corresponding to bases 40-3135 of SEQ ID NO:1, is the coding region for the polypeptide of SEQ ID NO:3.

TABLE 2

| cDNA Sequence for Murine TLR9 (5' to 3'; SEQ ID NO:1) | | | | | |
|---|---|---|---|---|---|
| tgtcagaggg | agcctcggga | gaatcctcca | tctcccaaca | tggttctccg | tcgaaggact | 60 |
| ctgcacccct | tgtccctcct | ggtacaggct | gcagtgctgg | ctgagactct | ggccctgggt | 120 |
| accctgcctg | ccttcctacc | ctgtgagctg | aagcctcatg | gcctggtgga | ctgcaattgg | 180 |
| ctgttcctga | agtctgtacc | ccgtttctct | gcggcagcat | cctgctccaa | catcacccgc | 240 |
| ctctccttga | tctccaaccg | tatccaccac | ctgcacaact | ccgacttcgt | ccacctgtcc | 300 |
| aacctgcggc | agctgaacct | caagtggaac | tgtccaccca | ctggccttag | cccctgcac | 360 |
| ttctcttgcc | acatgaccat | tgagcccaga | accttcctgg | ctatgcgtac | actggaggag | 420 |
| ctgaacctga | gctataatgg | tatcaccact | gtgccccgac | tgcccagctc | cctggtgaat | 480 |
| ctgagcctga | gccacaccaa | catcctggtt | ctagatgcta | acagcctcgc | cggcctatac | 540 |
| agcctgcgcg | ttctcttcat | ggacgggaac | tgctactaca | agaaccctg | cacaggagcg | 600 |
| gtgaagtga | ccccaggcgc | cctcctgggc | ctgagcaatc | tcacccatct | gtctctgaag | 660 |
| tataacaacc | tcacaaaggt | gccccgccaa | ctgcccccca | gctggagta | cctcctggtg | 720 |
| tcctataacc | tcattgtcaa | gctgggcct | gaagacctgg | ccaatctgac | ctcccttcga | 780 |
| gtacttgatg | tgggtgggaa | ttgccgtcgc | tgcgaccatg | cccccaatcc | ctgtatagaa | 840 |
| tgtggccaaa | agtccctcca | cctgcaccct | gagaccttcc | atcacctgag | ccatctggaa | 900 |
| ggcctggtgc | tgaaggacag | ctctctccat | acactgaact | cttcctggtt | ccaaggtctg | 960 |
| gtcaacctct | cggtgctgga | cctaagcgag | aactttctct | atgaaagcat | caaccacacc | 1020 |
| aatgcctttc | agaacctaac | ccgcctgcgc | aagctcaacc | tgtccttcaa | ttaccgcaag | 1080 |
| aaggtatcct | ttgcccgcct | ccacctggca | agttccttca | agaacctggt | gtcactgcag | 1140 |
| gagctgaaca | tgaacggcat | cttcttccgc | tcgctcaaca | agtacacgct | cagatggctg | 1200 |
| gccgatctgc | ccaaactcca | cactctgcat | cttcaaatga | acttcatcaa | ccaggcacag | 1260 |
| ctcagcatct | ttggtacctt | ccgagccctt | cgctttgtgg | acttgtcaga | caatcgcatc | 1320 |
| agtgggcctt | caacgctgtc | agaagccacc | cctgaagagg | cagatgatgc | agagcaggag | 1380 |
| gagctgttgt | ctgcggatcc | tcacccagct | ccactgagca | ccctgcttc | taagaacttc | 1440 |

TABLE 2-continued

| cDNA Sequence for Murine TLR9 (5' to 3'; SEQ ID NO:1) | |
|---|---|
| atggacaggt gtaagaactt caagttcacc atggacctgt ctcggaacaa cctggtgact | 1500 |
| atcaagccag agatgtttgt caatctctca cgcctccagt gtcttagcct gagccacaac | 1560 |
| tccattgcac aggctgtcaa tggctctcag ttcctgccgc tgactaatct gcaggtgctg | 1620 |
| gacctgtccc ataacaaact ggacttgtac cactggaaat cgttcagtga gctaccacag | 1680 |
| ttgcaggccc tggacctgag ctacaacagc cagcccttta gcatgaaggg tataggacac | 1740 |
| aatttcagtt ttgtgggccca tctgtccatg ctacacagcc ttagcctggc acacaatgac | 1800 |
| attcatacccg tgtgtcctc acatctcaac agcaactcag tgaggtttct tgacttcagc | 1860 |
| ggcaacggta tgggccgcat gtgggatgag ggggccttt atctccattt cttccaaggc | 1920 |
| ctgagtggcc tgctgaagct ggacctgtct caaaataacc tgcatatcct ccggccccag | 1980 |
| aaccttgaca acctccccaa gagcctgaag ctgctgagcc tccgagacaa ctacctatct | 2040 |
| ttctttaact ggaccagtct gtccttcctg cccaacctgg aagtcctaga cctggcaggc | 2100 |
| aaccagctaa aggccctgac caatggcacc ctgcctaatg caccctcct ccagaaactg | 2160 |
| gatgtcagca gcaacagtat cgtctctgtg gtcccagcct tcttcgctct ggcggtcgag | 2220 |
| ctgaaagagg tcaacctcag ccacaacatt ctcaagacgg tggatcgctc ctggtttggg | 2280 |
| cccattgtga tgaacctgac agttctagac gtgagaagca accctctgca ctgtgcctgt | 2340 |
| ggggcagcct tcgtagactt actgttggag gtgcagacca aggtgcctgg cctggctaat | 2400 |
| ggtgtgaagt gtggcagccc cggccagctg cagggccgta gcatcttcgc acaggacctg | 2460 |
| cggctgtgcc tggatgaggt cctctcttgg gactgctttg gcctttcact cttggctgtg | 2520 |
| gccgtgggca tggtggtgcc tatactgcac catctctgcg gctgggacgt ctggtactgt | 2580 |
| tttcatctgt gcctggcatg gctaccttg ctggcccgca gccgacgcag cgcccaagct | 2640 |
| ctcccctatg atgccttcgt ggtgttcgat aaggcacaga gcgcagttgc ggactgggtg | 2700 |
| tataacgagc tgcgggtgcg gctggaggag cggcgcggtc gccgagccct acgcttgtgt | 2760 |
| ctggaggacc gagattggct gcctggccag acgctcttcg agaacctctg gcttccatc | 2820 |
| tatgggagcc gcaagactct atttgtgctg gcccacacgg accgcgtcag tggcctcctg | 2880 |
| cgcaccagct cctgctggc tcagcagcgc ctgttggaag accgcaagga cgtggtggtg | 2940 |
| ttggtgatcc tgcgtccgga tgcccaccgc tcccgctatg tgcgactgcg ccagcgtctc | 3000 |
| tgccgccaga gtgtgctctt ctggccccag cagcccaacg ggcagggggg cttctgggcc | 3060 |
| cagctgagta cagccctgac tagggacaac cgccacttct ataaccagaa cttctgccgg | 3120 |
| ggacctacag cagaatagct cagagcaaca gctggaaaca gctgcatctt catgcctggt | 3180 |
| tcccgagttg ctctgcctgc | 3200 |

TABLE 3

| Coding region for murine TLR9 (SEQ ID NO:2) | |
|---|---|
| atggttctcc gtcgaaggac tctgcacccc ttgtccctcc tggtacaggc tgcagtgctg | 60 |
| gctgagactc tggccctggg taccctgcct gccttcctac cctgtgagct gaagcctcat | 120 |
| ggcctggtgg actgcaattg gctgttcctg aagtctgtac ccgtttctc tgcggcagca | 180 |
| tcctgctcca acatcacccg cctctccttg atctccaacc gtatccacca cctgcacaac | 240 |
| tccgacttcg tccacctgtc caacctgcgg cagctgaacc tcaagtggaa ctgtccaccc | 300 |

TABLE 3-continued

Coding region for murine TLR9 (SEQ ID NO:2)

| | | | | |
|---|---|---|---|---|
| actggcctta | gcccctgca | cttctcttgc | cacatgacca | ttgagcccag aaccttcctg | 360 |
| gctatgcgta | cactggagga | gctgaacctg | agctataatg | gtatcaccac tgtgccccga | 420 |
| ctgcccagct | ccctggtgaa | tctgagcctg | agccacacca | acatcctggt tctagatgct | 480 |
| aacagcctcg | ccggcctata | cagcctgcgc | gttctcttca | tggacgggaa ctgctactac | 540 |
| aagaacccct | gcacaggagc | ggtgaaggtg | accccaggcg | ccctcctggg cctgagcaat | 600 |
| ctcacccatc | tgtctctgaa | gtataacaac | ctcacaaagg | tgccccgcca actgcccccc | 660 |
| agcctggagt | acctcctggt | gtcctataac | ctcattgtca | agctggggcc tgaagacctg | 720 |
| gccaatctga | cctcccttcg | agtacttgat | gtgggtggga | attgccgtcg ctgcgaccat | 780 |
| gcccccaatc | cctgtataga | atgtggccaa | aagtccctcc | acctgcaccc tgagaccttc | 840 |
| catcacctga | gccatctgga | aggcctggtg | ctgaaggaca | gctctctcca tacactgaac | 900 |
| tcttcctggt | tccaaggtct | ggtcaacctc | tcggtgctgg | acctaagcga aactttctc  | 960 |
| tatgaaagca | tcaaccacac | caatgccttt | cagaacctaa | cccgcctgcg caagctcaac | 1020 |
| ctgtccttca | attaccgcaa | gaaggtatcc | tttgcccgcc | tccacctggc aagttccttc | 1080 |
| aagaacctgg | tgtcactgca | ggagctgaac | atgaacggca | tcttcttccg ctcgctcaac | 1140 |
| aagtacacgc | tcagatggct | ggccgatctg | cccaaactcc | acactctgca tcttcaaatg | 1200 |
| aacttcatca | ccaggcaca  | gctcagcatc | tttggtacct | tccgagccct tcgctttgtg | 1260 |
| gacttgtcag | acaatcgcat | cagtgggcct | tcaacgctgt | cagaagccac ccctgaagag | 1320 |
| gcagatgatg | cagagcagga | ggagctgttg | tctgcggatc | ctcacccagc tccactgagc | 1380 |
| accctgcttt | ctaagaactt | catggacagg | tgtaagaact | tcaagttcac catgaccctg | 1440 |
| tctcggaaca | acctggtgac | tatcaagcca | gagatgtttg | tcaatctctc acgcctccag | 1500 |
| tgtcttagcc | tgagccacaa | ctccattgca | caggctgtca | atggctctca gttcctgccg | 1560 |
| ctgactaatc | tgcaggtgct | ggacctgtcc | cataacaaac | tggacttgta ccactggaaa | 1620 |
| tcgttcagtg | agctaccaca | gttgcaggcc | ctggacctga | gctacaacag ccagcccttt | 1680 |
| agcatgaagg | gtataggcca | caatttcagt | tttgtggccc | atctgtccat gctacacagc | 1740 |
| cttagcctgg | cacacaatga | cattcatacc | cgtgtgtcct | cacatctcaa cagcaactca | 1800 |
| gtgaggtttc | ttgacttcag | cggcaacggt | atgggccgca | tgtgggatga ggggggcctt | 1860 |
| tatctccatt | tcttccaagg | cctgagtggc | ctgctgaagc | tggacctgtc tcaaaataac | 1920 |
| ctgcatatcc | tccggcccca | gaaccttgac | aacctcccca | agagcctgaa gctgctgagc | 1980 |
| ctccgagaca | actacctatc | tttctttaac | tggaccagtc | tgtccttcct gcccaacctg | 2040 |
| gaagtcctag | acctggcagg | caaccagcta | aaggccctga | ccaatggcac cctgcctaat | 2100 |
| ggcacccctcc | tccagaaact | ggatgtcagc | agcaacagta | tcgtctctgt ggtcccagcc | 2160 |
| ttcttcgctc | tggcggtcga | gctgaaagag | gtcaacctca | gccacaacat tctcaagacg | 2220 |
| gtggatcgct | cctggtttgg | gcccattgtg | atgaacctga | cagttctaga cgtgagaagc | 2280 |
| aaccctctgc | actgtgcctg | tgggcagcc  | ttcgtagact | tactgttgga ggtgcagacc | 2340 |
| aaggtgcctg | gcctggctaa | tggtgtgaag | tgtggcagcc | ccggccagct gcagggccgt | 2400 |
| agcatcttcg | cacaggacct | gcggctgtgc | ctggatgagg | tcctctcttg ggactgcttt | 2460 |
| ggcctttcac | tcttggctgt | ggccgtgggc | atggtggtgc | ctatactgca ccatctctgc | 2520 |
| ggctgggacg | tctggtactg | ttttcatctg | tgcctggcat | ggctaccttt gctggccgc  | 2580 |
| agccgacgca | gcgcccaagc | tctcccctat | gatgccttcg | tggtgttcga taaggcacag | 2640 |

TABLE 3-continued

Coding region for murine TLR9 (SEQ ID NO:2)

```
agcgcagttg cggactgggt gtataacgag ctgcgggtgc ggctggagga gcggcgcggt  2700
cgccgagccc tacgcttgtg tctggaggac cgagattggc tgcctggcca gacgctcttc  2760
gagaacctct gggcttccat ctatgggagc cgcaagactc tatttgtgct ggcccacacg  2820
gaccgcgtca gtggcctcct gcgcaccagc ttcctgctgg ctcagcagcg cctgttggaa  2880
gaccgcaagg acgtggtggt gttggtgatc ctgcgtccgg atgcccaccg ctcccgctat  2940
gtgcgactgc gccagcgtct ctgccgccag agtgtgctct tctggcccca gcagcccaac  3000
gggcagggg gcttctgggc ccagctgagt acagccctga ctagggacaa ccgccacttc  3060
tataaccaga acttctgccg gggacctaca gcagaa                             3096
```

The deduced amino acid sequence for murine TLR9 (SEQ ID NO:3), comprising 1032 amino acid residues, is shown in Table 4 below in the aligned sequence comparison as mtlr932e.pep. The deduced amino acid sequence for human TLR9 (SEQ ID NO:6), comprising 1032 amino acid residues, is shown in Table 4 below in the aligned sequence comparison as htlr9.pro.

TABLE 4

Amino Acid Sequence of Murine and Human TLR9

```
                        .         :         .         :         .         :         .         :         .         :         60
htlr9.pro       MGFCRSALHPLSLLVQAIMLAMTLALGTLPAFLPCELQPHGLVNCNWLFLKSVPHFSMAA   60
mtlr932e.pep    MVLRRRTLHPLSLLVQAAVLAETLALGTLPAFLPCELKPHGLVDCNWLFLKSVPRFSAAA   60

.         :         .         :         .         :         .         :         .         :        120
htlr9.pro       PRGNVTSLSLSSNRIHHLHDSDFAHLPSLRHLNLKWNCFFVGLSPMHFPCHMTIEPSTFL  120
mtlr932e.pep    SCSNITRLSLISNRIHHLHNSDFVHLSNLRQLNLKWNCPPTGLSPLHFSCHMTIEPRTFL  120

.         :         .         :         .         :         .         :         .         :        180
htlr9.pro       AVFTLEELNLSYNNIMTVPALPKSLISLSLSHTNILMLDSASLAGLHALRFLFMDGNCYY  180
mtlr932e.pep    AMRTLEELNLSYNGITTVFRLPSSLVNLSLSHTNILVLDANSLAGLYSLRVLFNDGNCYY  180

.         :         .         :         .         :         .         :         .         :        240
htlr9.pro       KNPCRQALEVAPGALLGLGNLTHLSLKYNNLTVVPRNLPSSLEYLLLSYNRIVKLAPEDL  240
mtlr932e.pep    KNPCTGAVKVTPGALLGLSNLTHLSLKYNNLTKVPRQLPPSLEYLLVSYNLIVKLGPEDL  240

.         :         .         :         .         :         .         :         .         :        300
htlr9.pro       ANLTALRVLDVGGNCRRCDHAPNPCMECPRHFPQLHPDTFSHLSRLEGLVLKDSSLSWLN  300
mtlr932e.pep    ANLTSLRVLDVGGNCRRCDNAPNPCIECGQKSLHLHPETFHHLSHLEGLVLKDSSLHTLN  300

.         :         .         :         .         :         .         :         .         :        360
aa197442.pep                                                    LNLSFNYRKKVSFARLHLASSF   22
htlr9.pro       ASWFRGLGNLRVLDLSENFLYKCITKTKAFQGLTQLRKLNLSFNYQKRVSFAHLSLAPSF  360
mtlr932e.pep    SSWFQGLVNLSVLDLSENFLYESINHTNAFQNLTRLRKLNLSFNYRKKVSFARLHLASSF  360

.         :         .         :         .         :         .         :         .         :        420
mousepep1                                                                            C    1
aa197442.pep    KNLVSLQELNMNGIFFRLLNKYTLRWLADLPKLHTLHLQMNFINQAQLSIFGTFRALRFV   82
htlr9.pro       GSLVALKELDMHGIFFRSLDETTLRPLARLPMLQTLRLQMNFINQAQLGIFRAFPGLRYV  420
mtlr932e.pep    KNLVSLQELNMNGIFFRSLNKYTLRWLADLPKLHTLHLQMNFINQAQLSIFGTFRALRFV  420

.         :         .         :         .         :         .         :         .         :        480
mousepepi       DLSDNRISGPSTLSEA                                                17
humanpepi                                               PAPVDTPSSEDFRPNC             16
aa197442.pep    DLSDNRISGFSTLSEATPEEADDAEQEELLSADPHPAPLSTPASKNFMDRCKNFKFNMDL  142
htlr9.pro       DLSDNRISGASELT-ATMGEADGGEKVWLQPGDLAPAPVDTPSSEDFRPNCSTLNFTLDL  479
mtlr932e.pep    DLSDNRISGPSTLSEATPEEADDAEQEELLSADPHPAPLSTPASKNFMDRCKNFKFTMDL  480

.         :         .         :         .         :         .         :         .         :        540
aa197442.pep    SRNNLVTITAEMFVNLSRLQCLSLSHNSIAQAVNGS                            178
htlr9.pro       SRNNLVTVQPEMFAQLSHLQCLRLSHNCISQAVNGSQFLPLTGLQVLDLSRNKLDLYHEH  539
mtlr932e.pep    SRNNLVTIKPEMFVNLSRLQCLSLSHNSIAQAVNGSQFLPLTNLQVLDLSHNKLDLYHWK  540
```

TABLE 4-continued

Amino Acid Sequence of Murine and Human TLR9

```
                                                                       600
              .    :    .    :    .    :    .    :    .    :
aa162495.pep                      YNSQPFSMKGIGHNFSFVTHLSMLQSLSLAHNDIHTRVSSHLNSNS    46
htlr9.pro     SFTELPRLEALDLSYNSQPFGMQGVGHNFSFVAHLRTLRHLSLAHNNIHSQVSQQLCSTS   599
mtlr932e.pep  SFSELPQLQALDLSYNSQPFSMKGIGHNFSFVAHLSMLHSLSLAHNDIHTRVSSHLNSNS   600

660
              .    :    .    :    .    :    .    :    .    :
aa162495.pep  VRFLDFSGNGMGRMWDEGGLYLHFFQGLSGVLKLDLSQNNLHILRPQNLDNLPKSLKLLS   106
htlr9.pro     LRALDFSGNALGHMWAEGDLYLHFFQGLSGLIWLDLSQNRLHTLLPQTLRNLPKSLQVLR   659
mtlr932e.pep  VRFLDFSGNGMGRMWDEGGLYLHFFQGLSGLLKLDLSQNNLHILRPQNLDNLPKSLKLLS   660

720
              .    :    .    :    .    :    .    :    .    :
aa162495.pep  LRDNYLSFFNWTSLSFLPNLEVLDLAGNQLKALTNGTLPNGTLLQKLDVSSNSIVS       162
htlr9.pro     LRDNYLAFFKWWSLHFLPKLEVLDLAGNRLKALTNGSLPAGTRLRRLDVSCNSISFVAPG   719
mtlr932e.pep  LRDNYLSFFNWTSLSFLPNLEVLDLAGNQLKALTNGTLPNGTLLQKLDVSSNSIVSVVPA   720

780
              .    :    .    :    .    :    .    :    .    :
ai451215.pep                           PIVMNLTVLDVRSNPLHCACGAAFVDLLLEVQT    33
htlr9.pro     FFSKAKELRELNLSANALKTVDHSWFGPLASALQILDVSANPLHCACGAAFMDFLLEVQA   779
mtlr932e.pep  FFALAVELKEVNLSHNILKTVDRSWFGPIVMNLTVLDVRSNPLHCACGAAFVDLLLEVQT   780

840
              .    :    .    :    .    :    .    :    .    :
ai451215.pep  KVPGLANGVKCGSPGQLQGRSIFAQDLRLCLDEVLSWDCFGLSLLAVAVGHVVPILHHLC    93
htlr9.pro     AVPGLPSRVKCGSPGQLQGLSIFAQDLRLCLDEALSWDCFALSLLAVALGLGVPMLHHLC   839
mtlr932e.pep  KVPGLANGVKCGSPGQLQGRSIFAQDLRLCLDEVLSWDCFGLSLLAVAVGMVVPILHHLC   840

900
              .    :    .    :    .    :    .    :    .    :
ai451215.pep  GWDVWYCFHLCLAWLPLLAR-SRRSAQTLPYDAFVVFDKAQSAVADWVYNELRVRLEERR   152
htlr9.pro     GWDLWYCFHLCLAWLPWRGRQSGRDEDALPYDAFVVFDKTQSAVADWVYNELRGQLEECR   899
mtlr932e.pep  GWDVWYCFHLCLAWLPLLAR-SRRSAQALPYDAFVVFDKAQSAVADWVYNELRVRLEERR   899

960
              .    :    .    :    .    :    .    :    .    :
aa273731.pep                                AHTDRVSGLLRTSFLLAQQRLL         22
ai463056.pep              EDRDWLPGQTLFENLWASIYGSRKTLFVLAHTDRVSGLLRTSFLLAQQRLL    51
ai451215.pep  GR                                                            154
htlr9.pro     GRWALRLCLEERDWLPGKTLFENLWASVYGSRKTLFVLAHTDRVSGLLRASFLLAQQRLL   959
mtlr932e.pep  GRRALRLCLEDRDWLPGQTLFENLWASIYGSRKTLFVLAHTDRVSGLLRTSFLLAQQRLL   959

1020
              .    :    .    :    .    :    .    :    .    :
humanpep2                                                             H     1
mousepep2                                                             H     1
aa273731.pep  EDRKDVVVLVILRPDAXPSRYVRLRQRLCRQSVLFWPQRPNGQGGFWAQLSTALTRDNRH    82
ai463056.pep  EDRKDVVVLVILRPDAHRSRYVRLRQRLCRQSVLFWPQQPNGQGGFWAQLSTALTRDNRH   111
htlr9.pro     EDRKDVVVLVILSPDGRRSRYVRLRQRLCRQSVLLWPHQPSGQRSFWAQLGMALTRDNHH  1019
mtlr932e.pep  EDRKDVVVLVILRPDAHRSRYVRLRQRLCRQSVLFWPQQPNGQGGFWAQLSTALTRDNRH  1019

1080
              .    :    .    :    .    :    .    :    .    :
humanpep2     FYNRNFCQGPTAE                                                  14
mousepep2     FYNQNFCRGPTAE                                                  14
aa273731.pep  FYNQNFCRGPTAE                                                  95
ai463056.pep  FYNQNFCRGPTA                                                  123
htlr9.pro     FYNRNFCQGPTAE                                                1032
mtlr932e.pep  FYNQNFCRGPTAE                                                1032
```

The following SEQ ID NOs correspond to the sequences as shown in Table 4: htlr9.pro: SEQ ID NO:6; mtlr932e.pep: SEQ ID NO:3; aa197442.pep: SEQ ID NO:8; mousepep1: SEQ ID NO:17; humanpep1: SEQ ID NO:19; aa162495.pep: SEQ ID NO:14; ai451215.pep: SEQ ID NO:16; aa273731.pep: SEQ ID NO:10; ai463056.pep: SEQ ID NO:12; humanpep2: SEQ ID NO:20; and mousepep2: SEQ ID NO:18.

Example 2

Reconstitution of TLR9 Signaling in 293 Fibroblasts

The cloned mouse TLR9 cDNA (see above) and human TLR9 cDNA (gift from B. Beutler, Howard Hughes Medical Institute, Dallas, Tex.) in pT-Adv vector (from Clonetech) were cloned into the expression vector pcDNA3.1 (−) from Invitrogen using the EcoRI site. Utilizing a "gain of function" assay it was possible to reconstitute human TLR (hTLR9) and murine TLR9 (mTLR9) signaling in CpG DNA non-responsive human 293 fibroblasts (ATCC, CRL-1573). The expression vectors mentioned above were transfected into 293 fibroblast cells using the calcium phosphate method.

Figure 1A:
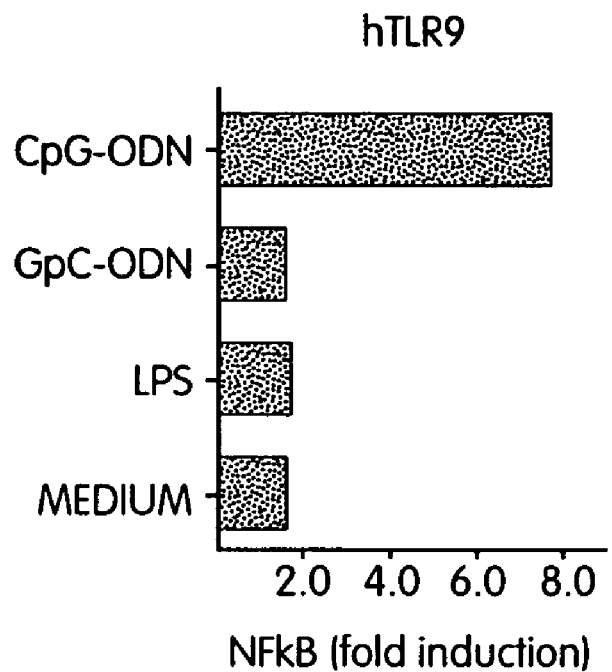
FIG. 1 is two paired bar graphs showing (A) the induction of NF-κB and (B) the amount of IL-8 produced by 293 fibroblast cells transfected with human TLR9 in response to exposure to various stimuli, including CpG-ODN, GpC-ODN, LPS, and medium.
Figure 1B:
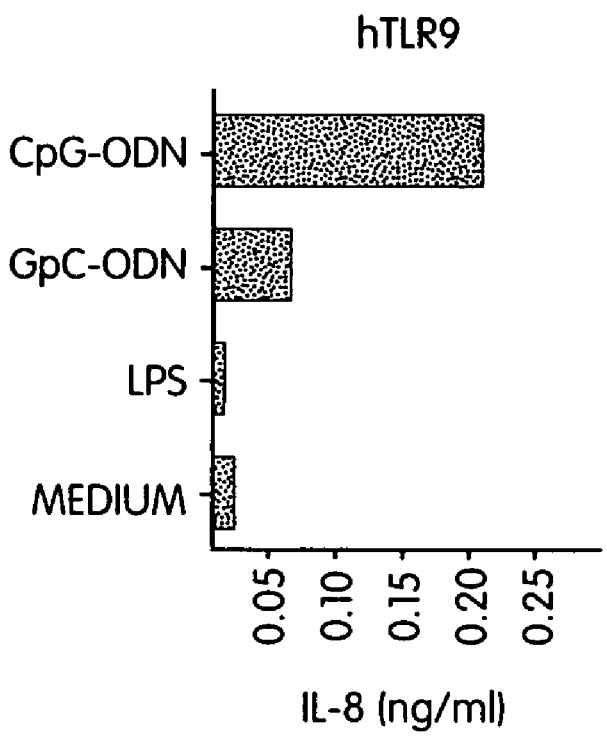

Since NF-κB activation is central to the IL-1/TLR signal transduction pathway (Medzhitov R et al., Mol Cell 2:253-258 (1998); Muzio M et al., J Exp Med 187:2097-2101 (1998)), cells were transfected with hTLR9 or co-transfected with hTLR9 and a NF-κB-driven luciferase reporter construct. Human fibroblast 293 cells were transiently transfected with (FIG. 1A) hTLR9 and a six-times NF-κB-luciferase reporter plasmid (NF-κB-luc, kindly provided by Patrick Baeuerle, Munich, Germany) or (FIG. 1B) with hTLR9 alone. After stimulus with CpG-ODN (2006, 2 μM, T CGTCGTTTTGTCGTTTTGTCGTT, SEQ ID NO:112), GpC-ODN (2006-GC, 2 μM, TGCTGCTTTTGT-GCTTTTGTGCTT, SEQ ID NO:118), LPS (100 ng/ml) or media, NF-κB activation by luciferase readout (8 h, FIG. 1A)

or IL-8 production by ELISA (48 h, FIG. 1B) were monitored. Results are representative of three independent experiments. FIG. 1 shows that cells expressing hTLR9 responded to CpG-DNA but not to LPS.

Figure 2:
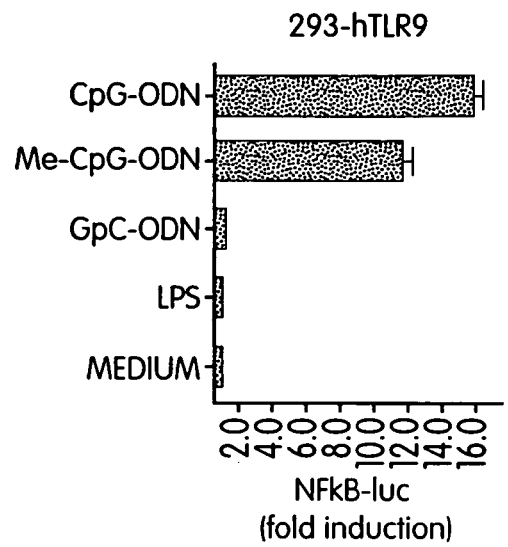
FIG. 2 is a bar graph showing the induction of NF-κB produced by 293 fibroblast cells transfected with murine TLR9 in response to exposure to various stimuli, including CpG-ODN, methylated CpG-ODN (Me-CpG-ODN), GpC-ODN, LPS, and medium.

FIG. 2 demonstrates the same principle for the transfection of mTLR9. Human fibroblast 293 cells were transiently transfected with mTLR9 and the NF-κB-luc construct (FIG. 2). Similar data was obtained for IL-8 production (not shown). Thus expression of TLR9 (human or mouse) in 293 cells results in a gain of function for CpG-DNA stimulation similar to hTLR4 reconstitution of LPS responses.

Figure 3:
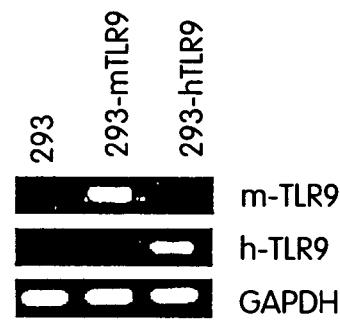
FIG. 3 is a series of gel images depicting the results of reverse transcriptase-polymerase chain reaction (RT-PCR) assays for murine TLR9 (mTLR9), human TLR9 (hTLR9), and glyceraldehyde-3-phosphate dehydrogenase (GAPDH) in untransfected control 293 cells, 293 cells transfected with mTLR9 (293-mTLR9), and 293 cells transfected with hTLR9 (293-hTLR9).

To generate stable clones expressing human TLR9, murine TLR9, or either TLR9 with the NF-κB-luc reporter plasmid, 293 cells were transfected in 10 cm plates ($2 \times 10^6$ cells/plate) with 16 μg of DNA and selected with 0.7 mg/ml G418 (PAA Laboratories GmbH, Cölbe, Germany). Clones were tested for TLR9 expression by RT-PCR, for example as shown in FIG. 3. The clones were also screened for IL-8 production or NF-κB-luciferase activity after stimulation with ODN. Four different types of clones were generated.

293-hTLR9-luc: expressing human TLR9 and 6-fold NF-κB-luciferase reporter
293-mTLR9-luc: expressing murine TLR9 and 6-fold NF-κB-luciferase reporter
293-hTLR9: expressing human TLR9
293-mTLR9: expressing murine TLR9

Figure 4:
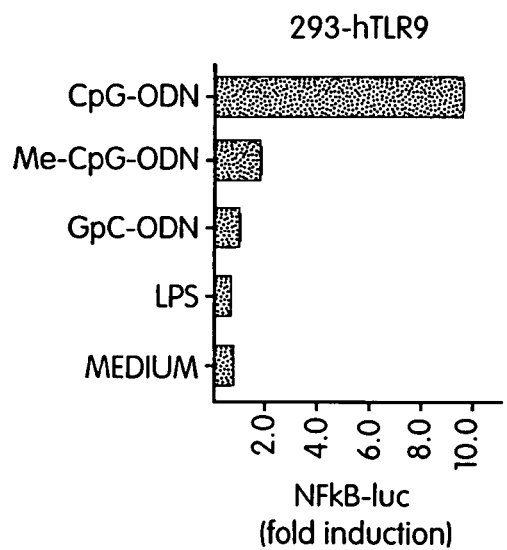
FIG. 4 is a graph showing the degree of induction of NF-κB-luc by various stimuli in stably transfected 293-hTLR9 cells.
Figure 5:
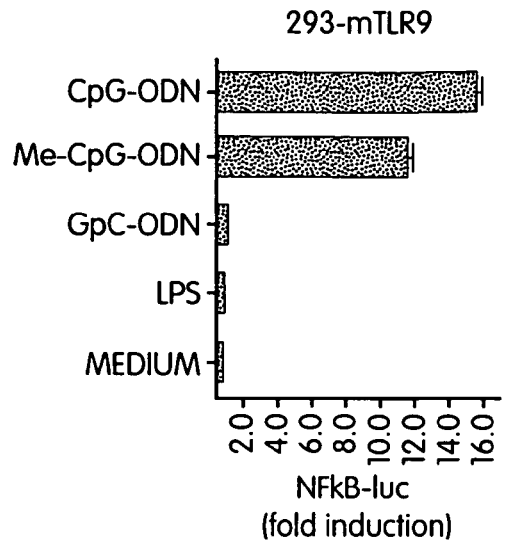
FIG. 5 is a graph showing the degree of induction of NF-κB-luc by various stimuli in stably transfected 293-mTLR9 cells.

FIG. 4 demonstrates the responsiveness of a stable 293-hTLR9-luc clone after stimulation with CpG-ODN (2006, 2 μM), GpC-ODN (2006-GC, 2 μM), Me-CpG-ODN (2006 methylated, 2 μM; TZGTZGTTTTGTZGTTTTGTZGTT, Z=5-methylcytidine, SEQ ID NO:128), LPS (100 ng/ml) or media, as measured by monitoring NF-κB activation. Similar results were obtained utilizing IL-8 production with the stable clone 293-hTLR9. 293-mTLR9-luc were also stimulated with CpG-ODN (1668, 2 μM; TCCATGA CGTTCCTGATGCT, SEQ ID NO:84), GpC-ODN (1668-GC, 2 μM; TCCATGAGCTTCCTGATGCT, SEQ ID NO:85), Me-CpG-ODN (1668 methylated, 2 μM; TCCAT-GAZGTTCCTGATGCT, Z=5-methylcytidine, SEQ ID NO:207), LPS (100 ng/ml) or media, as measured by monitoring NF-κB activation (FIG. 5). Similar results were obtained utilizing IL-8 production with the stable clone 293-mTLR9. Results are representative of at least two independent experiments. These results demonstrate that CpG-DNA non-responsive cell lines can be stably genetically complemented with TLR9 to become responsive to CpG DNA in a motif-specific manner. These cells can be used for screening of optimal ligands for innate immune responses driven by TLR9 in multiple species.

Example 3

Expression of Soluble Recombinant Human TLR9 in Yeast Cells (*Pichia pastoris*)

Figure 6:
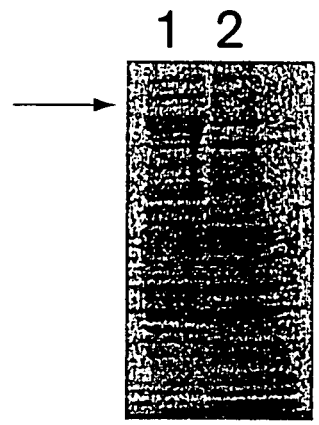
FIG. 6 is an image of a Coomassie-stained polyacrylamide gel depicting the presence of soluble hTLR9 in the supernatants of yeast cells transfected with hTLR9, either induced (lane 1) or not induced (lane 2).

Human TLR9 cDNA coding for amino acids 1 to 811 was amplified by PCR using the primers 5'-ATAGAAT-TCAATAATGGGTTTCTGCCGCAGCGCCCT-3' (SEQ ID NO:194) and 5'-ATATCTAGATCCAGGCAGAGGCGCAG-GTC-3' (SEQ ID NO:195), digested with EcoRI and XbaI, cloned into the yeast expression vector pPICZB (Invitrogen, Groningen, Netherlands) and transfected into yeast cells (*Pichia pastoris*). Clones were selected with the antibiotic zeozin and protein production of soluble human TLR9 was induced with methanol (see FIG. 6: SDS-PAGE, Coomassie stained, arrow marks hTLR9; lane 1: supernatant of culture induced with methanol; lane 2: supernatant of culture not induced). Thus TLR9 protein can be isolated from transfectants and further utilized for protein studies and vaccination purposes.

Example 4 hTLR9 Expression Correlates with CpG-DNA Responsiveness

Figure 7:
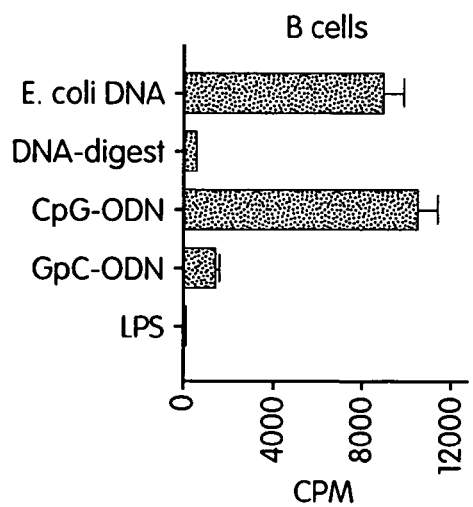
FIG. 7 is a graph showing proliferation of human B cells in response to various stimuli, including *Escherichia coli* (*E. coli*) DNA, DNase-digested *E. coli* DNA, CpG-ODN, GpC-ODN, and LPS.

Bacterial DNA has been described as a mitogen for both murine and human B cells. Although LPS is also mitogenic for murine B cells, it is generally accepted that LPS is not a mitogen for human B cells. FIG. 7 demonstrates that human B cells proliferate after stimulation with *E. coli* DNA or a CpG-ODN but not Dnase-digested *E. coli* DNA or a control GpC-ODN. Purified human B cells were stimulated with 50 μg/ml *E. coli* DNA, a comparable amount of DNase I-digested *E. coli* DNA, 2 μM CpG-ODN (2006), 2 μM GpC-ODN (2006-GC) or 100 ng/ml LPS. B cell proliferation was monitored at day two by $^3$H-thymidine uptake. These data demonstrate that it was DNA within the *E. coli* DNA preparation that was mitogenic and that a CpG-motif within the ODN was required.

Figure 8:
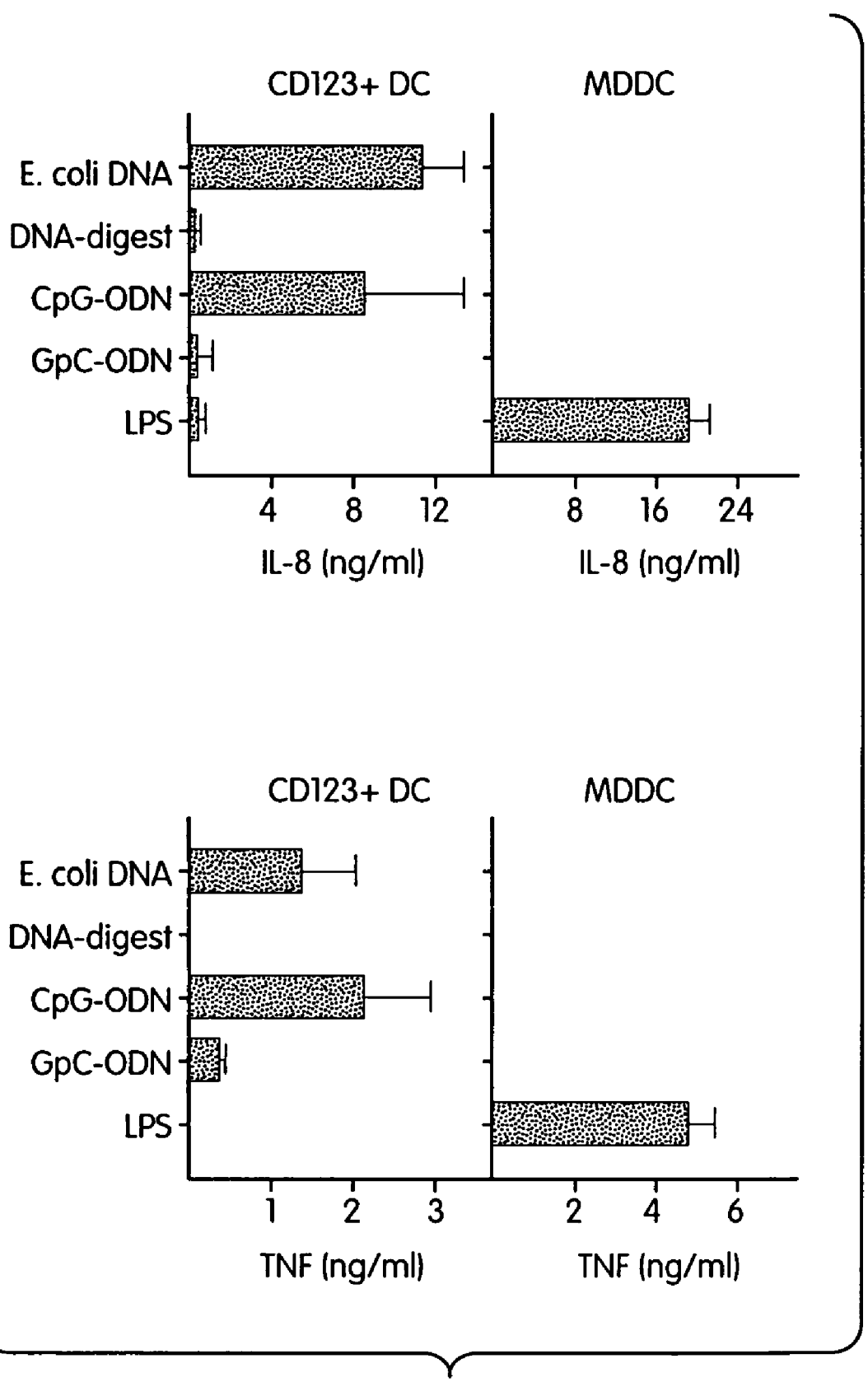
FIG. 8 is two paired bar graphs showing induction of (top) IL-8 and (bottom) TNF in plasmacytoid dendritic cells (CD123+ DC) and monocyte-derived dendritic cells (MDDC) in response to various stimuli, including *E. coli* DNA, DNase-digested *E. coli* DNA, CpG-ODN, GpC-ODN, and LPS.

Human dendritic cells (DC) have been claimed to be responsive to CpG-DNA. While analyzing human dendritic cell responses to CpG-DNA, we noted that plasmacytoid DC (CD123+DC) produced IFN-α, TNF, GM-CSF, and IL-8 upon exposure to CpG-DNA but not to LPS (FIG. 8 and unpublished data). The converse was true for stimulation of monocyte-derived dendritic cells (MDDC) (FIG. 8 and unpublished data). Purified CD123+DC or MDDC were stimulated with 50 μg/ml *E. coli* DNA, a comparable amount of DNase I-digested *E. coli* DNA, 2 μM CpG-ODN (2006), 2 μM GpC-ODN (2006-GC) or 100 ng/ml LPS (FIG. 8). IL-8 and TNF concentration was determined by enzyme-linked immunosorbent assay (ELISA). The CD123+DC response was DNA- and CpG-motif restricted. Monocyte-derived dendritic cells (MDDC) however demonstrated the converse response pattern, a response to LPS but not CpG-DNA. Due to this segregated response we analyzed TLR expression.

Figure 9:
FIG. 9 is a series of images of stained gels showing results of semi-quantitative RT-PCR comparing relative levels of human TLR9, TLR2, and TLR4 mRNA expression in human peripheral blood cells: MDDC (lane 1), purified CD14+ monocytes (lane 2), B cells (lane 3), CD123+ DC (lane 4), CD4+ T cells (lane 5), and CD8+ T cells (lane 6). GAPDH is a control for equalizing amounts of cDNA.

We have shown that CpG-DNA utilizes the Toll/IL-1R (TIR) signal transduction pathway implying the need for a TIR domain in the CpG-DNA signaling receptor. Häcker H et al., *J Exp Med* 192:595-600 (2000). It was further demonstrated that TLR9-deficient mice are non-responsive to CpG-ODN. Hemmi H et al., *Nature* 408:740-5. By semi-quantitative RT-PCR both B cells and CD123+ DC yielded positive signals for hTLR9 while MDDC, monocytes and T cells were weak to negative (FIG. 9). The cDNAs were prepared from monocyte-derived dendritic cells (MDDC), lane 1; purified CD14+ monocytes, lane 2; B cells, lane 3; CD123+ DC, lane 4; CD4+ T cells, lane 5; and CD8+ T cells, lane 6. cDNA amounts were normalized based on GAPDH amount determined by TAG-MAN PCR (Perkin-Elmer). RT-PCR was performed for 30 cycles on normalized cDNA diluted 1:5 for human TLR2, 4 and 9, while GAPDH was diluted 1:125. We also tested for hTLR2 and hTLR4 expression. MDDC and monocytes were positive while B cells, T cells and CD123+ DC were weak to negative (FIG. 9). Weak signals delivered by PCR could be explained by contaminating cells, however a strong positive signal implies expression. These data demonstrated a clear correlation between hTLR9 mRNA expression and B cell or CD123+DC responsiveness to CpG-DNA (FIGS. 7 and 8). A correlation could also be shown for hTLR2 and hTLR4 expression and MDDC responsiveness to LPS (FIG. 8). This data demonstrates that hTLR9 is a relevant receptor for CpG-DNA responses and that its expression determines responsiveness. If TLR9 expression could be modulated, agonism or antagonism of CpG-DNA responses could be achieved.

Example 5

Species Specificity of TLR9 Signaling

Figure 10A:
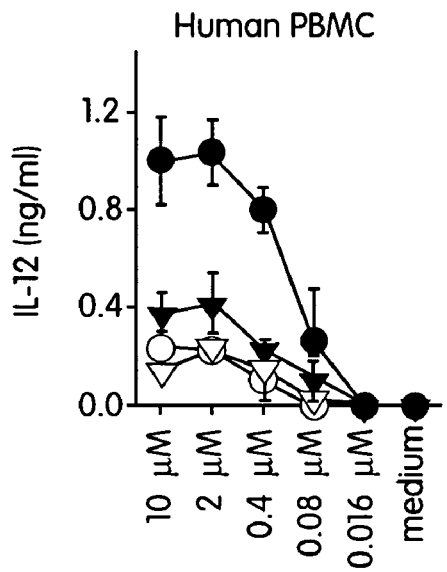
FIG. 10 is a pair of graphs showing amounts of IL-12 induced in (A) human peripheral blood mononuclear cells (PBMC) and (B) murine splenocytes in response to shown concentrations of various ODN, including ODN 2006 (filled circles; SEQ ID NO:112), 2006-GC (open circles; SEQ ID NO:118), 1668 (filled triangles; SEQ ID NO:84), and 1668-GC (open triangles; SEQ ID NO:85).
Figure 10B:
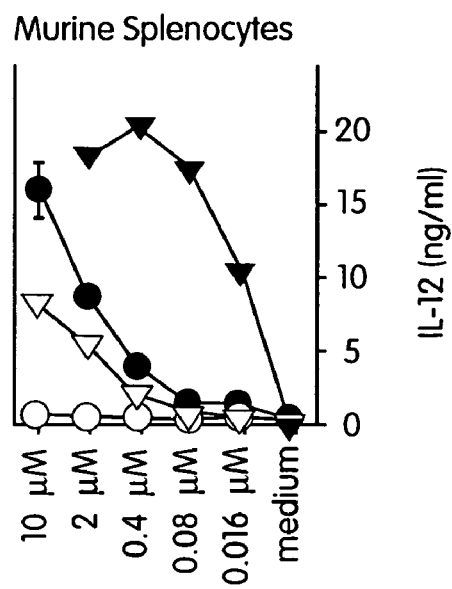

By iterative examination of the flanking sequences surrounding CG dinucleotides, CpG-motifs have been identified. Paradoxically, or by twist of nature, the human optimal CpG-motif, GTCGTT (SEQ ID NO:66), is different from the murine motif, GACGTT (SEQ ID NO:129). Human peripheral blood mononuclear cells (PBMC) (FIG. 10A) and murine splenocytes (FIG. 10B) were stimulated with ODN 2006 (filled circle, TCGTCGTTTTGTCGTTTTGTCGTT, SEQ ID NO:112), ODN 2006-GC (open circle), ODN 1668 (filled triangle, TCCATGACGTTCCTGATGCT, SEQ ID NO:84) or ODN 1668-GC (open triangle, TCCATGAGCTTCCTGATGCT, SEQ ID NO:85) at indicated concentrations and IL-12 production was monitored after 8 hours. FIG. 10A shows that titration of the optimal human ODN, 2006, on PBMC induces IL-12 production. The optimal murine sequence, 1668, however was much less effective in eliciting IL-12 from PBMC. The two control GpC-ODNs were essentially negative. The converse was true for murine splenocytes (FIG. 10B), in that the murine sequence induced optimal IL-12 while the human sequence was much less effective. It should also be noted that the $K_{ac}$ (concentration of half-maximal activation) of murine splenocytes for 1668 was greater than human PBMC for 2006 (compare FIG. 10A to FIG. 10B).

Figure 11:
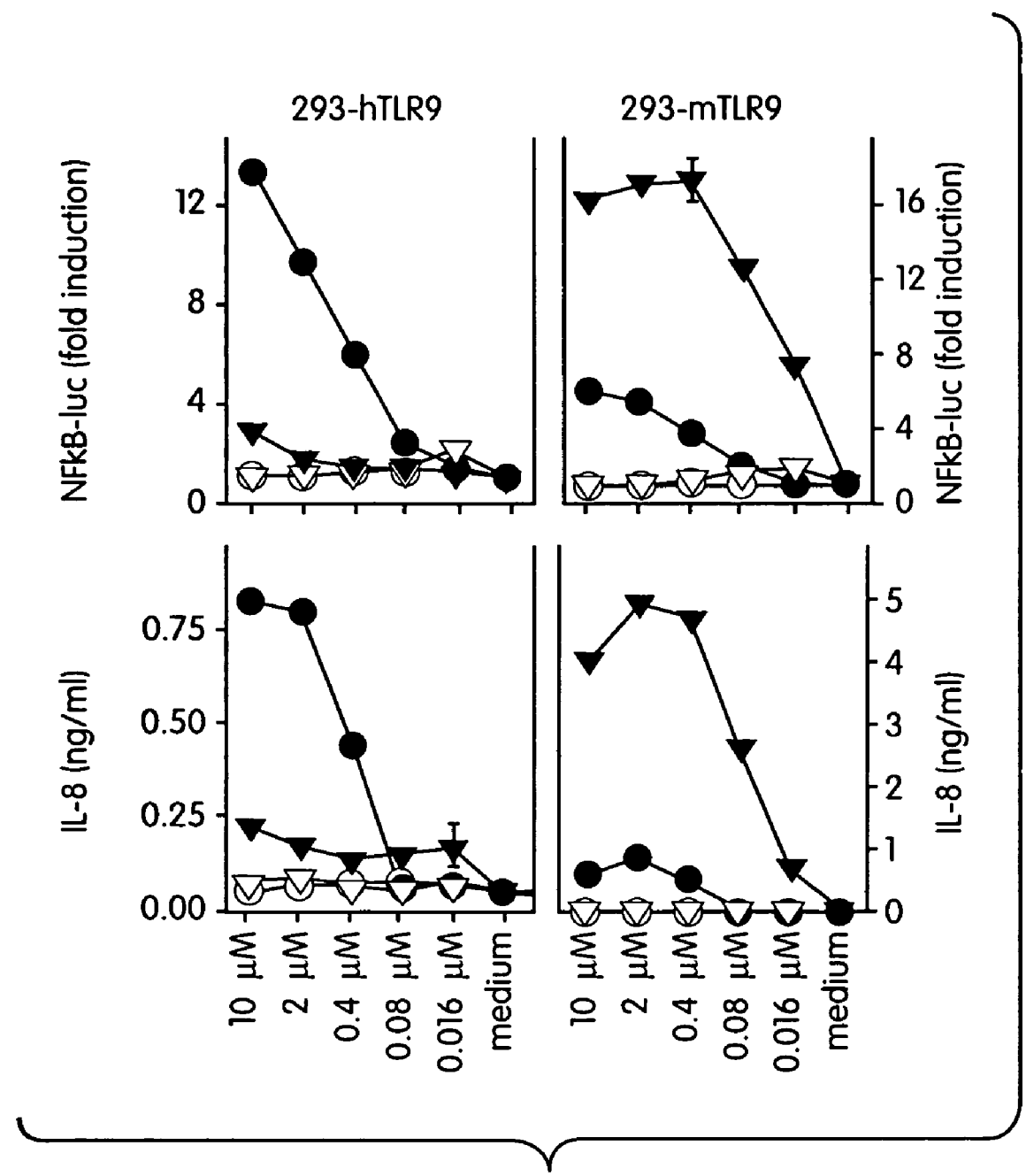
FIG. 11 is a quartet of graphs depicting responsiveness of 293 cells transfected with hTLR9 (left panels) or mTLR9 (right panels) upon stimulation with shown concentrations of various ODN, including ODN 2006 (filled circles; SEQ ID NO:112), 2006-GC (open circles; SEQ ID NO:118), 1668 (filled triangles; SEQ ID NO:84), and 1668-GC (open triangles; SEQ ID NO:85). Responses are shown in terms of induction of NF-κB-luc (upper panels) and IL-8 (lower panels).

Because stable TLR9 transfectants mirrored primary cell responsiveness to CpG-DNA (FIGS. 4 and 5), it was hypothesized that stable transfectants could potentially discern species-specific CpG-motifs through TLR9 receptors. Therefore 293-hTLR9-luc (expressing human TLR9 and 6-fold NF-κB-luc reporter), 293-mTLR9-luc (expressing murine TLR9 and 6-fold NF-κB-luc reporter), 293-hTLR9 (expressing human TLR9) and 293-mTLR9 (expressing murine TLR9) clones were tested for CpG-DNA motif responsiveness. FIG. 11 shows titration curves for 2006 or 1668 and their controls versus either hTLR9 or mTLR9 cells. Depicted are both NF-κB-driven luciferase and IL-8 production as readout. In both 293 hTLR9-luc and 293-mTLR9-luc cells stimulation with CpG-DNA resulted in NF-κB activation, as determined by measurement of the induced expression of firefly luciferase under the control of a minimal promotor containing six tandem NF-κB-binding sites. After lysis of the cells luciferase can be detected photometrically based on an enzymatic reaction by luciferase which creates photons. IL-8 production was monitored using enzyme-linked immunosorbent assay (ELISA). FIG. 11 depicts clones stimulated with ODN 2006 (filled circle), ODN 2006-GC (open circle), ODN 1668 (filled triangle) or ODN 1668-GC (open triangle) at indicated concentrations and NF-κB activation or IL-8 production were measured after 10 and 48 hours, respectively. Results shown in FIG. 11 are representative of three independent experiments. Strikingly, CpG-motif sequence specificity was conferred in a species-specific manner by TLR9. Additionally, the half-maximal concentration for either 2006 or 1668 appears nearly the same as those determined on primary cells (compare FIG. 10 and FIG. 11). These data demonstrate that TLR9 is the CpG-DNA receptor and that exquisite specificity to CpG-DNA sequence is conferred by TLR9.

Example 6

Figure 12:
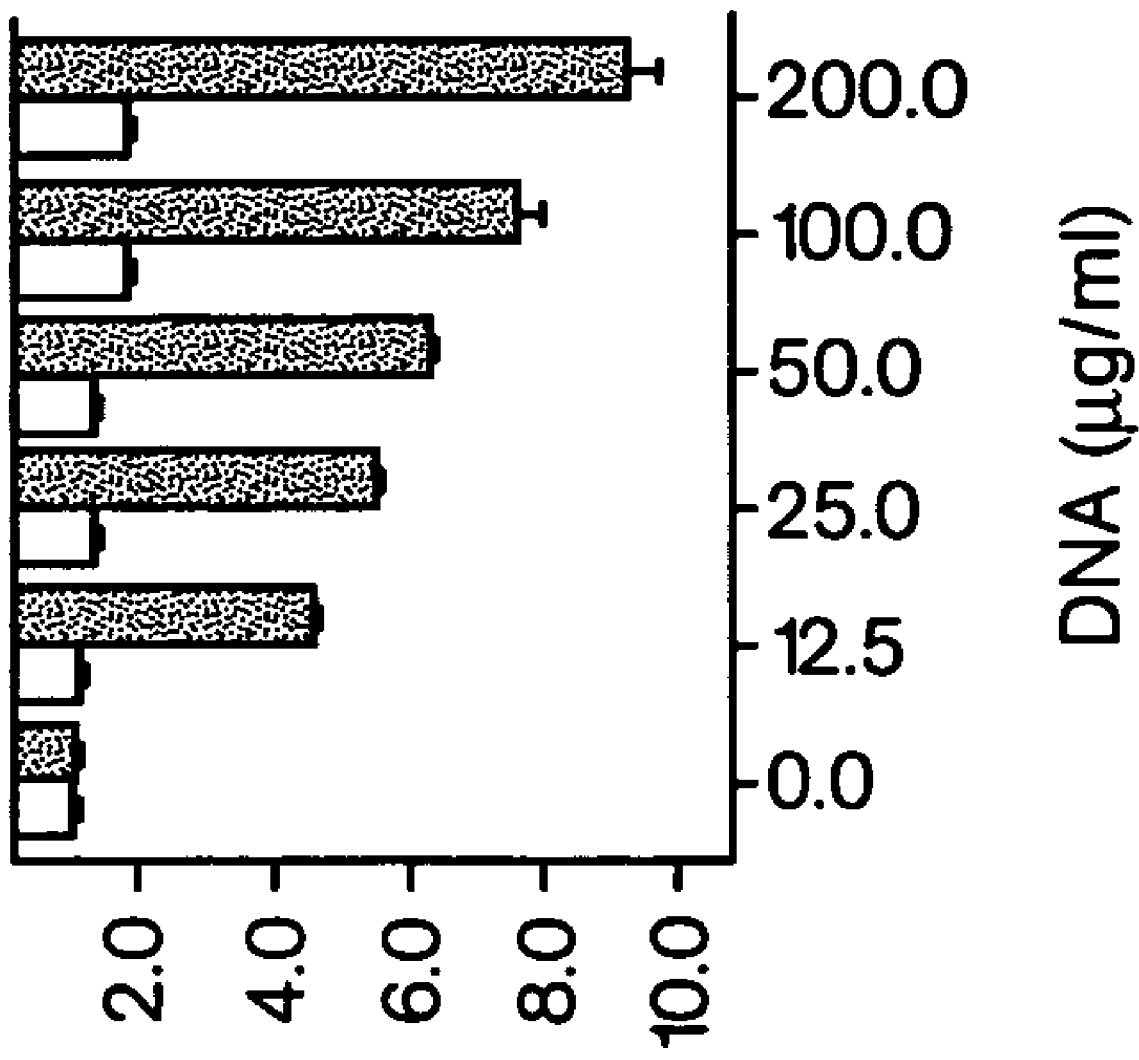
FIG. 12 is a bar graph depicting the dose-response of 293-hTLR9 cells to *E. coli* DNA (black bars) and to DNase-digested *E. coli* DNA (gray bars).

Use of Stable TLR9 Clones to Test Responsiveness to Substances Other than Phosphorothioate ODN As described in the foregoing Examples, the stable TLR9 clones were initially screened for fidelity of phosphorothioate CpG-ODN reactivity. The 293-hTLR9 cells demonstrated reactivity to CpG-DNA and not LPS in a CpG-motif dependent manner (FIGS. 4 and 5). In the present example the stable TLR9 transfectants were tested for responsiveness to additional DNAs. NF-κB activation was monitored after stimulation with *E. coli* DNA (black bars) or *E. coli* DNA digested with DNAse I (gray bars) in 293-hTLR9-luc cells. FIG. 12 demonstrates an *E. coli* DNA dose-dependent induction of NF-κB-driven luciferase expression to a level comparable to phosphorothioate CpG-ODN (FIG. 11). Activity was destroyed by DNase I digestion, indicating specificity of response to DNA and not contaminant bacterial products. The stable TLR9 transfectants can be used to screen the activity of DNAs from various species or vector DNAs intended for immune system stimulation. In particular, TLR9 transfectants can be used to screen and compare the immunostimulatory activity of DNAs from various species of pathogens, DNA constructs, DNAs intended for use as vaccines, gene replacement therapeutics, and nucleic acid vectors.

Figure 13A:
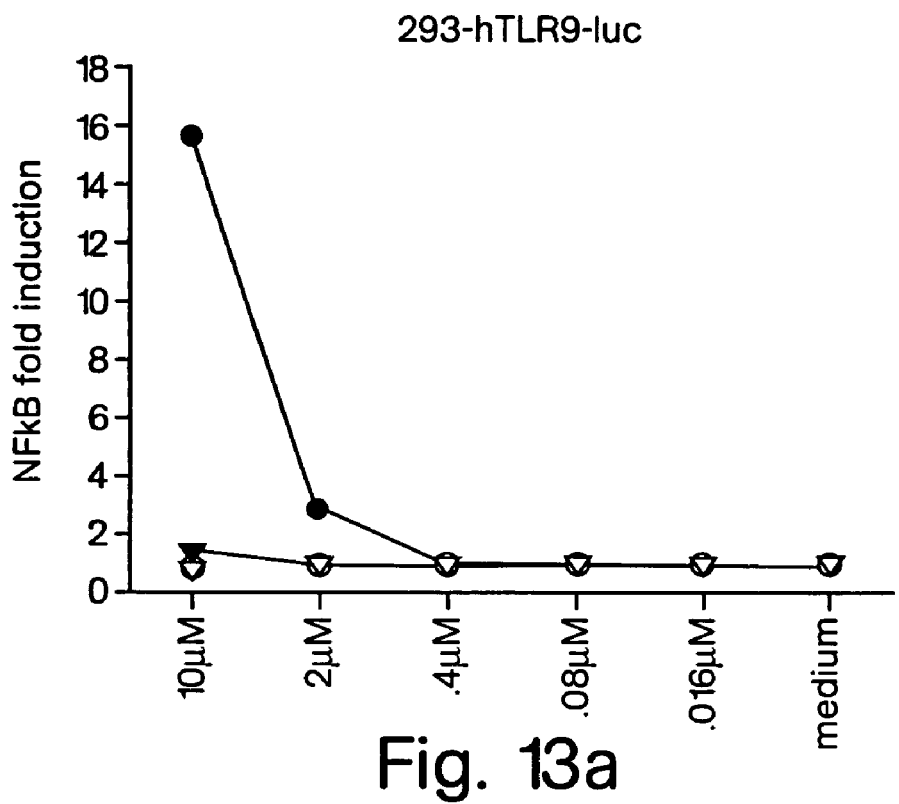
FIG. 13 is a pair of graphs showing the responsiveness of (A) 293-hTLR9 and (B) 293-mTLR9 cells to shown concentrations of phosphodiester versions of ODN 2006 (filled circles; SEQ ID NO:112), 2006-GC (open circles; SEQ ID NO:118), 1668 (filled triangles; SEQ ID NO:84), and 1668-GC (open triangles; SEQ ID NO:85).
Figure 13B:
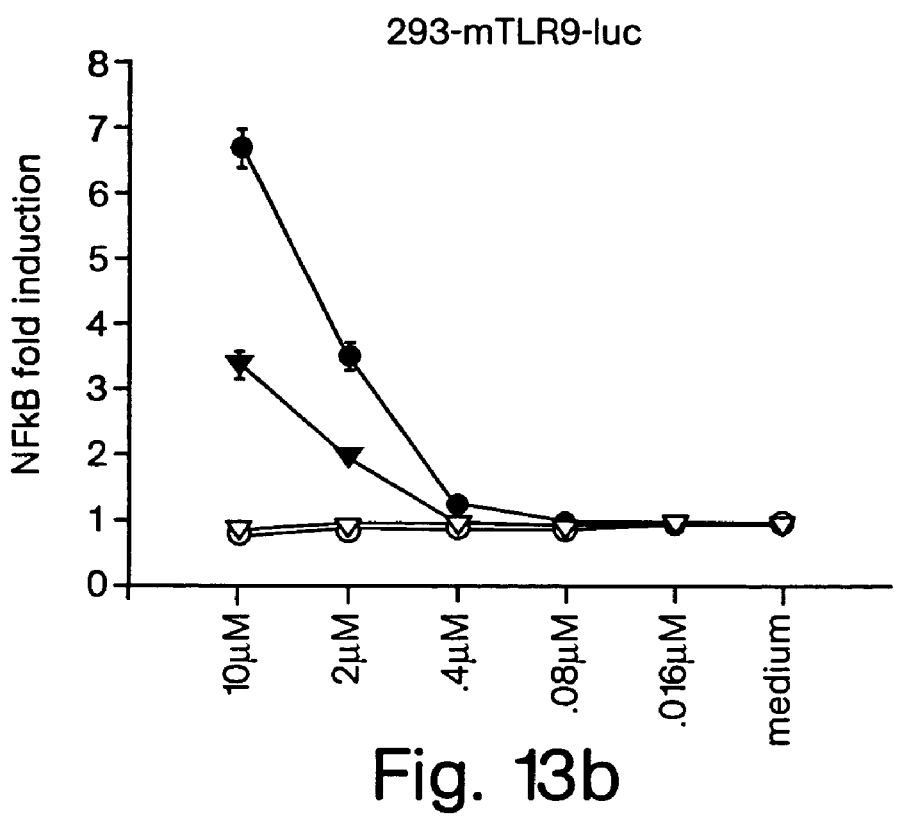

293-hTLR9-luc cells also were stimulated with the phosphodiester variants of ODN 2006 (filled circle), ODN 2006-GC (open circle), ODN 1668 (filled triangle) or ODN 1668-GC (open triangle) at indicated concentrations, and NF-κB activation was monitored after 12 hours (FIG. 13A). Likewise, 293-mTLR9-luc cells were stimulated with the phosphodiester variants of ODN 2006 (filled circle), ODN 2006-GC (open circle), ODN 1668 (filled triangle) or ODN 1668-GC (open triangle) at indicated concentrations, and NF-κB activation was monitored after 12 hours (FIG. 13B). These assays show that the stable TLR9 transfectants responded to DNAs other than phosphorothioate-modified ODN. These data demonstrate the utility of stable TLR transfectants for screening for agonists of the TLR9 receptor.

Example 7

TLR9 Determines CpG-ODN Activity

Figure 14:
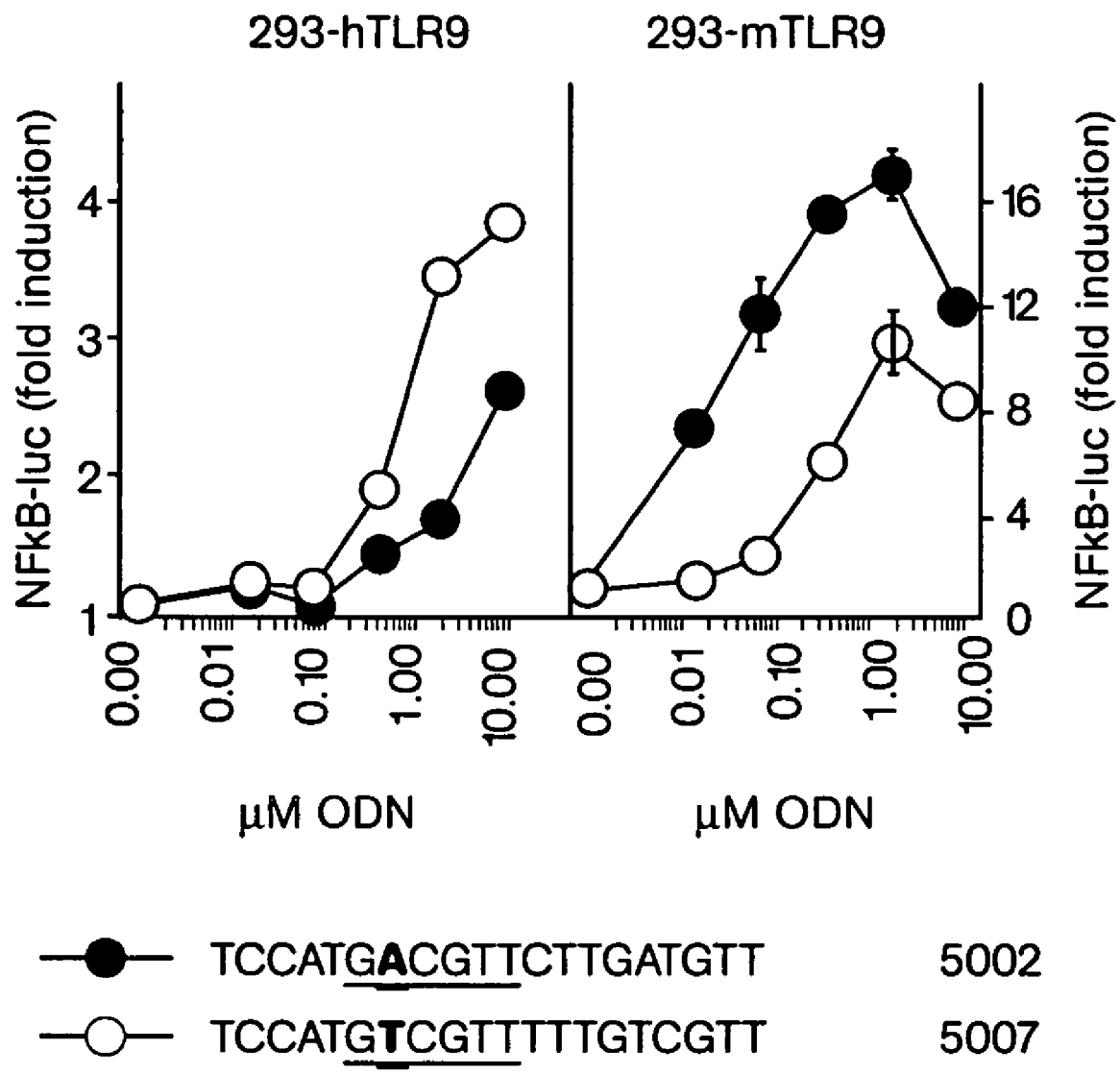
FIG. 14 is a pair of graphs showing the responsiveness of 293-hTLR9 and 293-mTLR9 cells to shown concentrations of ODN 5002 (filled circles; SEQ ID NO:132) and ODN 5007 (open circles; SEQ ID NO:98).

Although 2006 and 1668 are discussed in terms of CpG-motif differences, they are very different in several aspects (see Table 5 for comparison). The lengths are different, 24 versus 20 nucleotides, and 2006 has four CG dinucleotides compared to one in 1668. Additional differences are the CG position relative to the 5' and 3' ends and also 5' sequence differences. In order to determine if motif specificity is a quality of the motif and not the global sequence environment, for this experiment several sequences were produced holding these variables constant. As a starting point, the 1668 sequence was modified by converting the central C to T and the distal TG to CG, thereby creating a second CG in the resulting sequence 5000 (SEQ ID NO:130, Table 5). Then point nucleotide changes were made, progressing toward a 2006-like sequence, 5007 (SEQ ID NO:98). The ODN 5002 (SEQ ID NO:132) is most like 1668 with the exception that C's at positions 12 and 19 have been converted to T's. The last 16 nucleotides of ODN 5007 are the same as the last 15 nucleotides of 2006 with the exception of an additional T. The ODN concentration of half-maximal activation ($K_{ac}$) was determined by producing ODN titration curves using either 293-hTLR9-luc or 293-mTLR9-luc cells and NF-κB-driven luciferase expression as a readout. Example curves are given in FIG. 14. Stable transfectants 293-hTLR9-luc and 293-mTLR9-luc were stimulated with ODN 5002 (filled circle) or ODN 5007 (open circle) at indicated concentrations and NF-κB activation was monitored after 12 hours. Results shown in FIG. 14 are representative of three independent experiments. Values for $K_{ac}$ for multiple ODN are given in Table 5. Similar results were obtained for those ODN tested with 293-hTLR9 and 293-mTLR9 cells utilizing IL-8 as readout.

TABLE 5

CpG-DNA sequence specificity of human and murine TLR9 signaling activity

| CpG DNA | Sequence | 293-hTLR9 $K_{ac}$ (nM) | 293-mTLR9 $K_{ac}$ (nM) | SEQ ID NO: |
|---|---|---|---|---|
| 1668 | TCCAT<u>GACGTT</u>CCTGATGCT | >10,000 | 70 | 84 |
| 1668-GC | TCCATGAGCTTCCTGATGCT | >10,000 | >10,000 | 85 |
| 2006 | TC<u>GTCGTTT</u>T<u>GTCGTTT</u>T<u>GTCGTT</u> | 400 | >10,000 | 112 |
| 2006-GC | TGCTGCTTTTGTGCTTTTGTGCTT | >10,000 | >10,000 | 118 |
| 5000 | TCCAT<u>GACGTT</u>CTTGACGCT | 10,000 | 82 | 130 |
| 5001 | TCCATGACGTTCTTGACGTT | 7,000 | 55 | 131 |
| 5002 | TCCATGACGTTCTTGATGTT | 7,000 | 30 | 132 |
| 5003 | TCCATGACGTTTTTGATGTT | 10,000 | 30 | 133 |
| 5004 | TCCATGTCGTTCTTGATGTT | 5,000 | 400 | 134 |
| 5005 | TCCATGTCGTTTTTGATGTT | 3,000 | 2,000 | 135 |
| 5006 | TCCATGTCGTTTTTGTTGTT | 3,000 | 650 | 136 |
| 5007 | TCCAT<u>GTCGTTTT</u><u>GTCGTT</u> | 700 | 1,000 | 98 |
| 5002 | TCCAT<u>GACGTT</u>CTTGATGTT | ND | 30 | 132 |
| 5008 | TCCATGACGTTATTGATGTT | ND | 40 | 137 |
| 5009 | TCCATGACGTCCTTGATGTT | ND | >10,000 | 138 |
| 5010 | TCCATGACGTCATTGATGTT | ND | >10,000 | 139 |

In previous unpublished work by the inventors, it had been noted that a CA substitution converting the mouse CpG-motif from GACGT<u>TC</u> to GACGT<u>CA</u> was deleterious. To extend our examination of the motif, three more ODN were created to dissect this effect (5008-5010, SEQ ID NOs:137-139, Table 5).

The activity displayed by the 293-hTLR9-luc clone increased with progressive nucleotide substitutions converting the mouse sequence toward the human sequence (Table 5, sequences 5000-5007). The converse was true for the 293-mTLR9-luc clone, which showed highest activity for the mouse sequences. The originally hypothesized CpG-motif was purine-purine-CG-pyrimidine-pyrimidine. Most notable to motif definition as determined by TLR9 genetic complementation was the non-conservative pyrimidine for purine change A to T immediately 5' of the CG (Table 5). These changes improved 293-hTLR9-luc responsiveness but diminished 293-mTLR9-luc responsiveness. These results support the notion that the preferred mouse motif contains ACG while the preferred human sequence contains TCG. The conservative pyrimidine for pyrimidine change T to C in the mouse motif, ACGTT versus ACGTC (5002 versus 5009), completely destroyed 293-mTLR9 responsiveness. Although not a complete iterative analysis of the CpG-motif, the data refine our understanding of the motif. More importantly these data strongly support direct CpG-motif engagement by TLR9.

Example 8

Antagonist Definition

Figure 15:
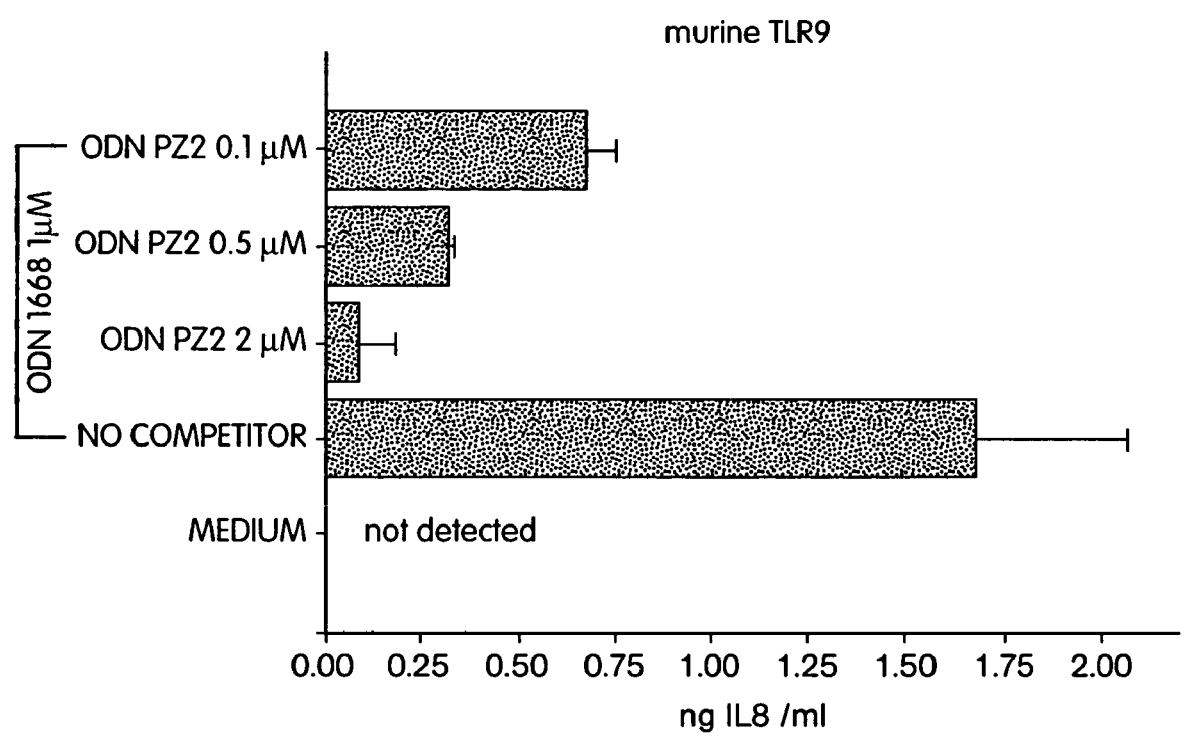
FIG. 15 is a bar graph showing the response of 293 cells transfected with mTLR9 to CpG-ODN 1668 (SEQ ID NO:84) is inhibited in a dose-dependent manner by co-exposure to non-CpG-ODN PZ2 (SEQ ID NO:43).

It has been demonstrated that DNA uptake and endosomal maturation are required for signal initiation by CpG-DNA. It has been hypothesized that in order for DNA to enter the endosomal/lysosomal compartment a non-CpG dependent uptake receptor may be required. 293 cells were transiently transfected with mTLR9 treated with either medium only or 1.0 μM CpG-ODN 1668 (FIG. 15). Additionally the 1668-treated TLR9 transfectants were simultaneously exposed to various doses of a non-CpG ODN (PZ2; 5'-CTC-CTAGTGGGGGTGTCCTAT-3', SEQ ID NO:43). IL-8 production was monitored after 48 h by ELISA. FIG. 15 shows that PZ2, in a dose-dependent manner, was able to antagonize the activation of TLR9-transfected cells stimulated with a CpG ODN.

Figure 16:
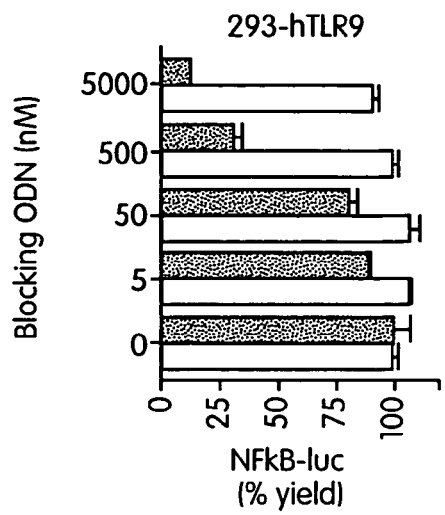
FIG. 16 is a bar graph showing the response of 293-hTLR9 cells to CpG-ODN (black bars) or to TNF (gray bars) in the presence of shown amounts of blocking non-CpG-ODN.

FIG. 16 demonstrates that the stable TLR9 transfectants, 293-hTLR9-luc cells, are sensitive to non-CpG-ODN blockade. 293-hTLR9-luc cells were incubated with CpG-ODN (0.5 μM) (black bars) or TNF-α (10 ng/ml) (gray bars) and increasing concentrations of a blocking ODN (5'-HHHHH-HHHHHHHHHWGGGGG-3', SEQ ID NO:140; H=A, T, C; W=A, T) as indicated. NF-κB activation was monitored after 12 hours and is presented as percent yields. Thus both mTLR9 and hTLR9 activity can be blocked by non-stimulatory ODN. The blockade is specific to blocking ODN since the TNF-driven NF-κB signal was not diminished. Antagonism of CpG-DNA responses could thus be defined in stable TLR9 cells and therefore high throughput screening can be done for TLR9 antagonist.

Figure 17:
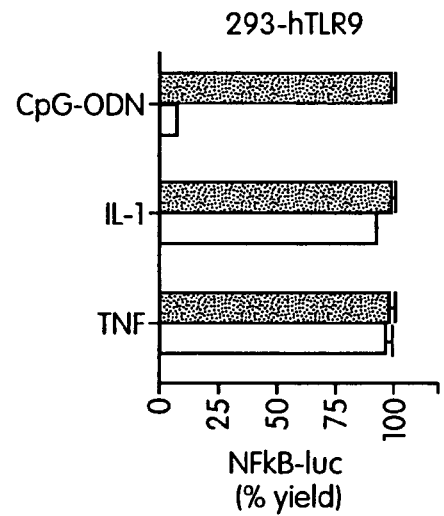
FIG. 17 is a bar graph showing blockade of response of 293-hTLR9 cells to CpG-ODN, but not to IL-1 or TNF, in the presence of Bafilomycin A (gray bars). Control treatment with dimethyl sulfoxide (DMSO) is shown in black bars.

Bafilomycin A poisons the proton pump needed for H⁺ transport into endosomes, which is required for endosomal maturation. FIG. 17 shows that blockade of endosomal maturation in 293-hTLR9-luc cells fully blocks CpG-ODN induction of NF-κB. 293-hTLR9-luc cells were preincubated with 10 nM Bafilomycin A (gray bars) or dimethylsulfoxide (DMSO) control (black bars) for 30 min and stimulated with CpG-ODN (2006, 0.5 μM), IL-1 (10 ng/ml) or TNF-α (10 ng/ml) as indicated. NF-κB activation was monitored after 12 hours and is presented as percent yields. The blockade was specific to CpG-DNA generated signal because both IL-1 and TNF induction of NF-κB was unaffected. These data demonstrate that 293 cells stably complemented with hTLR9 behave in a manner similar to primary CpG-DNA responsive cells, in that cellular uptake and endosomal maturation are required for induction of signal by CpG-DNA. Thus the stable transfectants can be used as indicator for TLR9 drug antagonist.

Figure 18:
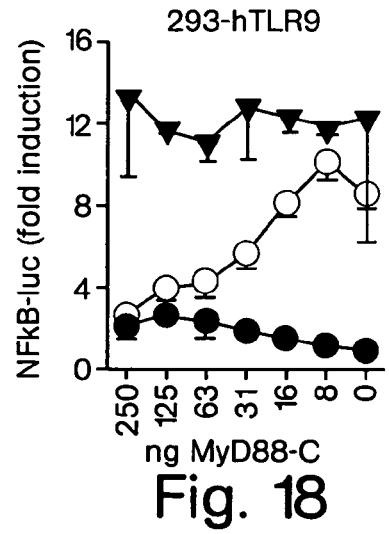
FIG. 18 is a graph showing the effect of varying concentrations of dominant negative human MyD88 on the induction of NF-κB in 293-hTLR9 cells stimulated with CpG-ODN (open circles), TNF-α (filled circles), or control (filled triangles).

CpG-DNA signaling appears to occur via a Toll/IL-1R-like pathway. It was shown in the mouse that CpG-DNA signaling is dependent on MyD88, IRAK and TRAF6. Häcker H et al., *J Exp Med* 192:595-600 (2000). Hemmi et al. demonstrated that mTLR9-deficient mice lack activation of IRAK upon CpG-ODN stimulation. Hemmi H et al., *Nature* 408:740-5 (2000). FIG. 18 shows that CpG-DNA signaling via human TLR9 was MyD88 dependent. hTLR9 (293-hTLR9) was co-transfected with a six-times NF-κB luciferase reporter plasmid and increasing concentrations of the dominant negative human MyD88 expression vector. Cells were not stimulated (filled circles), stimulated with CpG-ODN (2006, 2 µM) (open circles) or TNF-α (10 ng/ml) (filled triangles) and NF-κB activation was monitored after 12 hours. Results are representative of at least two independent experiments. FIG. 18 demonstrates that dominant negative MyD88 blocks NF-κB induction in 293-hTLR9 cells following CpG-DNA stimulation. The blockade of MyD88 did not affect NF-κB induction via TNF induced signal transduction. In general these data confirm the central role of MyD88 to TLR signaling and specifically the role of MyD88 in CpG-DNA initiation of signal. Thus human cells transfected with TLR9 can be used as indicators to find molecules to antagonize CpG-DNA via genetic mechanisms.

Example 9

Antibody Production

Peptides for human and mouse TLR9 were designed for coupling to a carrier protein and injected into rabbits to obtain anti-peptide polyclonal antisera. Mouse peptide 1 (mousepep1, see Table 4) can be found in EST aa197442 and peptide 2 (mousepep2, see Table 4) in EST aa273731 and ai463056. Human peptide 1 (humanpep1, see Table 4) and peptide 2 (humanpep2, see Table 4) were taken from the published human sequence.

Figure 19:
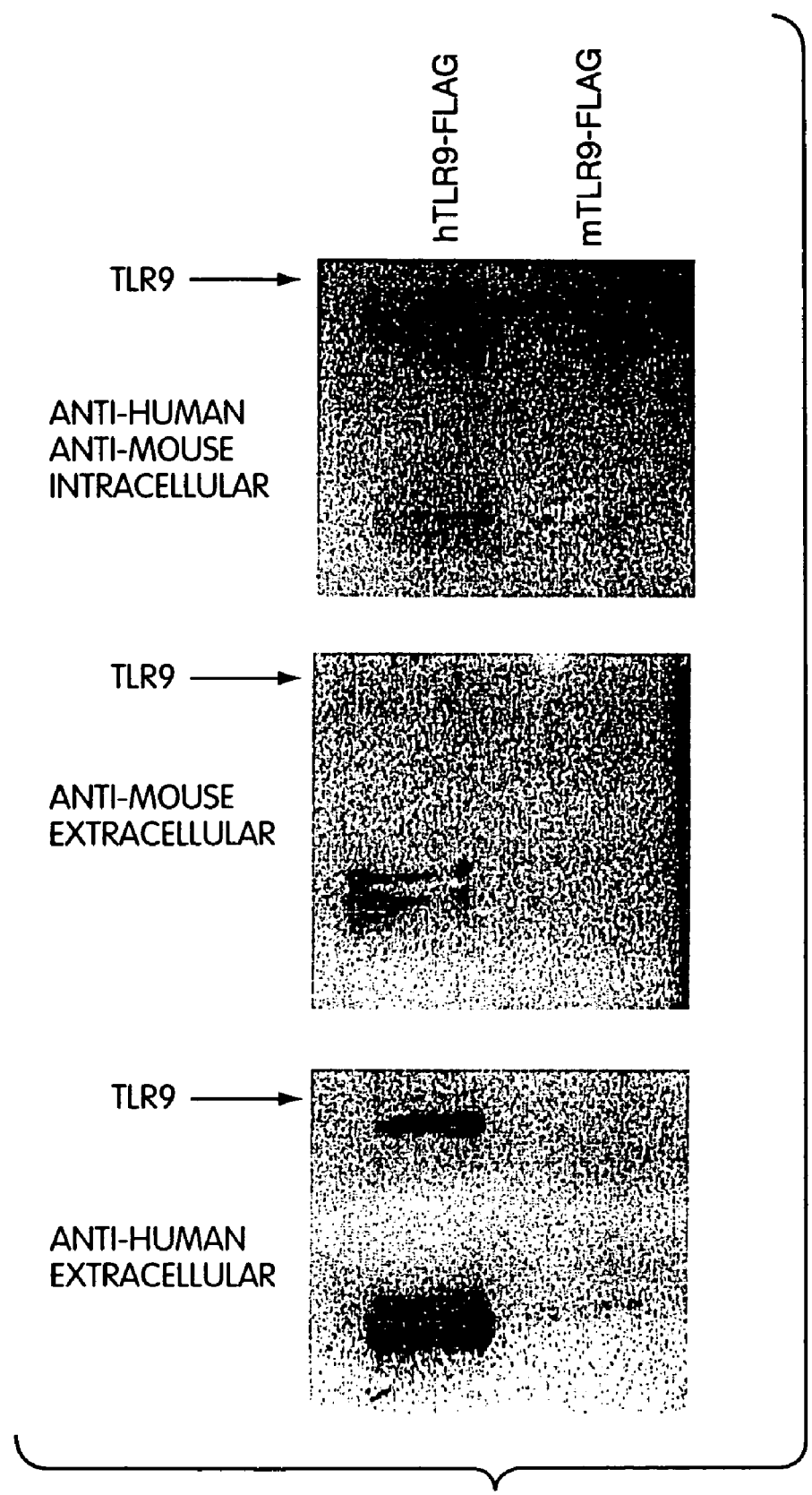
FIG. 19 is a series of three Western blot images showing the response of various polyclonal antibodies to purified hTLR9-FLAG and mTLR9-FLAG: upper panel, anti-human and anti-mouse intracellular; middle, anti-mouse extracellular; and lower, anti-human extracellular. Arrows indicate position of TLR9 in each blot.

Three rabbit antisera were generated by this method: anti-mousepep1, specific for the extracellular domain of murine TLR9; anti-humanpep1, specific for the extracellular domain of hTLR9; and antisera against a combination of mousepep2 and humanpep2, specific for the cytoplasmic domain of both murine and human TLR9. Immunoprecipitates with anti-FLAG antibody were electrophoresed by PAGE and, using standard Western blotting techniques, transferred to membrane and probed with the various antisera. FIG. 19 shows the response to hTLR9-FLAG and mTLR9-FLAG. The TLR9 in these blots are indicated with arrows, while the lower molecular weight bands represent anti-FLAG antibody.

Example 10

Mutation Adjacent to the CXXC-Domain
(hTLR9-CXXCm, mTLR9-CXXCh)

The CXXC motif resembles a zinc finger motif and is found in DNA-binding proteins and in certain specific CpG binding proteins, e.g. methyl-CpG binding protein-1 (MBD-1). Fujita N et al., *Mol Cell Biol* 20:5107-5118 (2000). Human and murine TLR9 contain two CXXC motifs. The CXXC domain is highly conserved between human and murine TLR9 but followed by 6 amino acids (aa) which differ quite substantially in polarity and size. By the use of a site-specific mutagenesis kit (Stratagene, La Jolla, Calif., USA) these six amino acid residues (human: PRHFPQ 269-274); mouse: GQKSLH 269-274) were interchanged between human and murine TLR9. These mutations were generated by the use of the primers 5'-CTGCATGGAGTGCGGCCAAAAGTC-CCTCCACCTACATCCCGATAC-3' (SEQ ID NO:141) and 5'-GTATCGGGATGTAGGTGGAGG-GACTTTTGGCCGCACTCCATGCAG-3' (SEQ ID NO:142) for human TLR9 and the primers 5'-CTGTATA-GAATGTCCTCGTCACTTCCCCCAGCTG-CACCCTGAGAC-3' (SEQ ID NO:143) and 5'-GTCT-CAGGGTGCAGCTGGGGGAAGTGACGAGGACATTC TATACAG-3' (SEQ ID NO:144) for murine TLR9 according to the manufacturer's protocol.

| | | |
|---|---|---|
| CXXC motif: | CXXCXXXXXXCXXC | SEQ ID NO:145 |
| Wildtype hTLR9: | CRRCDHAPNPCMECPRHFPQ | SEQ ID NO:146 aa 255-274 |
| hTLR9-CXXCm: | CRRCDHAPNPCMEC<u>GQKSLH</u> | SEQ ID NO:147 aa 255-274 |
| Wildtype mTLR9: | CRRCDHAPNPCMICGQKSLH | SEQ ID NO:148 aa 255-274 |
| mTLR9-CXXCh: | CRRCDHAPNPCMIC<u>PRHFPQ</u> | SEQ ID NO:149 aa 255-274 |

Figure 20:
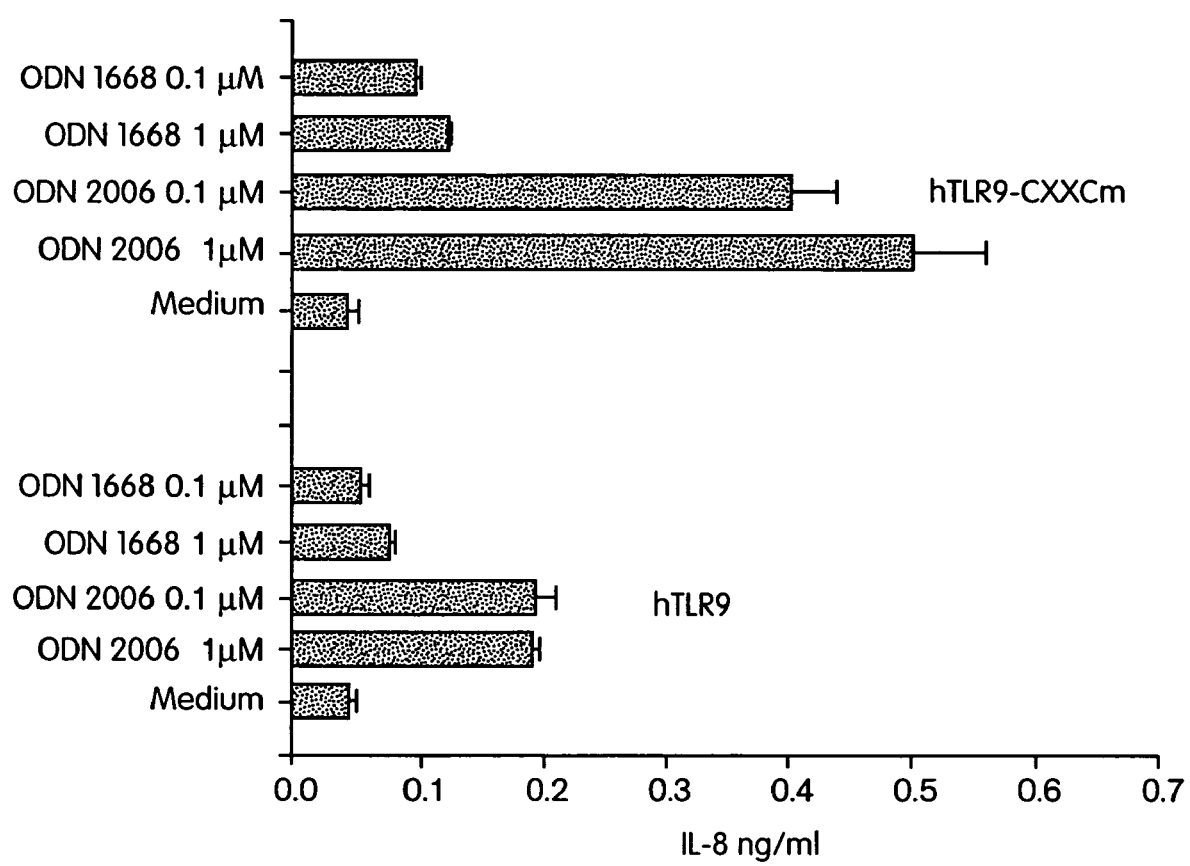
FIG. 20 is a bar graph depicting the responsiveness of native form hTLR9 and hTLR9 variant form hTLR9-CXXCm to various stimuli at different concentrations. ODN are as follows: ODN 1668 (SEQ ID NO:84) and ODN 2006 (SEQ ID NO:112).
Figure 21:
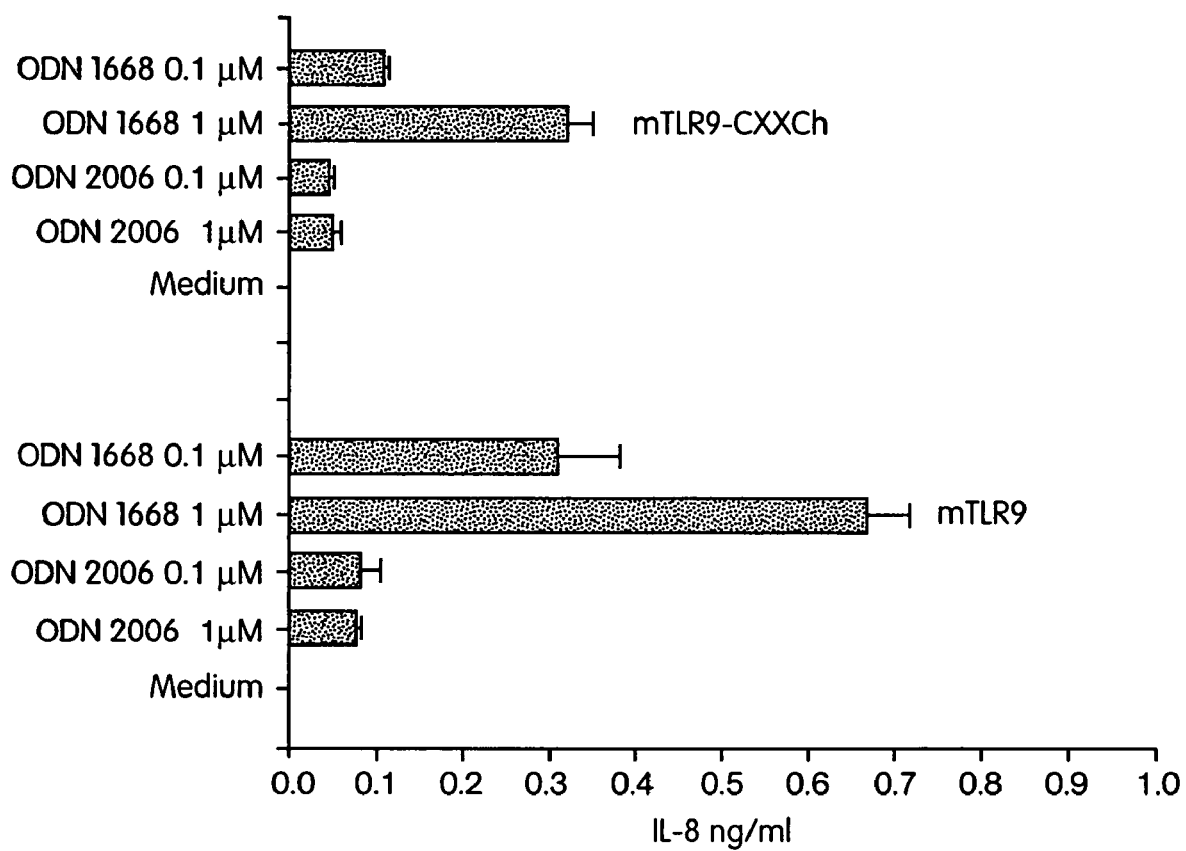
FIG. 21 is a bar graph depicting the responsiveness of native form mTLR9 and mTLR9 variant form mTLR9-

For the stimulation of the hTLR9 variant hTLR9-CXXCm, 293 cells were transiently transfected with hTLR9 or hTLR9-CXXCm and stimulated after 16 hours with ODN 2006 and ODN 1668 at concentrations indicated (FIG. 20). 48 hours after stimulation supernatant was harvested and IL-8 production was measured by ELISA. The data show that hTLR9 can be improved by converting the human CXXC domain to the murine CXXC domain. For the stimulation of the mTLR9 variant mTLR9-CXXCh, 293 cells were transiently transfected with mTLR9 or mTLR9-CXXCh and stimulated after 16 hours with ODN 2006 and ODN 1668 at concentrations indicated (FIG. 21). 48 hours after stimulation supernatant was harvested and IL-8 production was measured by ELISA. It appears that the human CXXC domain may diminish mTLR9-CXXCh activity relative to the wild type mTLR9.

Example 11

Mutation in the MBD Motif (hTLR9-MBDmut, mTLR9-MBDmut)

The MBD motif is a domain recently described for CpG binding in the protein MBD-1. Fujita N et al., *Mol Cell Biol* 20:5107-5118 (2000); Ohki I et al., *EMBO J.* 18:6653-6661 (1999). Human and murine TLR9 contain this motif at position 524-554 and 525-555, respectively.

| | | |
|---|---|---|
| MBD-1 | R-XXXXXXX-R-X-D-X-Y-XXXXXXXXX-R-S-XXXXXX-Y | SEQ ID NO:125 |
| hTLR9 | Q-XXXXXXX-K-X-D-X-Y-XXXXXXXXX-R-L-XXXXXX-Y | SEQ ID NO:126 |
| mTLR9 | Q-XXXXXXX-K-X-D-X-Y-XXXXXXXXX-Q-L-XXXXXX-Y | SEQ ID NO:127 |

The core of this domain consists of D-L-Y in human TLR9 (aa 534-536) and mouse TLR9 (aa 535-537). Through site-specific mutagenesis D534 and Y536 in human TLR9, and D535 and Y537 in murine TLR9, were mutated to alanines creating the sequence A-L-A for human (aa 534-536) and murine TLR9 (aa 535-537). These mutations were generated by the use of the primers 5'-CACAATAAGCTGGC-CCTCGCCCACGAGCACTC-3' (SEQ ID NO:150) and 5'-GAGTGCTCGTGGGCGAGGGCCAGCTTATTGTG-3' (SEQ ID NO:151) for human TLR9 and the primers 5'-CAT-AACAAACTGGCCTTGGCCCACTGGAAATC-3' (SEQ ID NO:152) and 5'-GATTTCCAGTGGGCCAAGGC-CAGTTTGTTATG-3' (SEQ ID NO:153) for murine TLR9 according to the manufacturer's protocol.

For the stimulation of mTLR9 variant, mTLR9-MBDmut, 293 cells were transiently transfected with mTLR9 or mTLR9-MBD-mut and stimulated after 16 hours with ODN 2006 and ODN 1668 at concentrations indicated (FIG. 22). 48 hours after stimulation supernatant was harvested and IL-8 production was measured by ELISA. For the stimulation of hTLR9 variant, hTLR9-MBDmut, 293 cells were transiently transfected with hTLR9 or hTLR9-MBD-mut and stimulated after 16 hours with ODN 2006 and ODN 1668 at concentrations indicated (FIG. 23). 48 hours after stimulation supernatant was harvested and IL-8 production was measured by ELISA. The disruption of the putative CpG binding domain DXY in TLR9 destroyed receptor activity. These data demonstrate that the MBD motif is most likely involved in CpG-DNA binding and can be thus be manipulated to better understand CpG-DNA binding and efficacy.

Example 12

Proline to Histidine Mutation in the TIR-Domain (hTLR9-PHmut, mTLR9-PHmut)

Toll-like receptors have a cytoplasmic Toll/IL-1 receptor (TIR) homology domain which initiates signaling after binding of the adapter molecule MyD88. Medzhitov R et al., *Mol Cell* 2:253-8 (1998); Kopp E B et al., *Curr Opin Immunol* 11:15-8 (1999). Reports by others have shown that a single-point mutation in the signaling TIR-domain in murine TLR4 (Pro712 to His) or human TLR2 (Pro681 to His) abolishes host immune response to lipopolysaccharide or gram-positive bacteria, respectively. Poltorak A et al., *Science* 282:2085-8 (1998); Underhill D M et al., *Nature* 401:811-5 (1999). Through site-specific mutagenesis the equivalent Proline at position 915 of human and murine TLR9 were mutated to Histidine (Pro915 to His). These mutations were generated by the use of the primers 5'-GCGACTGGCTG-CATGGCAAAACCCTCTTTG-3' (SEQ ID NO:154) and 5'-CAAAGAGGGTTTTGCCATGCAGCCAGTCGC-3' (SEQ ID NO:155) for human TLR9 and the primers 5'-CGAGATTGGCTGCATGGCCAGACGCTCTTC-3' (SEQ ID NO:156) and 5'-GAAGAGCGTCTGGCCATG-CAGCCAATCTCG-3' (SEQ ID NO:157) for murine TLR9 according to the manufacturer's protocol.

For the stimulation of mTLR9 variant, mTLR9-PHmut, 293 cells were transiently transfected with mTLR9 or mTLR9-PHmut and stimulated after 16 hours with ODN 2006 and ODN 1668 at concentrations indicated (FIG. 22). 48 hours after stimulation supernatant was harvested and IL-8 production was measured by ELISA. For the stimulation of hTLR9 variant, hTLR9-PHmut, 293 cells were transiently transfected with hTLR9 or hTLR9-PHmut and stimulated after 16 hours with ODN 2006 and ODN 1668 at concentrations indicated (FIG. 23). 48 hours after stimulation supernatant was harvested and IL-8 production was measured by ELISA. These data demonstrate that TLR9 activity can be destroyed by the Pro to His mutation. This mutation has the potential to be used as a dominant negative to block TLR9 activity thus a genetic variant could compete for ligand or signaling partners and disrupt signaling.

Example 13

Exchange of the TIR-Domain Between Murine and Human TLR9 (hTLR9-TIRm, mTLR9-TIRh)

Toll-like receptors have a cytoplasmic Toll/IL-1 receptor (TIR) homology domain that initiates signaling after binding of the adapter molecule MyD88. Medzhitov R et al., *Mol Cell* 2:253-8 (1998); Kopp E B et al., *Curr Opin Immunol* 11:15-8 (1999). This is also true for TLR9. To generate molecules consisting of human extracellular TLR9 and murine TIR domain (hTLR9-TIRm) or murine extracellular TLR9 and human TIR domain (mTLR9-TIRh), the following approach was chosen. Through site-specific mutagenesis a ClaI restriction site was introduced in human and murine TLR9. For human TLR9 the DNA sequence 5'-GGCCTCAGCATCTTT-3' (3026-3040, SEQ ID NO:158) was mutated to 5'-GGCCT ATCGATTTTT-3' (SEQ ID NO:159), introducing a ClaI site (underlined in the sequence) but leaving the amino acid sequence (GLSIF, aa 798-802) unchanged. For murine TLR9 the DNA sequence 5'-GGCCGTAGCATCTTC-3' (2434-2447, SEQ ID NO:160) was mutated to 5'-GGCCT ATCGATTTTT-3' (SEQ ID NO:161), introducing a ClaI site and creating the amino acid sequence (GLSIF, aa 799-803) which differs in one position (aa 800) from the wildtype murine TLR9 sequence (GRSIF, aa 799-803) but is identical to the human sequence.

hTLR9-TIRm. The primers used for human TLR9 were 5'-CAGCTCCAGGGCCTATCGATTTTTGCACAGGACC-3' (SEQ ID NO:162) and 5'-GGTCCTGTGCAAAAATC-GATAGGCCCTGGAGCTG-3' (SEQ ID NO:163). For creating an expression vector containing the extracellular portion of human TLR9 connected to the murine TIR domain, the human expression vector was cut with ClaI and limiting amounts of EcoRI and the fragment coding for the murine TIR domain generated by a ClaI and EcoRI digestion of murine TLR9 expression vector was ligated in the vector fragment containing the extracellular portion of hTLR9. Transfection into *E. coli* yielded the expression vector hTLR9-TIRm (human extracellular TLR9-murine TIR-domain).

mTLR9-TIRh. The primers used for murine TLR9 were 5'-CAGCTGCAGGGCCTATCGATTTTCGCACAGGACC-3' (SEQ ID NO:164) and 5'-GGTCCTGTGCGAAAATC-GATAGGCCCTGCAGCTG-3' (SEQ ID NO:165). For creating an expression vector containing the extracellular portion of murine TLR9 connected to the human TIR domain, the murine expression vector was cut with ClaI and limiting amounts of EcoRI and the fragment coding for the human TIR domain generated by a ClaI and EcoRI digestion of human TLR9 expression vector was ligated in the vector fragment containing the extracellular portion of mTLR9. Transfection into *E. coli* yielded the expression vector mTLR9-TIRh (murine extracellular TLR9-human TIR-domain).

For the stimulation of the mTLR9 variant, mTLR9-TIRh, 293 cells were transiently transfected with mTLR9 or mTLR9-TIRh and stimulated after 16 hours with ODN 2006 and ODN 1668 at concentrations indicated (FIG. 24). 48 hours after stimulation supernatant was harvested and IL-8 production was measured by ELISA. For the stimulation of the hTLR9 variant, hTLR9-TIRm, 293 cells were transiently transfected with hTLR9 or hTLR9-TIRm and stimulated after 16 hours with ODN 2006 and ODN 1668 at concentrations indicated (FIG. 25). 48 hours after stimulation supernatant was harvested and IL-8 production was measured by ELISA. Replacement of the murine TLR9-TIR domain with human does not significantly affect mTLR9 activity. Replacement of the human TLR9-TIR with murine however appears to have a negative effect on hTLR9. These data demonstrate that manipulations could be made to influence TLR9 activities.

Example 14

TLR9-Fusion Protein with Green-Fluorescent-Protein (hTLR9-GFP, mTLR9-GFP)

Human and murine TLR9 were individually cloned into the vector pEGFP-N1 (Clontech, Palo Alto, Calif., USA) to create expression vectors encoding human and murine fusion proteins consisting of an N-terminal TLR9 protein fused to C-terminal green-fluorescent protein (GFP). These constructs can be used to trace TLR9 localization and expression. Such detections can be used for staining in FACS analysis, confocal microscopy and Western blot, or for purification of polypeptides and subsequent antibody production.

Example 15

TLR9-Fusion Protein with FLAG-Peptide (hTLR9-FLAG, mTLR9-FLAG)

Human and murine TLR9 were individually cloned into the vector pFLAG-CMV-1 (Sigma, St. Louis, Mo., USA) to create expression vectors encoding human and murine fusion proteins consisting of an N-terminal leader peptide (preprotrypsin, which is cleaved intracellularly during processing of the protein), FLAG-peptide (DYKDDDDK) and TLR9 protein which does not contain its own signal peptide. These constructs can be used to trace TLR9 localization and expression, e.g., using anti-FLAG antibodies. Such detections can be used for staining in FACS analysis, confocal microscopy and Western blot, or for purification of polypeptides and subsequent antibody production.

Example 16

Method of Cloning Human TLR7

Two accession numbers in the GenBank database, AF245702 and AF240467, describe the DNA sequence for human TLR7. To create an expression vector for human TLR7, human TLR7 cDNA was amplified from a cDNA made from human peripheral mononuclear blood cells (PBMC) using the primers 5'-CACCTCTCATGCTCT-GCTCTCTTC-3' (SEQ ID NO:166) and 5'-GCTAGAC-CGTTTCCTTGAACACCTG-3' (SEQ ID NO:167). The fragment was cloned into pGEM-T Easy vector (Promega), cut with the restriction enzyme NotI and ligated into a NotI-digested pcDNA3.1 expression vector (Invitrogen). The insert was fully sequenced and translated into protein. The cDNA sequence for hTLR7 is SEQ ID NO:168, is presented in Table 6. The open reading frame starts at base 124, ends at base 3273, and codes for a protein of 1049 amino acids. SEQ ID NO:169 (Table 7), corresponding to bases 124-3273 of SEQ ID NO:168 (Table 6), is the coding region for the polypeptide of SEQ ID NO:170 (Table 8).

The protein sequence of the cloned hTLR7 cDNA matches the sequence described under the GenBank accession number AF240467. The sequence deposited under GenBank accession number AF245702 contains two amino acid changes at position 725 (L to H) and 738 (L to P).

TABLE 6

| cDNA Sequence for Human TLR7 (5' to 3'; SEQ ID NO:168) | | | | | | |
|---|---|---|---|---|---|---|
| agctggctag | cgtttaaacg | ggccctctag | actcgagcgg | ccgcgaattc | actagtgatt | 60 |
| cacctctcat | gctctgctct | cttcaaccag | acctctacat | tccattttgg | aagaagacta | 120 |
| aaaatggtgt | ttccaatgtg | gacactgaag | agacaaattc | ttatccttt | taacataatc | 180 |
| ctaatttcca | aactccttgg | ggctagatgg | tttcctaaaa | ctctgccctg | tgatgtcact | 240 |
| ctggatgttc | caaagaacca | tgtgatcgtg | gactgcacag | acaagcattt | gacagaaatt | 300 |
| cctggaggta | ttcccacgaa | caccacgaac | ctcaccctca | ccattaacca | cataccagac | 360 |
| atctccccag | cgtcctttca | cagactggac | catctggtag | agatcgattt | cagatgcaac | 420 |
| tgtgtaccta | ttccactggg | gtcaaaaaac | aacatgtgca | tcaagaggct | gcagattaaa | 480 |
| cccagaagct | ttagtggact | cacttattta | aaatcccttt | acctggatgg | aaaccagcta | 540 |
| ctagagatac | cgcagggcct | cccgcctagc | ttacagcttc | tcagccttga | ggccaacaac | 600 |
| atcttttcca | tcagaaaaga | gaatctaaca | gaactggcca | acatagaaat | actctacctg | 660 |
| ggccaaaact | gttattatcg | aaatccttgt | tatgtttcat | attcaataga | gaaagatgcc | 720 |
| ttcctaaact | tgacaaagtt | aaaagtgctc | tccctgaaag | ataacaatgt | cacagccgtc | 780 |
| cctactgttt | tgccatctac | tttaacagaa | ctatatctct | acaacaacat | gattgcaaaa | 840 |
| atccaagaag | atgattttaa | taacctcaac | caattacaaa | ttcttgacct | aagtggaaat | 900 |
| tgccctcgtt | gttataatgc | cccatttcct | tgtgcgccgt | gtaaaaataa | ttctccccta | 960 |
| cagatccctg | taaatgcttt | tgatgcgctg | acagaattaa | aagttttacg | tctacacagt | 1020 |
| aactctcttc | agcatgtgcc | cccaagatgg | tttaagaaca | tcaacaaact | ccaggaactg | 1080 |
| gatctgtccc | aaaacttctt | ggccaaagaa | attggggatg | ctaaatttct | gcattttctc | 1140 |

TABLE 6-continued

| cDNA Sequence for Human TLR7 (5' to 3'; SEQ ID NO:168) | |
|---|---|
| cccagcctca tccaattgga tctgtctttc aattttgaac ttcaggtcta tcgtgcatct | 1200 |
| atgaatctat cacaagcatt ttcttcactg aaaagcctga aaattctgcg gatcagagga | 1260 |
| tatgtctttta aagagttgaa aagctttaac ctctcgccat tacataatct tcaaaatctt | 1320 |
| gaagttcttg atcttggcac taactttata aaaattgcta acctcagcat gtttaaacaa | 1380 |
| tttaaaagac tgaaagtcat agatctttca gtgaataaaa tatcaccttc aggagattca | 1440 |
| agtgaagttg gcttctgctc aaatgccaga acttctgtag aaagttatga accccaggtc | 1500 |
| ctggaacaat tacattattt cagatatgat aagtatgcaa ggagttgcag attcaaaaac | 1560 |
| aaagaggctt ctttcatgtc tgttaatgaa agctgctaca agtatgggca gaccttggat | 1620 |
| ctaagtaaaa atagtatatt ttttgtcaag tcctctgatt ttcagcatct ttctttcctc | 1680 |
| aaatgcctga atctgtcagg aaatctcatt agccaaactc ttaatggcag tgaattccaa | 1740 |
| cctttagcag agctgagata tttggacttc tccaacaacc ggcttgattt actccattca | 1800 |
| acagcatttg aagagcttca caaactggaa gttctggata taagcagtaa tagccattat | 1860 |
| tttcaatcag aaggaattac tcatatgcta aactttacca gaacctaaa ggttctgcag | 1920 |
| aaactgatga tgaacgacaa tgacatctct tcctccacca gcaggaccat ggagagtgag | 1980 |
| tctcttagaa ctctggaatt cagaggaaat cacttagatg ttttatggag agaaggtgat | 2040 |
| aacagatact tacaattatt caagaatctg ctaaaattag aggaattaga catctctaaa | 2100 |
| aattccctaa gttcttgcc ttctggagtt tttgatggta tgcctccaaa tctaaagaat | 2160 |
| ctctctttgg ccaaaaatgg gctcaaatct ttcagttgga agaaactcca gtgtctaaag | 2220 |
| aacctggaaa ctttggacct cagccacaac caactgacca ctgtccctga gagattatcc | 2280 |
| aactgttcca gaagcctcaa gaatctgatt cttaagaata tcaaatcag gagtctgacg | 2340 |
| aagtattttc tacaagatgc cttccagttg cgatatctgg atctcagctc aaataaaatc | 2400 |
| cagatgatcc aaaagaccag cttcccagaa aatgtcctca caatctgaa gatgttgctt | 2460 |
| ttgcatcata atcggtttct gtgcacctgt gatgctgtgt ggtttgtctg gtgggttaac | 2520 |
| catacggagg tgactattcc ttacctggcc acagatgtga cttgtgtggg gccaggagca | 2580 |
| cacaagggcc aaagtgtgat ctccctggat ctgtacacct gtgagttaga tctgactaac | 2640 |
| ctgattctgt tctcactttc catatctgta tctctctttc tcatggtgat gatgacagca | 2700 |
| agtcacctct atttctggga tgtgtggtat atttaccatt tctgtaaggc caagataaag | 2760 |
| gggtatcagc gtctaatatc accagactgt tgctatgatg ctttattgt gtatgacact | 2820 |
| aaagacccag ctgtgaccga gtgggttttg gctgagctgg tggccaaact ggaagaccca | 2880 |
| agagagaaac atttttaattt atgtctcgag gaaagggact ggttaccagg gcagccagtt | 2940 |
| ctggaaaacc tttcccagag catacagctt agcaaaaaga cagtgtttgt gatgacagac | 3000 |
| aagtatgcaa agactgaaaa ttttaagata gcattttact tgtcccatca gaggctcatg | 3060 |
| gatgaaaaag ttgatgtgat tatcttgata tttcttgaga agccttttca gaagtccaag | 3120 |
| ttcctccagc tccggaaaag gctctgtggg agttctgtcc ttgagtggcc aacaaacccg | 3180 |
| caagctcacc atacttctg gcagtgtcta agaacgccc tggccacaga caatcatgtg | 3240 |
| gcctatagtc aggtgttcaa ggaaacggtc tagaatcgaa ttcccgcggc cgccactgtg | 3300 |
| ctggatatct gcagaattcc accacactgg actagtggat ccgagctcgg taccaagctt | 3360 |
| aagtttaaac cgc | 3373 |

TABLE 7

| Coding Region for Human TLR7 (5' to 3'; SEQ ID NO:169) | |
|---|---|
| atggtgtttc caatgtggac actgaagaga caaattctta tccttttttaa cataatccta | 60 |
| atttccaaac tccttggggc tagatggttt cctaaaactc tgccctgtga tgtcactctg | 120 |
| gatgttccaa agaaccatgt gatcgtggac tgcacagaca agcatttgac agaaattcct | 180 |
| ggaggtattc ccacgaacac cacgaacctc accctcacca ttaaccacat accagacatc | 240 |
| tccccagcgt cctttcacag actggaccat ctggtagaga tcgatttcag atgcaactgt | 300 |
| gtacctattc cactggggtc aaaaaacaac atgtgcatca agaggctgca gattaaaccc | 360 |
| agaagcttta gtggactcac ttatttaaaa tcccttttacc tggatggaaa ccagctacta | 420 |
| gagataccgc agggcctccc gcctagctta cagcttctca gccttgaggc caacaacatc | 480 |
| ttttccatca gaaagagaa tctaacagaa ctggccaaca tagaaatact ctacctgggc | 540 |
| caaaactgtt attatcgaaa tccttgttat gtttcatatt caatagagaa agatgccttc | 600 |
| ctaaacttga caaagttaaa agtgctctcc ctgaaagata caatgtcac agccgtccct | 660 |
| actgttttgc catctacttt aacagaacta tatctctaca caacatgat tgcaaaaatc | 720 |
| caagaagatg attttaataa cctcaaccaa ttacaaattc ttgacctaag tggaaattgc | 780 |
| cctcgttgtt ataatgcccc atttccttgt gcgccgtgta aaaataattc tcccctacag | 840 |
| atccctgtaa atgcttttga tgcgctgaca gaattaaaag ttttacgtct acacagtaac | 900 |
| tctcttcagc atgtgccccc aagatggttt aagaacatca caaactcca ggaactggat | 960 |
| ctgtcccaaa acttcttggc caagaaaatt ggggatgcta aatttctgca ttttctcccc | 1020 |
| agcctcatcc aattggatct gtctttcaat tttgaacttc aggtctatcg tgcatctatg | 1080 |
| aatctatcac aagcattttc ttcactgaaa agcctgaaaa ttctgcggat cagaggatat | 1140 |
| gtctttaaag agttgaaaag ctttaacctc tcgccattac ataatcttca aaatcttgaa | 1200 |
| gttcttgatc ttggcactaa ctttataaaa attgctaacc tcagcatgtt taaacaattt | 1260 |
| aaaagactga aagtcataga tctttcagtg aataaaatat caccttcagg agattcaagt | 1320 |
| gaagttggct tctgctcaaa tgccagaact tctgtagaaa gttatgaacc ccaggtcctg | 1380 |
| gaacaattac attatttcag atatgataag tatgcaagga gttgcagatt caaaaacaaa | 1440 |
| gaggcttctt tcatgtctgt taatgaaagc tgctacaagt atgggcagac cttggatcta | 1500 |
| agtaaaaata gtatattttt tgtcaagtcc tctgattttc agcatctttc tttcctcaaa | 1560 |
| tgcctgaatc tgtcaggaaa tctcattagc caaactctta atggcagtga attccaacct | 1620 |
| ttagcagagc tgagatattt ggacttctcc aacaaccggc ttgatttact ccattcaaca | 1680 |
| gcatttgaag agcttcacaa actggaagtt ctggatataa gcagtaatag ccattatttt | 1720 |
| caatcagaag gaattactca tatgctaaac tttaccaaga acctaaaggt tctgcagaaa | 1800 |
| ctgatgatga cgacaatga catctcttcc tccaccagca ggaccatgga gagtgagtct | 1860 |
| cttagaactc tggaattcag aggaaatcac ttagatgttt atggagaga aggtgataac | 1920 |
| agatacttac aattattcaa gaatctgcta aaattagagg aattagacat ctctaaaaat | 1980 |
| tccctaagtt tcttgccttc tggagttttt gatggtatgc ctccaaatct aaagaatctc | 2040 |
| tctttggcca aaaatgggct caaatctttc agttggaaga actccagtg tctaaagaac | 2100 |
| ctggaaactt tggacctcag ccacaaccaa ctgaccactg tccctgagag attatccaac | 2160 |
| tgttccagaa gcctcaagaa tctgattctt aagaataatc aaatcaggag tctgacgaag | 2220 |
| tattttctac aagatgcctt ccagttgcga tatctggatc tcagctcaaa taaaatccag | 2280 |
| atgatccaaa agaccagctt cccagaaaat gtcctcaaca atctgaagat gttgcttttg | 2340 |

TABLE 7-continued

Coding Region for Human TLR7 (5' to 3'; SEQ ID NO:169)

```
catcataatc ggtttctgtg cacctgtgat gctgtgtggt ttgtctggtg ggttaaccat   2400
acggaggtga ctattcctta cctggccaca gatgtgactt gtgtggggcc aggagcacac   2460
aagggccaaa gtgtgatctc cctggatctg tacacctgtg agttagatct gactaacctg   2520
attctgttct cactttccat atctgtatct ctctttctca tggtgatgat gacagcaagt   2580
cacctctatt tctgggatgt gtggtatatt taccatttct gtaaggccaa gataaagggg   2640
tatcagcgtc taatatcacc agactgttgc tatgatgctt ttattgtgta tgacactaaa   2700
gacccagctg tgaccgagtg ggttttggct gagctggtgg ccaaactgga agacccaaga   2760
gagaaacatt ttaatttatg tctcgaggaa agggactggt taccagggca gccagttctg   2820
gaaaaccttt cccagagcat acagcttagc aaaaagacag tgtttgtgat gacagacaag   2880
tatgcaaaga ctgaaaattt taagatagca ttttacttgt cccatcagag gctcatggat   2940
gaaaaagttg atgtgattat cttgatattt cttgagaagc cttttcagaa gtccaagttc   3000
ctccagctcc ggaaaaggct ctgtgggagt tctgtccttg agtggccaac aaacccgcaa   3060
gctcacccat acttctggca gtgtctaaag aacgccctgg ccacagacaa tcatgtggcc   3120
tatagtcagg tgttcaagga aacggtc                                       3147
```

TABLE 8

Amino Acid Sequence of Human TLR7

```
                          .         :         .         :         .         :      60
AF240467.pep   MVFPMWTLKRQILILFNIILISKLLGARWFPKTLPCDVTLDVPKNHVIVDCTDKHLTEIP    60
hTLR7.pep      MVFPMWTLKRQILILFNIILISKLLGARWFPKTLPCDVTLDVPKNHVIVDCTDKHLTEIP    60
AF245702.pep   MVFPMWTLKRQILILFNIILISKLLGARWFPKTLPCDVTLDVPKNHVIVDCTDKHLTEIP    60

.         :         .         :         .         :     120
AF240467.pep   GGIPTNTTNLTLTINHIPDISPASFHRLDHLVEIDFRCNCVPIPLGSKNNMCIKRLQIKP   120
hTLR7.pep      GGIPTNTTNLTLTINHIPDISPASFHRLDHLVEIDFRCNCVPIPLGSKNNMCIKRLQIKP   120
AF245702.pep   GGIPTNTTNLTLTINHIPDISPASFHRLDHLVEIDFRCNCVPIPLGSKNNMCIKRLQIKP   120

.         :         .         :         .         :     180
                                                                                   180
AF240467.pep   RSFSGLTYLKSLYLDGNQLLEIPQGLPPSLQLLSLEANNIFSIRKENLTELANIEILYLG   180
hTLR7.pep      RSFSGLTYLKSLYLDGNQLLEIPQGLPPSLQLLSLEANNIFSIRKENLTELANIEILYLG   180
AF245702.pep   RSFSGLTYLKSLYLDGNQLLEIPQGLPPSLQLLSLEANNIFSIRKENLTELANIEILYLG   180

.         :         .         :         .         :     240
AF240467.pep   QNCYYRNPCYVSYSIEKDAFLNLTKLKVLSLKDNNVTAVFTVLPSTLTELYLYNNMIAKI   240
hTLR7.pep      QNCYYRNPCYVSYSIEKDAFLNLTKLKVLSLKDNNVTAVFTVLPSTLTELYLYNNMIAKI   240
AF245702.pep   QNCYYRNPCYVSYSIEKDAFLNLTKLKVLSLKDNNVTAVFTVLPSTLTELYLYNNMIAKI   240

.         :         .         :         .         :     300
AF240467.pep   QEDDFNNLNQLQILDLSGNCPRCYNAPFPCAPCKNNSPLQIPVNAFDALTELKVLRLHSN   300
hTLR7.pep      QEDDFNNLNQLQILDLSGNCPRCYNAPFPCAPCKNNSPLQIPVNAFDALTELKVLRLHSN   300
AF245702.pep   QEDDFNNLNQLQILDLSGNCPRCYNAPFPCAPCKNNSPLQIPVNAFDALTELKVLRLHSN   300

.         :         .         :         .         :     360
AF240467.pep   SLQHVPPRWFKNINKLQELDLSQNFLAKEIGDAKFLHFLPSLIQLDLSFNFELQVYRASM   360
hTLR7.pep      SLQHVPPRWFKNINKLQELDLSQNFLAKEIGDAKFLHFLPSLIQLDLSFNFELQVYRASM   360
AF245702.pep   SLQHVPPRWFKNINKLQELDLSQNFLAKEIGDAKFLHFLPSLIQLDLSFNFELQVYRASM   360

.         :         .         :         .         :     420
AF240467.pep   NLSQAFSSLKSLKILRIRGYVFKELKSFNLSPLHNLQNLEVLDLGTNFIKIANLSMFKQF   420
hTLR7.pep      NLSQAFSSLKSLKILRIRGYVFKELKSFNLSPLHNLQNLEVLDLGTNFIKIANLSMFKQF   420
AF245702.pep   NLSQAFSSLKSLKILRIRGYVFKELKSFNLSPLHNLQNLEVLDLGTNFIKIANLSMFKQF   420

.         :         .         :         .         :     480
AF240467.pep   KRLKVIDLSVNKISPSGDSSEVGFCSNARTSVESYEPQVLEQLHYFRYDKYARSCRFKNK   480
hTLR7.pep      KRLKVIDLSVNKISPSGDSSEVGFCSNARTSVESYEPQVLEQLHYFRYDKYARSCRFKNK   480
AF245702.pep   KRLKVIDLSVNKISPSGDSSEVGFCSNARTSVESYEFQVLEQLHYFRYDKYARSCRFKNK   480
```

TABLE 8-continued

Amino Acid Sequence of Human TLR7

```
                                                                            540
AF240467.pep  EASFMSVNESCYKYGQTLDLSKNSIFFVKSSDFQHLSFLKCLNLSGNLISQTLNGSEFQF   540
hTLR7.pep     EASFMSVNESCYKYGQTLDLSKNSIFFVKSSDFQHLSFLKCLNLSGNLISQTLNGSEFQF   540
AF245702.pep  EASFMSVNESCYKYGQTLDLSKNSIFFVKSSDFQHLSFLKCLNLSGNLISQTLNGSEFQF   540

600
AF240467.pep  LAELRYLDFSNNRLDLLHSTAFEELHKLEVLDISSNSHYFQSEGITHMLNFTKNLKVLQK   600
hTLR7.pep     LAELRYLDFSNNRLDLLHSTAFEELHKLEVLDISSNSHYFQSEGITHMLNFTKNLKVLQK   600
AF245702.pep  LAELRYLDFSNNRLDLLHSTAFEELHKLEVLDISSNSHYFQSEGITHMLNFTKNLKVLQK   600

660
AF240467.pep  LMMNDNDISSSTSRTMESESLRTLEFRGNHLDVLWREGDNRYLQLFKNLLKLEELDISKN   660
hTLR7.pep     LMMNDNDISSSTSRTMESESLRTLEFRGNHLDVLWREGDNRYLQLFKNLLKLEELDISKN   660
AF245702.pep  LMMNDNDISSSTSRTMESESLRTLEFRGNHLDVLWREGDNRYLQLFKNLLKLEELDISKN   660

720
AF240467.pep  SLSFLPSGVFDGMPPNLKNLSLAKNGLKSFSWKKLQCLKNLETLDLSHNQLTTVPERLSN   720
hTLR7.pep     SLSFLPSGVFDGMPPNLKNLSLAKNGLKSFSWKKLQCLKNLETLDLSHNQLTTVPERLSN   720
AF245702.pep  SLSFLPSGVFDGMPPNLKNLSLAKNGLKSFSWKKLQCLKNLETLDLSHNQLTTVPERLSN   720

780
AF240467.pep  CSRSLKNLILKNNQIRSLTKYFLQDAFQLRYLDLSSNKIQMIQKTSFPENVLNNLKMLLL   780
hTLR7.pep     CSRSLKNLILKNNQIRSLTKYFLQDAFQLRYLDLSSNKIQMIQKTSFpENVLNNLKMLLL   780
AF245702.pep  CSRSHKNLILKNNQIRSPTKYFLQDAFQLRYLDLSSNKIQMIQKTSFPENVLNNLKMLLL   780

840
AF240467.pep  HHNRFLCTCDAVWFVWWVNHTEVTIPYLATDVTCVGPGAHKGQSVISLDLYTCELDLTNL   840
hTLR7.pep     HHNRFLCTCDAVWFVWWVNHTEVTIPYLATDVTCVGPGAHKGQSVISLDLYTCELDLTNL   840
AF245702.pep  HHNRFLCTCDAVWFVWWVNHTEVTIPYLATDVTCVGPGAHKGQSVISLDLYTCELDLTNL   840

900
AF240467.pep  ILFSLSISVSLFLMVMNTASHLYFWDVWYIYHFCKAKIKGYQRLISPDCCYDAFIVYDTK   900
hTLR7.pep     ILFSLSISVSLFLMVMMTASHLYFWDVWYIYHFCKAKIKGYQRLISPDCCYDAFIVYDTK   900
AF245702.pep  ILFSLSISVSLFLMVMMTASHLYFWDVWYIYHFCKAKIKGYQRLISPDCCYDAFIVYDTK   900

960
AF240467.pep  DPAVTEWVLAELVAKLEDPREKHFNLCLEERDWLPGQPVLENLSQSIQLSKKTVFVMTDK   960
hTLR7.pep     DPAVTEWVLAELVAKLEDPREKHFNLCLEERDWLPGQPVLENLSQSIQLSKKTVFVMTDK   960
AF245702.pep  DPAVTEWVLAELVAKLEDPREKHFNLCLEERDWLPGQPVLENLSQSIQLSKKTVEVMTDK   960

1020
AF240467.pep  YAKTENFKIAFYLSHQRLMDEKVDVIILIFLEKPFQKSKFLQLRKRLCGSSVLEWPTNPQ  1020
hTLR7.pep     YAKTENFKIAFYLSHQRLMDEKVDVIILIFLEKPFQKSKFLQLRKRLCGSSVLEWPTNPQ  1020
AF245702.pep  YAKTENFKIAFYLSHQRLMDEKVDVIILIFLEKPFQKSKFLQLRKRLCGSSVLEWPTNPQ  1020

1080
AF240467.pep  AHPYFWQCLKNALATDNHVAYSQVFKETV                                 1049
hTLR7.pep     AHPYFWQCLKNALATDNHVAYSQVFKETV                                 1049
AF245702.pep  AHPYFWQCLKNALATDNHVAYSQVFKETV                                 1049
```

In Table 8 the sequences are assigned as follows: hTLR7.pep, SEQ ID NO:170; AF240467.pep, SEQ ID NO:171; AF245702.pep, SEQ ID NO:172.

Example 17

Method of Cloning the Murine TLR7

Alignment of human TLR7 protein sequence with mouse EST database using tfasta yielded 4 hits with mouse EST sequences bbl 16163, aa266744, bb210780 and aa276879. Two primers were designed that bind to aa266744 sequence for use in a RACE-PCR to amplify 5' and 3' ends of the murine TLR7 cDNA. The library used for the RACE PCR was a mouse spleen marathon-ready cDNA commercially available from Clontech. A 5' fragment with a length of 3000 bp obtained by this method was cloned into Promega pGEM-T Easy vector. After sequencing of the 5' end, additional primers were designed for amplification of the complete murine TLR7 cDNA. The primer for the 5' end was obtained from the sequence of the 5' RACE product whereas the primer for the 3' end was selected from the mouse EST sequence aa266744.

Three independent PCR reactions were set up using a murine macrophage RAW264.7 (ATCC TIB-71) cDNA as a template with the primers 5'-CTCCTCCACCAGACCTCT-TGATTCC-3' (SEQ ID NO:208) and 5'-CAAGGCATGTC-CTAGGTGGTGACATTC-3' (SEQ ID NO:209). The resulting amplification products were cloned into pGEM-T Easy vector and fully sequenced (SEQ ID NO:173; Table 9). The open reading frame of mTLR7 (SEQ ID NO:174; Table 10) starts at base 49, ends at base 3201 and codes for a protein of 1050 amino acids (SEQ ID NO:175; Table 11). To create an expression vector for murine TLR7 cDNA, pGEM-T Easy vector plus mTLR7 insert was cut with NotI, the fragment isolated and ligated into a NotI digested pcDNA3.1 expression vector (Invitrogen).

TABLE 9

| cDNA Seqence for Murine TLR7 (5' to 3'; SEQ ID NO:173) | |
|---|---|
| ATTCTCCTCC ACCAGACCTC TTGATTCCAT TTTGAAAGAA AACTGAAAAT GGTGTTTTCG | 60 |
| ATGTGGACAC GGAAGAGACA AATTTTGATC TTTTTAAATA TGCTCTTAGT TTCTAGAGTC | 120 |
| TTTGGGTTTC GATGGTTTCC TAAAACTCTA CCTTGTGAAG TTAAAGTAAA TATCCCAGAG | 180 |
| GCCCATGTGA TCGTGGACTG CACAGACAAG CATTTGACAG AAATCCCTGA GGGCATTCCC | 240 |
| ACTAACACCA CCAATCTTAC CCTTACCATC AACCACATAC CAAGCATCTC TCCAGATTCC | 300 |
| TTCCGTAGGC TGAACCATCT GGAAGAAATC GATTTAAGAT GCAATTGTGT ACCTGTTCTA | 360 |
| GTGGGGTCCA AAGCCAATGT GTGTACCAAG AGGCTGCAGA TTAGACCTGG AAGCTTTAGT | 420 |
| GGACTCTCTG ACTTAAAAGC CCTTTACCTG GATGGAAACC AACTTCTGGA GATACCACAG | 480 |
| GATCTGCCAT CCAGCTTACA TCTTCTGAGC CTTGAGGCTA ACAACATCTT CTCCATCACG | 540 |
| AAGGAGAATC TAACAGAACT GGTCAACATT GAAACACTCT ACCTGGGTCA AAACTGTTAT | 600 |
| TATCGAAATC CTTGCAATGT TTCCTATTCT ATTGAAAAAG ATGCTTTCCT AGTTATGAGA | 660 |
| AATTTGAAGG TTCTCTCACT AAAAGATAAC AATGTCACAG CTGTCCCCAC CACTTTGCCA | 720 |
| CCTAATTTAC TAGAGCTCTA TCTTTATAAC AATATCATTA AGAAAATCCA AGAAAATGAT | 780 |
| TTTAATAACC TCAATGAGTT GCAAGTTCTT GACCTAAGTG GAAATTGCCC TCGATGTTAT | 840 |
| AATGTCCCAT ATCCGTGTAC ACCGTGTGAA ATAATTCCC CCTTACAGAT CCATGACAAT | 900 |
| GCTTTCAATT CATTGACAGA ATTAAAAGTT TTACGTTTAC ACAGTAATTC TCTTCAGCAT | 960 |
| GTGCCCCCAA CATGGTTTAA AAACATGAGA AACCTCCAGG AACTAGACCT CTCCCAAAAC | 1020 |
| TACTTGGCCA GAGAAATTGA GGAGGCCAAA TTTTTGCATT TTCTTCCCAA CCTTGTTGAG | 1080 |
| TTGGATTTTT CTTTCAATTA TGAGCTGCAG GTCTACCATG CATCTATAAC TTTACCACAT | 1140 |
| TCACTCTCTT CATTGGAAAA CTTGAAAATT CTGCGTGTCA AGGGGTATGT CTTTAAAGAG | 1200 |
| CTGAAAAACT CCAGTCTTTC TGTATTGCAC AAGCTTCCCA GGCTGGAAGT TCTTGACCTT | 1260 |
| GGCACTAACT TCATAAAAAT TGCTGACCTC AACATATTCA AACATTTGA AAACCTCAAA | 1320 |
| CTCATAGACC TTTCAGTGAA TAAGATATCT CCTTCAGAAG AGTCAAGAGA AGTTGGCTTT | 1380 |
| TGTCCTAATG CTCAAACTTC TGTAGACCGT CATGGGCCCC AGGTCCTTGA GGCCTTACAC | 1440 |
| TATTTCCGAT ACGATGAATA TGCACGGAGC TGCAGGTTCA AAAACAAAGA GCCACCTTCT | 1500 |
| TTCTTGCCTT TCAATGCAGA CTGCCACATA TATGGGCAGA CCTTAGACTT AAGTAGAAAT | 1560 |
| AACATATTTT TTATTAAACC TTCTGATTTT CAGCATCTTT CATTCCTCAA ATGCCTCAAC | 1620 |
| TTATCAGGAA ACACCATTGG CCAAACTCTT AATGGCAGTG AACTCTGGCC GTTGAGAGAG | 1680 |
| TTGCGGTACT TAGACTTCTC CAACAACCGG CTTGATTTAC TCTACTCAAC AGCCTTTGAA | 1740 |
| GAGCTCCAGA GTCTTGAAGT TCTGGATCTA AGTAGTAACA GCCACTATTT TCAAGCAGAA | 1800 |
| GGAATTACTC ACATGCTAAA CTTTACCAAG AAATTACGGC TTCTGGACAA ACTCATGATG | 1860 |
| AATGATAATG ACATCTCTAC TTCGGCCAGC AGGACCATGG AAAGTGACTC TCTTCGAATT | 1920 |
| CTGGAGTTCA GAGGCAACCA TTTAGATGTT CTATGGAGAG CCGGTGATAA CAGATACTTG | 1980 |
| GACTTCTTCA AGAATTTGTT CAATTTAGAG GTATTAGATA TCTCCAGAAA TTCCCTGAAT | 2040 |
| TCCTTGCCTC CTGAGGTTTT TGAGGGTATG CCGCCAAATC TAAAGAATCT CTCCTTGGCC | 2100 |
| AAAAATGGGC TCAAATCTTT CTTTTGGGAC AGACTCCAGT TACTGAAGCA TTTGGAAATT | 2160 |
| TTGGACCTCA GCCATAACCA GCTGACAAAA GTACCTGAGA GATTGGCCAA CTGTTCCAAA | 2220 |
| AGTCTCACAA CACTGATTCT TAAGCATAAT CAAATCAGGC AATTGACAAA ATATTTTCTA | 2280 |
| GAAGATGCTT TGCAATTGCG CTATCTAGAC ATCAGTTCAA ATAAAATCCA GGTCATTCAG | 2340 |

TABLE 9-continued cDNA Seqence for Murine TLR7 (5'to 3'; SEQ ID NO:173)

| | | | | | |
|---|---|---|---|---|---|
| AAGACTAGCT | TCCCAGAAAA | TGTCCTCAAC | AATCTGGACA | TGTTGGTTTT | ACATCACAAT | 2400 |
| CGCTTTCTTT | GCAACTGTGA | TGCTGTGTGG | TTTGTCTGGT | GGGTTAACCA | TACAGATGTT | 2460 |
| ACTATTCCAT | ACCTGGCCAC | TGATGTGACT | TGTGTAGGTC | CAGGAGCACA | CAAAGGTCAA | 2520 |
| AGTGTCATAT | CCCTTGATCT | GTATACGTGT | GAGTTAGATC | TCACAAACCT | GATTCTGTTC | 2580 |
| TCAGTTTCCA | TATCATCAGT | CCTCTTTCTT | ATGGTAGTTA | TGACAACAAG | TCACCTCTTT | 2640 |
| TTCTGGGATA | TGTGGTACAT | TTATTATTTT | TGGAAAGCAA | AGATAAAGGG | GTATCAGCAT | 2700 |
| CTGCAATCCA | TGGAGTCTTG | TTATGATGCT | TTTATTGTGT | ATGACACTAA | AAACTCAGCT | 2760 |
| GTGACAGAAT | GGGTTTTGCA | GGAGCTGGTG | GCAAAATTGG | AAGATCCAAG | AGAAAAACAC | 2820 |
| TTCAATTTGT | GTCTAGAAGA | AAGAGACTGG | CTACCAGGAC | AGCCAGTTCT | AGAAAACCTT | 2880 |
| TCCCAGAGCA | TACAGCTCAG | CAAAAAGACA | GTGTTTGTGA | TGACACAGAA | ATATGCTAAG | 2940 |
| ACTGAGAGTT | TTAAGATGGC | ATTTTATTTG | TCTCATCAGA | GGCTCCTGGA | TGAAAAGTG | 3000 |
| GATGTGATTA | TCTTGATATT | CTTGGAAAAG | CCTCTTCAGA | AGTCTAAGTT | TCTTCAGCTC | 3060 |
| AGGAAGAGAC | TCTGCAGGAG | CTCTGTCCTT | GAGTGGCCTG | CAAATCCACA | GGCTCACCCA | 3120 |
| TACTTCTGGC | AGTGCCTGAA | AAATGCCCTG | ACCACAGACA | ATCATGTGGC | TTATAGTCAA | 3180 |
| ATGTTCAAGG | AAACAGTCTA | GCTCTCTGAA | GAATGTCACC | ACCTAGGACA | TGCCTTGAAT | 3240 |
| CGA | | | | | | 3243 |

TABLE 10

Coding Region for Murine TLR7 (5' to 3'; SEQ ID NO:174)

| | | | | | |
|---|---|---|---|---|---|
| ATGGTGTTTT | CGATGTGGAC | ACGGAAGAGA | CAAATTTTGA | TCTTTTTAAA | TATGCTCTTA | 60 |
| GTTTCTAGAG | TCTTTGGGTT | TCGATGGTTT | CCTAAAACTC | TACCTTGTGA | AGTTAAAGTA | 120 |
| AATATCCCAG | AGGCCCATGT | GATCGTGGAC | TGCACAGACA | AGCATTTGAC | AGAAATCCCT | 180 |
| GAGGGCATTC | CCACTAACAC | CACCAATCTT | ACCCTTACCA | TCAACCACAT | ACCAAGCATC | 240 |
| TCTCCAGATT | CCTTCCGTAG | GCTGAACCAT | CTGGAAGAAA | TCGATTTAAG | ATGCAATTGT | 300 |
| GTACCTGTTC | TACTGGGGTC | CAAAGCCAAT | GTGTGTACCA | AGAGGCTGCA | GATTAGACCT | 360 |
| GGAAGCTTTA | GTGGACTCTC | TGACTTAAAA | GCCCTTTACC | TGGATGGAAA | CCAACTTCTG | 420 |
| GAGATACCAC | AGGATCTGCC | ATCCAGCTTA | CATCTTCTGA | GCCTTGAGGC | TAACAACATC | 480 |
| TTCTCCATCA | CGAAGGAGAA | TCTAACAGAA | CTGGTCAACA | TTGAAACACT | CTACCTGGGT | 540 |
| CAAAACTGTT | ATTATCGAAA | TCCTTGCAAT | GTTTCCTATT | CTATTGAAAA | AGATGCTTTC | 600 |
| CTAGTTATGA | GAAATTTGAA | GGTTCTCTCA | CTAAAAGATA | CAATGTCAC | AGCTGTCCCC | 660 |
| AGCACTTTGC | CACCTAATTT | ACTAGAGCTC | TATCTTTATA | CAATATCAT | TAAGAAAATG | 720 |
| CAAGAAAATG | ATTTTAATAA | CCTCAATGAG | TTGCAAGTTC | TTGACCTAAG | TGGAAATTGC | 780 |
| CCTCGATGTT | ATAATGTCCC | ATATCCGTGT | ACACCGTGTG | AAAATAATTC | CCCCTTACAG | 840 |
| ATCCATGACA | ATGCTTTCAA | TTCATTGACA | GAATTAAAAG | TTTTACGTTT | ACACAGTAAT | 900 |
| TCTCTTCAGC | ATGTGCCCCC | AACATGGTTT | AAAAACATGA | GAAACCTCCA | GGAACTAGAC | 960 |
| CTCTCCCAAA | ACTACTTGGC | CAGAGAAATT | GAGGAGGCCA | ATTTTTGCA | TTTTCTTCCC | 1020 |
| AACCTTGTTG | AGTTGGATTT | TTCTTTGAAT | TATGAGCTGC | AGGTGTACCA | TGCATCTATA | 1080 |
| ACTTTACCAC | ATTCACTCTC | TTCATTGGAA | AACTTGAAAA | TTCTGCGTGT | CAAGGGGTAT | 1140 |

TABLE 10-continued

Coding Region for Murine TLR7 (5' to 3'; SEQ ID NO:174)

```
GTCTTTAAAG AGCTGAAAAA CTCCAGTCTT TCTGTATTGC ACAAGCTTCC CAGGCTGGAA  1200
GTTCTTGACC TTGGCACTAA CTTCATAAAA ATTGCTGACC TCAACATATT CAAACATTTT  1260
GAAAACCTCA AACTCATAGA CCTTTCAGTG AATAAGATAT CTCCTTCAGA AGAGTCAAGA  1320
GAAGTTGGCT TTTGTCCTAA TGCTCAAACT TCTGTAGACC GTCATGGGCC CCAGGTCCTT  1380
GAGGCCTTAC ACTATTTCCG ATACGATGAA TATGCACGGA GCTGCAGGTT CAAAACAAA   1440
GAGCCACCTT CTTTCTTGCC TTTGAATGCA GACTGCCACA TATATGGGCA GACCTTAGAC  1500
TTAAGTAGAA ATAACATATT TTTTATTAAA CCTTCTGATT TTCAGCATCT TTCATTCCTC  1560
AAATGCCTCA ACTTATCAGG AAACACCATT GGCCAAACTC TTAATGGCAG TGAACTCTGG  1620
CCGTTGAGAG AGTTGCGGTA CTTAGACTTC TCCAACAACC GGCTTGATTT ACTCTACTCA  1680
ACAGCCTTTG AAGAGCTCCA GAGTCTTGAA GTTCTGGATC TAAGTAGTAA CAGCCACTAT  1740
TTTCAAGCAG AAGGAATTAC TCACATGCTA AACTTTACCA AGAAATTACG GCTTCTGGAC  1800
AAACTCATGA TGAATGATAA TGACATCTCT ACTTCGGCCA GCAGGACCAT GGAAAGTGAC  1860
TCTCTTCGAA TTCTGGAGTT CAGAGGCAAC CATTTAGATG TTCTATGGAG AGCCGGTGAT  1920
AACAGATACT GGACTTCTT CAAGAATTTG TTCAATTTAG AGGTATTAGA TATCTCCAGA   1980
AATTCCCTGA ATTCCTTGCC TCCTGAGGTT TTTGAGGGTA TGCCGCCAAA TCTAAAGAAT  2040
CTCTCCTTGG CCAAAAATGG GCTCAAATCT TTCTTTTGGG ACAGACTCCA GTTACTGAAG  2100
CATTTGGAAA TTTTGGACCT CAGCCATAAC CAGCTGACAA AAGTACCTGA GAGATTGGCC  2160
AACTGTTCCA AAAGTCTCAC AACACTGATT CTTAAGCATA ATCAAATCAG GCAATTGACA  2220
AAATATTTTC TAGAAGATGC TTTGCAATTG CGCTATCTAG ACATCAGTTC AAATAAAATC  2280
CAGGTCATTC AGAAGACTAG CTTCCCAGAA AATGTCCTCA ACAATCTGGA GATGTTGGTT  2340
TTACATCACA ATCGCTTTCT TTGCAACTGT GATGCTGTGT GGTTTGTCTG GTGGGTTAAC  2400
CATACAGATG TTACTATTCC ATACCTGGCC ACTGATGTGA CTTGTGTAGG TCCAGGAGCA  2460
CACAAAGGTC AAAGTGTCAT ATCCCTTGAT CTGTATACGT GTGAGTTAGA TCTCACAAAC  2520
CTGATTCTGT TCTCAGTTTC CATATCATCA GTCCTCTTTC TTATGGTAGT TATGACAACA  2580
AGTCACCTCT TTTTCTGGGA TATGTGGTAC ATTTATTATT TTTGGAAAGC AAAGATAAAG  2640
GGGTATCAGC ATCTGCAATC CATGGAGTCT TGTTATGATG CTTTTATTGT GTATGACACT  2700
AAAAACTCAG CTGTGACAGA ATGGGTTTTG CAGGAGCTGG TGGCAAAATT GGAAGATCCA  2760
AGAGAAAAAC ACTTCAATTT GTGTCTAGAA GAAAGAGACT GGCTACCAGG ACAGCCAGTT  2820
CTAGAAAACC TTTCCCAGAG CATACAGCTC AGCAAAAGA CAGTGTTTGT GATGACACAG   2880
AAATATGCTA AGACTGAGAG TTTTAAGATG GCATTTTATT TGTCTCATCA GAGGCTCCTG  2940
GATGAAAAAG TGGATGTGAT TATCTTGATA TTCTTGGAAA AGCCTCTTCA GAAGTCTAAG  3000
TTTCTTCAGC TCAGGAAGAG ACTCTGCAGG AGCTGTGTGC TTGAGTGGCC TGCAAATCCA  3060
CAGGCTCACC CATACTTCTG GCAGTGCCTG AAAAATGCCC TGACCACAGA CAATCATGTG  3120
GCTTATAGTC AAATGTTCAA GGAAACAGTC                                  3150
```

TABLE 11

Amino Acid Sequences of Murine TLR7 and Human TLR7

```
                       .         :         .         :         .         :
                                                                              60
hTLR7.pep   MVFPMWTLKRQILILFNIILISKLLGARWFPKTLPCDVTLDVPKNHVIVDCTDKHLTEIP   60
mTLR7.pep   MVFSMWTRKRQILIFLNMLLVSRVFGFRWFPKTLPCEVKVNIPEAHVIVDCTDKHLTEIP   60

.         :         .         :         .         :
                                                                             120
hTLR7.pep   GGIPTNTTNLTLTINHIPDISPASFHRLDHLVEIDFRCNCVPIPLGSKNNMCIKRLQIKP  120
mTLR7.pep   EGIPTNTTNLTLTINHIPSISPDSFRRLNHLEEIDLRCNCVPVLLGSKANVCTKRLQIRP  120

.         :         .         :         .         :
                                                                             180
hTLR7.pep   RSFSGLTYLKSLYLDGNQLLEIPQGLPPSLQLLSLEANNIFSIRKENLTELANIEILYLG  180
mTLR7.pep   GSFSGLSDLKALYLDGNQLLEIPQDLPSSLHLLSLEANNIFSITKENLTELVNIETLYLG  180

.         :         .         :         .         :
                                                                             240
hTLR7.pep   QNCYYRNPCYVSYSIEKDAFLNLTKLKVLSLKDNNVTAVPTVLPSTLTELYLYNNMIAKI  240
mTLR7.pep   QNCYYRNPCNVSYSIEKDAFLVMRNLKVLSLKDNNVTAVPTTLPPNLLELYLYNNIIKKI  240

.         :         .         :         .         :
                                                                             300
hTLR7.pep   QEDDFNNLNQLQILDLSGNCPRCYNAPFPCAPCKNNSPLQIPVNAFDALTELKVLRLHSN  300
mTLR7.pep   QENDFNNLNELQVLDLSGNCPRCYNVPYPCTPCENNSPLQIHDNAENSLTELKVLRLHSN  300

.         :         .         :         .         :
                                                                             360
hTLR7.pep   SLQHVPPRWFKNINKLQELDLSQNFLAKEIGDAKFLHFLPSLIQLDLSFNFELQVYRASM  360
mTLR7.pep   SLQHVPPTWFKNMRNLQELDLSQNYLAREIEEAKFLHFLPNLVELDFSFNYELQVYHASI  360

.         :         .         :         .         :
                                                                             420
hTLR7.pep   NLSQAFSSLKSLKILRIRGYVFKELKSFNLSPLHNLQNLEVLDLGTNFIKIANLSMFKQF  420
mTLR7.pep   TLPHSLSSLENLKILRVKGYVFKELKNSSLSVLHKLPRLEVLDLGTNFIKIADLNIFKHF  420

.         :         .         :         .         :
                                                                             480
hTLR7.pep   KRLKVIDLSVNKISPSGDSSEVGFCSNARTSVESYEPQVLEQLHYFRYDKYARSCRFKNK  480
mTLR7.pep   ENLKLIDLSVNKISPSEESREVGFCPNAQTSVDRHGPQVLEALHYFRYDEYARSCRFKNK  480

.         :         .         :         .         :
                                                                             540
hTLR7.pep   EA-SFMSVNESCYKYGQTLDLSKNSIFFVKSSDFQHLSFLKCLNLSGNLISQTLNGSEFQ  539
mTLR7.pep   EPPSFLPLNADCHIYGQTLDLSRNNIFFIKPSDFQHLSFLKCLNLSGNTIGQTLNGSELW  540

.         :         .         :         .         :
                                                                             600
hTLR7.pep   PLAELRYLDFSNNRLDLLHSTAFEELHKLEVLDISSNSHYFQSEGITHNLNFTKNLKVLQ  599
mTLR7.pep   PLRELRYLDFSNNRLDLLYSTAFEELQSLEVLDLSSNSHYFQAEGITHMLNFTKKLRLLD  600

.         :         .         :         .         :
                                                                             660
hTLR7.pep   KLMMNDNDISSSTSRTMESESLRTLEFRGNHLOVLWREGDNRYLQLFKNLLKLEELDISK  659
mTLR7.pep   KLMMNDNDISTSASRTMESDSLRILEFRGNHLOVLWRAGDNRYLDFFKNLFNLEVLDISR  660

.         :         .         :         .         :
                                                                             720
hTLR7.pep   NSLSFLPSGVFOGMPPNLKNLSLAKNGLKSFSWKKLQCLKNLETLDLSHNQLTTVPERLS  719
mTLR7.pep   NSLNSLPPEVFEGMFPNLKNLSLAKNGLKSFFWDRLQLLKHLEILDLSHNQLTKVPERLA  720

.         :         .         :         .         :
                                                                             780
hTLR7.pep   NCSRSLKNLILKNNQIRSLTKYFLQDAFQLRYLDLSSNKIQMIQKTSFPENVLNNLGNLL  779
mTLR7.pep   NCSKSLTTLILKHNQIRQLTKYFLEOALQLRYLDISSNKIQVIQKTSFPENvVNNLEMLV  780

.         :         .         :         .         :
                                                                             840
hTLR7.pep   LHHNRFLCTCDAVWFVWWVNHTEVTIPYLATDVTCVGPGAHKGQSVISLDLYTCELDLTN  839
mTLR7.pep   LHHNRFLCNCDAVWFVWWVNHTDVTIFYLATDVTCVGFGAHKGQSVISLDLYTCELDLTN  840

.         :         .         :         .         :
                                                                             900
hTLR7.pep   LILFSLSISVSLFLMVMMTASHLYFWDVWYIYHFCKAKIKGYQRLISPOCCYDAFIVYDT  899
mTLR7.pep   LILFSVSISSVLFLMVVMTTSHLFFWDMWYIYYFWKAKIKGYQHLQSMESCYDAFIVYDT  900

.         :         .         :         .         :
                                                                             960
hTLR7.pep   KDPAVTEWVLAELVAKLEDPREKHFNLCLEERDWLPGQPVLENLSQSIQLSKKTVFVMTD  959
mTLR7.pep   KNSAVTEWVLQELVAKLEDPREKHFNLCLEERDWLPGQPVLENLSQSIQLSKKTVFVMTQ  960

.         :         .         :         .         :
                                                                            1020
bb210788.pep                         VDVIILIFLVKPFQKFNFL*LRKRISRSSVLECPPNP   37
aa276879.pep                                   QKSKFLQLRKRLCRSSVLEWPANP   24
aa266744.pep                                  LGKPLQKSKFLQLRKRLCRSSVLEWFANP   29
bb116163.pep        IETFQMPSFLSIQRLLDDKVDVIILIFLE*PL*KSKFLQLRKRFCRSSVLEWPANP   56
hTLR7.pep   KYAKTENFKIAFYLSHQRLMDEKVDVIILIFLEKPFQKSKFLQLRKRLCGSSVLEWPTNP 1019
mTLR7.pep   KYAKTESFKMAFYLSHQRLLOEKVDVIILIFLEKPLQKSKFLQLRKRLCRSSvLEWFANP 1020

.         :         .         :         .         :
                                                                            1080
bb210788.pep   QAHPYFWQCLKNALTTDNHVAYSQMFKETV   67
aa276879.pep   QAHPYFWQCLKNALTTDNHVAYSQMFKETV   54
aa266744.pep   QAHPYFWQCLKNALTTDNHVAYSQMFKETV   59
bb116163.pep   QAHPYFWQCLKNALTTDNHVAYSQMFKETV   86
```

TABLE 11-continued

Amino Acid Sequences of Murine TLR7 and Human TLR7

| | | |
|---|---|---|
| hTLR7.pep | QAHPYFWQCLKNALTTDNHVAYSQVFKETV | 1049 |
| mTLR7.pep | QAHPYFWQCLKNALTTDNHVAYSQMFKETV | 1050 |

In Table 11 the sequences are assigned as follows: mTLR7.pep, SEQ ID NO:175; hTLR7.pep, SEQ ID NO:170; bb210788.pep, SEQ ID NO:176; aa276879.pep, SEQ ID NO:177; aa266744.pep, SEQ ID NO:178; and bb116163.pep, SEQ ID NO:179.

Example 18

Method of Cloning Human TLR8

Two accession numbers in the GenBank database, AF245703 and AF246971, describe the DNA sequence for human TLR8. To create an expression vector for human TLR8, human TLR8 cDNA was amplified from a cDNA made from human peripheral mononuclear blood cells (PBMC) using the primers 5'-CTGCGCTGCTGCAAGT-TACGGAATG-3' (SEQ ID NO:180) and 5'-GCGCGAAAT-CATGACTTAACGTCAG-3 (SEQ ID NO:181). The fragment was cloned into pGEM-T Easy vector (Promega), cut with the restriction enzyme NotI and ligated into a NotI-digested pcDNA3.1 expression vector (Invitrogen). The insert was fully sequenced and translated into protein. The cDNA sequence for hTLR8 is SEQ ID NO:182, is presented in Table 12. The open reading frame starts at base 83, ends at base 3208, and codes for a protein of 1041 amino acids. SEQ ID NO:183 (Table 13), corresponding to bases 83-3205 of SEQ ID NO:182 (Table 12), is the coding region for the polypeptide of SEQ ID NO:184 (Table 14).

The protein sequence of the cloned hTLR8 cDNA matches the sequence described under the GenBank accession number AF245703. The sequence deposited under GenBank accession number AF246971 contains an insertion at the N-terminus of 15 amino acids (MKESSLQNSSCSLGKETKK; SEQ ID NO:185) and three single amino acid changes at positions 217 (P to S), 266 (L to P) and 867 (V to I).

TABLE 12 cDNA Seguence for Human TLR8 (5'to 3'; SEQ ID NO:182)

| | | | | | |
|---|---|---|---|---|---|
| gctcccggcc | gccatggcgg | ccgcgggaat | tcgattctgc | gctgctgcaa | gttacggaat | 60 |
| gaaaaattag | aacaacagaa | acatggaaaa | catgttcctt | cagtcgtcaa | tgctgacctg | 120 |
| cattttcctg | ctaatatctg | gttcctgtga | gttatgcgcc | gaagaaaatt | tttctagaag | 180 |
| ctatccttgt | gatgagaaaa | agcaaaatga | ctcagttatt | gcagagtgca | gcaatcgtcg | 240 |
| actacaggaa | gttccccaaa | cggtgggcaa | atatgtgaca | gaactagacc | tgtctgataa | 300 |
| tttcatcaca | cacataacga | atgaatcatt | tcaagggctg | caaaatctca | ctaaaataaa | 360 |
| tctaaaccac | aaccccaatg | tacagcacca | gaacgaaaat | cccggtatac | aatcaaatgg | 420 |
| cttgaatatc | acagacgggg | cattcctcaa | cctaaaaaac | ctaagggagt | tactgcttga | 480 |
| agacaaccag | ttaccccaaa | taccctctgg | tttgccagag | tctttgacag | aacttagtct | 540 |
| aattcaaaac | aatatataca | acataactaa | agagggcatt | tcaagactta | taaacttgaa | 600 |
| aaatctctat | ttggcctgga | actgctattt | taacaaagtt | tgcgagaaaa | ctaacataga | 660 |
| agatggagta | tttgaaacgc | tgacaaattt | ggagttgcta | tcactatctt | tcaattctct | 720 |
| ttcacacgtg | ccacccaaac | tgccaagctc | cctacgcaaa | cttttctga | gcaacaccca | 780 |
| gatcaaatac | attagtgaag | aagatttcaa | gggattgata | aatttaacat | tactagattt | 840 |
| aagcgggaac | tgtccgaggt | gcttcaatgc | cccatttcca | tgcgtgcctt | gtgatggtgg | 900 |
| tgcttcaatt | aatatagatc | gttttgcttt | tcaaaacttg | acccaacttc | gatacctaaa | 960 |
| cctctctagc | acttccctca | ggaagattaa | tgctgcctgg | tttaaaaata | tgcctcatct | 1020 |
| gaaggtgctg | gatcttgaat | tcaactattt | agtgggagaa | atagcctctg | ggcattttt | 1080 |
| aacgatgctg | ccccgcttag | aaatacttga | cttgtctttt | aactatataa | aggggagtta | 1140 |
| tccacagcat | attaatattt | ccagaaactt | ctctaaactt | ttgtctctac | gggcattgca | 1200 |
| tttaagaggt | tatgtgttcc | aggaactcag | agaagatgat | ttccagcccc | tgatgcagct | 1260 |
| tccaaactta | tcgactatca | acttgggtat | taattttatt | aagcaaatcg | atttcaaact | 1320 |

TABLE 12-continued cDNA Sequence for Human TLR8 (5' to 3'; SEQ ID NO:182)

```
tttccaaaat ttctccaatc tggaaattat ttacttgtca gaaaacagaa tatcaccgtt    1380
ggtaaaagat acccggcaga gttatgcaaa tagttcctct tttcaacgtc atatccggaa    1440
acgacgctca acagattttg agtttgaccc acattcgaac ttttatcatt tcacccgtcc    1500
tttaataaag ccacaatgtg ctgcttatgg aaaagcctta gatttaagcc tcaacagtat    1560
tttcttcatt gggccaaacc aatttgaaaa tcttcctgac attgcctgtt taaatctgtc    1620
tgcaaatagc aatgctcaag tgttaagtgg aactgaattt tcagccattc ctcatgtcaa    1680
atatttggat ttgacaaaca atagactaga ctttgataat gctagtgctc ttactgaatt    1740
gtccgacttg gaagttctag atctcagcta taattcacac tatttcagaa tagcaggcgt    1800
aacacatcat ctagaattta ttcaaaattt cacaaatcta aaagttttaa acttgagcca    1860
caacaacatt tatactttaa cagataagta taacctggaa agcaagtccc tggtagaatt    1920
agttttcagt ggcaatcgcc ttgacatttt gtggaatgat gatgacaaca ggtatatctc    1980
cattttcaaa ggtctcaaga atctgacacg tctggattta tcccttaata ggctgaagca    2040
catcccaaat gaagcattcc ttaatttgcc agcgagtctc actgaactac atataaatga    2100
taatatgtta aagtttttta actggacatt actccagcag tttcctcgtc tcgagttgct    2160
tgacttacgt ggaaacaaac tactcttttt aactgatagc ctatctgact ttacatcttc    2220
ccttcggaca ctgctgctga gtcataacag gatttcccac ctaccctctg gctttctttc    2280
tgaagtcagt agtctgaagc acctcgattt aagttccaat ctgctaaaaa caatcaacaa    2340
atccgcactt gaaactaaga ccaccaccaa attatctatg ttggaactac acggaaaccc    2400
ctttgaatgc acctgtgaca ttggagattt ccgaagatgg atggatgaac atctgaatgt    2460
caaaattccc agactggtag atgtcatttg tgccagtcct ggggatcaaa gagggaagag    2520
tattgtgagt ctggagctaa caacttgtgt ttcagatgtc actgcagtga tattattttt    2580
cttcacgttc tttatcacca ccatggttat gttggctgcc ctggctcacc atttgttta    2640 ctgggatgtt tggttatat ataatgtgtg tttagctaag gtaaaaggct acaggtctct    2700
ttccacatcc caaactttct atgatgctta catttcttat gacaccaaag acgcctctgt    2760
tactgactgg gtgataaatg agctgcgcta ccaccttgaa gagagccgag acaaaaacgt    2820
tctcctttgt ctagaggaga gggattggga cccgggattg gccatcatcg acaacctcat    2880
gcagagcatc aaccaaagca agaaaacagt atttgtttta accaaaaaat atgcaaaaag    2940
ctggaacttt aaaacagctt tttacttggc tttgcagagg ctaatggatg agaacatgga    3000
tgtgattata tttatcctgc tggagccagt gttacagcat tctcagtatt tgaggctacg    3060
gcagcggatc tgtaagagct ccatcctcca gtggcctgac aacccgaagg cagaaggctt    3120
gttttggcaa actctgagaa atgtggtctt gactgaaaat gattcacggt ataacaatat    3180
gtatgtcgat tccattaagc aatactaact gacgttaagt catgatttcg cgcaatcact    3240
agtgaattcg cggccgcctg caggtcgacc atatgggaga gctcccaacg cgttggatgc    3300
atagcttgag                                                          3310
```

TABLE 13

| Coding Region for Human TLR8 (5' to 3'; SEQ ID NO:183) | |
|---|---|
| atggaaaaca tgttccttca gtcgtcaatg ctgacctgca ttttcctgct aatatctggt | 60 |
| tcctgtgagt tatgcgccga agaaaatttt tctagaagct atccttgtga tgagaaaaag | 120 |
| caaaatgact cagttattgc agagtgcagc aatcgtcgac tacaggaagt tccccaaacg | 180 |
| gtgggcaaat atgtgacaga actagacctg tctgataatt tcatcacaca cataacgaat | 240 |
| gaatcatttc aagggctgca aaatctcact aaaataaatc taaaccacaa ccccaatgta | 300 |
| cagcaccaga acggaaatcc cggtatacaa tcaaatggct tgaatatcac agacggggca | 360 |
| ttcctcaacc taaaaaacct aagggagtta ctgcttgaag acaaccagtt accccaaata | 420 |
| ccctctggtt tgccagagtc tttgacagaa cttagtctaa ttcaaaacaa tatatacaac | 480 |
| ataactaaag agggcatttc aagacttata aacttgaaaa atctctattt ggcctggaac | 540 |
| tgctatttta caaagtttg cgagaaaact aacatagaag atggagtatt tgaaacgctg | 600 |
| acaaatttgg agttgctatc actatctttc aattctcttt cacacgtgcc acccaaactg | 660 |
| ccaagctccc tacgcaaact ttttctgagc aacacccaga tcaaatacat tagtgaagaa | 720 |
| gatttcaagg gattgataaa tttaacatta ctagatttaa gcgggaactg tccgaggtgc | 780 |
| ttcaatgccc catttccatg cgtgccttgt gatggtggtg cttcaattaa tatagatcgt | 840 |
| tttgcttttc aaaacttgac ccaacttcga tacctaaacc tctctagcac ttccctcagg | 900 |
| aagattaatg ctgcctggtt taaaaatatg cctcatctga aggtgctgga tcttgaattc | 960 |
| aactatttag tgggagaaat agcctctggg gcatttttaa cgatgctgcc ccgcttagaa | 1020 |
| atacttgact tgtcttttaa ctatataaag gggagttatc cacagcatat taatatttcc | 1080 |
| agaaacttct ctaaactttt gtctctacgg gcattgcatt taagaggtta tgtgttccag | 1140 |
| gaactcagag aagatgattt ccagccctg atgcagcttc caaacttatc gactatcaac | 1200 |
| ttgggtatta attttattaa gcaaatcgat ttcaaacttt tccaaaattt ctccaatctg | 1260 |
| gaaattattt acttgtcaga aaacagaata tcaccgttgg taaaagatac ccggcagagt | 1320 |
| tatgcaaata gttcctcttt tcaacgtcat atccggaaac gacgctcaac agattttgag | 1380 |
| tttgacccac attcgaactt ttatcatttc acccgtcctt aataaagcc acaatgtgct | 1440 |
| gcttatggaa aagccttaga tttaagcctc aacagtattt tcttcattgg gccaaaccaa | 1500 |
| tttgaaaatc ttcctgacat tgcctgttta aatctgtctg caaatagcaa tgctcaagtg | 1560 |
| ttaagtggaa ctgaattttc agccattcct catgtcaaat atttggattt gacaaacaat | 1620 |
| agactagact ttgataatgc tagtgctctt actgaattgt ccgacttgga agttctagat | 1680 |
| ctcagctata attcacacta tttcagaata gcaggcgtaa cacatcatct agaatttatt | 1740 |
| caaaatttca caaatctaaa agttttaaac ttgagccaca caacattta tactttaaca | 1800 |
| gataagtata acctggaaag caagtccctg gtagaattag ttttcagtgg caatcgcctt | 1860 |
| gacatttgt ggaatgatga tgacaacagg tatatctcca ttttcaaagg tctcaagaat | 1920 |
| ctgacacgtc tggatttatc ccttaatagg ctgaagcaca tcccaaatga agcattcctt | 1980 |
| aatttgccag cgagtctcac tgaactacat ataaatgata atatgttaaa gttttttaac | 2040 |
| tggacattac tccagcagtt tcctcgtctc gagttgcttg acttacgtgg aaacaaacta | 2100 |
| ctcttttaa ctgatagcct atctgacttt acatcttccc ttcggacact gctgctgagt | 2160 |
| cataacagga tttcccacct accctctggc tttctttctg aagtcagtag tctgaagcac | 2220 |
| ctcgatttaa gttccaatct gctaaaaaca atcaacaaat ccgcacttga aactaagacc | 2280 |
| accaccaaat tatctatgtt ggaactacac ggaaacccct ttgaatgcac ctgtgacatt | 2340 |

TABLE 13-continued

Coding Region for Human TLR8 (5' to 3'; SEQ ID NO:183)

```
ggagatttcc gaagatggat ggatgaacat ctgaatgtca aaattcccag actggtagat    2400
gtcatttgtg ccagtcctgg ggatcaaaga gggaagagta ttgtgagtct ggagctaaca    2460
acttgtgttt cagatgtcac tgcagtgata ttatttttct tcacgttctt tatcaccacc    2520
atggttatgt tggctgccct ggctcaccat ttgtttact gggatgtttg gtttatatat      2580
aatgtgtgtt tagctaaggt aaaaggctac aggtctcttt ccacatccca aactttctat    2640
gatgcttaca tttcttatga caccaaagac gcctctgtta ctgactgggt gataaatgag    2700
ctgcgctacc accttgaaga gagccgagac aaaaacgttc tcctttgtct agaggagagg    2760
gattgggacc cgggattggc catcatcgac aacctcatgc agagcatcaa ccaaagcaag    2820
aaaacagtat ttgttttaac caaaaaatat gcaaaaagct ggaactttaa aacagctttt     2880
tacttggctt tgcagaggct aatggatgag aacatggatg tgattatatt tatcctgctg    2940
gagccagtgt tacagcattc tcagtatttg aggctacggc agcggatctg taagagctcc    3000
atcctccagt ggcctgacaa cccgaaggca gaaggcttgt tttggcaaac tctgagaaat    3060
gtggtcttga ctgaaaatga ttcacggtat aacaatatgt atgtcgattc cattaagcaa    3120
tac                                                                   3123
```

TABLE 14

Amino Acid Sequence of Human TLR8

```
                              .         :         .         :         .         :    60
AF245703.pep                  MENMFLQSSMLTCIFLLISGSCELCAEENFSRSYFCDEKKQN    42
hTLR8.pep                     MENMFLQSSMLTCIFLLISGSCELCAEENFSRSYPCDEKKQN    42
AF246971.pep  MKESSLQNSSCSLGKETKKENMFLQSSMLTCIFLLISGSCELCAEENFSRSYPCDEKKQN    60

.         :         .         :         .         :   120
AF24 5703.pep DSVIAECSNRRLQEVPQTVGKYVTELDLSONFITHITNESFQGLQNLTKINLNHNPNVQH   102
hTLR8.pep     DSVIAECSNRRLQEVPQTVGKYVTELDLSDNFITHITNESFQGLQNLTKINLNHNPNVQH   102
AF24 6971.pep DSVIAECSNRRLQEVPQTVGKYVTELDLSDNFITHITNESFQGLQNLTKINLNHNPNVQH   120

.         :         .         :         .         :   180
AF245703.pep  QNGNPGIQSNGLNITDGAFLNLKNLRELLLEDNQLPQIPSGLPESLTELSLIQNNIYNIT   162
hTLR8.pep     QNGNPGIQSNGLNITDGAFLNLKNLRELLLEDNQLPQIPSGLPESLTELSLIQNNIYNIT   162
AF246971.pep  QNGNPGIQSNGLNITDGAFLNLKNLRELLLEDNQLFQIPSGLPESLTELSLIQNNIYNIT   180

.         :         .         :         .         :   240
AF245703.pep  KEGISRLINLKNLYLAWNCYFNKVCEKTNIEDGVFETLTNLELLSLSFNSLSHVPPKLPS   222
hTLR8.pep     KEGISRLINLKNLYLAWNCYFNKVCEKTNIEDGVFETLTNLELLSLSFNSLSHVPPKLPS   222
AF246971.pep  KEGISRLINLKNLYLAWNCYFNKVCEKTNIEDGVFETLTNLELLSLSFNSLSHVSPKLPS   240

.         :         .         :         .         :   300
AF245703.pep  SLRKLFLSNTQIKYISEEDFKGLINLTLLDLSGNCPRCFNAPFPCVPCDGGASINIDRFA   282
hTLR8.pep     SLRKLFLSNTQIKYISEEDFKGLINLTLLDLSGNCPRCFNAPFPCVPCDGGASINIDRFA   282
AF246971.pep  SLRKLFLSNTQIKYISEEDFKGLINLTLLDLSGNCPRCFNAFFPCVPCDGGASINIDRFA   300

.         :         .         :         .         :   360
AF245703.pep  FQNLTQLRYLNLSSTSLRKINAAWFKNMPHLKVLDLEFNYLVGEIASGAFLTMLPRLEIL   342
hTLR8.pep     FQNLTQLRYLNLSSTSLRKINAAWFKNNPHLKVLDLEFNYLVGEIASGAFLTMLPRLEIL   342
AF246971.pep  FQNLTQLRYLNLSSTSLRKINAAWFKNMPHLKVLDLEFNYLVGEIASGAFLTMLPRLEIL   360

.         :         .         :         .         :   420
AF245703.pep  DLSFNYIKGSYFQHINISRNFSKLLSLRALHLRGYVFQELREDDFQPLMQLPNLSTINLG   402
hTLR8.pep     DLSFNYIKGSYFQHINISRNFSKLLSLRALHLRGYVFQELREDDFQPLMQLPNLSTINLG   402
AF246971.pep  DLSFNYIKGSYPQHINISRNFSKPLSLRALHLRGYVFQELREODFQFLMQLPNLSTINLG   420

.         :         .         :         .         :   480
AF245703.pep  INFIKQIDFKLFQNFSNLEIIYLSENRISPLVKDTRQSYANSSSFQRHIRKRRSTDFEFD   462
hTLR8.pep     INFIKQIDFKLFQNFSNLEIIYLSENRISPLVKDTRQSYANSSSFQRHIRKRRSTDFEFD   462
AF246971.pep  INFIKQIDFKLFQNFSNLEIIYLSENRISPLVKOTRQSYANSSSFQRHIRKRRSTDFEFD   480

.         :         .         :         .         :   540
```

TABLE 14-continued

Amino Acid Sequence of Human TLR8

```
                                                                                             :
AF245703.pep  PHSNFYHFTRPLIKPQCAAYGKALDLSLNSIFFIGPNQFENLPDIACLNLSANSNAQVLS  522
hTLR8.pep     PHSNFYHFTRPLIKPQCAAYGKALDLSLNSIFFIGPNQFENLPDIACLNLSANSNAQVLS  522
AF246971.pep  PHSNFYHFTRFLIKPQCAAYGKALDLSLNSIFFIGPNQFENLPDIACLNLSANSNAQVLS  540

.         :         .         :         .         :         600
AF245703.pep  GTEFSAIPHVKYLDLTNNRLDFDNASALTELSDLEVLDLSYNSHYFRIAGVTHHLEFIQN  582
hTLR8.pep     GTEFSAIPHVKYLDLTNNRLDFDNASALTELSDLEVLDLSYNSHYFRIAGVTHHLEFIQN  582
AF246971.pep  GTEFSAIPHVKYLDLTNNRLDFDNASALTELSDLEVLDLSYNSHYFRIAGVTHHLEFIQN  600

.         :         .         :         .         :         660
AF245703.pep  FTNLKVLNLSHNNIYTLTDKYNLESKSLVELVFSGNRLDILWNDDDNRYISIFKGLKNLT  642
hTLR8.pep     FTNLKVLNLSHNNIYTLTDKYNLESKSLVELVFSGNRLDILWNDDDNRYISIFKGLKNLT  642
AF246971.pep  FTNLKVLNLSHNNIYTLTDKYNLESKSLVELVFSGNRLDILWNDDDNRYISIFKGLKNLT  660

.         :         .         :         .         :         720
AF245703.pep  RLDLSLNRLKHIPNEAFLNLPASLTELHINDNMLKFFNWTLLQQFPRLELLDLRGNKLLF  702
hTLR8.pep     RLDLSLNRLKHIPNEAFLNLPASLTELHINDNMLKFFNWTLLQQFPRLELLDLRGNKLLF  702
AF246971.pep  RLDLSLNRLKHIPNEAFLNLPASLTELHINDNMLKFFNWTLLQQFPRLELLDLRGNKLLF  720

.         :         .         :         .         :         780
AF245703.pep  LTOSLSDFTSSLRTLLLSHNRISHLPSGFLSEVSSLKHLDLSSNLLKTINKSALETKTTT  762
hTLR8.pep     LTDSLSDFTSSLRTLLLSHNRISHLPSGFLSEVSSLKHLDLSSNLLKTINKSALETKTTT  762
AF246971.pep  LTDSLSDFTSSLRTLLLSHNRISHLPSGFLSEVSSLKHLDLSSNLLKTINKSALETKTTT  780

.         :         .         :         .         :         840
AF245703.pep  KLSMLELHGNPFECTCDIGDFRRWMDEHLNVKIPRLVDVICASPGDQRGKSIVSLELTTC  822
hTLR8.pep     KLSMLELHGNPFECTCDIGDFRRWMDEHLNVKIPRLVDVICASPGDQRGKSIVSLELTTC  822
AF246971.pep  KLSMLELHGNPFECTCDIGDFRRWMDEHLNVKIPRLVODICAsPGDQRGKSIVSLELTTC  840

.         :         .         :         .         :         900
AF245703.pep  VSDVTAVILFFFTFFITTMVMLAALAHHLFYWDVWFIYNVCLAKVKGYRSLSTSQTFYDA  882
hTLR8.pep     VSDVTAVILFFFTFFITTMVMLAALAHHLFYWDVWFIYNVCLAKVKGYRSLSTSQTFYDA  882
AF246971.pep  VSDVTAVILFFFTFFITTMVMLAALAHHLFYWDVWFIYNVCLAKVKGYRSLSTSQTFYDA  900

.         :         .         :         .         :         960
AF245703.pep  YISYDTKDASVTDWVINELRYHLEESRDKNVLLCLEERDWDPGLAIIDNLMQSINQSKKT  942
hTLR8.pep     YISYDTKDASVTDWVINELRYHLEESRDKNVLLCLEERDWDPGLAIIDNLMQSINQSKKT  942
AF246971.pep  YISYDTKDASVTDWVINELRYHLEESRDKNVLLCLEERDWDPGLAIIDNLMQSINQSKKT  960

.         :         .         :         .         :        1020
AF245703.pep  VFVLTKKYAKSWNFKTAFYLALQRLMDENMDVIIFILLEPVLQHSQYLRLRQRICKSSIL 1002
hTLR8.pep     VFVLTKKYAKSWNFKTAFYLALQRLMDENMDVIIFILLEPVLQHSQYLRLRQRICKSSIL 1002
AF246971.pep  VFVLTKKYAKSWNFKTAFYLALQRLMDENMDVIIFILLEPVLQHSQYLRLRQRICKSSIL 1020

.         :         .         :    .         :             1080
AF245703.pep  QWPDNPKAEGLFWQTLRNVVLTENDSRYNNMYVDSIKQY                      1041
hTLR8.pep     QWPDNPKAEGLFWQTLRNVVLTENDSRYNNMYVDSIKQY                      1041
AF246971.pep  QWPDNPKAEGLFWQTLRNVVLTENDSRYNNMYVDSIKQY                      1059
```

In Table 14 the sequences are assigned as follows: hTLR8.pep, SEQ ID NO:184; AF245703.pep, SEQ ID NO:186; and AF246971.pep, SEQ ID NO:187.

Example 19

Method of Cloning the Murine TLR8

Alignment of human TLR8 protein sequence with mouse EST database using tfasta yielded 1 hit with mouse EST sequence bf135656. Two primers were designed that bind to bf135656 sequence for use in a RACE-PCR to amplify 5' and 3' ends of the murine TLR8 cDNA. The library used for the RACE PCR was a mouse spleen marathon-ready cDNA commercially available from Clontech. A 5' fragment with a length of 2900 bp and a 3' fragment with a length of 2900 bp obtained by this method were cloned into Promega pGEM-T Easy vector. After sequencing of the 5' end and 3' end of each fragment, partial sequences of mTLR8 were obtained and allowed the design of primers for amplification of the complete murine TLR8 cDNA.

Three independent PCR reactions were set up using a spleen murine cDNA from Clontech as a template with the primers 5'-GAGAGAAACAAACGTTTTACCTTC-3' (SEQ ID NO:188) and 5'-GATGGCAGAGTCGTGACTTCCC-3' (SEQ ID NO:189). The resulting amplification products were cloned into pGEM-T Easy vector, fully sequenced, translated into protein, and aligned to the human TLR8 protein sequence (GenBank accession number AF245703). The cDNA sequence for mTLR8 is SEQ ID NO:190, presented in Table 15. The open reading frame of mTLR8 starts at base 59, ends at base 3157, and codes for a protein of 1032 amino acids. SEQ ID NO:191 (Table 16), corresponding to bases 59-3154 of SEQ ID NO:190 (Table 15), is the coding region for the polypeptide of SEQ ID NO:192 (Table 17). To create an expression vector for murine TLR8, cDNA pGEM-T Easy vector with the mTLR8 insert was cut with NotI, the fragment isolated, and ligated into a NotI-digested pcDNA3.1 expression vector (Invitrogen).

TABLE 15

| cDNA Sequence for Murine TLR8 (5' to 3'; SEQ ID NO:190) | |
|---|---|
| attcagagtt ggatgttaag agagaaacaa acgttttacc ttcctttgtc tatagaacat | 60 |
| ggaaaacatg cccctcagt catggattct gacgtgcttt tgtctgctgt cctctggaac | 120 |
| cagtgccatc ttccataaag cgaactattc cagaagctat ccttgtgacg agataaggca | 180 |
| caactccctt gtgattgcag aatgcaacca tcgtcaactg catgaagttc cccaaactat | 240 |
| aggcaagtat gtgacaaaca tagacttgtc agacaatgcc attacacata taacgaaaga | 300 |
| gtcctttcaa aagctgcaaa acctcactaa aatcgatctg aaccacaatg ccaaacaaca | 360 |
| gcacccaaat gaaaataaaa atggtatgaa tattacagaa ggggcacttc tcagcctaag | 420 |
| aaatctaaca gttttactgc tggaagacaa ccagttatat actatacctg ctgggttgcc | 480 |
| tgagtctttg aaagaactta gcctaattca aacaatata tttcaggtaa ctaaaaacaa | 540 |
| cactttggg cttaggaact tggaaagact ctatttgggc tggaactgct attttaaatg | 600 |
| taatcaaacc tttaaggtag aagatggggc atttaaaaat cttatacact tgaaggtact | 660 |
| ctcattatct ttcaataacc ttttctatgt gccccccaaa ctaccaagtt ctctaaggaa | 720 |
| acttttctg agtaatgcca aaatcatgaa catcactcag gaagacttca aggactgga | 780 |
| aaatttaaca ttactagatc tgagtggaaa ctgtccaagg tgttacaatg ctccatttcc | 840 |
| ttgcacacct tgcaaggaaa actcatccat ccacatacat cctctggctt ttcaaagtct | 900 |
| cacccaactt ctctatctaa acctttccag cacttccctc aggacgattc cttctacctg | 960 |
| gtttgaaaat ctgtcaaatc tgaaggaact ccatcttgaa ttcaactatt tagttcaaga | 1020 |
| aattgcctcg ggggcatttt taacaaaact acccagttta caaatccttg atttgtcctt | 1080 |
| caactttcaa tataaggaat atttacaatt tattaatatt tcctcaaatt tctctaagct | 1140 |
| tcgttctctc aagaagttgc acttaagagg ctatgtgttc cgagaactta aaaagaagca | 1200 |
| tttcgagcat ctccagagtc ttccaaactt ggcaaccatc aacttgggca ttaactttat | 1260 |
| tgagaaaatt gatttcaaag cttttccagaa tttttccaaa ctcgacgtta tctatttatc | 1320 |
| aggaaatcgc atagcatctg tattagatgg tacagattat tcctcttggc gaaatcgtct | 1380 |
| tcggaaacct ctctcaacag acgatgatga gtttgatcca cacgtgaatt tttaccatag | 1440 |
| caccaaacct ttaataaagc cacagtgtac tgcttatggc aaggccttgg atttaagttt | 1500 |
| gaacaatatt ttcattattg ggaaaagcca atttgaaggt tttcaggata tcgcctgctt | 1560 |
| aaatctgtcc ttcaatgcca atactcaagt gtttaatggc acagaattct cctccatgcc | 1620 |
| ccacattaaa tatttggatt taaccaacaa cagactagct tttgatgata caatgctttt | 1680 |
| cagtgatctt cacgatctag aagtgctgga cctgagccac aatgcacact atttcagtat | 1740 |
| agcagggta acgcaccgtc taggatttat ccagaactta ataaacctca gggtgttaaa | 1800 |
| cctgagccac aatggcattt acaccctcac agaggaaagt gagctgaaaa gcatctcact | 1860 |
| gaaagaattg gttttcagtg gaaatcgtct tgaccatttg tggaatgcaa atgatggcaa | 1920 |
| atactggtcc atttttaaaa gtctccagaa tttgatacgc ctggacttat catacaataa | 1980 |
| ccttcaacaa atcccaaatg gagcattcct caatttgcct cagagcctcc aagagttact | 2040 |
| tatcagtggt aacaaattac gtttctttaa ttggacatta ctccagtatt ttcctcacct | 2100 |
| tcacttgctg gatttatcga gaatgagct gtattttcta cccaattgcc tatctaagtt | 2160 |
| tgcacattcc ctggagacac tgctactgag ccataatcat ttctctcacc taccctctgg | 2220 |
| cttcctctcc gaagccagga atctggtgca cctggatcta gtttcaaca caataaagat | 2280 |
| gatcaataaa tcctccctgc aaaccaagat gaaaacgaac ttgtctattc tggagctaca | 2340 |

TABLE 15-continued cDNA Sequence for Murine TLR8 (5' to 3'; SEQ ID NO:190)

| | | | | | |
|---|---|---|---|---|---|
| tgggaactat | tttgactgca | cgtgtgacat | aagtgatttt | cgaagctggc | tagatgaaaa | 2400 |
| tctgaatatc | acaattccta | aattggtaaa | tgttatatgt | tccaatcctg | gggatcaaaa | 2460 |
| atcaaagagt | atcatgagcc | tagatctcac | gacttgtgta | tcggatacca | ctgcagctgt | 2520 |
| cctgttttc | ctcacattcc | ttaccacctc | catggttatg | ttggctgctc | tggttcacca | 2580 |
| cctgttttac | tgggatgttt | ggtttatcta | tcacatgtgc | tctgctaagt | taaaaggcta | 2640 |
| caggacttca | tccacatccc | aaactttcta | tgatgcttat | atttcttatg | acaccaaaga | 2700 |
| tgcatctgtt | actgactggg | taatcaatga | actgcgctac | caccttgaag | agagtgaaga | 2760 |
| caaaagtgtc | ctcctttgtt | tagaggagag | ggattgggat | coaggattac | ccatcattga | 2820 |
| taacctcatg | cagagcataa | accagagcaa | gaaaacaatc | tttgttttaa | ccaagaaata | 2880 |
| tgccaagagc | tggaacttta | aaacagcttt | ctacttggcc | ttgcagaggc | taatggatga | 2940 |
| gaacatggat | gtgattattt | tcatcctcct | ggaaccagtg | ttacagtact | cacagtacct | 3000 |
| gaggcttcgg | cagaggatct | gtaagagctc | catcctccag | tggcccaaca | atcccaaagc | 3060 |
| agaaaacttg | ttttggcaaa | gtctgaaaaa | tgtggtcttg | actgaaaatg | attcacggta | 3120 |
| tgacgatttg | tacattgatt | ccattaggca | atactagtga | tgggaagtca | cgactctgcc | 3180 |
| atcataaaaa | cacacagctt | ctccttacaa | tgaaccgaat | | | 3220 |

TABLE 16

Coding Region for Murine TLR8 (5' to 3'; SEQ ID NO:191)

| | | | | | |
|---|---|---|---|---|---|
| atggaaaaca | tgccccctca | gtcatggatt | ctgacgtgct | tttgtctgct | gtcctctgga | 60 |
| accagtgcca | tcttccataa | agcgaactat | tccagaagct | atccttgtga | cgagataagg | 120 |
| cacaactccc | ttgtgattgc | agaatgcaac | catcgtcaac | tgcatgaagt | tccccaaact | 180 |
| ataggcaagt | atgtgacaaa | catagacttg | tcagacaatg | ccattacaca | tataacgaaa | 240 |
| gagtcctttc | aaaagctgca | aaacctcact | aaaatcgatc | tgaaccacaa | tgccaaacaa | 300 |
| cagcacccaa | atgaaaataa | aaatggtatg | aatattacag | aagggggcact | tctcagccta | 360 |
| agaaatctaa | cagtttact | gctggaagac | aaccagttat | atactataco | tgctgggttg | 420 |
| cctgagtctt | tgaaagaact | tagcctaatt | caaaacaata | tatttcaggt | aactaaaaac | 480 |
| aacacttttg | ggcttaggaa | cttggaaaga | ctctatttgg | gctggaactg | ctattttaaa | 540 |
| tgtaatcaaa | cctttaaggt | agaagatggg | gcatttaaaa | atcttataca | cttgaaggta | 600 |
| ctctcattat | ctttcaataa | ccttttctat | gtgcccccca | aactaccaag | ttctctaagg | 660 |
| aaacttttc | tgagtaatgc | caaaatcatg | aacatcactc | aggaagactt | caaggactg | 720 |
| gaaaatttaa | cattactaga | tctgagtgga | aactgtccaa | ggtgttacaa | tgctccattt | 780 |
| ccttgcacac | cttgcaagga | aaactcatcc | atccacatac | atcctctggc | ttttcaaagt | 840 |
| ctcacccaac | ttctctatct | aaacctttcc | agcacttccc | tcaggacgat | tccttctacc | 900 |
| tggtttgaaa | atctgtcaaa | tctgaaggaa | ctccatcttg | aattcaacta | tttagttcaa | 960 |
| gaaattgcct | cggggggcatt | tttaacaaaa | ctacccagtt | tacaaatcct | tgatttgtcc | 1020 |
| ttcaactttc | aatataagga | atatttacaa | tttattaata | tttcctcaaa | tttctctaag | 1080 |
| cttcgttctc | tcaagaagtt | gcacttaaga | ggctatgtgt | tccagaaact | taaaagaag | 1140 |
| catttcgagc | atctccagag | tcttccaaac | ttggcaacca | tcaacttggg | cattaacttt | 1200 |

TABLE 16-continued

Coding Region for Murine TLR8 (5' to 3'; SEQ ID NO:191)

```
attgagaaaa ttgatttcaa agctttccag aattttttcca aactcgacgt tatctatttta   1260
tcaggaaatc gcatagcatc tgtattagat ggtacagatt attcctcttg gcgaaatcgt   1320
cttcggaaac ctctctcaac agacgatgat gagtttgatc cacacgtgaa ttttttaccat   1380
agcaccaaac ctttaataaa gccacagtgt actgcttatg gcaaggcctt ggatttaagt   1440
ttgaacaata tttcattat tgggaaaagc caatttgaag gttttcagga tatcgcctgc   1500
ttaaatctgt ccttcaatgc caatactcaa gtgtttaatg gcacagaatt ctcctccatg   1560
ccccacatta aatatttgga tttaaccaac aacagactag actttgatga taacaatgct   1620
ttcagtgatc ttcacgatct agaagtgctg gacctgagcc acaatgcaca ctatttcagt   1680
atagcagggg taacgcaccg tctaggattt atccagaact aataaaccct cagggtgtta   1740
aacctgagcc acaatggcat ttacaccctc acagaggaaa gtgagctgaa aagcatctca   1800
ctgaaagaat tggttttcag tggaaatcgt cttgaccatt tgtggaatgc aaatgatggc   1860
aaatactggt ccatttttaa aagtctccag aatttgatac gcctggactt atcatacaat   1920
aaccttcaac aaatcccaaa tggagcattc ctcaatttgc ctcagagcct ccaagagtta   1980
cttatcagtg gtaacaaatt acgtttcttt aattggacat tactccagta ttttcctcac   2040
cttcacttgc tggatttatc gagaaatgag ctgtattttc tacccaattg cctatctaag   2100
tttgcacatt ccctggagac actgctactg agccataatc atttctctca cctaccctct   2160
ggcttcctct ccgaagccag gaatctggtg cacctggatc taagtttcaa cacaataaag   2220
atgatcaata aatcctccct gcaaaccaag atgaaaacga acttgtctat tctggagcta   2280
catgggaact attttgactg cacgtgtgac ataagtgatt ttcgaagctg gctagatgaa   2340
aatctgaata tcacaattcc taaattggta aatgttatat gttccaatcc tggggatcaa   2400
aaaatcaaaga gtatcatgag cctagatctc acgacttgtg tatcggatac cactgcagct   2460
gtcctgtttt tcctcacatt ccttaccacc tccatggtta tgttggctgc tctggttcac   2520
cacctgtttt actgggatgt ttggtttatc tatcacatgt gctctgctaa gttaaaaggc   2580
tacaggactt catccacatc ccaaactttc tatgatgctt atattctta tgacaccaaa   2640
gatgcatctg ttactgactg ggtaatcaat gaactgcgct accaccttga agagagtgaa   2700
gacaaaagtg tcctcctttg tttagaggag agggattggg atccaggatt acccatcatt   2760
gataacctca tgcagagcat aaaccagagc aagaaaacaa tctttgtttt aaccaagaaa   2820
tatgccaaga gctggaactt taaaacagct ttctacttgg ccttgcagag gctaatggat   2880
gagaacatgg atgtgattat tttcatcctc ctggaaccag tgttacagta ctcacagtac   2940
ctgaggcttc ggcagaggat ctgtaagagc tccatcctcc agtggcccaa caatcccaaa   3000
gcagaaaact tgttttggca aagtctgaaa aatgtggtct tgactgaaaa tgattcacgg   3060
tatgacgatt tgtacattga ttccattagg caatac                             3096
```

TABLE 17

Amino Acid Sequences of Murine TLR8 and Human TLR8

```
                  .         :         .         :         .         :         .         :         .         :      60
mTLR8.pep    MENMPPQSWILTCFCLLSSGTSAIFHKANYSRSYPCDEIRHNSLVIAECNHRQLHEVPQT    60
hTLR8.pep    MENMFLQSSMLTCIFLLISGSCELCAEENFSRSYPCDEKKQNDSVIAECSNRRLQEVPQT    60

.         :         .         :         .         :         .         :         .         :     120
```

TABLE 17-continued

Amino Acid Sequences of Murine TLR8 and Human TLR8

```
mTLR8.pep  IGKYVTNIDLSDNAITHITKESFQKLQNLTKIDLNHNAKQQH----PNENKNGMNITEGA  116
hTLR8.pep  VGKYVTELDLSDNFITHITNESFQGLQNLTKINLNHNPNVQHQNGNPGIQSNGLNITDGA  120

.         :         .         :         .         :
                                                                          180
mTLR8.pep  LLSLRNLTVLLLEDNQLYTIPAGLPESLKELSLIQNNIFQVTKNNTFGLRNLERLYLGWN  176
hTLR8.pep  FLNLKNLRELLLEDNQLFQIPSGLPESLTELSLIQNNIYNITKEGISRLINLKNLyLAWN  180

.         :         .         :         .         :
                                                                          240
mTLR8.pep  CYFK--CNQTFKVEDGAFKNLIHLKVLSLSFNNLFYVPPKLFSSLRKLFLSNAKIMNITQ  234
hTLR8.pep  CYFNKVCEKT-NIEDGVFETLTNLELLSLSFNSLSHVPPKLFSSLRKLFLSNTQIKYISE  239

.         :         .         :         .         :
                                                                          300
mTLR8.pep  EDFKGLENLTLLDLSGNCPRCYNAFFPCTPCKENSSIHIHPLAFQSLTQLLYLNLSSTSL  294
hTLR8.pep  EDFKGLINLTLLDLSGNCPRCFNAPFPCVPCDGGASINIDRFAFQNLTQLRYLNLSSTSL  299

.         :         .         :         .         :
                                                                          360
mTLR8.pep  RTIPSTWFENLSNLKELHLEFNYLVQEIASGAFLTKLPSLQILDLSFNFQYKEYLQFINI  354
hTLR8.pep  RKINAAWFKNMPHLKVLDLEFNYLVGEIASGAFLTMLPRLEILDLSFNYIKGSYPQHINI  359

.         :         .         :         .         :
                                                                          420
mTLR8.pep  SSNFSKLRSLKKLHLRGYVFRELKKKHFEHLQSLPNLATINLGINFIEKIDFKAFQNFSK  414
hTLR8.pep  SRNFSKLLSLRALHLRGYVFQELREDQFQPLMQLPNLSTINLGINFIKQIDFKLFQNFSN  419

.         :         .         :         .         :
                                                                          480
mTLR8.pep  LDVIYLSGNRIASVLDGT--DY---SSWRNRLRKPLSTDDDEFDPHVNFYHSTKPLIKPQ  469
hTLR8.pep  LEIIYLSENRISPLVKDTRQSYANSSSFQRHIRKRRSTQF-EFDPHSNFYHFTRPLIKPQ  478

.         :         .         :         .         :
                                                                          540
mTLR8.pep  CTAYGKALQLSLNNIFIIGKSQFEGFQDIACLNLSFNANTQVFNGTEFSSMPHIKYLDLT  529
hTLR8.pep  CAAYGKALDLSLNSIFFIGFNQFENLFDIACLNLSANSNAQVLSGTEFSAIPHvKYLDLT  538

.         :         .         :         .         :
                                                                          600
mTLRB.pep  NNRLDFDDNNAFSQLHDLEVLDLSHNAHYFSIAGVTHRLGFIQNLINLRVLNLSHNGIYT  589
hTLR8.pep  NNRLDFDNASALTELSDLEVLDLSYNSHYFRIAGVTHHLEFIQNFTNLKVLNLSHNNIYT  598

.         :         .         :         .         :
                                                                          660
mTLR8.pep  LTEESELKSISLKELVFSGNRLDHLWNANOGKYWSIFKSLQNLIRLDLSYNNLQQIPNGA  649
hTLR8.pep  LTDKYNLESKSLVELVFSGNRLDILWNDDDNRYISIFKGLKNLTRLDLSLNRLKHIPNEA  658

.         :         .         :         .         :
                                                                          720
mTLR8.pep  FLNLPQSLQELLISGNKLRFFNWTLLQYFPHLHLLQLSRNELYFLFNCLSKFAHSLETLL  709
hTLR8.pep  FLNLPASLTELHINDNMLKFFNWTLLQQFPRLELLDLRGNKLLFLTDSLSDFTSSLRTLL  718

.         :         .         :         .         :
                                                                          780
bf135656.pep     NHFSHLPSGFLSEARNLVHLDLSFNTIKMINKSSLQTKIMKTNLSILELHGNYFDCTC   57
mTLR8.pep  LSHNHFSHLFSGFLSEARNLVHLDLSFNTIKMINKSSLQTKMKTNLSILELHGNYFDCTC  769
hTLR8.pep  LSHNRISHLPSGFLSEVSSLKHLDLSSNLLKTINKSALETKTTTKLSMLELHGNPFECTC  778

.         :         .         :         .         :
                                                                          840
bf135656.pep  DISDFRSWLDENLNITIPKLVNVICSNPGDQKSKSIMSLDLTTCVSDTTAAVLFFLTFLT  117
mTLR8.pep  DISDFRSWLDENLNITIPKLVNVICSNPGDQKSKSIMSLDLTTCVSDTTAAVLFFLTFLT  829
hTLR8.pep  DIGDFRRWMDEHLNVKIPRLVDVICASPGDQRGKSIVSLELTTCVSDVTAVILFFFTFFI  838

.         :         .         :         .         :
                                                                          900
bf135656.pep  TSMVNLAALVHHLFYWDVWFIYHMCSAKLKGYRTSSTSQTFYDAYISYDTKDASVTDWVI  177
mTLR8.pep  TSMVMLAALVHHLFYWDVWFIYHMCSAKLKGYRTSSTSQTFYDAYISYDTKDASVTDWVI  889
hTLR8.pep  TTMVMLAALAHHLFYWDVWFIYNVCLAKVKGYRSLSTSQTFYDAYISYDTKDASVTDWVI  898

.         :         .         :         .         :
                                                                          960
bf135656.pep  NELRYHLE                                                      185
mTLR8.pep  NELRYHLEESEDKSVLLCLEERDWDPGLPIIDNLMQSINQSKKTIFVLTKKYAKSWNFKT  949
hTLR8.pep  NELRYHLEESRDKNVLLCLEERDWDPGLAIIDNLMQSINQSKKTVFVLTKKYAKSWNFKT  958

.         :         .         :         .         :
                                                                         1020
mTLR8.pep  AFYLALQRLMDENMDVIIFILLEPVLQYSQYLRLRQRICKSSILQWPNNPKAENLFWQSL  1009
hTLR8.pep  AFYLALQRLMDENMDVIIFILLEPVLQHSQYLRLRQRICKSSILQWPDNPKAEGLFWQTL  1018

.         :         .         :         .         :
                                                                         1080
mTLR8.pep  KNVVLTENDSRYDDLYIDSIRQY                                      1032
hTLR8.pep  RNVVLTENDSRYNNMYVDSIKQY                                      1041
```

In Table 17 the sequences are assigned as follows: mTLR8.pep, SEQ ID NO:192; hTLR8.pep, SEQ ID NO:184; and bf135656.pep, SEQ ID NO:193.

Example 20

Transient Transfectants Expressing TLR8 and TLR7

The cloned human TLR7 and human TLR8 cDNA (our result) were cloned into the expression vector pcDNA3.1 (−) from Invitrogen using the NotI site. Utilizing a "gain of function" assay, hTLR7 and hTLR8 expression vectors were transiently expressed in human 293 fibroblasts (ATCC, CRL-1573) using the calcium phosphate method. Activation was monitored by IL-8 production after stimulus with CpG-ODN (2006 or 1668, 2 μM) or LPS (100 ng/ml). None of the stimuli used activated 293 cells transfected with either hTLR7 or hTLR8.

Example 21

Screening for TLR9, 8 and 7 Modulators

Human TLR receptors 9, 8 and 7 are expressed differentially among tissues which may be due to differences in promoter structure. Du X et al., *Eur Cytokine Netw* 11:362-71 (2000); Chuang T H et al., *Eur Cytokine Netw* 11:372-8 (2000). For the human Toll-like receptors 9, 8 and 7 the genomic locus has been defined and sequenced. TLR9 is located on chromosome 3 (GenBank accession numbers NT_005985, AC006252), TLR7 on chromosome X (GenBank accession numbers NT_011774, AC005859, AC003046) and TLR8 close to TLR7 also on chromosome X (GenBank accession numbers NT_011774, AC005859). To verify differences in the promoter regions the putative promoter region of each gene are cloned in reporter vectors like pGL2-Basic (Promega, Madison, Wis., USA) which contains the luciferase gene (luc) adjacent to a multiple cloning site. After transient transfection of these constructs in various cell lines, different stimuli can be tested for the activation of the inserted promoter region which is detected by luciferase activity. The promoter regions defined by the cloning of mTLR9, mTLR8 and mTLR7 can be utilized in the same manner. Definition of compounds that agonize or antagonize TLR9, 8, or 7 expression can be used to enhance or dampen responses to nucleic acid ligands or to any TLR9, 8 or 7 ligand defined by screening. These constructs can be adapted to high throughput screening after stable transfection similar to the use of TLR9 stable transfectants.

Each of the foregoing patents, patent applications and references is hereby incorporated by reference. While the invention has been described with respect to certain embodiments, it should be appreciated that many modifications and changes may be made by those of ordinary skill in the art without departing from the spirit of the invention. It is intended that such modification, changes and equivalents fall within the scope of the following claims.

Example 22

Method Cloning the Murine and Human Extracellular TLR9 Domain Fused to Human IgG1 Fc Human IgG1 Fc was amplified from human B cell cDNA using the sense and antisense primers 5' TATGGATCCTCT-TGTGACAAAACTCACACATGC (SEQ ID NO:216) and 5' ATA AAGCTTTCATTTACCCGGAGACAGGGAGAG (SEQ ID NO:217) and ligated into pcDNA3.1 (−) (Invitrogen) after digestion with the restriction endonucleases BamHI and HindIII creating the vector pcDNA-IgGFc. The extracellular domain of human TLR9 (amino acids 1 to 815) was amplified with the sense and antisense primers 5' TAT-GAATTCCCACCATGGGTTTCTGCCGCAG (SEQ ID NO:218) and 5' ATAGGATCCCCGGGGCACCAGGCCGC-CGCCGCGGCCGCCGGAGAGGGCCTCAT CCAGGC (SEQ ID NO:219). The primers amplify the extracellular domain of human TLR9 and create adjacent to amino acid 815 an additional NotI restriction site, a glycine linker and thrombin protease recognition site. The translated sequence of this region starting at amino acid 812 is DEALSG-GRGGGLVPRGS (SEQ ID NO:220). The fragment was cut with EcoRI and BamHI and cloned into pcDNA-IgGFc, creating the vector coding for the fusion protein of the extracellular domain of human TLR9 fused to the Fc part of human IgG1 (pcDNAhTLR9IgGFc). Expressed extracellular TLR9 protein can be separated from the IgG1 Fc fragment by digestion with Thrombin (see figure).

The extracellular part of murine TLR9 (amino acids 1 to 816) was amplified with the sense and antisense primers 5' TATATGCGGCCGCCCACCATGGTTCTCCGTCGAAG (SEQ ID NO:221) and 5' TATATGCGGCCGCCAGAGAG-GACCTCATCCAGGC (SEQ ID NO:222) and cloned into pcDNAhTLR9IgGFc after NotI digestion of PCR fragment and vector. This procedure exchanged the human extracellular part of TLR9 with the murine counterpart.

Example 23

Method of Expression and Purification of the Extracellular Domain of TLR9 Fused to Human IgG1 Fc Vector DNA coding for the human or murine TLR9 human IgGFc fusion protein was transfected by $Ca_2PO_4$ method into 293 fibroblast cells. Transfected cells were selected with 0.7 mg/ml G418 and cloned. Expression of fusion protein was monitored by enzyme-linked immunosorbent assay (ELISA). Cells were lysed in lysis buffer (PBS, 1% Triton X-100) and supernatant was applied to ELISA plates coated with polyclonal antibody against human IgG-Fc. Bound fusion protein was detected by incubation with biotinylated polyclonal antibodies against human IgG-Fc and streptavidin-horseradish peroxidase conjugate.

For purification of the fusion protein cell lysates from $10^9$ cells were produced and incubated with Protein A sepharose which binds tightly to human IgG-Fc. Incubation with the protease thrombin releases the soluble extracellular domain of human TLR9. FIG. 27 shows an example of the TLR9 fusion protein visualized by a silver stained SDS-gel. FIG. 27 demonstrates that lysates of transfected cells included a strong band travelling between 100 and 150 kD which was not present either in lysates of mock-transfected cells or in supernatants transfected or mock-transfected cells. The apparent molecular weight of the band decreased following thrombin treatment, consistent with cleavage at the thrombin protease recognition site interposed between the extracellular TLR9 domain and the Fc fragment.

Example 24

Method of Cloning the Murine and Human Extracellular TLR7 and TLR8 Domain Fused to Human IgG1 Fc and its Expression in 293 Cells The extracellular domains of murine TLR7 (amino acids 1 to 837), human TLR7 (amino acids 1 to 836), murine TLR8 (amino acids 1 to 816) and human TLR8 (amino acids 1 to 825) were amplified with the primer pairs 5' TATATGCGGC-CGCCCACCATGGTGTTTTCGATGTGGACACG (SEQ ID NO:223) and 5'TATATGCGGCCGCCATCTAACTCA-CACGTATACAGATC (SEQ ID NO:224); 5' TATATGCG-GCCGCCCACCATGGTGTTTCCAATGTGGACACTG (SEQ ID NO:225) and 5' TATATGCGGCCGC-CATCTAACTCACAGGTGTACAGATC (SEQ ID NO:226); 5' TATATGCGGCCGCCCACCATGGAAAA-CATGCCCCCTCAG (SEQ ID NO:227) and 5' TATATGCG-GCCGCCATCCGATACACAAGTCGTGAGATC (SEQ ID NO:228); and 5' TATATGCGGCCGCCCACCATG-GAAAACATGTTCCTTCAGTC (SEQ ID NO:229) and 5' TATATGCGGCCGCCATCTGAAACA-CAAGTTGTTAGCTC (SEQ ID NO:230), respectively. Fragments were cloned into pcDNA-IgGFc after NotI digestion.

Vector DNA coding for the extracellular domain of human or murine TLR7 or TLR8 fused to human IgGFc fusion protein was transfected by $Ca_2PO_4$ method into 293 fibroblast cells. Transfected cells were selected with 0.7 mg/ml G418 and cloned. Expression of fusion protein was monitored by ELISA. Cells were lysed in lysis buffer (PBS, 1% Triton X-100) and supernatant was applied to ELISA plates coated with polyclonal antibody against human IgG-Fc. Bound fusion protein was detected by incubation with biotinylated polyclonal antibodies against human IgG-Fc and Streptavidin-horseradish peroxidase conjugate.

Example 25

Method of Antibody Production Against Murine and Human TLR9 and Characterization of Activity C57/B6 mice were immunized three times by intraperitoneal administration of 20 µg of the extracellular domain of human TLR9 mixed with 10 nmol of the CpG-ODN 1668. B cells taken from immunized mice were fused with a non antibody producing B-cell hybridoma P3XAG8 using standard protocols. Hybridoma supernatants were screened for reactivity in ELISA using murine and human TLR9 fusion proteins. For identification of positive hybridomas ELISA plates were coated with polyclonal antibody against human IgG Fc and incubated with lysate containing murine or human TLR9 IgGFc fusion protein. Plates were then incubated with individual hybridoma supernatants, and bound TLR9-specific antibodies were detected by incubation with biotinylated polyclonal antibodies against murine IgG and Streptavidin-horseradish peroxidase conjugate.

Ten antibodies have been isolated which are of IgG1, IgG2a and IgG2b isotype. They have been tested for reactivity against human and murine TLR9 and their performance in western blotting or intracellular staining. Table 18 shows the names (ID), isotypes, reactivity and performance in western blotting and intracellular staining.

All isolated antibodies were readily purified using standard protein A affinity chromatography.

TABLE 18

Monclonal Antibodies Raised Against Murine and Human TLR9

| # | ID | Isotype | Reactivity in ELISAh9 mTLR9 | hTLR9 | Western Blotting | Intracellular Staining |
|---|------|------|-----|-----|-----|-----|
| 1 | 1-3A11 | G1 | YES | YES | YES | NO |
| 2 | 1-1B1 | G1 | YES | YES | YES | NO |
| 3 | 1-2A9 | G2a | NO | YES | YES | YES |
| 4 | 1-3F2 | G1 | YES | YES | YES | NO |
| 5 | 2-1E2 | G2a | NO | YES | YES | YES |
| 6 | 1-5G5 | G2a | YES | YES | YES | YES |
| 7 | 1-2F1 | G1 | YES | YES | YES | NO |
| 8 | 1-5F12 | G2b | NO | YES | NO | NO |
| 9 | 1-3C9 | G2a | NO | YES | YES | YES |
| 10 | 1-3F5 | G2b | NO | YES | NO | NO |

Example 26

Method for Intracellular Staining

Mock transfected 293 cells and human TLR9 transfected 293 cells were seeded on cover slips and cultured overnight. The following day cells were washed in PBS and fixed with 2% formalin for 10 minutes at room temperature. Cells were permeabilized with 0.2% saponin in PBS and incubated with 2 µg/ml anti human TLR9-specific antibody 2-1E2 for 1 h. After two wash steps cells were incubated with Alexis488-conjugated goat anti-mouse IgG antibody and TLR9 was visualized utilizing confocal microscopy on a Zeiss LSM510 microscope. Results indicated that cytoplasms of human TLR9 transfected 293 cells, but not mock transfected 293 cells, stained positive for human TLR9.

Example 27

Method for Western Blotting

Lysates of 293 cells transfected with murine TLR9, human TLR9 or murine TLR2 IgG1-Fc fusion protein were separated by SDS-PAGE. Proteins were transferred to a nylon membrane utilizing a BioRad semi dry blotter according to the manufacturer's protocol. The membrane was incubated with 2 µg/ml of the human TLR9-specific antibody 2-1E2, and human TLR9 was detected by polyclonal goat anti-mouse peroxidase conjugate. Peroxidase activity was monitored with ECL reagent (Amersham) and incubation of the membrane on film (see FIG. 29).

What is claimed is:

1. A cell-free screening method for identifying a CpG nucleic acid as a candidate pharmacological agent comprising:
   contacting a cell-free assay system comprising an isolated polypeptide comprising a Toll-like receptor (TLR) extracytoplasmic domain or fragment thereof selected from the group consisting of TLR7, TLR8, and TLR9 with a test CpG nucleic acid molecule;
   detecting presence or absence of binding to the TLR extracytoplasmic domain or fragment thereof by the test CpG nucleic acid molecule; and
   determining the test CpG nucleic acid molecule is a candidate pharmacological agent when specific binding to the TLR extracytoplasmic domain or fragment thereof is detected, wherein the TLR extracytoplasmic domain fragment at least includes a methyl-CpG binding domain (MBD) motif, a CCXC motif or both a MBD motif and a CCXC motif.

2. The method of claim 1, wherein the screening method is performed on a plurality of test CpG nucleic acid molecules.

3. The method of claim 1, wherein the TLR extracytoplasmic domain or fragment thereof is part of a complex with an isolated non-TLR polypeptide selected from the group consisting of MyD88, IRAK, TRAF6, IκB, NF-κB, and functional homologues and derivatives thereof.

4. The method of claim 1, wherein the TLR extracytoplasmic domain or fragment thereof is immobilized on a solid support, selected form a group comprising a multiwell plate, a slide, a BIAcore chip, a bead, or a column.

5. The method of claim 1, wherein the TLR extracytoplasmic domain or fragment thereof is fused with an Fc fragment of an antibody.

6. The method of claim 5, wherein the Fc fragment comprises a thrombin protease recognition site.

7. The method of claim 1, wherein the measuring is accomplished by a method selected from the group consisting of enzyme-linked immunosorbent assay (ELISA), biomolecular interaction assay (BIA), electromobility shift assay (EMSA), radioimmunoassay (RIA), polyacrylamide gel electrophoresis (PAGE), and Western blotting.

8. The method of claim 1, wherein detecting presence or absence of binding to the TLR extracytoplasmic domain or fragment thereof by the test CpG nucleic acid molecule is accomplished by a method selected from the group consisting of labeled in vitro protein binding assays, and signaling assays using detectable molecules.

9. The method of claim 1, wherein the isolated polypeptide comprising a Toll-like receptor (TLR) extracytoplasmic domain or fragment thereof is produced recombinantly, isolated from biological extracts, or synthesized in vitro.

10. The method of claim 1, wherein the isolated polypeptide comprising a Toll-like receptor (TLR) extracytoplasmic domain or fragment thereof comprises a chimeric protein comprising a fusion of a TLR polypeptide with another polypeptide capable of providing or enhancing protein-protein binding, enhancing signaling capability, facilitating detection, or enhancing stability of the TLR polypeptide under assay conditions.

11. The method of claim 1, wherein the isolated polypeptide comprising a Toll-like receptor (TLR) extracytoplasmic domain or fragment thereof is a constituent of a membrane-encapsulated space.

12. The method of claim 11, wherein the membrane-encapsulated, isolated polypeptide comprising a Toll-like receptor (TLR) extracytoplasmic domain or fragment thereof is added to an assay mixture.

13. The method of claim 12, wherein the assay mixture comprises one or more reagents selected form a group consisting of salts, buffers, neutral proteins, detergents, protease inhibitors, nuclease inhibitors, and antimicrobial agents.

14. The method of claim 1, further comprising a separation step to separate bound from unbound components.

15. The method of claim 14, wherein at least one of the components is immobilized on a solid substrate, from which the unbound components are separated.

16. The method of claim 1, wherein the TLR extracytoplasmic domain comprises amino acids 1 to about 819 of murine TLR9.

17. The method of claim 1, wherein the TLR extracytoplasmic domain comprises leucine-rich repeats (LRR).

18. The method of claim 1, wherein the MBD motif is set forth as any one of SEQ ID NOs: 126, 127, 210, or 211.

19. The method of claim 1, wherein the CCXC motif is set forth as any one of SEQ ID NOs: 196, 197, or 198.

20. The method of claim 1, wherein the MBD motif is set forth as any one of SEQ ID NOs: 126, 127, 210, or 211, and the CCXC motif is set forth as any one of SEQ ID NOs: 196, 197, or 198.

* * * * *

SEQUENCE LISTING

<160> NUMBER OF SEQ ID NOS: 230

<210> SEQ ID NO 1
<211> LENGTH: 3200
<212> TYPE: DNA
<213> ORGANISM: Mus musculus
<220> FEATURE:
<221> NAME/KEY: misc_feature
<222> LOCATION: (0)...(0)
<223> OTHER INFORMATION: Murine TLR9 cDNA

<400> SEQUENCE: 1

| | | | | | |
|---|---|---|---|---|---|
| tgtcagaggg | agcctcggga | gaatcctcca | tctcccaaca | tggttctccg | tcgaaggact | 60 |
| ctgcacccct | tgtccctcct | ggtacaggct | gcagtgctgg | ctgagactct | ggccctgggt | 120 |
| accctgcctg | ccttcctacc | ctgtgagctg | aagcctcatg | gcctggtgga | ctgcaattgg | 180 |
| ctgttcctga | agtctgtacc | ccgtttctct | gcggcagcat | cctgctccaa | catcacccgc | 240 |
| ctctccttga | tctccaaccg | tatccaccac | ctgcacaact | ccgacttcgt | ccacctgtcc | 300 |
| aacctgcggc | agctgaacct | caagtggaac | tgtccaccca | ctggccttag | cccctgcac | 360 |
| ttctcttgcc | acatgaccat | tgagcccaga | accttcctgg | ctatgcgtac | actggaggag | 420 |
| ctgaacctga | gctataatgg | tatcaccact | gtgcccgac | tgcccagctc | cctggtgaat | 480 |
| ctgagcctga | gccacaccaa | catcctggtt | ctagatgcta | acagcctcgc | cggcctatac | 540 |
| agcctgcgcg | ttctcttcat | ggacgggaac | tgctactaca | agaaccctg | cacaggagcg | 600 |
| gtgaaggtga | ccccaggcgc | cctcctgggc | ctgagcaatc | tcacccatct | gtctctgaag | 660 |
| tataacaacc | tcacaaaggt | gccccgccaa | ctgcccccca | gcctggagta | cctcctggtg | 720 |
| tcctataacc | tcattgtcaa | gctggggcct | gaagacctgg | ccaatctgac | ctcccttcga | 780 |
| gtacttgatg | tgggtgggaa | ttgccgtcgc | tgcgaccatg | cccccaatcc | ctgtatagaa | 840 |
| tgtggccaaa | agtccctcca | cctgcaccct | gagaccttcc | atcacctgag | ccatctggaa | 900 |
| ggcctggtgc | tgaaggacag | ctctctccat | acactgaact | cttcctggtt | ccaaggtctg | 960 |
| gtcaacctct | cggtgctgga | cctaagcgag | aactttctct | atgaaagcat | caaccacacc | 1020 |
| aatgcctttc | agaacctaac | ccgcctgcgc | aagctcaacc | tgtccttcaa | ttaccgcaag | 1080 |
| aaggtatcct | ttgcccgcct | ccacctggca | agttccttca | agaacctggt | gtcactgcag | 1140 |
| gagctgaaca | tgaacggcat | cttcttccgc | tcgctcaaca | agtacacgct | cagatggctg | 1200 |
| gccgatctgc | ccaaactcca | cactctgcat | cttcaaatga | acttcatcaa | ccaggcacag | 1260 |
| ctcagcatct | ttggtacctt | ccgagcccctt | cgctttgtgg | acttgtcaga | caatcgcatc | 1320 |
| agtgggcctt | caacgctgtc | agaagccacc | cctgaagagg | cagatgatgc | agagcaggag | 1380 |
| gagctgttgt | ctgcggatcc | tcacccagct | ccactgagca | ccctgcttc | taagaacttc | 1440 |
| atggacaggt | gtaagaactt | caagttcacc | atggacctgt | ctcggaacaa | cctggtgact | 1500 |
| atcaagccag | agatgtttgt | caatctctca | cgcctccagt | gtcttagcct | gagccacaac | 1560 |
| tccattgcac | aggctgtcaa | tggctctcag | ttcctgccgc | tgactaatct | gcaggtgctg | 1620 |
| gacctgtccc | ataacaaact | ggacttgtac | cactggaaat | cgttcagtga | gctaccacag | 1680 |
| ttgcaggccc | tggacctgag | ctacaacagc | cagcccttta | gcatgaaggg | tataggccac | 1740 |
| aatttcagtt | ttgtggccca | tctgtccatg | ctacacagcc | ttagcctggc | acacaatgac | 1800 |
| attcataccc | gtgtgtcctc | acatctcaac | agcaactcag | tgaggtttct | tgacttcagc | 1860 |
| ggcaacggta | tgggccgcat | gtgggatgag | gggggcctt | atctccattt | cttccaaggc | 1920 |

```
ctgagtggcc tgctgaagct ggacctgtct caaaataacc tgcatatcct ccggccccag    1980
aaccttgaca acctccccaa gagcctgaag ctgctgagcc tccgagacaa ctacctatct    2040
ttctttaact ggaccagtct gtccttcctg cccaacctgg aagtcctaga cctggcaggc    2100
aaccagctaa aggccctgac caatggcacc ctgcctaatg cacctcct ccagaaactg     2160 gatgtcagca gcaacagtat cgtctctgtg gtcccagcct tcttcgctct ggcggtcgag    2220
ctgaaagagg tcaacctcag ccacaacatt tcaagacgg tggatcgctc ctggtttggg    2280
cccattgtga tgaacctgac agttctagac gtgagaagca accctctgca ctgtgcctgt    2340
ggggcagcct tcgtagactt actgttggag gtgcagacca aggtgcctgg cctggctaat    2400
ggtgtgaagt gtggcagccc cggccagctg cagggccgta gcatcttcgc acaggacctg    2460
cggctgtgcc tggatgaggt cctctcttgg gactgctttg gcctttcact cttggctgtg    2520
gccgtgggca tggtggtgcc tatactgcac catctctgcg gctgggacgt ctggtactgt    2580
tttcatctgt gcctggcatg gctacctttg ctggcccgca gccgacgcag cgcccaagct    2640
ctcccctatg atgccttcgt ggtgttcgat aaggcacaga gcgcagttgc ggactgggtg    2700
tataacgagc tgcgggtgcg gctggaggag cggcgcggtc gccgagccct acgcttgtgt    2760
ctggaggacc gagattggct gcctggccag acgctcttcg agaacctctg gcttccatc    2820 tatgggagcc gcaagactct atttgtgctg gcccacacgg accgcgtcag tggcctcctg    2880
cgcaccagct cctgctggc tcagcagcgc ctgttggaag accgcaagga cgtggtggtg    2940
ttggtgatcc tgcgtccgga tgcccaccgc tcccgctatg tgcgactgcg ccagcgtctc    3000
tgccgccaga gtgtgctctt ctggccccag cagcccaacg ggcaggggg cttctgggcc    3060 cagctgagta cagcccctgac tagggacaac cgccacttct ataaccagaa cttctgccgg    3120
ggacctacag cagaatagct cagagcaaca gctggaaaca gctgcatctt catgcctggt    3180
tcccgagttg ctctgcctgc                                                3200

<210> SEQ ID NO 2
<211> LENGTH: 3096
<212> TYPE: DNA
<213> ORGANISM: Mus musculus
<220> FEATURE:
<221> NAME/KEY: misc_feature
<222> LOCATION: (0)...(0)
<223> OTHER INFORMATION: Murine TLR9 ORF

<400> SEQUENCE: 2
atggttctcc gtcgaaggac tctgcacccc ttgtccctcc tggtacaggc tgcagtgctg      60
gctgagactc tggccctggg taccctgcct gccttcctac cctgtgagct gaagcctcat     120
ggcctggtgg actgcaattg ctgttcctg aagtctgtac cccgtttctc tgcggcagca     180
tcctgctcca acatcacccg cctctccttg atctccaacc gtatccacca cctgcacaac    240
tccgacttcg tccacctgtc caacctgcgg cagctgaacc tcaagtggaa ctgtccaccc    300
actggcctta gccccctgca cttctcttgc cacatgacca ttgagcccag aaccttcctg    360
gctatgcgta cactggagga gctgaacctg agctataatg gtatcaccac tgtgccccga    420
ctgcccagct ccctggtgaa tctgagcctg agccacacca catcctggt tctagatgct    480 aacagcctcg ccggcctata cagcctgcgc gttctcttca tggacgggaa ctgctactac    540
aagaacccct gcacaggagc ggtgaaggtg accccaggcg ccctcctggg cctgagcaat    600
ctcacccatc tgtctctgaa gtataacaac ctcacaaagg tgccccgcca actgccccc    660
```

```
agcctggagt acctcctggt gtcctataac ctcattgtca agctggggcc tgaagacctg    720
gccaatctga cctcccttcg agtacttgat gtgggtggga attgccgtcg ctgcgaccat    780
gcccccaatc cctgtataga atgtggccaa aagtccctcc acctgcaccc tgagaccttc    840
catcacctga gccatctgga aggcctggtg ctgaaggaca gctctctcca tacactgaac    900
tcttcctggt tccaaggtct ggtcaacctc tcggtgctgg acctaagcga gaactttctc    960
tatgaaagca tcaaccacac caatgccttt cagaacctaa cccgcctgcg caagctcaac   1020
ctgtccttca attaccgcaa gaaggtatcc tttgcccgcc tccacctggc aagttccttc   1080
aagaacctgg tgtcactgca ggagctgaac atgaacggca tcttcttccg ctcgctcaac   1140
aagtacacgc tcagatggct ggccgatctg cccaaactcc acactctgca tcttcaaatg   1200
aacttcatca accaggcaca gctcagcatc tttggtacct tccgagccct tcgctttgtg   1260
gacttgtcag acaatcgcat cagtgggcct tcaacgctgt cagaagccac ccctgaagag   1320
gcagatgatg cagagcagga ggagctgttg tctgcggatc ctcacccagc tccactgagc   1380
accctgctt ctaagaactt catggacagg tgtaagaact tcaagttcac catggacctg   1440
tctcggaaca acctggtgac tatcaagcca gagatgtttg tcaatctctc acgcctccag   1500
tgtcttagcc tgagccacaa ctccattgca caggctgtca atggctctca gttcctgccg   1560
ctgactaatc tgcaggtgct ggacctgtcc cataacaaac tggacttgta ccactggaaa   1620
tcgttcagtg agctaccaca gttgcaggcc ctggacctga gctacaacag ccagcccttt   1680
agcatgaagg gtataggcca caatttcagt tttgtggccc atctgtccat gctacacagc   1740
cttagcctgg cacacaatga cattcatacc cgtgtgtcct cacatctcaa cagcaactca   1800
gtgaggtttc ttgacttcag cggcaacggt atgggccgca tgtgggatga gggggggcctt   1860
tatctccatt tcttccaagg cctgagtggc ctgctgaagc tggacctgtc tcaaaataac   1920
ctgcatatcc tccggcccca gaaccttgac aacctcccca agagcctgaa gctgctgagc   1980
ctccgagaca actacctatc tttctttaac tggaccagtc tgtccttcct gcccaacctg   2040
gaagtcctag acctggcagg caaccagcta aaggccctga ccaatggcac cctgcctaat   2100
ggcacctcc tccagaaact ggatgtcagc agcaacagta tcgtctctgt ggtcccagcc   2160
ttcttcgctc tggcggtcga gctgaaagag gtcaacctca ccacaacat tctcaagacg   2220
gtggatcgct cctggttgg gcccattgtg atgaacctga cagttctaga cgtgagaagc   2280
aaccctctgc actgtgcctg tgggcagcc ttcgtagact tactgttgga ggtgcagacc   2340
aaggtgcctg gcctggctaa tggtgtgaag tgtggcagcc ccggccagct gcagggccgt   2400
agcatcttcg cacaggacct gcggctgtgc ctggatgagg tcctctcttg ggactgcttt   2460
ggcctttcac tcttggctgt ggccgtgggc atggtggtgc ctatactgca ccatctctgc   2520
ggctgggacg tctggtactg ttttcatctg tgcctggcat ggctaccttt gctggcccgc   2580
agccgacgca gcgcccaagc tctcccctat gatgccttcg tggtgttcga taaggcacag   2640
agcgcagttg cggactgggt gtataacgag ctgcgggtgc ggctggagga gcggcgcggt   2700
cgccgagccc tacgcttgtg tctggaggac cgagattggc tgcctggcca gacgctcttc   2760
gagaacctct gggcttccat ctatgggagc cgcaagactc tatttgtgct ggcccacacg   2820
gaccgcgtca gtgccctcct cgcaccagc ttcctgctgg ctcagcagcg cctgttggaa   2880
gaccgcaagg acgtggtggt gttggtgatc ctgcgtccgg atgcccaccg ctcccgctat   2940
gtgcgactgc gccagcgtct ctgccgccag agtgtgctct tctggcccca gcagcccaac   3000
gggcagggg gcttctgggc ccagctgagt acagccctga ctagggacaa ccgccacttc   3060
```

-continued

```
tataaccaga acttctgccg gggacctaca gcagaa                                     3096
```

<210> SEQ ID NO 3
<211> LENGTH: 1032
<212> TYPE: PRT
<213> ORGANISM: Mus musculus

<400> SEQUENCE: 3

| Met | Val | Leu | Arg | Arg | Thr | Leu | His | Pro | Leu | Ser | Leu | Leu | Val | Gln |
|-----|-----|-----|-----|-----|-----|-----|-----|-----|-----|-----|-----|-----|-----|-----|
| 1   |     |     |     | 5   |     |     |     |     | 10  |     |     |     |     | 15  |

| Ala | Ala | Val | Leu | Ala | Glu | Thr | Leu | Ala | Leu | Gly | Thr | Leu | Pro | Ala | Phe |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

Leu Pro Cys Glu Leu Lys Pro His Gly Leu Val Asp Cys Asn Trp Leu
            35                  40                  45

Phe Leu Lys Ser Val Pro Arg Phe Ser Ala Ala Ser Cys Ser Asn
 50                  55                  60

Ile Thr Arg Leu Ser Leu Ile Ser Asn Arg Ile His His Leu His Asn
 65                  70                  75                  80

Ser Asp Phe Val His Leu Ser Asn Leu Arg Gln Leu Asn Leu Lys Trp
                 85                  90                  95

Asn Cys Pro Pro Thr Gly Leu Ser Pro Leu His Phe Ser Cys His Met
            100                 105                 110

Thr Ile Glu Pro Arg Thr Phe Leu Ala Met Arg Thr Leu Glu Glu Leu
        115                 120                 125

Asn Leu Ser Tyr Asn Gly Ile Thr Thr Val Pro Arg Leu Pro Ser Ser
130                 135                 140

Leu Val Asn Leu Ser Leu Ser His Thr Asn Ile Leu Val Leu Asp Ala
145                 150                 155                 160

Asn Ser Leu Ala Gly Leu Tyr Ser Leu Arg Val Leu Phe Met Asp Gly
                165                 170                 175

Asn Cys Tyr Tyr Lys Asn Pro Cys Thr Gly Ala Val Lys Val Thr Pro
            180                 185                 190

Gly Ala Leu Leu Gly Leu Ser Asn Leu Thr His Leu Ser Leu Lys Tyr
        195                 200                 205

Asn Asn Leu Thr Lys Val Pro Arg Gln Leu Pro Pro Ser Leu Glu Tyr
210                 215                 220

Leu Leu Val Ser Tyr Asn Leu Ile Val Lys Leu Gly Pro Glu Asp Leu
225                 230                 235                 240

Ala Asn Leu Thr Ser Leu Arg Val Leu Asp Val Gly Gly Asn Cys Arg
                245                 250                 255

Arg Cys Asp His Ala Pro Asn Pro Cys Ile Glu Cys Gly Gln Lys Ser
            260                 265                 270

Leu His Leu His Pro Glu Thr Phe His His Leu Ser His Leu Glu Gly
        275                 280                 285

Leu Val Leu Lys Asp Ser Ser Leu His Thr Leu Asn Ser Ser Trp Phe
290                 295                 300

Gln Gly Leu Val Asn Leu Ser Val Leu Asp Leu Ser Glu Asn Phe Leu
305                 310                 315                 320

Tyr Glu Ser Ile Asn His Thr Asn Ala Phe Gln Asn Leu Thr Arg Leu
                325                 330                 335

Arg Lys Leu Asn Leu Ser Phe Asn Tyr Arg Lys Lys Val Ser Phe Ala
            340                 345                 350

Arg Leu His Leu Ala Ser Ser Phe Lys Asn Leu Val Ser Leu Gln Glu
        355                 360                 365

-continued

```
Leu Asn Met Asn Gly Ile Phe Phe Arg Ser Leu Asn Lys Tyr Thr Leu
    370                 375                 380

Arg Trp Leu Ala Asp Leu Pro Lys Leu His Thr Leu His Leu Gln Met
385                 390                 395                 400

Asn Phe Ile Asn Gln Ala Gln Leu Ser Ile Phe Gly Thr Phe Arg Ala
                405                 410                 415

Leu Arg Phe Val Asp Leu Ser Asp Asn Arg Ile Ser Gly Pro Ser Thr
                420                 425                 430

Leu Ser Glu Ala Thr Pro Glu Glu Ala Asp Ala Glu Gln Glu Glu
            435                 440                 445

Leu Leu Ser Ala Asp Pro His Pro Ala Pro Leu Ser Thr Pro Ala Ser
    450                 455                 460

Lys Asn Phe Met Asp Arg Cys Lys Asn Phe Lys Phe Thr Met Asp Leu
465                 470                 475                 480

Ser Arg Asn Asn Leu Val Thr Ile Lys Pro Glu Met Phe Val Asn Leu
                485                 490                 495

Ser Arg Leu Gln Cys Leu Ser Leu Ser His Asn Ser Ile Ala Gln Ala
            500                 505                 510

Val Asn Gly Ser Gln Phe Leu Pro Leu Thr Asn Leu Gln Val Leu Asp
            515                 520                 525

Leu Ser His Asn Lys Leu Asp Leu Tyr His Trp Lys Ser Phe Ser Glu
    530                 535                 540

Leu Pro Gln Leu Gln Ala Leu Asp Leu Ser Tyr Asn Ser Gln Pro Phe
545                 550                 555                 560

Ser Met Lys Gly Ile Gly His Asn Phe Ser Phe Val Ala His Leu Ser
                565                 570                 575

Met Leu His Ser Leu Ser Leu Ala His Asn Asp Ile His Thr Arg Val
            580                 585                 590

Ser Ser His Leu Asn Ser Asn Ser Val Arg Phe Leu Asp Phe Ser Gly
    595                 600                 605

Asn Gly Met Gly Arg Met Trp Asp Glu Gly Gly Leu Tyr Leu His Phe
    610                 615                 620

Phe Gln Gly Leu Ser Gly Leu Leu Lys Leu Asp Leu Ser Gln Asn Asn
625                 630                 635                 640

Leu His Ile Leu Arg Pro Gln Asn Leu Asp Asn Leu Pro Lys Ser Leu
                645                 650                 655

Lys Leu Leu Ser Leu Arg Asp Asn Tyr Leu Ser Phe Phe Asn Trp Thr
            660                 665                 670

Ser Leu Ser Phe Leu Pro Asn Leu Glu Val Leu Asp Leu Ala Gly Asn
    675                 680                 685

Gln Leu Lys Ala Leu Thr Asn Gly Thr Leu Pro Asn Gly Thr Leu Leu
    690                 695                 700

Gln Lys Leu Asp Val Ser Ser Asn Ser Ile Val Ser Val Pro Ala
705                 710                 715                 720

Phe Phe Ala Leu Ala Val Glu Leu Lys Glu Val Asn Leu Ser His Asn
                725                 730                 735

Ile Leu Lys Thr Val Asp Arg Ser Trp Phe Gly Pro Ile Val Met Asn
            740                 745                 750

Leu Thr Val Leu Asp Val Arg Ser Asn Pro Leu His Cys Ala Cys Gly
    755                 760                 765

Ala Ala Phe Val Asp Leu Leu Leu Glu Val Gln Thr Lys Val Pro Gly
770                 775                 780
```

-continued

| | | | | | | | | | | | | | |
|---|---|---|---|---|---|---|---|---|---|---|---|---|---|
| Leu | Ala | Asn | Gly | Val | Lys | Cys | Gly | Ser | Pro | Gly | Gln | Leu | Gln | Gly | Arg |
| 785 | | | | 790 | | | | | 795 | | | | | 800 |

Ser Ile Phe Ala Gln Asp Leu Arg Leu Cys Leu Asp Glu Val Leu Ser
            805                 810                 815

Trp Asp Cys Phe Gly Leu Ser Leu Leu Ala Val Ala Val Gly Met Val
        820                 825                 830

Val Pro Ile Leu His His Leu Cys Gly Trp Asp Val Trp Tyr Cys Phe
    835                 840                 845

His Leu Cys Leu Ala Trp Leu Pro Leu Leu Ala Arg Ser Arg Arg Ser
    850                 855                 860

Ala Gln Ala Leu Pro Tyr Asp Ala Phe Val Val Phe Asp Lys Ala Gln
865                 870                 875                 880

Ser Ala Val Ala Asp Trp Val Tyr Asn Glu Leu Arg Val Arg Leu Glu
                885                 890                 895

Glu Arg Arg Gly Arg Arg Ala Leu Arg Leu Cys Leu Glu Asp Arg Asp
                900                 905                 910

Trp Leu Pro Gly Gln Thr Leu Phe Glu Asn Leu Trp Ala Ser Ile Tyr
            915                 920                 925

Gly Ser Arg Lys Thr Leu Phe Val Leu Ala His Thr Asp Arg Val Ser
        930                 935                 940

Gly Leu Leu Arg Thr Ser Phe Leu Leu Ala Gln Gln Arg Leu Leu Glu
945                 950                 955                 960

Asp Arg Lys Asp Val Val Val Leu Val Ile Leu Arg Pro Asp Ala His
                965                 970                 975

Arg Ser Arg Tyr Val Arg Leu Arg Gln Arg Leu Cys Arg Gln Ser Val
            980                 985                 990

Leu Phe Trp Pro Gln Gln Pro Asn Gly Gln Gly Gly Phe Trp Ala Gln
        995                 1000                1005

Leu Ser Thr Ala Leu Thr Arg Asp Asn Arg His Phe Tyr Asn Gln Asn
    1010                1015                1020

Phe Cys Arg Gly Pro Thr Ala Glu
1025                1030

<210> SEQ ID NO 4
<211> LENGTH: 3352
<212> TYPE: DNA
<213> ORGANISM: Homo sapiens
<220> FEATURE:
<221> NAME/KEY: misc_feature
<222> LOCATION: (0)...(0)
<223> OTHER INFORMATION: Human TLR9 per GenBank AF245704

<400> SEQUENCE: 4

```
aggctggtat aaaaatctta cttcctctat tctctgagcc gctgctgccc ctgtgggaag      60
ggacctcgag tgtgaagcat ccttccctgt agctgctgtc cagtctgccc gccagaccct     120
ctggagaagc ccctgccccc cagcatgggt ttctgccgca cgccctgca cccgctgtct      180 ctcctggtgc aggccatcat gctggccatg accctggccc tgggtacctt gcctgccttc     240
ctaccctgtg agctccagcc ccacggcctg gtgaactgca actggctgtt cctgaagtct     300
gtgccccact ctccatggc agcaccccgt ggcaatgtca ccagcctttc cttgtcctcc      360
aaccgcatcc accacctcca tgattctgac tttgcccacc tgcccagcct gcggcatctc     420
aacctcaagt ggaactgccc gccggttggc tcagcccca tgcacttccc ctgccacatg     480
accatcgagc ccagcacctt cttggctgtg cccaccctgg aagagctaaa cctgagctac    540
aacaacatca tgactgtgcc tgcgctgccc aaatccctca tatccctgtc cctcagccat    600
```

-continued

```
accaacatcc tgatgctaga ctctgccagc ctcgccggcc tgcatgccct gcgcttccta    660
ttcatggacg gcaactgtta ttacaagaac ccctgcaggc aggcactgga ggtggccccg    720
ggtgccctcc ttggcctggg caacctcacc cacctgtcac tcaagtacaa caacctcact    780
gtggtgcccc gcaacctgcc ttccagcctg gagtatctgc tgttgtccta caaccgcatc    840
gtcaaactgg cgcctgagga cctggccaat ctgaccgccc tgcgtgtgct cgatgtgggc    900
ggaaattgcc gccgctgcga ccacgctccc aaccctgca tggagtgccc tcgtcacttc     960
ccccagctac atcccgatac cttcagccac ctgagccgtc ttgaaggcct ggtgttgaag   1020
gacagttctc tctcctggct gaatgccagt tggttccgtg ggctgggaaa cctccgagtg   1080
ctggacctga gtgagaactt cctctacaaa tgcatcacta aaaccaaggc cttccagggc   1140
ctaacacagc tgcgcaagct taacctgtcc ttcaattacc aaaagagggt gtcctttgcc   1200
cacctgtctc tggccccttc cttcgggagc ctggtcgccc tgaaggagct ggacatgcac   1260
ggcatcttct tccgctcact cgatgagacc acgctccggc cactggcccg cctgcccatg   1320
ctccagactc tgcgtctgca gatgaacttc atcaaccagg cccagctcgg catcttcagg   1380
gccttccctg gcctgcgcta cgtggacctg tcggacaacc gcatcagcgg agcttcggag   1440
ctgacagcca ccatggggga ggcagatgga ggggagaagg tctggctgca gcctggggac   1500
cttgctccgg ccccagtgga cactcccagc tctgaagact tcaggcccaa ctgcagcacc   1560
ctcaacttca ccttggatct gtcacggaac aacctggtga ccgtgcagcc ggagatgttt   1620
gcccagctct cgcacctgca gtgcctgcgc ctgagccaca actgcatctc gcaggcagtc   1680
aatggctccc agttcctgcc gctgaccggt ctgcaggtgc tagacctgtc ccgcaataag   1740
ctggacctct accacgagca tcattcacg gagctaccgc gactggaggc cctggacctc   1800
agctacaaca gccagccctt tggcatgcag ggcgtgggcc acaacttcag cttcgtggct   1860
cacctgcgca cctgcgcca cctcagcctg gcccacaaca acatccacag ccaagtgtcc   1920
cagcagctct gcagtacgtc gctgcgggcc ctggacttca gcggcaatgc actgggccat   1980
atgtgggccg agggagacct ctatctgcac ttcttccaag gcctgagcgg tttgatctgg   2040
ctggacttgt cccagaaccg cctgcacacc ctcctgcccc aaaccctgcg caacctcccc   2100
aagagcctac aggtgctgcg tctccgtgac aattacctgg ccttctttaa gtggtggagc   2160
ctccacttcc tgcccaaact ggaagtcctc gacctggcag gaaaccggct gaaggccctg   2220
accaatggca gctgcctgc tggcacccgg ctccggaggc tggatgtcag ctgcaacagc   2280
atcagcttcg tggcccccgg cttctttttcc aaggccaagg agctgcgaga gctcaacctt   2340
agcgccaacg ccctcaagac agtggaccac tcctggtttg gccccctggc gagtgccctg   2400
caaatactag atgtaagcgc caaccctctg cactgcgcct gtgggcggc ctttatggac    2460 ttcctgctgg aggtgcaggc tgccgtgccc ggtctgccca gccgggtgaa gtgtggcagt   2520
ccgggccagc tccagggcct cagcatcttt gcacaggacc tgcgcctctg cctggatgag   2580
gccctctcct gggactgttt cgccctctcg ctgctggctg tggctctggg cctggtgtg    2640 cccatgctgc atcacctctg tggctgggac ctctggtact gcttccacct gtgcctggcc   2700
tggcttccct ggcgggggcg gcaaagtggg cgagatgagg atgccctgcc ctacgatgcc   2760
ttcgtggtct tcgacaaaac gcagagcgca gtggcagact gggtgtacaa cgagcttcgg   2820
gggcagctgg aggagtgccg tgggcgctgg gcactccgcc tgtgcctgga ggaacgcgac   2880
tggctgcctg gcaaaaccct cttttgagaac ctgtgggcct cggtctatgg cagccgcaag   2940
```

| | | | | |
|---|---|---|---|---|
| acgctgtttg | tgctggccca | cacggaccgg | gtcagtggtc | tcttgcgcgc | cagcttcctg | 3000 |
| ctggcccagc | agcgcctgct | ggaggaccgc | aaggacgtcg | tggtgctggt | gatcctgagc | 3060 |
| cctgacggcc | gccgctcccg | ctacgtgcgg | ctgcgccagc | gcctctgccg | ccagagtgtc | 3120 |
| ctcctctggc | cccaccagcc | cagtggtcag | cgcagcttct | gggcccagct | gggcatggcc | 3180 |
| ctgaccaggg | acaaccacca | cttctataac | cggaacttct | gccagggacc | cacggccgaa | 3240 |
| tagccgtgag | ccggaatcct | gcacggtgcc | acctccacac | tcacctcacc | tctgcctgcc | 3300 |
| tggtctgacc | ctcccctgct | cgcctccctc | accccacacc | tgacacagag | ca | 3352 |

<210> SEQ ID NO 5
<211> LENGTH: 3868
<212> TYPE: DNA
<213> ORGANISM: Homo sapiens
<220> FEATURE:
<221> NAME/KEY: misc_feature
<222> LOCATION: (0)...(0)
<223> OTHER INFORMATION: Human TLR9 per GenBank NM_017442

<400> SEQUENCE: 5

| | | | | | |
|---|---|---|---|---|---|
| ggaggtcttg | tttccggaag | atgttgcaag | gctgtggtga | aggcaggtgc | agcctagcct | 60 |
| cctgctcaag | ctacaccctg | gccctccacg | catgaggccc | tgcagaactc | tggagatggt | 120 |
| gcctacaagg | gcagaaaagg | acaagtcggc | agccgctgtc | ctgagggcac | cagctgtggt | 180 |
| gcaggagcca | agacctgagg | gtggaagtgt | cctcttagaa | tggggagtgc | ccagcaaggt | 240 |
| gtacccgcta | ctggtgctat | ccagaattcc | catctctccc | tgctctctgc | ctgagctctg | 300 |
| ggccttagct | cctccctggg | cttggtagag | acaggtgtg | aggccctcat | gggatgtagg | 360 |
| ctgtctgaga | ggggagtgga | aagaggaagg | ggtgaaggag | ctgtctgcca | tttgactatg | 420 |
| caaatggcct | ttgactcatg | ggaccctgtc | ctcctcactg | ggggcagggt | ggagtggagg | 480 |
| gggagctact | aggctggtat | aaaaatctta | cttcctctat | tctctgagcc | gctgctgccc | 540 |
| ctgtgggaag | ggacctcgag | tgtgaagcat | ccttccctgt | agctgctgtc | cagtctgccc | 600 |
| gccagaccct | ctggagaagc | ccctgccccc | cagcatgggt | ttctgccgca | gcgccctgca | 660 |
| cccgctgtct | ctcctggtgc | aggccatcat | gctggccatg | accctggccc | tgggtacctt | 720 |
| gcctgccttc | ctaccctgtg | agctccagcc | ccacggcctg | gtgaactgca | actggctgtt | 780 |
| cctgaagtct | gtgcccact | tctccatggc | agcacccgt | ggcaatgtca | ccagcctttc | 840 |
| cttgtcctcc | aaccgcatcc | accacctcca | tgattctgac | tttgcccacc | tgcccagcct | 900 |
| gcggcatctc | aacctcaagt | ggaactgccc | gccggttggc | ctcagcccca | tgcacttccc | 960 |
| ctgccacatg | accatcgagc | ccagcacctt | cttggctgtg | cccaccctgg | aagagctaaa | 1020 |
| cctgagctac | aacaacatca | tgactgtgcc | tgcgctgccc | aaatccctca | tatccctgtc | 1080 |
| cctcagccat | accaacatcc | tgatgctaga | ctctgccagc | ctcgccggcc | tgcatgccct | 1140 |
| gcgcttccta | ttcatggacg | gcaactgtta | ttacaagaac | ccctgcaggc | aggcactgga | 1200 |
| ggtggccccg | ggtgccctcc | ttggcctggg | caacctcacc | cacctgtcac | tcaagtacaa | 1260 |
| caacctcact | gtggtgcccc | gcaacctgcc | ttccagcctg | gagtatctgc | tgttgtccta | 1320 |
| caaccgcatc | gtcaaactgg | cgcctgagga | cctggccaat | ctgaccgccc | tgcgtgtgct | 1380 |
| cgatgtgggc | ggaaattgcc | gccgctgcga | ccacgctccc | aaccccctgca | tggagtgccc | 1440 |
| tcgtcacttc | ccccagctac | atcccgatac | cttcagccac | ctgagccgtc | ttgaaggcct | 1500 |
| ggtgttgaag | gacagttctc | tctcctggct | gaatgccagt | tggttccgtg | gctgggaaa | 1560 |
| cctccgagtg | ctggacctga | gtgagaactt | cctctacaaa | tgcatcacta | aaaccaaggc | 1620 |

```
cttccagggc ctaacacagc tgcgcaagct taacctgtcc ttcaattacc aaaagagggt      1680
gtcctttgcc cacctgtctc tggcccctttc cttcgggagc ctggtcgccc tgaaggagct     1740
ggacatgcac ggcatcttct tccgctcact cgatgagacc acgctccggc cactggcccg      1800
cctgcccatg ctccagactc tgcgtctgca gatgaacttc atcaaccagg cccagctcgg      1860
catcttcagg gccttccctg gcctgcgcta cgtggacctg tcggacaacc gcatcagcgg      1920
agcttcggag ctgacagcca ccatgggggga ggcagatgga ggggagaagg tctggctgca     1980
gcctggggac cttgctccgg ccccagtgga cactcccagc tctgaagact tcaggcccaa      2040
ctgcagcacc ctcaacttca ccttggatct gtcacggaac aacctggtga ccgtgcagcc      2100
ggagatgttt gcccagctct cgcacctgca gtgcctgcgc ctgagccaca actgcatctc      2160
gcaggcagtc aatggctccc agttcctgcc gctgaccggt ctgcaggtgc tagacctgtc      2220
ccacaataag ctggacctct accacgagca ctcattcacg gagctaccac gactggaggc      2280
cctggacctc agctacaaca gccagccctt tggcatgcag ggcgtgggcc acaacttcag      2340
cttcgtggct cacctgcgca ccctgcgcca cctcagcctg gcccacaaca catccacag      2400 ccaagtgtcc cagcagctct gcagtacgtc gctgcgggcc ctggacttca gcggcaatgc      2460
actgggccat atgtgggccg agggagacct ctatctgcac ttcttccaag gcctgagcgg      2520
tttgatctgg ctggacttgt cccagaaccg cctgcacacc ctcctgcccc aaaccctgcg      2580
caacctcccc aagagcctac aggtgctgcg tctccgtgac aattacctgg ccttctttaa      2640
gtggtggagc ctccacttcc tgcccaaact ggaagtcctc gacctggcag aaaccagct     2700 gaaggccctg accaatggca gcctgcctgc tggcacccgg ctccggaggc tggatgtcag      2760
ctgcaacagc atcagcttcg tggccccccgg cttctttttcc aaggccaagg agctgcgaga    2820
gctcaacctt agcgccaacg ccctcaagac agtggaccac tcctggttttg ggccctggc    2880 gagtgccctg caaatactag atgtaagcgc caaccctctg cactgcgcct gtggggcggc     2940
ctttatggac ttcctgctgg aggtgcaggc tgccgtgccc ggtctgccca gccgggtgaa      3000
gtgtggcagt ccgggccagc tccagggcct cagcatctttt gcacaggacc tgcgcctctg    3060
cctggatgag gccctctcct gggactgttt cgccctctcg ctgctggctg tggctctggg     3120
cctgggtgtg cccatgctgc atcacctctg tggctgggac ctctggtact gcttccacct     3180
gtgcctggcc tggcttccct ggcgggggcg gcaaagtggg cgagatgagg atgccctgcc     3240
ctacgatgcc ttcgtggtct tcgacaaaac gcagagcgca gtggcagact gggtgtacaa      3300
cgagcttcgg gggcagctgg aggagtgccg tgggcgctgg gcactccgcc tgtgcctgga     3360
ggaacgcgac tggctgcctg gcaaaaccct ctttgagaac ctgtgggcct cggtctatgg     3420
cagccgcaag acgctgtttg tgctggccca cacggaccgg gtcagtggtc tcttgcgcgc     3480
cagcttcctg ctgcccagc agcgcctgct ggaggaccgc aaggacgtcg tggtgctggt     3540
gatcctgagc cctgacggcc gccgctcccg ctacgtgcgg ctgcgccagc gcctctgccg      3600
ccagagtgtc ctcctctggc cccaccagcc cagtggtcag cgcagcttct gggcccagct     3660
gggcatggcc ctgaccaggg acaaccacca cttctataac cggaacttct gccagggacc     3720
cacggccgaa tagccgtgag ccggaatcct gcacggtgcc acctccacac tcacctcacc     3780
tctgcctgcc tggtctgacc ctccccctgct cgcctccctc accccacacc tgacacagag    3840
caggcactca ataaatgcta ccgaaggc                                         3868

<210> SEQ ID NO 6
```

-continued

<211> LENGTH: 1032
<212> TYPE: PRT
<213> ORGANISM: Homo sapiens

<400> SEQUENCE: 6

```
Met Gly Phe Cys Arg Ser Ala Leu His Pro Leu Ser Leu Leu Val Gln
 1               5                  10                  15

Ala Ile Met Leu Ala Met Thr Leu Ala Leu Gly Thr Leu Pro Ala Phe
             20                  25                  30

Leu Pro Cys Glu Leu Gln Pro His Gly Leu Val Asn Cys Asn Trp Leu
         35                  40                  45

Phe Leu Lys Ser Val Pro His Phe Ser Met Ala Ala Pro Arg Gly Asn
     50                  55                  60

Val Thr Ser Leu Ser Leu Ser Ser Asn Arg Ile His His Leu His Asp
 65                  70                  75                  80

Ser Asp Phe Ala His Leu Pro Ser Leu Arg His Leu Asn Leu Lys Trp
                 85                  90                  95

Asn Cys Pro Pro Val Gly Leu Ser Pro Met His Phe Pro Cys His Met
            100                 105                 110

Thr Ile Glu Pro Ser Thr Phe Leu Ala Val Pro Thr Leu Glu Glu Leu
        115                 120                 125

Asn Leu Ser Tyr Asn Asn Ile Met Thr Val Pro Ala Leu Pro Lys Ser
    130                 135                 140

Leu Ile Ser Leu Ser Leu Ser His Thr Asn Ile Leu Met Leu Asp Ser
145                 150                 155                 160

Ala Ser Leu Ala Gly Leu His Ala Leu Arg Phe Leu Phe Met Asp Gly
                165                 170                 175

Asn Cys Tyr Tyr Lys Asn Pro Cys Arg Gln Ala Leu Glu Val Ala Pro
            180                 185                 190

Gly Ala Leu Leu Gly Leu Gly Asn Leu Thr His Leu Ser Leu Lys Tyr
        195                 200                 205

Asn Asn Leu Thr Val Val Pro Arg Asn Leu Pro Ser Ser Leu Glu Tyr
    210                 215                 220

Leu Leu Leu Ser Tyr Asn Arg Ile Val Lys Leu Ala Pro Glu Asp Leu
225                 230                 235                 240

Ala Asn Leu Thr Ala Leu Arg Val Leu Asp Val Gly Gly Asn Cys Arg
                245                 250                 255

Arg Cys Asp His Ala Pro Asn Pro Cys Met Glu Cys Pro Arg His Phe
            260                 265                 270

Pro Gln Leu His Pro Asp Thr Phe Ser His Leu Ser Arg Leu Glu Gly
        275                 280                 285

Leu Val Leu Lys Asp Ser Ser Leu Ser Trp Leu Asn Ala Ser Trp Phe
    290                 295                 300

Arg Gly Leu Gly Asn Leu Arg Val Leu Asp Leu Ser Glu Asn Phe Leu
305                 310                 315                 320

Tyr Lys Cys Ile Thr Lys Thr Lys Ala Phe Gln Gly Leu Thr Gln Leu
                325                 330                 335

Arg Lys Leu Asn Leu Ser Phe Asn Tyr Gln Lys Arg Val Ser Phe Ala
            340                 345                 350

His Leu Ser Leu Ala Pro Ser Phe Gly Ser Leu Val Ala Leu Lys Glu
        355                 360                 365

Leu Asp Met His Gly Ile Phe Phe Arg Ser Leu Asp Glu Thr Thr Leu
    370                 375                 380

Arg Pro Leu Ala Arg Leu Pro Met Leu Gln Thr Leu Arg Leu Gln Met
```

-continued

```
            385                 390                 395                 400
Asn Phe Ile Asn Gln Ala Gln Leu Gly Ile Phe Arg Ala Phe Pro Gly
                405                 410                 415

Leu Arg Tyr Val Asp Leu Ser Asp Asn Arg Ile Ser Gly Ala Ser Glu
                420                 425                 430

Leu Thr Ala Thr Met Gly Glu Ala Asp Gly Gly Glu Lys Val Trp Leu
                435                 440                 445

Gln Pro Gly Asp Leu Ala Pro Ala Val Asp Thr Pro Ser Ser Glu
    450                 455                 460

Asp Phe Arg Pro Asn Cys Ser Thr Leu Asn Phe Thr Leu Asp Leu Ser
465                 470                 475                 480

Arg Asn Asn Leu Val Thr Val Gln Pro Glu Met Phe Ala Gln Leu Ser
                485                 490                 495

His Leu Gln Cys Leu Arg Leu Ser His Asn Cys Ile Ser Gln Ala Val
                500                 505                 510

Asn Gly Ser Gln Phe Leu Pro Leu Thr Gly Leu Gln Val Leu Asp Leu
                515                 520                 525

Ser Arg Asn Lys Leu Asp Leu Tyr His Glu His Ser Phe Thr Glu Leu
    530                 535                 540

Pro Arg Leu Glu Ala Leu Asp Leu Ser Tyr Asn Ser Gln Pro Phe Gly
545                 550                 555                 560

Met Gln Gly Val Gly His Asn Phe Ser Phe Val Ala His Leu Arg Thr
                565                 570                 575

Leu Arg His Leu Ser Leu Ala His Asn Asn Ile His Ser Gln Val Ser
                580                 585                 590

Gln Gln Leu Cys Ser Thr Ser Leu Arg Ala Leu Asp Phe Ser Gly Asn
                595                 600                 605

Ala Leu Gly His Met Trp Ala Glu Gly Asp Leu Tyr Leu His Phe Phe
                610                 615                 620

Gln Gly Leu Ser Gly Leu Ile Trp Leu Asp Leu Ser Gln Asn Arg Leu
625                 630                 635                 640

His Thr Leu Leu Pro Gln Thr Leu Arg Asn Leu Pro Lys Ser Leu Gln
                645                 650                 655

Val Leu Arg Leu Arg Asp Asn Tyr Leu Ala Phe Phe Lys Trp Trp Ser
                660                 665                 670

Leu His Phe Leu Pro Lys Leu Glu Val Leu Asp Leu Ala Gly Asn Arg
                675                 680                 685

Leu Lys Ala Leu Thr Asn Gly Ser Leu Pro Ala Gly Thr Arg Leu Arg
                690                 695                 700

Arg Leu Asp Val Ser Cys Asn Ser Ile Ser Phe Val Ala Pro Gly Phe
705                 710                 715                 720

Phe Ser Lys Ala Lys Glu Leu Arg Glu Leu Asn Leu Ser Ala Asn Ala
                725                 730                 735

Leu Lys Thr Val Asp His Ser Trp Phe Gly Pro Leu Ala Ser Ala Leu
                740                 745                 750

Gln Ile Leu Asp Val Ser Ala Asn Pro Leu His Cys Ala Cys Gly Ala
                755                 760                 765

Ala Phe Met Asp Phe Leu Leu Glu Val Gln Ala Val Pro Gly Leu
                770                 775                 780

Pro Ser Arg Val Lys Cys Gly Ser Pro Gly Gln Leu Gln Gly Leu Ser
785                 790                 795                 800

Ile Phe Ala Gln Asp Leu Arg Leu Cys Leu Asp Glu Ala Leu Ser Trp
                805                 810                 815
```

```
Asp Cys Phe Ala Leu Ser Leu Leu Ala Val Ala Leu Gly Leu Gly Val
            820                 825                 830

Pro Met Leu His His Leu Cys Gly Trp Asp Leu Trp Tyr Cys Phe His
            835                 840                 845

Leu Cys Leu Ala Trp Leu Pro Trp Arg Gly Arg Gln Ser Gly Arg Asp
            850                 855                 860

Glu Asp Ala Leu Pro Tyr Asp Ala Phe Val Phe Asp Lys Thr Gln
865                 870                 875                 880

Ser Ala Val Ala Asp Trp Val Tyr Asn Glu Leu Arg Gly Gln Leu Glu
                    885                 890                 895

Glu Cys Arg Gly Arg Trp Ala Leu Arg Leu Cys Leu Glu Glu Arg Asp
            900                 905                 910

Trp Leu Pro Gly Lys Thr Leu Phe Glu Asn Leu Trp Ala Ser Val Tyr
            915                 920                 925

Gly Ser Arg Lys Thr Leu Phe Val Leu Ala His Thr Asp Arg Val Ser
            930                 935                 940

Gly Leu Leu Arg Ala Ser Phe Leu Leu Ala Gln Gln Arg Leu Leu Glu
945                 950                 955                 960

Asp Arg Lys Asp Val Val Leu Val Ile Leu Ser Pro Asp Gly Arg
                965                 970                 975

Arg Ser Arg Tyr Val Arg Leu Arg Gln Arg Leu Cys Arg Gln Ser Val
            980                 985                 990

Leu Leu Trp Pro His Gln Pro Ser Gly Gln Arg Ser Phe Trp Ala Gln
            995                 1000                1005

Leu Gly Met Ala Leu Thr Arg Asp Asn His His Phe Tyr Asn Arg Asn
            1010                1015                1020

Phe Cys Gln Gly Pro Thr Ala Glu
1025                1030

<210> SEQ ID NO 7
<211> LENGTH: 557
<212> TYPE: DNA
<213> ORGANISM: Mus musculus

<400> SEQUENCE: 7
ggctttcaac ctaaccgctg gcactcaacc tgtccttcaa ttaccgcaag aaggtatcct      60
ttgcccgcct ccacctggca agttcctttt agaacctggt gtcactgcag gagctgaaca     120
tgaacggcat cttcttccgc ttgctcaaca gtacacgct cagatggctg ccgatctgc      180 ccaaactcca cactctgcat cttcaaatga acttcatcaa ccaggcacag ctcagcatct     240
ttggtacctt ccgagccctt cgctttgtgg acttgtcaga caatcgcatc agtgggcctt     300
caacgctgtc agaagccacc cctgaagagg cagatgatgc agagcaggag gagctgttgt     360
ctgcggatcc tcacccagct ccgctgagca cccctgcttc taagaacttc atggacaggt     420
gtaagaactt caagttcaac atggacctgt ctcggaacaa cctggtgact atcacagcag     480
agatgtttgt aaatctctca cgcctccagt gtcttagcct gagccacaac tcaattgcac     540
aggctgtcaa tggctct                                                    557

<210> SEQ ID NO 8
<211> LENGTH: 178
<212> TYPE: PRT
<213> ORGANISM: Mus musculus

<400> SEQUENCE: 8
```

```
Leu Asn Leu Ser Phe Asn Tyr Arg Lys Lys Val Ser Phe Ala Arg Leu
1               5                   10                  15

His Leu Ala Ser Ser Phe Lys Asn Leu Val Ser Leu Gln Glu Leu Asn
            20                  25                  30

Met Asn Gly Ile Phe Phe Arg Leu Leu Asn Lys Tyr Thr Leu Arg Trp
        35                  40                  45

Leu Ala Asp Leu Pro Lys Leu His Thr Leu His Leu Gln Met Asn Phe
    50                  55                  60

Ile Asn Gln Ala Gln Leu Ser Ile Phe Gly Thr Phe Arg Ala Leu Arg
65                  70                  75                  80

Phe Val Asp Leu Ser Asp Asn Arg Ile Ser Gly Pro Ser Thr Leu Ser
                85                  90                  95

Glu Ala Thr Pro Glu Glu Ala Asp Asp Ala Glu Gln Glu Glu Leu Leu
            100                 105                 110

Ser Ala Asp Pro His Pro Ala Pro Leu Ser Thr Pro Ala Ser Lys Asn
            115                 120                 125

Phe Met Asp Arg Cys Lys Asn Phe Lys Phe Asn Met Asp Leu Ser Arg
        130                 135                 140

Asn Asn Leu Val Thr Ile Thr Ala Glu Met Phe Val Asn Leu Ser Arg
145                 150                 155                 160

Leu Gln Cys Leu Ser Leu Ser His Asn Ser Ile Ala Gln Ala Val Asn
                165                 170                 175

Gly Ser
```

<210> SEQ ID NO 9
<211> LENGTH: 497
<212> TYPE: DNA
<213> ORGANISM: Mus musculus
<220> FEATURE:
<221> NAME/KEY: misc_feature
<222> LOCATION: (380)...(380)
<223> OTHER INFORMATION: any

<400> SEQUENCE: 9

```
gtgggtttgg tgtctatctt cactctcctg aaagatgcat gggaagaaaa ctacccttta      60
cagccaacct ttgctccgtg ggcctggtgg cttggtagca tatattgcgc acttgccaaa     120
tagcggtgta gtaagacaga gcaaggcagg cagagcaact cgggaaccag acatgaagat     180
gcagctgttt ccagctgttg ctctgagcta ttctgctgta ggtccccggc agaagttctg     240
gttatagaag tggcggttgt ccctagtcag ggctgtactc agctgggccc agaagccccc     300
ctgcccgttg ggtcgctggg gccagaagag cacactctgg cggcagagac gctggcgcag     360
tcgcacatag cgggacggtn gggcatccgg acgcaggatc accaacacca ccacgtcctt     420
gcggtcttcc aacaggcgct gctgagccag caggaagctg gtgcgcagga ggccactgac     480
gcggtccgtg tgggcca                                                    497
```

<210> SEQ ID NO 10
<211> LENGTH: 95
<212> TYPE: PRT
<213> ORGANISM: Mus musculus
<220> FEATURE:
<221> NAME/KEY: misc_feature
<222> LOCATION: (39)...(39)
<223> OTHER INFORMATION: any

<400> SEQUENCE: 10

```
Ala His Thr Asp Arg Val Ser Gly Leu Leu Arg Thr Ser Phe Leu Leu
1               5                   10                  15
```

```
Ala Gln Gln Arg Leu Leu Glu Asp Arg Lys Asp Val Val Leu Val
            20                  25                  30

Ile Leu Arg Pro Asp Ala Xaa Pro Ser Arg Tyr Val Arg Leu Arg Gln
        35                  40                  45

Arg Leu Cys Arg Gln Ser Val Leu Phe Trp Pro Gln Arg Pro Asn Gly
    50                  55                  60

Gln Gly Gly Phe Trp Ala Gln Leu Ser Thr Ala Leu Thr Arg Asp Asn
65                  70                  75                  80

Arg His Phe Tyr Asn Gln Asn Phe Cys Arg Gly Pro Thr Ala Glu
                85                  90                  95

<210> SEQ ID NO 11
<211> LENGTH: 373
<212> TYPE: DNA
<213> ORGANISM: Mus musculus

<400> SEQUENCE: 11
tggaggaccg agattggctg cctggccaga cgctcttcga gaacctctgg gcttccatct     60
atgggagccg caagactcta tttgtgctgg cccacacgga ccgcgtcagt ggcctcctgc    120
gcaccagctt cctgctggct cagcagcgcc tgttggaaga ccgcaaggac gtggtggtgt    180
tggtgatcct cgtccggat gcccaccgct ccgctatgt cgactgcgc cagcgtctct      240 gccgccagag tgtgctcttc tggccccagc agcccaacgg gcagggggc ttctgggccc    300 agctgagtac agccctgact agggacaacc gccacttcta taaccagaac ttctgccggg    360
gacctacagc aga                                                       373

<210> SEQ ID NO 12
<211> LENGTH: 123
<212> TYPE: PRT
<213> ORGANISM: Mus musculus

<400> SEQUENCE: 12

Glu Asp Arg Asp Trp Leu Pro Gly Gln Thr Leu Phe Glu Asn Leu Trp
1               5                   10                  15

Ala Ser Ile Tyr Gly Ser Arg Lys Thr Leu Phe Val Leu Ala His Thr
            20                  25                  30

Asp Arg Val Ser Gly Leu Leu Arg Thr Ser Phe Leu Leu Ala Gln Gln
        35                  40                  45

Arg Leu Leu Glu Asp Arg Lys Asp Val Val Leu Val Ile Leu Arg
    50                  55                  60

Pro Asp Ala His Arg Ser Arg Tyr Val Arg Leu Arg Gln Arg Leu Cys
65                  70                  75                  80

Arg Gln Ser Val Leu Phe Trp Pro Gln Gln Pro Asn Gly Gln Gly Gly
                85                  90                  95

Phe Trp Ala Gln Leu Ser Thr Ala Leu Thr Arg Asp Asn Arg His Phe
            100                 105                 110

Tyr Asn Gln Asn Phe Cys Arg Gly Pro Thr Ala
        115                 120

<210> SEQ ID NO 13
<211> LENGTH: 489
<212> TYPE: DNA
<213> ORGANISM: Mus musculus

<400> SEQUENCE: 13
gctacaacag ccagcccttt agcatgaagg gtataggcca caatttcagt tttgtgaccc     60
```

-continued

```
atctgtccat gctacagagc cttagcctgg cacacaatga cattcatacc cgtgtgtcct      120
cacatctcaa cagcaactca gtgaggtttc ttgacttcag cggcaacggt atgggccgca      180
tgtgggatga gggggggcctt tatctccatt tcttccaagg cctgagtggc gtgctgaagc      240
tggacctgtc tcaaaataac ctgcatatcc tccggcccca gaaccttgac aacctcccca      300
agagcctgaa gctgctgagc ctccgagaca actacctatc tttctttaac tggaccagtc      360
tgtccttcct acccaacctg gaagtcctag acctggcagg caaccagcta aaggccctga      420
ccaatggcac cctgcctaat ggcacccctcc tccagaaact cgatgtcagt agcaacagta      480
tcgtctctg                                                               489
```

<210> SEQ ID NO 14
<211> LENGTH: 162
<212> TYPE: PRT
<213> ORGANISM: Mus musculus
<400> SEQUENCE: 14

```
Tyr Asn Ser Gln Pro Phe Ser Met Lys Gly Ile Gly His Asn Phe Ser
1               5                   10                  15

Phe Val Thr His Leu Ser Met Leu Gln Ser Leu Ser Leu Ala His Asn
            20                  25                  30

Asp Ile His Thr Arg Val Ser Ser His Leu Asn Ser Asn Ser Val Arg
        35                  40                  45

Phe Leu Asp Phe Ser Gly Asn Gly Met Gly Arg Met Trp Asp Glu Gly
    50                  55                  60

Gly Leu Tyr Leu His Phe Phe Gln Gly Leu Ser Gly Val Leu Lys Leu
65                  70                  75                  80

Asp Leu Ser Gln Asn Asn Leu His Ile Leu Arg Pro Gln Asn Leu Asp
                85                  90                  95

Asn Leu Pro Lys Ser Leu Lys Leu Leu Ser Leu Arg Asp Asn Tyr Leu
            100                 105                 110

Ser Phe Phe Asn Trp Thr Ser Leu Ser Phe Leu Pro Asn Leu Glu Val
        115                 120                 125

Leu Asp Leu Ala Gly Asn Gln Leu Lys Ala Leu Thr Asn Gly Thr Leu
    130                 135                 140

Pro Asn Gly Thr Leu Leu Gln Lys Leu Asp Val Ser Ser Asn Ser Ile
145                 150                 155                 160

Val Ser
```

<210> SEQ ID NO 15
<211> LENGTH: 462
<212> TYPE: DNA
<213> ORGANISM: Mus musculus
<400> SEQUENCE: 15

```
gcggccgcgc cgctcctcca gccgcacccg cagctcgtta tacacccagt cggcaactgc      60
gctctgtgcc ttatcgaaca ccacgaaggc atcataaggg agagtttggg cgctgcgtcg     120
gctgcgggct agcaaaggta gccatgccag gcacagatga aaacagtacc agacgtccca     180
gccgcagaga tggtgcagta taggcaccac catgcccacg gccacagcca agagtgaaag     240
gccaaagcag tcccaagaga ggacctcatc caggcacagc cgcaggtcct cgcgcaagat     300
gctacgcccc tgcagctggc cggggctgcc acacttcaca ccattagcca ggccaggcac     360
cttggtctgc acctccaaca gtaagtctac gaaggctgcc ccacaggcac agtgcagagg     420
```
gttgcttctc acgtctagaa ctgtcaggtt catcacaatg gg          462

```
<210> SEQ ID NO 16
<211> LENGTH: 154
<212> TYPE: PRT
<213> ORGANISM: Mus musculus

<400> SEQUENCE: 16
```

Pro Ile Val Met Asn Leu Thr Val Leu Asp Val Arg Ser Asn Pro Leu
1               5                   10                  15

His Cys Ala Cys Gly Ala Ala Phe Val Asp Leu Leu Leu Glu Val Gln
            20                  25                  30

Thr Lys Val Pro Gly Leu Ala Asn Gly Val Lys Cys Gly Ser Pro Gly
        35                  40                  45

Gln Leu Gln Gly Arg Ser Ile Phe Ala Gln Asp Leu Arg Leu Cys Leu
    50                  55                  60

Asp Glu Val Leu Ser Trp Asp Cys Phe Gly Leu Ser Leu Leu Ala Val
65                  70                  75                  80

Ala Val Gly Met Val Val Pro Ile Leu His His Leu Cys Gly Trp Asp
                85                  90                  95

Val Trp Tyr Cys Phe His Leu Cys Leu Ala Trp Leu Pro Leu Leu Ala
            100                 105                 110

Arg Ser Arg Ser Ala Gln Thr Leu Pro Tyr Asp Ala Phe Val Val
        115                 120                 125

Phe Asp Lys Ala Gln Ser Ala Val Ala Asp Trp Val Tyr Asn Glu Leu
    130                 135                 140

Arg Val Arg Leu Glu Glu Arg Arg Gly Arg
145                 150

```
<210> SEQ ID NO 17
<211> LENGTH: 17
<212> TYPE: PRT
<213> ORGANISM: Mus musculus

<400> SEQUENCE: 17
```

Cys Asp Leu Ser Asp Asn Arg Ile Ser Gly Pro Ser Thr Leu Ser Glu
1               5                   10                  15

Ala

```
<210> SEQ ID NO 18
<211> LENGTH: 14
<212> TYPE: PRT
<213> ORGANISM: Mus musculus

<400> SEQUENCE: 18
```

His Phe Tyr Asn Gln Asn Phe Cys Arg Gly Pro Thr Ala Glu
1               5                   10

```
<210> SEQ ID NO 19
<211> LENGTH: 16
<212> TYPE: PRT
<213> ORGANISM: Homo sapiens

<400> SEQUENCE: 19
```

Pro Ala Pro Val Asp Thr Pro Ser Ser Glu Asp Phe Arg Pro Asn Cys
1               5                   10                  15

```
<210> SEQ ID NO 20
<211> LENGTH: 14
<212> TYPE: PRT
```

-continued

```
<213> ORGANISM: Homo sapiens

<400> SEQUENCE: 20

His Phe Tyr Asn Arg Asn Phe Cys Gln Gly Pro Thr Ala Glu
  1               5                  10

<210> SEQ ID NO 21
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 21 aacgttct                                                                    8

<210> SEQ ID NO 22
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 22
aagcgaaaat gaaattgact                                                      20

<210> SEQ ID NO 23
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 23
accatggacg aactgtttcc cctc                                                 24

<210> SEQ ID NO 24
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 24
accatggacg acctgtttcc cctc                                                 24

<210> SEQ ID NO 25
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 25
accatggacg agctgtttcc cctc                                                 24

<210> SEQ ID NO 26
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 26
accatggacg atctgtttcc cctc                                                 24
```

<210> SEQ ID NO 27
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 27
accatggacg gtctgtttcc cctc                                          24

<210> SEQ ID NO 28
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 28
accatggacg tactgtttcc cctc                                          24

<210> SEQ ID NO 29
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 29
accatggacg ttctgtttcc cctc                                          24

<210> SEQ ID NO 30
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 30
agatttctag gaattcaatc                                               20

<210> SEQ ID NO 31
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 31 agcggggcg agcggggcg                                                 20

<210> SEQ ID NO 32
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 32
agctatgacg ttccaagg                                                 18

<210> SEQ ID NO 33
<211> LENGTH: 20
<212> TYPE: DNA
<213> ORGANISM: Artificial Sequence
<220> FEATURE:
<223> OTHER INFORMATION: Synthetic oligonucleotide

```
<400> SEQUENCE: 33
atcgactctc gagcgttctc                                            20

<210> SEQ ID NO 34
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 34
atgacgttcc tgacgtt                                               17

<210> SEQ ID NO 35
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 35
atggaaggtc caacgttctc                                            20

<210> SEQ ID NO 36
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 36
atggaaggtc cagcgttctc                                            20

<210> SEQ ID NO 37
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 37
atggactctc cagcgttctc                                            20

<210> SEQ ID NO 38
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 38
atggaggctc catcgttctc                                            20

<210> SEQ ID NO 39
<211> LENGTH: 7
<212> TYPE: DNA
<213> ORGANISM: Artificial Sequence
<220> FEATURE:
<223> OTHER INFORMATION: Synthetic oligonucleotide

<400> SEQUENCE: 39 caacgtt                                                           7

<210> SEQ ID NO 40
```

```
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 40
cacgttgagg ggcat                                                    15

<210> SEQ ID NO 41
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 41
caggcataac ggttccgtag                                               20

<210> SEQ ID NO 42
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 42 ccaacgtt                                                             8

<210> SEQ ID NO 43
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 43
ctcctagtgg gggtgtccta t                                             21

<210> SEQ ID NO 44
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 44
ctgatttccc cgaaatgatg                                               20

<210> SEQ ID NO 45
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 45
ctgctgagac tggag                                                    15

<210> SEQ ID NO 46
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 46
```
gagaacgatg gaccttccat                                                    20

<210> SEQ ID NO 47
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 47
gagaacgctc cagcactgat                                                    20

<210> SEQ ID NO 48
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 48
gagaacgctc gaccttccat                                                    20

<210> SEQ ID NO 49
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 49
gagaacgctc gaccttcgat                                                    20

<210> SEQ ID NO 50
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 50
gagaacgctg gaccttccat                                                    20

<210> SEQ ID NO 51
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 51
gagcaagctg gaccttccat                                                    20

<210> SEQ ID NO 52
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 52
gattgcctga cgtcagagag                                                    20

<210> SEQ ID NO 53
<211> LENGTH: 15
<212> TYPE: DNA

```
<213> ORGANISM: Artificial Sequence
<220> FEATURE:
<223> OTHER INFORMATION: Synthetic oligonucleotide

<400> SEQUENCE: 53
gcatgacgtt gagct                                                     15

<210> SEQ ID NO 54
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 54
gcggcgggcg gcgcgcgccc                                                20

<210> SEQ ID NO 55
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 55
gcgtgcgttg tcgttgtcgt t                                              21

<210> SEQ ID NO 56
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 56
gctagacgtt agcgt                                                     15

<210> SEQ ID NO 57
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 57
gctagacgtt agtgt                                                     15

<210> SEQ ID NO 58
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 58
gctagatgtt agcgt                                                     15

<210> SEQ ID NO 59
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 59
gcttgatgac tcagccggaa                                                20
```

```
<210> SEQ ID NO 60
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 60
ggaatgacgt tccctgtg                                                 18

<210> SEQ ID NO 61
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 61
ggggtcaacg ttgacgggg                                                19

<210> SEQ ID NO 62
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 62
ggggtcagtc ttgacgggg                                                19

<210> SEQ ID NO 63
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 63
gtatttccca gaaaaggaac                                               20

<210> SEQ ID NO 64
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 64
gtccatttcc cgtaaatctt                                               20

<210> SEQ ID NO 65
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 65 gtcgct                                                               6

<210> SEQ ID NO 66
<211> LENGTH: 6
<212> TYPE: DNA
<213> ORGANISM: Artificial Sequence
<220> FEATURE:
```

```
<223> OTHER INFORMATION: Synthetic oligonucleotide

<400> SEQUENCE: 66 gtcgtt                                                                          6

<210> SEQ ID NO 67
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 67
taccgcgtgc gaccctct                                                            18

<210> SEQ ID NO 68
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 68
tatgcatatt cctgtaagtg                                                          20

<210> SEQ ID NO 69
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 69 tcaacgtc                                                                        8

<210> SEQ ID NO 70
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 70 tcaacgtt                                                                        8

<210> SEQ ID NO 71
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 71 tcaagctt                                                                        8

<210> SEQ ID NO 72
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 72 tcagcgct                                                                        8
```

```
<210> SEQ ID NO 73
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 73
tcagcgtgcg cc                                                             12

<210> SEQ ID NO 74
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 74 tcatcgat                                                                   8

<210> SEQ ID NO 75
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 75
tccacgacgt tttcgacgtt                                                     20

<210> SEQ ID NO 76
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 76
tccaggactt ctctcaggtt                                                     20

<210> SEQ ID NO 77
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 77
tccataacgt tcctgatgct                                                     20

<210> SEQ ID NO 78
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 78
tccatagcgt tcctagcgtt                                                     20

<210> SEQ ID NO 79
<211> LENGTH: 20
<212> TYPE: DNA
<213> ORGANISM: Artificial Sequence
<220> FEATURE:
<223> OTHER INFORMATION: Synthetic oligonucleotide
```

```
<400> SEQUENCE: 79
tccatcacgt gcctgatgct                                              20

<210> SEQ ID NO 80
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 80
tccatgacgg tcctgatgct                                              20

<210> SEQ ID NO 81
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 81
tccatgacgt ccctgatgct                                              20

<210> SEQ ID NO 82
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 82
tccatgacgt gcctgatgct                                              20

<210> SEQ ID NO 83
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 83
tccatgacgt tcctgacgtt                                              20

<210> SEQ ID NO 84
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 84
tccatgacgt tcctgatgct                                              20

<210> SEQ ID NO 85
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 85
tccatgagct tcctgatgct                                              20

<210> SEQ ID NO 86
<211> LENGTH: 20
```

```
<212> TYPE: DNA
<213> ORGANISM: Artificial Sequence
<220> FEATURE:
<223> OTHER INFORMATION: Synthetic oligonucleotide

<400> SEQUENCE: 86
tccatgccgg tcctgatgct                                               20

<210> SEQ ID NO 87
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 87
tccatgcgtg cgtgcgtttt                                               20

<210> SEQ ID NO 88
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 88
tccatgcgtt gcgttgcgtt                                               20

<210> SEQ ID NO 89
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 89
tccatgctgg tcctgatgct                                               20

<210> SEQ ID NO 90
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 90
tccatggcgg tcctgatgct                                               20

<210> SEQ ID NO 91
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 91
tccatgtcga tcctgatgct                                               20

<210> SEQ ID NO 92
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 92
```
tccatgtcgc tcctgatgct 20

<210> SEQ ID NO 93
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 93
tccatgtcgg tcctgatgct 20

<210> SEQ ID NO 94
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 94
tccatgtcgg tcctgctgat 20

<210> SEQ ID NO 95
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 95
tccatgtcgt ccctgatgct 20

<210> SEQ ID NO 96
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 96
tccatgtcgt tcctgatgct 20

<210> SEQ ID NO 97
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 97
tccatgtcgt tcctgtcgtt 20

<210> SEQ ID NO 98
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 98
tccatgtcgt ttttgtcgtt 20

<210> SEQ ID NO 99
<211> LENGTH: 19
<212> TYPE: DNA
<213> ORGANISM: Artificial Sequence

```
<220> FEATURE:
<223> OTHER INFORMATION: Synthetic oligonucleotide

<400> SEQUENCE: 99
tcctgacgtt cctgacgtt                                                  19

<210> SEQ ID NO 100
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 100
tcctgtcgtt cctgtcgtt                                                  19

<210> SEQ ID NO 101
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 101
tcctgtcgtt ccttgtcgtt                                                 20

<210> SEQ ID NO 102
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 102
tcctgtcgtt ttttgtcgtt                                                 20

<210> SEQ ID NO 103
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 103
tccttgtcgt tcctgtcgtt                                                 20

<210> SEQ ID NO 104
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 104
tcgatcgggg cggggcgagc                                                 20

<210> SEQ ID NO 105
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 105
tcgtcgctgt ctccgcttct t                                               21
```

<210> SEQ ID NO 106
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 106
tcgtcgctgt ctccgcttct tcttgcc                                    27

<210> SEQ ID NO 107
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 107
tcgtcgctgt ctgcccttct t                                          21

<210> SEQ ID NO 108
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 108
tcgtcgctgt tgtcgtttct t                                          21

<210> SEQ ID NO 109
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 109
tcgtcgtcgt cgtt                                                  14

<210> SEQ ID NO 110
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 110
tcgtcgttgt cgttgtcgtt                                            20

<210> SEQ ID NO 111
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 111
tcgtcgttgt cgttttgtcg tt                                         22

<210> SEQ ID NO 112
<211> LENGTH: 24
<212> TYPE: DNA
<213> ORGANISM: Artificial Sequence
<220> FEATURE:
<223> OTHER INFORMATION: Synthetic oligonucleotide

```
<400> SEQUENCE: 112
tcgtcgtttt gtcgttttgt cgtt                                          24

<210> SEQ ID NO 113
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 113
tctcccagcg cgcgccat                                                 18

<210> SEQ ID NO 114
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 114
tctcccagcg ggcgcat                                                  17

<210> SEQ ID NO 115
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 115
tctcccagcg tgcgccat                                                 18

<210> SEQ ID NO 116
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 116 tcttcgaa                                                             8

<210> SEQ ID NO 117
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 117
tgcagattgc gcaatctgca                                               20

<210> SEQ ID NO 118
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 118
tgctgctttt gtgcttttgt gctt                                          24

<210> SEQ ID NO 119
```

```
<211> LENGTH: 7
<212> TYPE: DNA
<213> ORGANISM: Artificial Sequence
<220> FEATURE:
<223> OTHER INFORMATION: Synthetic oligonucleotide

<400> SEQUENCE: 119 tgtcgct                                                                  7

<210> SEQ ID NO 120
<211> LENGTH: 7
<212> TYPE: DNA
<213> ORGANISM: Artificial Sequence
<220> FEATURE:
<223> OTHER INFORMATION: Synthetic oligonucleotide

<400> SEQUENCE: 120 tgtcgtt                                                                  7

<210> SEQ ID NO 121
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 121
tgtcgttgtc gtt                                                          13

<210> SEQ ID NO 122
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 122
tgtcgttgtc gttgtcgtt                                                    19

<210> SEQ ID NO 123
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 123
tgtcgttgtc gttgtcgttg tcgtt                                             25

<210> SEQ ID NO 124
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 124
tgtcgtttgt cgtttgtcgt t                                                 21

<210> SEQ ID NO 125
<211> LENGTH: 31
<212> TYPE: PRT
<213> ORGANISM: Unknown
<220> FEATURE:
<221> NAME/KEY: misc_feature
<222> LOCATION: (2)...(8)
<223> OTHER INFORMATION: unknown
```

```
<220> FEATURE:
<221> NAME/KEY: misc_feature
<222> LOCATION: (10)...(10)
<223> OTHER INFORMATION: unknown
<220> FEATURE:
<221> NAME/KEY: misc_feature
<222> LOCATION: (12)...(12)
<223> OTHER INFORMATION: unknown
<220> FEATURE:
<221> NAME/KEY: misc_feature
<222> LOCATION: (14)...(22)
<223> OTHER INFORMATION: unknown
<220> FEATURE:
<221> NAME/KEY: misc_feature
<222> LOCATION: (25)...(30)
<223> OTHER INFORMATION: unknown

<400> SEQUENCE: 125

Arg Xaa Xaa Xaa Xaa Xaa Xaa Xaa Arg Xaa Asp Xaa Tyr Xaa Xaa Xaa
 1               5                  10                  15

Xaa Xaa Xaa Xaa Xaa Xaa Arg Ser Xaa Xaa Xaa Xaa Xaa Tyr
            20                  25                  30

<210> SEQ ID NO 126
<211> LENGTH: 31
<212> TYPE: PRT
<213> ORGANISM: Homo sapiens
<220> FEATURE:
<221> NAME/KEY: misc_feature
<222> LOCATION: (2)...(8)
<223> OTHER INFORMATION: unknown
<220> FEATURE:
<221> NAME/KEY: misc_feature
<222> LOCATION: (10)...(10)
<223> OTHER INFORMATION: unknown
<220> FEATURE:
<221> NAME/KEY: misc_feature
<222> LOCATION: (12)...(12)
<223> OTHER INFORMATION: unknown
<220> FEATURE:
<221> NAME/KEY: misc_feature
<222> LOCATION: (14)...(22)
<223> OTHER INFORMATION: unknown
<220> FEATURE:
<221> NAME/KEY: misc_feature
<222> LOCATION: (25)...(30)
<223> OTHER INFORMATION: unknown

<400> SEQUENCE: 126

Gln Xaa Xaa Xaa Xaa Xaa Xaa Xaa Lys Xaa Asp Xaa Tyr Xaa Xaa Xaa
 1               5                  10                  15

Xaa Xaa Xaa Xaa Xaa Xaa Arg Leu Xaa Xaa Xaa Xaa Xaa Tyr
            20                  25                  30

<210> SEQ ID NO 127
<211> LENGTH: 31
<212> TYPE: PRT
<213> ORGANISM: Mus musculus
<220> FEATURE:
<221> NAME/KEY: misc_feature
<222> LOCATION: (2)...(8)
<223> OTHER INFORMATION: unknown
<220> FEATURE:
<221> NAME/KEY: misc_feature
<222> LOCATION: (10)...(10)
<223> OTHER INFORMATION: unknown
<220> FEATURE:
<221> NAME/KEY: misc_feature
<222> LOCATION: (12)...(12)
<223> OTHER INFORMATION: unknown
<220> FEATURE:
<221> NAME/KEY: misc_feature
<222> LOCATION: (14)...(22)
```

```
<223> OTHER INFORMATION: unknown
<220> FEATURE:
<221> NAME/KEY: misc_feature
<222> LOCATION: (25)...(30)
<223> OTHER INFORMATION: unknown

<400> SEQUENCE: 127

Gln Xaa Xaa Xaa Xaa Xaa Xaa Xaa Lys Xaa Asp Xaa Tyr Xaa Xaa Xaa
 1               5                  10                  15

Xaa Xaa Xaa Xaa Xaa Xaa Gln Leu Xaa Xaa Xaa Xaa Xaa Tyr
            20                  25                  30

<210> SEQ ID NO 128
<211> LENGTH: 24
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (2)...(2)
<223> OTHER INFORMATION: m5c
<220> FEATURE:
<221> NAME/KEY: modified_base
<222> LOCATION: (5)...(5)
<223> OTHER INFORMATION: m5c
<220> FEATURE:
<221> NAME/KEY: modified_base
<222> LOCATION: (13)...(13)
<223> OTHER INFORMATION: m5c
<220> FEATURE:
<221> NAME/KEY: modified_base
<222> LOCATION: (21)...(21)
<223> OTHER INFORMATION: m5c

<400> SEQUENCE: 128
tcgtcgtttt gtcgttttgt cgtt                                          24

<210> SEQ ID NO 129
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 129 gacgtt                                                               6

<210> SEQ ID NO 130
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 130
tccatgacgt tcttgacgct                                               20

<210> SEQ ID NO 131
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 131
tccatgacgt tcttgacgtt                                               20
```

```
<210> SEQ ID NO 132
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 132
tccatgacgt tcttgatgtt                                               20

<210> SEQ ID NO 133
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 133
tccatgacgt ttttgatgtt                                               20

<210> SEQ ID NO 134
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 134
tccatgtcgt tcttgatgtt                                               20

<210> SEQ ID NO 135
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 135
tccatgtcgt ttttgatgtt                                               20

<210> SEQ ID NO 136
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 136
tccatgtcgt ttttgttgtt                                               20

<210> SEQ ID NO 137
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 137
tccatgacgt tattgatgtt                                               20

<210> SEQ ID NO 138
<211> LENGTH: 20
<212> TYPE: DNA
<213> ORGANISM: Artificial Sequence
<220> FEATURE:
<223> OTHER INFORMATION: Synthetic oligonucleotide
```

```
<400> SEQUENCE: 138
tccatgacgt ccttgatgtt                                           20

<210> SEQ ID NO 139
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 139
tccatgacgt cattgatgtt                                           20

<210> SEQ ID NO 140
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 140
hhhhhhhhhh hhhhwggggg                                           20

<210> SEQ ID NO 141
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 141
ctgcatggag tgcggccaaa agtccctcca cctacatccc gatac               45

<210> SEQ ID NO 142
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 142
gtatcgggat gtaggtggag ggacttttgg ccgcactcca tgcag               45

<210> SEQ ID NO 143
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 143
ctgtatagaa tgtcctcgtc acttcccccca gctgcaccct gagac              45

<210> SEQ ID NO 144
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 144
gtctcagggt gcagctgggg gaagtgacga ggacattcta tacag               45

<210> SEQ ID NO 145
<211> LENGTH: 14
```

```
<212> TYPE: PRT
<213> ORGANISM: Artificial Sequence
<220> FEATURE:
<223> OTHER INFORMATION: Mutated from human
<220> FEATURE:
<221> NAME/KEY: misc_feature
<222> LOCATION: (2)...(3)
<223> OTHER INFORMATION: unknown
<220> FEATURE:
<221> NAME/KEY: misc_feature
<222> LOCATION: (5)...(10)
<223> OTHER INFORMATION: unknown
<220> FEATURE:
<221> NAME/KEY: misc_feature
<222> LOCATION: (12)...(13)
<223> OTHER INFORMATION: unknown

<400> SEQUENCE: 145

Cys Xaa Xaa Cys Xaa Xaa Xaa Xaa Xaa Xaa Cys Xaa Xaa Cys
 1               5                  10

<210> SEQ ID NO 146
<211> LENGTH: 20
<212> TYPE: PRT
<213> ORGANISM: Homo sapiens

<400> SEQUENCE: 146

Cys Arg Arg Cys Asp His Ala Pro Asn Pro Cys Met Glu Cys Pro Arg
 1               5                  10                  15

His Phe Pro Gln
            20

<210> SEQ ID NO 147
<211> LENGTH: 20
<212> TYPE: PRT
<213> ORGANISM: Unknown
<220> FEATURE:
<223> OTHER INFORMATION: Mutated from human

<400> SEQUENCE: 147

Cys Arg Arg Cys Asp His Ala Pro Asn Pro Cys Met Glu Cys Gly Gln
 1               5                  10                  15

Lys Ser Leu His
            20

<210> SEQ ID NO 148
<211> LENGTH: 20
<212> TYPE: PRT
<213> ORGANISM: Mus musculus

<400> SEQUENCE: 148

Cys Arg Arg Cys Asp His Ala Pro Asn Pro Cys Met Ile Cys Gly Gln
 1               5                  10                  15

Lys Ser Leu His
            20

<210> SEQ ID NO 149
<211> LENGTH: 20
<212> TYPE: PRT
<213> ORGANISM: Unknown
<220> FEATURE:
<223> OTHER INFORMATION: Mutated from mouse

<400> SEQUENCE: 149

Cys Arg Arg Cys Asp His Ala Pro Asn Pro Cys Met Ile Cys Pro Arg
 1               5                  10                  15
```

His Phe Pro Gln
            20

<210> SEQ ID NO 150
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 150
cacaataagc tggccctcgc ccacgagcac tc                          32

<210> SEQ ID NO 151
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 151
gagtgctcgt gggcgagggc cagcttattg tg                          32

<210> SEQ ID NO 152
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 152
cataacaaac tggccttggc ccactggaaa tc                          32

<210> SEQ ID NO 153
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 153
gatttccagt gggccaaggc cagtttgtta tg                          32

<210> SEQ ID NO 154
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 154
gcgactggct gcatggcaaa accctctttg                             30

<210> SEQ ID NO 155
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 155
caaagagggt tttgccatgc agccagtcgc                             30

<210> SEQ ID NO 156
<211> LENGTH: 30
<212> TYPE: DNA

```
<213> ORGANISM: Artificial Sequence
<220> FEATURE:
<223> OTHER INFORMATION: Synthetic oligonucleotide

<400> SEQUENCE: 156
cgagattggc tgcatggcca gacgctcttc                                              30

<210> SEQ ID NO 157
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 157
gaagagcgtc tggccatgca gccaatctcg                                              30

<210> SEQ ID NO 158
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 158
ggcctcagca tcttt                                                              15

<210> SEQ ID NO 159
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 159
ggcctatcga ttttt                                                              15

<210> SEQ ID NO 160
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 160
ggccgtagca tcttc                                                              15

<210> SEQ ID NO 161
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 161
ggcctatcga ttttt                                                              15

<210> SEQ ID NO 162
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 162
cagctccagg gcctatcgat ttttgcacag gacc                                         34
```

<210> SEQ ID NO 163
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 163
ggtcctgtgc aaaaatcgat aggccctgga gctg                         34

<210> SEQ ID NO 164
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 164
cagctgcagg gcctatcgat tttcgcacag gacc                         34

<210> SEQ ID NO 165
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 165
ggtcctgtgc gaaaatcgat aggccctgca gctg                         34

<210> SEQ ID NO 166
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 166
cacctctcat gctctgctct cttc                                    24

<210> SEQ ID NO 167
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 167
gctagaccgt ttccttgaac acctg                                   25

<210> SEQ ID NO 168
<211> LENGTH: 3373
<212> TYPE: DNA
<213> ORGANISM: Homo sapiens
<220> FEATURE:
<221> NAME/KEY: misc_feature
<222> LOCATION: (0)...(0)
<223> OTHER INFORMATION: Human TLR7 cDNA

<400> SEQUENCE: 168
agctggctag cgtttaaacg ggccctctag actcgagcgg ccgcgaattc actagtgatt    60
cacctctcat gctctgctct cttcaaccag acctctacat tccatttggg aagaagacta   120
aaaatggtgt tccaatgtgt gacactgaag agacaaattc ttatccttttt taacataatc   180

```
ctaatttcca aactccttgg ggctagatgg tttcctaaaa ctctgccctg tgatgtcact    240
ctggatgttc caaagaacca tgtgatcgtg gactgcacag acaagcattt gacagaaatt    300
cctggaggta ttcccacgaa caccacgaac ctcaccctca ccattaacca cataccagac    360
atctccccag cgtcctttca cagactggac catctggtag agatcgattt cagatgcaac    420
tgtgtaccta ttccactggg gtcaaaaaac aacatgtgca tcaagaggct gcagattaaa    480
cccagaagct ttagtggact cacttattta aaatcccttt acctggatgg aaaccagcta    540
ctagagatac cgcagggcct cccgcctagc ttacagcttc tcagccttga ggccaacaac    600
atcttttcca tcagaaaaga gaatctaaca gaactggcca acatagaaat actctacctg    660
ggccaaaact gttattatcg aaatccttgt tatgtttcat attcaataga gaaagatgcc    720
ttcctaaact tgacaaagtt aaaagtgctc tccctgaaag ataacaatgt cacagccgtc    780
cctactgttt tgccatctac tttaacagaa ctatatctct acaacaacat gattgcaaaa    840
atccaagaag atgattttaa taacctcaac caattacaaa ttcttgacct aagtggaaat    900
tgccctcgtt gttataatgc cccatttcct tgtgcgccgt gtaaaaataa ttctccccta    960
cagatccctg taaatgcttt tgatgcgctg acagaattaa aagttttacg tctacacagt   1020
aactctcttc agcatgtgcc cccaagatgg tttaagaaca tcaacaaact ccaggaactg   1080
gatcgtcccc aaaacttctt ggccaaagaa attggggatg ctaaatttct gcattttctc   1140
cccagcctca tccaattgga tctgtctttc aattttgaac ttcaggtcta tcgtgcatct   1200
atgaatctat cacaagcatt tcttcactg aaaagcctga aaattctgcg gatcagagga   1260
tatgtcttta aagagttgaa aagctttaac ctctcgccat tacataatct tcaaaatctt   1320
gaagttcttg atcttggcac taactttata aaaattgcta acctcagcat gtttaaacaa   1380
tttaaaagac tgaaagtcat agatctttca gtgaataaaa tatcaccttc aggagattca   1440
agtgaagttg gcttctgctc aaatgccaga acttctgtag aaagttatga accccaggtc   1500
ctggaacaat tacattattt cagatatgat aagtatgcaa ggagttgcag attcaaaaac   1560
aaagaggctt ctttcatgtc tgttaatgaa agctgctaca agtatgggca gaccttggat   1620
ctaagtaaaa atagtatatt ttttgtcaag tcctctgatt ttcagcatct ttctttcctc   1680 aaaatgcctga atctgtcagg aaatctcatt agccaaactc ttaatggcag tgaattccaa   1740
cctttagcag agctgagata tttggacttc tccaacaacc ggcttgattt actccattca   1800
acagcatttg aagagcttca caaactggaa gttctggata taagcagtaa tagccattat   1860
tttcaatcag aaggaattac tcatatgcta aactttacca agaacctaaa ggttctgcag   1920
aaactgatga tgaacgacaa tgacatctct tcctccacca gcaggaccat ggagagtgag   1980
tctcttagaa ctctggaatt cagaggaaat cacttagatg tttttatggag agaaggtgat   2040 aacagatact tacaattatt caagaatctg ctaaaattag aggaattaga catctctaaa   2100
aattccctaa gtttcttgcc ttctggagtt tttgatggta tgcctccaaa tctaaagaat   2160
ctctctttgg ccaaaaatgg gctcaaatct ttcagttgga gaaaactcca gtgtctaaag   2220
aacctggaaa ctttggacct cagccacaac caactgacca ctgtccctga gagattatcc   2280
aactgttcca gaagcctcaa gaatctgatt cttaagaata tcaaatcag gagtctgacg   2340 aagtattttc tacaagatgc cttccagttg cgatatctgg atctcagctc aaataaaatc   2400
cagatgatcc aaaagaccag cttcccagaa aatgtcctca acaatctgaa gatgttgctt   2460
ttgcatcata atcggtttct gtgcacctgt gatgctgtgt ggtttgtctg gtgggttaac   2520
catacggagg tgactattcc ttacctggcc acagatgtga cttgtgtggg gccaggagca   2580
```

| | |
|---|---|
| cacaagggcc aaagtgtgat ctccctggat ctgtacacct gtgagttaga tctgactaac | 2640 |
| ctgattctgt tctcactttc catatctgta tctctctttc tcatggtgat gatgacagca | 2700 |
| agtcacctct atttctggga tgtgtggtat atttaccatt tctgtaaggc caagataaag | 2760 |
| gggtatcagc gtctaatatc accagactgt tgctatgatg cttttattgt gtatgacact | 2820 |
| aaagacccag ctgtgaccga gtgggttttg gctgagctgg tggccaaact ggaagaccca | 2880 |
| agagagaaac attttaattt atgtctcgag gaaagggact ggttaccagg gcagccagtt | 2940 |
| ctggaaaacc tttcccagag catacagctt agcaaaaaga cagtgtttgt gatgacagac | 3000 |
| aagtatgcaa agactgaaaa ttttaagata gcattttact tgtcccatca gaggctcatg | 3060 |
| gatgaaaaag ttgatgtgat tatcttgata tttcttgaga agccttttca gaagtccaag | 3120 |
| ttcctccagc tccggaaaag gctctgtggg agttctgtcc ttgagtggcc aacaaacccg | 3180 |
| caagctcacc catacttctg gcagtgtcta agaacgccc tggccacaga caatcatgtg | 3240 |
| gcctatagtc aggtgttcaa ggaaacggtc tagaatcgaa ttcccgcggc cgccactgtg | 3300 |
| ctggatatct gcagaattcc accacactgg actagtggat ccgagctcgg taccaagctt | 3360 |
| aagtttaaac cgc | 3373 |

<210> SEQ ID NO 169
<211> LENGTH: 3147
<212> TYPE: DNA
<213> ORGANISM: Homo sapiens
<220> FEATURE:
<221> NAME/KEY: misc_feature
<222> LOCATION: (0)...(0)
<223> OTHER INFORMATION: Human TLR7 ORF

<400> SEQUENCE: 169

| | |
|---|---|
| atggtgtttc aatgtggac actgaagaga caaattctta tccttttaa cataatccta | 60 |
| atttccaaac tccttggggc tagatggttt cctaaaactc tgccctgtga tgtcactctg | 120 |
| gatgttccaa agaaccatgt gatcgtggac tgcacagaca gcatttgac agaaattcct | 180 |
| ggaggtattc ccacgaacac cacgaacctc accctcacca ttaaccacat ccagacatc | 240 |
| tccccagcgt cctttcacag actggaccat ctggtagaga tcgatttcag atgcaactgt | 300 |
| gtacctattc cactggggtc aaaaaacaac atgtgcatca gaggctgca gattaaaccc | 360 |
| agaagcttta gtggactcac ttatttaaaa tcccttttacc tggatggaaa ccagctacta | 420 |
| gagataccgc agggcctccc gcctagctta cagcttctca gccttgaggc aacaacatc | 480 |
| ttttccatca gaaaagagaa tctaacagaa ctggccaaca tagaaatact ctacctgggc | 540 |
| caaaactgtt attatcgaaa tccttgttat gtttcatatt caatagagaa agatgccttc | 600 |
| ctaaacttga caaagttaaa agtgctctcc ctgaaagata caatgtcac agccgtccct | 660 |
| actgttttgc catctacttt aacagaacta tatctctaca acaacatgat tgcaaaaatc | 720 |
| caagaagatg attttaataa cctcaaccaa ttacaaattc ttgacctaag tggaaattgc | 780 |
| cctcgttgtt ataatgcccc atttcctgt gcgccgtgta aaataattc tcccctacag | 840 |
| atccctgtaa atgcttttga tgcgctgaca gaattaaaag ttttacgtct acacagtaac | 900 |
| tctcttcagc atgtgccccc aagatggttt aagaacatca caaactcca ggaactggat | 960 |
| ctgtcccaaa acttcttggc caaagaaatt ggggatgcta atttctgca ttttctcccc | 1020 |
| agcctcatcc aattggatct gtcttttcaat tttgaacttc aggtctatcg tgcatctatg | 1080 |
| aatctatcac aagcattttc ttcactgaaa agcctgaaaa ttctgcggat cagaggatat | 1140 |

```
gtctttaaag agttgaaaag ctttaacctc tcgccattac ataatcttca aaatcttgaa    1200
gttcttgatc ttggcactaa ctttataaaa attgctaacc tcagcatgtt taaacaattt    1260
aaaagactga aagtcataga tctttcagtg aataaaatat caccttcagg agattcaagt    1320
gaagttggct tctgctcaaa tgccagaact tctgtagaaa gttatgaacc ccaggtcctg    1380
gaacaattac attatttcag atatgataag tatgcaagga gttgcagatt caaaaacaaa    1440
gaggcttctt tcatgtctgt taatgaaagc tgctacaagt atgggcagac cttggatcta    1500
agtaaaaata gtatttttt tgtcaagtcc tctgattttc agcatctttc tttcctcaaa    1560
tgcctgaatc tgtcaggaaa tctcattagc caaactctta atggcagtga attccaacct    1620
ttagcagagc tgagatattt ggacttctcc aacaaccggc ttgatttact ccattcaaca    1680
gcatttgaag agcttcacaa actggaagtt ctggatataa cagtaatag ccattatttt    1740 caatcagaag gaattactca tatgctaaac tttaccaaga acctaaaggt tctgcagaaa    1800
ctgatgatga cgacaatga catctcttcc tccaccagca ggaccatgga gagtgagtct    1860
cttagaactc tggaattcag aggaaatcac ttagatgttt tatggagaga aggtgataac    1920
agatacttac aattattcaa gaatctgcta aaattagagg aattagacat ctctaaaaat    1980
tccctaagtt tcttgccttc tggagttttt gatggtatgc ctccaaatct aaagaatctc    2040
tctttggcca aaaatgggct caaatctttc agttggaaga actccagtg tctaaagaac    2100 ctggaaactt tggacctcag ccacaaccaa ctgaccactg tccctgagag attatccaac    2160
tgttccagaa gcctcaagaa tctgattctt aagaataatc aaatcaggag tctgacgaag    2220
tattttctac aagatgcctt ccagttgcga tatctggatc tcagctcaaa taaaatccag    2280
atgatccaaa agaccagctt cccagaaaat gtcctcaaca atctgaagat gttgcttttg    2340
catcataatc ggtttctgtg cacctgtgat gctgtgtggt ttgtctggtg ggttaaccat    2400
acggaggtga ctattcctta cctggccaca gatgtgactt gtgtggggcc aggagcacac    2460
aagggccaaa gtgtgatctc cctggatctg tacacctgtg agttagatct gactaacctg    2520
attctgttct cactttccat atctgtatct ctctttctca tggtgatgat gacagcaagt    2580
cacctctatt tctgggatgt gtggtatatt taccatttct gtaaggccaa gataaagggg    2640
tatcagcgtc taatatcacc agactgttgc tatgatgctt ttattgtgta tgacactaaa    2700
gacccagctg tgaccgagtg ggttttggct gagctggtgg ccaaactgga agacccaaga    2760
gagaaacatt ttaatttatg tctcgaggaa agggactggt taccagggca gccagttctg    2820
gaaaaccttt cccagagcat acagcttagc aaaaagacag tgtttgtgat gacagacaag    2880
tatgcaaaga ctgaaaattt taagatagca ttttacttgt cccatcagag gctcatggat    2940
gaaaaagttg atgtgattat cttgatattt cttgagaagc ttttcagaa gtccaagttc    3000 ctccagctcc ggaaaaggct ctgtgggagt tctgtccttg agtggccaac aaacccgcaa    3060
gctcacccat acttctggca gtgtctaaag aacgccctgg ccacagacaa tcatgtggcc    3120
tatagtcagg tgttcaagga aacggtc                                      3147
```

<210> SEQ ID NO 170
<211> LENGTH: 1049
<212> TYPE: PRT
<213> ORGANISM: Homo sapiens

<400> SEQUENCE: 170

Met Val Phe Pro Met Trp Thr Leu Lys Arg Gln Ile Leu Ile Leu Phe
1               5                   10                  15

```
Asn Ile Ile Leu Ile Ser Lys Leu Leu Gly Ala Arg Trp Phe Pro Lys
             20                  25                  30

Thr Leu Pro Cys Asp Val Thr Leu Asp Val Pro Lys Asn His Val Ile
         35                  40                  45

Val Asp Cys Thr Asp Lys His Leu Thr Glu Ile Pro Gly Gly Ile Pro
 50                  55                  60

Thr Asn Thr Thr Asn Leu Thr Leu Thr Ile Asn His Ile Pro Asp Ile
 65                  70                  75                  80

Ser Pro Ala Ser Phe His Arg Leu Asp His Leu Val Glu Ile Asp Phe
                 85                  90                  95

Arg Cys Asn Cys Val Pro Ile Pro Leu Gly Ser Lys Asn Asn Met Cys
             100                 105                 110

Ile Lys Arg Leu Gln Ile Lys Pro Arg Ser Phe Ser Gly Leu Thr Tyr
         115                 120                 125

Leu Lys Ser Leu Tyr Leu Asp Gly Asn Gln Leu Leu Glu Ile Pro Gln
 130                 135                 140

Gly Leu Pro Pro Ser Leu Gln Leu Leu Ser Leu Glu Ala Asn Asn Ile
145                 150                 155                 160

Phe Ser Ile Arg Lys Glu Asn Leu Thr Glu Leu Ala Asn Ile Glu Ile
             165                 170                 175

Leu Tyr Leu Gly Gln Asn Cys Tyr Tyr Arg Asn Pro Cys Tyr Val Ser
         180                 185                 190

Tyr Ser Ile Glu Lys Asp Ala Phe Leu Asn Leu Thr Lys Leu Lys Val
         195                 200                 205

Leu Ser Leu Lys Asp Asn Asn Val Thr Ala Val Pro Thr Val Leu Pro
         210                 215                 220

Ser Thr Leu Thr Glu Leu Tyr Leu Tyr Asn Asn Met Ile Ala Lys Ile
225                 230                 235                 240

Gln Glu Asp Asp Phe Asn Asn Leu Asn Gln Leu Gln Ile Leu Asp Leu
             245                 250                 255

Ser Gly Asn Cys Pro Arg Cys Tyr Asn Ala Pro Phe Pro Cys Ala Pro
             260                 265                 270

Cys Lys Asn Asn Ser Pro Leu Gln Ile Pro Val Asn Ala Phe Asp Ala
         275                 280                 285

Leu Thr Glu Leu Lys Val Leu Arg Leu His Ser Asn Ser Leu Gln His
 290                 295                 300

Val Pro Pro Arg Trp Phe Lys Asn Ile Asn Lys Leu Gln Glu Leu Asp
305                 310                 315                 320

Leu Ser Gln Asn Phe Leu Ala Lys Glu Ile Gly Asp Ala Lys Phe Leu
             325                 330                 335

His Phe Leu Pro Ser Leu Ile Gln Leu Asp Leu Ser Phe Asn Phe Glu
         340                 345                 350

Leu Gln Val Tyr Arg Ala Ser Met Asn Leu Ser Gln Ala Phe Ser Ser
         355                 360                 365

Leu Lys Ser Leu Lys Ile Leu Arg Ile Arg Gly Tyr Val Phe Lys Glu
         370                 375                 380

Leu Lys Ser Phe Asn Leu Ser Pro Leu His Asn Leu Gln Asn Leu Glu
385                 390                 395                 400

Val Leu Asp Leu Gly Thr Asn Phe Ile Lys Ile Ala Asn Leu Ser Met
                 405                 410                 415

Phe Lys Gln Phe Lys Arg Leu Lys Val Ile Asp Leu Ser Val Asn Lys
             420                 425                 430

Ile Ser Pro Ser Gly Asp Ser Ser Glu Val Gly Phe Cys Ser Asn Ala
```

-continued

```
            435                 440                 445
Arg Thr Ser Val Glu Ser Tyr Glu Pro Gln Val Leu Glu Gln Leu His
450                     455                 460
Tyr Phe Arg Tyr Asp Lys Tyr Ala Arg Ser Cys Arg Phe Lys Asn Lys
465                 470                  475                 480
Glu Ala Ser Phe Met Ser Val Asn Glu Ser Cys Tyr Lys Tyr Gly Gln
                485                 490                 495
Thr Leu Asp Leu Ser Lys Asn Ser Ile Phe Phe Val Lys Ser Ser Asp
            500                 505                 510
Phe Gln His Leu Ser Phe Leu Lys Cys Leu Asn Leu Ser Gly Asn Leu
            515                 520                 525
Ile Ser Gln Thr Leu Asn Gly Ser Glu Phe Gln Pro Leu Ala Glu Leu
530                 535                 540
Arg Tyr Leu Asp Phe Ser Asn Asn Arg Leu Asp Leu Leu His Ser Thr
545                 550                 555                 560
Ala Phe Glu Glu Leu His Lys Leu Glu Val Leu Asp Ile Ser Ser Asn
                565                 570                 575
Ser His Tyr Phe Gln Ser Glu Gly Ile Thr His Met Leu Asn Phe Thr
            580                 585                 590
Lys Asn Leu Lys Val Leu Gln Lys Leu Met Met Asn Asp Asn Asp Ile
            595                 600                 605
Ser Ser Ser Thr Ser Arg Thr Met Glu Ser Glu Ser Leu Arg Thr Leu
610                 615                 620
Glu Phe Arg Gly Asn His Leu Asp Val Leu Trp Arg Glu Gly Asp Asn
625                 630                 635                 640
Arg Tyr Leu Gln Leu Phe Lys Asn Leu Leu Lys Leu Glu Glu Leu Asp
                645                 650                 655
Ile Ser Lys Asn Ser Leu Ser Phe Leu Pro Ser Gly Val Phe Asp Gly
            660                 665                 670
Met Pro Pro Asn Leu Lys Asn Leu Ser Leu Ala Lys Asn Gly Leu Lys
            675                 680                 685
Ser Phe Ser Trp Lys Lys Leu Gln Cys Leu Lys Asn Leu Glu Thr Leu
690                 695                 700
Asp Leu Ser His Asn Gln Leu Thr Thr Val Pro Glu Arg Leu Ser Asn
705                 710                 715                 720
Cys Ser Arg Ser Leu Lys Asn Leu Ile Leu Lys Asn Asn Gln Ile Arg
                725                 730                 735
Ser Leu Thr Lys Tyr Phe Leu Gln Asp Ala Phe Gln Leu Arg Tyr Leu
            740                 745                 750
Asp Leu Ser Ser Asn Lys Ile Gln Met Ile Gln Lys Thr Ser Phe Pro
            755                 760                 765
Glu Asn Val Leu Asn Asn Leu Lys Met Leu Leu Leu His His Asn Arg
770                 775                 780
Phe Leu Cys Thr Cys Asp Ala Val Trp Phe Val Trp Trp Val Asn His
785                 790                 795                 800
Thr Glu Val Thr Ile Pro Tyr Leu Ala Thr Asp Val Thr Cys Val Gly
                805                 810                 815
Pro Gly Ala His Lys Gly Gln Ser Val Ile Ser Leu Asp Leu Tyr Thr
            820                 825                 830
Cys Glu Leu Asp Leu Thr Asn Leu Ile Leu Phe Ser Leu Ser Ile Ser
            835                 840                 845
Val Ser Leu Phe Leu Met Val Met Met Thr Ala Ser His Leu Tyr Phe
850                 855                 860
```

Trp Asp Val Trp Tyr Ile Tyr His Phe Cys Lys Ala Lys Ile Lys Gly
865                 870                 875                 880

Tyr Gln Arg Leu Ile Ser Pro Asp Cys Cys Tyr Asp Ala Phe Ile Val
                885                 890                 895

Tyr Asp Thr Lys Asp Pro Ala Val Thr Glu Trp Val Leu Ala Glu Leu
            900                 905                 910

Val Ala Lys Leu Glu Asp Pro Arg Glu Lys His Phe Asn Leu Cys Leu
                915                 920                 925

Glu Glu Arg Asp Trp Leu Pro Gly Gln Pro Val Leu Glu Asn Leu Ser
930                 935                 940

Gln Ser Ile Gln Leu Ser Lys Lys Thr Val Phe Val Met Thr Asp Lys
945                 950                 955                 960

Tyr Ala Lys Thr Glu Asn Phe Lys Ile Ala Phe Tyr Leu Ser His Gln
                965                 970                 975

Arg Leu Met Asp Glu Lys Val Asp Val Ile Leu Ile Phe Leu Glu
            980                 985                 990

Lys Pro Phe Gln Lys Ser Lys Phe Leu Gln Leu Arg Lys Arg Leu Cys
                995                 1000                1005

Gly Ser Ser Val Leu Glu Trp Pro Thr Asn Pro Gln Ala His Pro Tyr
    1010                1015                1020

Phe Trp Gln Cys Leu Lys Asn Ala Leu Ala Thr Asp Asn His Val Ala
1025                1030                1035                1040

Tyr Ser Gln Val Phe Lys Glu Thr Val
                1045

<210> SEQ ID NO 171
<211> LENGTH: 989
<212> TYPE: PRT
<213> ORGANISM: Homo sapiens

<400> SEQUENCE: 171

Met Val Phe Pro Met Trp Thr Leu Lys Arg Gln Ile Leu Ile Leu Phe
1               5                   10                  15

Asn Ile Ile Leu Ile Ser Lys Leu Leu Gly Ala Arg Trp Phe Pro Lys
                20                  25                  30

Thr Leu Pro Cys Asp Val Thr Leu Asp Val Pro Lys Asn His Val Ile
            35                  40                  45

Val Asp Cys Thr Asp Lys His Leu Thr Glu Ile Pro Gly Gly Ile Pro
50                  55                  60

Thr Asn Thr Thr Asn Leu Thr Leu Thr Ile Asn His Ile Pro Asp Ile
65                  70                  75                  80

Ser Pro Ala Ser Phe His Arg Leu Asp His Leu Val Glu Ile Asp Phe
                85                  90                  95

Arg Cys Asn Cys Val Pro Ile Pro Leu Gly Ser Lys Asn Asn Met Cys
            100                 105                 110

Ile Lys Arg Leu Gln Ile Lys Pro Arg Ser Phe Ser Gly Leu Thr Tyr
        115                 120                 125

Leu Lys Ser Leu Tyr Leu Asp Gly Asn Gln Leu Leu Glu Ile Pro Gln
130                 135                 140

Gly Leu Pro Pro Ser Leu Gln Leu Leu Ser Leu Glu Ala Asn Asn Ile
145                 150                 155                 160

Phe Ser Ile Arg Lys Glu Asn Leu Thr Glu Leu Ala Asn Ile Glu Ile
                165                 170                 175

Leu Tyr Leu Gly Gln Asn Cys Tyr Tyr Arg Asn Pro Cys Tyr Val Ser

-continued

```
                180                 185                 190
Tyr Ser Ile Glu Lys Asp Ala Phe Leu Asn Leu Thr Lys Leu Lys Val
            195                 200                 205
Leu Ser Leu Lys Asp Asn Asn Val Thr Ala Val Pro Thr Val Leu Pro
        210                 215                 220
Ser Thr Leu Thr Glu Leu Tyr Leu Tyr Asn Asn Met Ile Ala Lys Ile
225                 230                 235                 240
Gln Glu Asp Asp Phe Asn Asn Leu Asn Gln Leu Gln Ile Leu Asp Leu
                245                 250                 255
Ser Gly Asn Cys Pro Arg Cys Tyr Asn Ala Pro Phe Pro Cys Ala Pro
            260                 265                 270
Cys Lys Asn Asn Ser Pro Leu Gln Ile Pro Val Asn Ala Phe Asp Ala
        275                 280                 285
Leu Thr Glu Leu Lys Val Leu Arg Leu His Ser Asn Ser Leu Gln His
        290                 295                 300
Val Pro Pro Arg Trp Phe Lys Asn Ile Asn Lys Leu Gln Glu Leu Asp
305                 310                 315                 320
Leu Ser Gln Asn Phe Leu Ala Lys Glu Ile Gly Asp Ala Lys Phe Leu
                325                 330                 335
His Phe Leu Pro Ser Leu Ile Gln Leu Asp Leu Ser Phe Asn Phe Glu
            340                 345                 350
Leu Gln Val Tyr Arg Ala Ser Met Asn Leu Ser Gln Ala Phe Ser Ser
        355                 360                 365
Leu Lys Ser Leu Lys Ile Leu Arg Ile Arg Gly Tyr Val Phe Lys Glu
        370                 375                 380
Leu Lys Ser Phe Asn Leu Ser Pro Leu His Asn Leu Gln Asn Leu Glu
385                 390                 395                 400
Val Leu Asp Leu Gly Thr Asn Phe Ile Lys Ile Ala Asn Leu Ser Met
                405                 410                 415
Phe Lys Gln Phe Lys Arg Leu Lys Val Ile Asp Leu Ser Val Asn Lys
            420                 425                 430
Ile Ser Pro Ser Gly Asp Ser Ser Glu Val Gly Phe Cys Ser Asn Ala
        435                 440                 445
Arg Thr Ser Val Glu Ser Tyr Glu Pro Gln Val Leu Glu Gln Leu His
        450                 455                 460
Tyr Phe Arg Tyr Asp Lys Tyr Ala Arg Ser Cys Arg Phe Lys Asn Lys
465                 470                 475                 480
Glu Ala Ser Phe Met Ser Val Asn Glu Ser Cys Tyr Lys Tyr Gly Gln
                485                 490                 495
Thr Leu Asp Leu Ser Lys Asn Ser Ile Phe Phe Val Lys Ser Ser Asp
            500                 505                 510
Phe Gln His Leu Ser Phe Leu Lys Cys Leu Asn Leu Ser Gly Asn Leu
        515                 520                 525
Ile Ser Gln Thr Leu Asn Gly Ser Glu Phe Gln Pro Leu Met Met Asn
        530                 535                 540
Asp Asn Asp Ile Ser Ser Ser Thr Ser Arg Thr Met Glu Ser Glu Ser
545                 550                 555                 560
Leu Arg Thr Leu Glu Phe Arg Gly Asn His Leu Asp Val Leu Trp Arg
                565                 570                 575
Glu Gly Asp Asn Arg Tyr Leu Gln Leu Phe Lys Asn Leu Leu Lys Leu
            580                 585                 590
Glu Glu Leu Asp Ile Ser Lys Asn Ser Leu Ser Phe Leu Pro Ser Gly
        595                 600                 605
```

Val Phe Asp Gly Met Pro Pro Asn Leu Lys Asn Leu Ser Leu Ala Lys
    610                 615                 620

Asn Gly Leu Lys Ser Phe Ser Trp Lys Lys Leu Gln Cys Leu Lys Asn
625                 630                 635                 640

Leu Glu Thr Leu Asp Leu Ser His Asn Gln Leu Thr Thr Val Pro Glu
                645                 650                 655

Arg Leu Ser Asn Cys Ser Arg Ser Leu Lys Asn Leu Ile Leu Lys Asn
                660                 665                 670

Asn Gln Ile Arg Ser Leu Thr Lys Tyr Phe Leu Gln Asp Ala Phe Gln
            675                 680                 685

Leu Arg Tyr Leu Asp Leu Ser Ser Asn Lys Ile Gln Met Ile Gln Lys
    690                 695                 700

Thr Ser Phe Pro Glu Asn Val Leu Asn Asn Leu Lys Met Leu Leu Leu
705                 710                 715                 720

His His Asn Arg Phe Leu Cys Thr Cys Asp Ala Val Trp Phe Val Trp
                725                 730                 735

Trp Val Asn His Thr Glu Val Thr Ile Pro Tyr Leu Ala Thr Asp Val
                740                 745                 750

Thr Cys Val Gly Pro Gly Ala His Lys Gly Gln Ser Val Ile Ser Leu
            755                 760                 765

Asp Leu Tyr Thr Cys Glu Leu Asp Leu Thr Asn Leu Ile Leu Phe Ser
    770                 775                 780

Leu Ser Ile Ser Val Ser Leu Phe Leu Met Val Met Met Thr Ala Ser
785                 790                 795                 800

His Leu Tyr Phe Trp Asp Val Trp Tyr Ile Tyr His Phe Cys Lys Ala
                805                 810                 815

Lys Ile Lys Gly Tyr Gln Arg Leu Ile Ser Pro Asp Cys Cys Tyr Asp
            820                 825                 830

Ala Phe Ile Val Tyr Asp Thr Lys Asp Pro Ala Val Thr Glu Trp Val
    835                 840                 845

Leu Ala Glu Leu Val Ala Lys Leu Glu Asp Pro Arg Glu Lys His Phe
850                 855                 860

Asn Leu Cys Leu Glu Glu Arg Asp Trp Leu Pro Gly Gln Pro Val Leu
865                 870                 875                 880

Glu Asn Leu Ser Gln Ser Ile Gln Leu Ser Lys Lys Thr Val Phe Val
                885                 890                 895

Met Thr Asp Lys Tyr Ala Lys Thr Glu Asn Phe Lys Ile Ala Phe Tyr
            900                 905                 910

Leu Ser His Gln Arg Leu Met Asp Glu Lys Val Asp Val Ile Ile Leu
    915                 920                 925

Ile Phe Leu Glu Lys Pro Phe Gln Lys Ser Lys Phe Leu Gln Leu Arg
930                 935                 940

Lys Arg Leu Cys Gly Ser Ser Val Leu Glu Trp Pro Thr Asn Pro Gln
945                 950                 955                 960

Ala His Pro Tyr Phe Trp Gln Cys Leu Lys Asn Ala Leu Ala Thr Asp
                965                 970                 975

Asn His Val Ala Tyr Ser Gln Val Phe Lys Glu Thr Val
            980                 985

<210> SEQ ID NO 172
<211> LENGTH: 1049
<212> TYPE: PRT
<213> ORGANISM: Homo sapiens

<400> SEQUENCE: 172

```
Met Val Phe Pro Met Trp Thr Leu Lys Arg Gln Ile Leu Ile Leu Phe
 1               5                  10                  15
Asn Ile Ile Leu Ile Ser Lys Leu Leu Gly Ala Arg Trp Phe Pro Lys
             20                  25                  30
Thr Leu Pro Cys Asp Val Thr Leu Asp Val Pro Lys Asn His Val Ile
         35                  40                  45
Val Asp Cys Thr Asp Lys His Leu Thr Glu Ile Pro Gly Gly Ile Pro
 50                  55                  60
Thr Asn Thr Thr Asn Leu Thr Leu Thr Ile Asn His Ile Pro Asp Ile
65                  70                  75                  80
Ser Pro Ala Ser Phe His Arg Leu Asp His Leu Val Glu Ile Asp Phe
                 85                  90                  95
Arg Cys Asn Cys Val Pro Ile Pro Leu Gly Ser Lys Asn Asn Met Cys
            100                 105                 110
Ile Lys Arg Leu Gln Ile Lys Pro Arg Ser Phe Ser Gly Leu Thr Tyr
        115                 120                 125
Leu Lys Ser Leu Tyr Leu Asp Gly Asn Gln Leu Leu Glu Ile Pro Gln
130                 135                 140
Gly Leu Pro Pro Ser Leu Gln Leu Leu Ser Leu Glu Ala Asn Asn Ile
145                 150                 155                 160
Phe Ser Ile Arg Lys Glu Asn Leu Thr Glu Leu Ala Asn Ile Glu Ile
                165                 170                 175
Leu Tyr Leu Gly Gln Asn Cys Tyr Tyr Arg Asn Pro Cys Tyr Val Ser
            180                 185                 190
Tyr Ser Ile Glu Lys Asp Ala Phe Leu Asn Leu Thr Lys Leu Lys Val
        195                 200                 205
Leu Ser Leu Lys Asp Asn Asn Val Thr Ala Val Pro Thr Val Leu Pro
210                 215                 220
Ser Thr Leu Thr Glu Leu Tyr Leu Tyr Asn Asn Met Ile Ala Lys Ile
225                 230                 235                 240
Gln Glu Asp Asp Phe Asn Asn Leu Asn Gln Leu Gln Ile Leu Asp Leu
                245                 250                 255
Ser Gly Asn Cys Pro Arg Cys Tyr Asn Ala Pro Phe Pro Cys Ala Pro
            260                 265                 270
Cys Lys Asn Asn Ser Pro Leu Gln Ile Pro Val Asn Ala Phe Asp Ala
        275                 280                 285
Leu Thr Glu Leu Lys Val Leu Arg Leu His Ser Asn Ser Leu Gln His
290                 295                 300
Val Pro Pro Arg Trp Phe Lys Asn Ile Asn Lys Leu Gln Glu Leu Asp
305                 310                 315                 320
Leu Ser Gln Asn Phe Leu Ala Lys Glu Ile Gly Asp Ala Lys Phe Leu
                325                 330                 335
His Phe Leu Pro Ser Leu Ile Gln Leu Asp Leu Ser Phe Asn Phe Glu
            340                 345                 350
Leu Gln Val Tyr Arg Ala Ser Met Asn Leu Ser Gln Ala Phe Ser Ser
        355                 360                 365
Leu Lys Ser Leu Lys Ile Leu Arg Ile Arg Gly Tyr Val Phe Lys Glu
370                 375                 380
Leu Lys Ser Phe Asn Leu Ser Pro Leu His Asn Leu Gln Asn Leu Glu
385                 390                 395                 400
Val Leu Asp Leu Gly Thr Asn Phe Ile Lys Ile Ala Asn Leu Ser Met
                405                 410                 415
```

-continued

Phe Lys Gln Phe Lys Arg Leu Lys Val Ile Asp Leu Ser Val Asn Lys
                420                 425                 430

Ile Ser Pro Ser Gly Asp Ser Ser Glu Val Gly Phe Cys Ser Asn Ala
            435                 440                 445

Arg Thr Ser Val Glu Ser Tyr Glu Pro Gln Val Leu Glu Gln Leu His
    450                 455                 460

Tyr Phe Arg Tyr Asp Lys Tyr Ala Arg Ser Cys Arg Phe Lys Asn Lys
465                 470                 475                 480

Glu Ala Ser Phe Met Ser Val Asn Glu Ser Cys Tyr Lys Tyr Gly Gln
                485                 490                 495

Thr Leu Asp Leu Ser Lys Asn Ser Ile Phe Phe Val Lys Ser Ser Asp
            500                 505                 510

Phe Gln His Leu Ser Phe Leu Lys Cys Leu Asn Leu Ser Gly Asn Leu
        515                 520                 525

Ile Ser Gln Thr Leu Asn Gly Ser Glu Phe Gln Pro Leu Ala Glu Leu
    530                 535                 540

Arg Tyr Leu Asp Phe Ser Asn Asn Arg Leu Asp Leu Leu His Ser Thr
545                 550                 555                 560

Ala Phe Glu Glu Leu His Lys Leu Glu Val Leu Asp Ile Ser Ser Asn
                565                 570                 575

Ser His Tyr Phe Gln Ser Glu Gly Ile Thr His Met Leu Asn Phe Thr
            580                 585                 590

Lys Asn Leu Lys Val Leu Gln Lys Leu Met Met Asn Asp Asn Asp Ile
        595                 600                 605

Ser Ser Ser Thr Ser Arg Thr Met Glu Ser Glu Ser Leu Arg Thr Leu
    610                 615                 620

Glu Phe Arg Gly Asn His Leu Asp Val Leu Trp Arg Glu Gly Asp Asn
625                 630                 635                 640

Arg Tyr Leu Gln Leu Phe Lys Asn Leu Leu Lys Leu Glu Glu Leu Asp
                645                 650                 655

Ile Ser Lys Asn Ser Leu Ser Phe Leu Pro Ser Gly Val Phe Asp Gly
            660                 665                 670

Met Pro Pro Asn Leu Lys Asn Leu Ser Leu Ala Lys Asn Gly Leu Lys
        675                 680                 685

Ser Phe Ser Trp Lys Lys Leu Gln Cys Leu Lys Asn Leu Glu Thr Leu
    690                 695                 700

Asp Leu Ser His Asn Gln Leu Thr Thr Val Pro Glu Arg Leu Ser Asn
705                 710                 715                 720

Cys Ser Arg Ser His Lys Asn Leu Ile Leu Lys Asn Asn Gln Ile Arg
                725                 730                 735

Ser Pro Thr Lys Tyr Phe Leu Gln Asp Ala Phe Gln Leu Arg Tyr Leu
            740                 745                 750

Asp Leu Ser Ser Asn Lys Ile Gln Met Ile Gln Lys Thr Ser Phe Pro
        755                 760                 765

Glu Asn Val Leu Asn Asn Leu Lys Met Leu Leu Leu His His Asn Arg
    770                 775                 780

Phe Leu Cys Thr Cys Asp Ala Val Trp Phe Val Trp Trp Val Asn His
785                 790                 795                 800

Thr Glu Val Thr Ile Pro Tyr Leu Ala Thr Asp Val Thr Cys Val Gly
                805                 810                 815

Pro Gly Ala His Lys Gly Gln Ser Val Ile Ser Leu Asp Leu Tyr Thr
            820                 825                 830

```
Cys Glu Leu Asp Leu Thr Asn Leu Ile Leu Phe Ser Leu Ser Ile Ser
            835                 840                 845

Val Ser Leu Phe Leu Met Val Met Met Thr Ala Ser His Leu Tyr Phe
        850                 855                 860

Trp Asp Val Trp Tyr Ile Tyr His Phe Cys Lys Ala Lys Ile Lys Gly
865                 870                 875                 880

Tyr Gln Arg Leu Ile Ser Pro Asp Cys Cys Tyr Asp Ala Phe Ile Val
                885                 890                 895

Tyr Asp Thr Lys Asp Pro Ala Val Thr Glu Trp Val Leu Ala Glu Leu
                900                 905                 910

Val Ala Lys Leu Glu Asp Pro Arg Glu Lys His Phe Asn Leu Cys Leu
            915                 920                 925

Glu Glu Arg Asp Trp Leu Pro Gly Gln Pro Val Leu Glu Asn Leu Ser
        930                 935                 940

Gln Ser Ile Gln Leu Ser Lys Lys Thr Val Phe Val Met Thr Asp Lys
945                 950                 955                 960

Tyr Ala Lys Thr Glu Asn Phe Lys Ile Ala Phe Tyr Leu Ser His Gln
                965                 970                 975

Arg Leu Met Asp Glu Lys Val Asp Val Ile Leu Ile Phe Leu Glu
                980                 985                 990

Lys Pro Phe Gln Lys Ser Lys Phe Leu Gln Leu Arg Lys Arg Leu Cys
            995                 1000                1005

Gly Ser Ser Val Leu Glu Trp Pro Thr Asn Pro Gln Ala His Pro Tyr
        1010                1015                1020

Phe Trp Gln Cys Leu Lys Asn Ala Leu Ala Thr Asp Asn His Val Ala
1025                1030                1035                1040

Tyr Ser Gln Val Phe Lys Glu Thr Val
                1045
```

<210> SEQ ID NO 173
<211> LENGTH: 3243
<212> TYPE: DNA
<213> ORGANISM: Mus musculus
<220> FEATURE:
<221> NAME/KEY: misc_feature
<222> LOCATION: (0)...(0)
<223> OTHER INFORMATION: Murine TLR7 cDNA

<400> SEQUENCE: 173

```
attctcctcc accagacctc ttgattccat tttgaaagaa aactgaaaat ggtgttttcg      60
atgtggacac ggaagagaca aatttttgatc tttttaaata tgctcttagt ttctagagtc    120
tttgggtttc gatggtttcc taaaactcta ccttgtgaag ttaaagtaaa tatcccagag    180
gcccatgtga tcgtggactg cacagacaag catttgacga aaatccctga ggcattcccc    240
actaacacca ccaatcttac ccttaccatc aaccacatac caagcatctc tccagattcc    300
ttccgtaggc tgaaccatct ggaagaaatc gatttaagat gcaattgtgt acctgttcta    360
ctggggtcca agccaatgt gtgtaccaag aggctgcaga ttagacctgg aagctttagt    420
ggactctctg acttaaaagc cctttacctg atggaaacc aacttctgga gataccacag    480
gatctgccat ccagcttaca tcttctgagc cttgaggcta acaacatctt ctccatcacg    540
aaggagaatc taacagaact ggtcaacatt gaaacactct acctgggtca aaactgttat    600
tatcgaaatc cttgcaatgt ttcctattct attgaaaaag atgctttcct agttatgaga    660
aatttgaagg ttctctcact aaaagataac aatgtcacag ctgtcccac cactttgcca    720 cctaatttac tagagctcta tctttataac aatatcatta agaaaatcca gaaaaatgat    780
```

```
tttaataacc tcaatgagtt gcaagttctt gacctaagtg gaaattgccc tcgatgttat    840
aatgtcccat atccgtgtac accgtgtgaa ataattccc ccttacagat ccatgacaat    900
gctttcaatt cattgacaga attaaaagtt ttacgtttac acagtaattc cttcagcat    960
gtgcccccaa catggtttaa aaacatgaga acctccagg aactagacct ctcccaaaac   1020
tacttggcca gagaaattga ggaggccaaa tttttgcatt ttcttcccaa ccttgttgag   1080
ttggattttt ctttcaatta tgagctgcag gtctaccatg catctataac tttaccacat   1140
tcactctctt cattggaaaa cttgaaaatt ctgcgtgtca aggggtatgt ctttaaagag   1200
ctgaaaaact ccagtctttc tgtattgcac aagcttccca ggctggaagt tcttgacctt   1260
ggcactaact tcataaaaat tgctgacctc aacatattca acatttga aaacctcaaa    1320
ctcatagacc tttcagtgaa taagatatct ccttcagaag agtcaagaga agttggcttt   1380
tgtcctaatg ctcaaacttc tgtagaccgt catgggcccc aggtccttga ggccttacac   1440
tatttccgat acgatgaata tgcacggagc tgcaggttca aaaacaaaga gccaccttct   1500
ttcttgcctt tgaatgcaga ctgccacata tatgggcaga ccttagactt aagtagaaat   1560
aacatatttt ttattaaacc ttctgatttt cagcatcttt cattcctcaa atgcctcaac   1620
ttatcaggaa acaccattgg ccaaactctt aatggcagtg aactctggcc gttgagagag   1680
ttgcggtact tagacttctc caacaaccgg cttgatttac tctactcaac agcctttgaa   1740
gagctccaga gtcttgaagt tctggatcta agtagtaaca gccactattt tcaagcagaa   1800
ggaattactc acatgctaaa ctttaccaag aaattacggc ttctggacaa actcatgatg   1860
aatgataatg acatctctac ttcggccagc aggaccatgg aaagtgactc tcttcgaatt   1920
ctggagttca gaggcaacca tttagatgtt ctatggagag ccggtgataa cagatacttg   1980
gacttcttca agaatttgtt caatttagag gtattagata tctccagaaa ttccctgaat   2040
tccttgcctc ctgaggtttt tgagggtatg ccgccaaatc taaagaatct ctccttggcc   2100
aaaaatgggc tcaaatcttt cttttgggac agactccagt tactgaagca tttggaaatt   2160
ttggacctca gccataacca gctgacaaaa gtacctgaga gattggccaa ctgttccaaa   2220
agtctcacaa cactgattct taagcataat caaatcaggc aattgacaaa atattttcta   2280
gaagatgctt gcaattgcg ctatctagac atcagttcaa ataaaatcca ggtcattcag   2340
aagactagct tcccagaaaa tgtcctcaac aatctggaga tgttggtttt acatcacaat   2400
cgctttcttt gcaactgtga tgctgtgtgg tttgtctggt gggttaacca tacagatgtt   2460
actattccat acctggccac tgatgtgact tgtgtaggtc caggagcaca caaaggtcaa   2520
agtgtcatat cccttgatct gtatacgtgt gagttagatc tcacaaacct gattctgttc   2580
tcagttttcca tatcatcagt cctctttctt atggtagtta tgacaacaag tcacctcttt   2640
ttctgggata tgtggtacat ttattatttt tggaaagcaa agataaaggg gtatcagcat   2700
ctgcaatcca tggagtcttg ttatgatgct tttattgtgt atgacactaa aaactcagct   2760
gtgacagaat gggttttgca ggagctggtg gcaaaattgg aagatccaag agaaaaacac   2820
ttcaatttgt gtctagaaga aagagactgg ctaccaggac agccagttct agaaaacctt   2880
tcccagagca tacagctcag caaaagaca gtgtttgtga tgcacagaa atatgctaag   2940
actgagagtt ttaagatggc atttttatttg tctcatcaga ggctcctgga tgaaaaagtg   3000
gatgtgatta tcttgatatt cttggaaaag cctcttcaga agtctaagtt tcttcagctc   3060
aggaagagac tctgcaggag ctctgtcctt gagtggcctg caaatccaca ggctcaccca   3120
```

```
tacttctggc agtgcctgaa aaatgccctg accacagaca atcatgtggc ttatagtcaa    3180
atgttcaagg aaacagtcta gctctctgaa gaatgtcacc acctaggaca tgccttgaat    3240
cga                                                                  3243
```

<210> SEQ ID NO 174
<211> LENGTH: 3150
<212> TYPE: DNA
<213> ORGANISM: Mus musculus
<220> FEATURE:
<221> NAME/KEY: misc_feature
<222> LOCATION: (0)...(0)
<223> OTHER INFORMATION: Murine TLR7 ORF

<400> SEQUENCE: 174

```
atggtgtttt cgatgtggac acggaagaga caaattttga tcttttttaaa tatgctctta     60 gtttctagag tctttgggtt tcgatggttt cctaaaactc taccttgtga agttaaagta    120
aatatcccag aggcccatgt gatcgtggac tgcacagaca agcatttgac agaaatccct    180
gagggcattc ccactaacac caccaatctt acccttacca tcaaccacat accaagcatc    240
tctccagatt cctccgtag gctgaaccat ctggaagaaa tcgatttaag atgcaattgt    300
gtacctgttc tactggggtc caaagccaat gtgtgtacca agaggctgca gattagacct    360
ggaagcttta gtggactctc tgacttaaaa gcccttatacc tggatggaaa ccaacttctg    420
gagataccac aggatctgcc atccagctta catcttctga gccttgaggc taacaacatc    480
ttctccatca cgaaggagaa tctaacagaa ctggtcaaca ttgaaacact ctacctgggt    540
caaaactgtt attatcgaaa tccttgcaat gtttcctatt ctattgaaaa agatgctttc    600
ctagttatga gaatttgaa ggttctctca ctaaaagata caatgtcac agctgtcccc    660 accactttgc cacctaattt actagagctc tatctttata caatatcat taagaaaatc    720 caagaaaatg attttaataa cctcaatgag ttgcaagttc ttgacctaag tgaaattgc    780 cctcgatgtt ataatgtccc atatccgtgt acaccgtgtg aaaataattc ccccttacag    840
atccatgaca atgctttcaa ttcattgaca gaattaaaag ttttacgttt acacagtaat    900
tctcttcagc atgtgccccc aacatggttt aaaaacatga gaaacctcca ggaactagac    960
ctctcccaaa actacttggc cagagaaatt gaggaggcca aattttgtca ttttcttccc   1020
aaccttgttg agttggattt ttcttcaat tatgagctgc aggtctacca tgcatctata   1080
actttaccac attcactctc ttcattggaa aacttgaaaa ttctgcgtgt caaggggtat   1140
gtctttaaag agctgaaaaa ctccagtctt tctgtattgc acaagcttcc caggctggaa   1200
gttcttgacc ttggcactaa cttcataaaa attgctgacc tcaacatatt caaacatttt   1260
gaaaacctca actcataga cctttcagtg aataagatat ctccttcaga agagtcaaga   1320
gaagttggct tttgtcctaa tgctcaaact tctgtagacc gtcatgggcc ccaggtcctt   1380
gaggccttac actatttccg atacgatgaa tatgcacgga gctgcaggtt caaaaacaaa   1440
gagccacctt ctttcttgcc tttgaatgca gactgccaca tatatgggca gaccttagac   1500
ttaagtagaa ataacatatt ttttattaaa ccttctgatt tcagcatctt tcattcctc   1560 aaatgcctca acttatcagg aaacaccatt ggccaaactc ttaatggcag tgaactctgg   1620
ccgttgagag agttgcggta cttagacttc tccaacaacc ggcttgattt actctactca   1680
acagcctttg aagagctcca gagtcttgaa gttctggatc taagtagtaa cagccactat   1740
tttcaagcag aaggaattac tcacatgcta aactttacca gaaattacg gcttctggac   1800 aaactcatga tgaatgataa tgacatctct acttcggcca gcaggaccat ggaaagtgac   1860
```

-continued

```
tctcttcgaa ttctggagtt cagaggcaac catttagatg ttctatggag agccggtgat    1920
aacagatact tggacttctt caagaatttg ttcaatttag aggtattaga tatctccaga    1980
aattccctga attccttgcc tcctgaggtt tttgagggta tgccgccaaa tctaaagaat    2040
ctctccttgg ccaaaaatgg gctcaaatct ttcttttggg acagactcca gttactgaag    2100
catttggaaa ttttggacct cagccataac cagctgacaa agtacctga gagattggcc     2160 aactgttcca aaagtctcac aacactgatt cttaagcata atcaaatcag gcaattgaca    2220
aaatattttc tagaagatgc tttgcaattg cgctatctag acatcagttc aaataaaatc    2280
caggtcattc agaagactag cttcccagaa aatgtcctca acaatctgga gatgttggtt    2340
ttacatcaca atcgctttct ttgcaactgt gatgctgtgt ggtttgtctg gtgggttaac    2400
catacagatg ttactattcc atacctggcc actgatgtga cttgtgtagg tccaggagca    2460
cacaaaggtc aaagtgtcat atcccttgat ctgtatacgt gtgagttaga tctcacaaac    2520
ctgattctgt tctcagtttc catatcatca gtcctctttc ttatggtagt tatgacaaca    2580
agtcacctct ttttctggga tatgtggtac atttattatt tttggaaagc aaagataaag    2640
gggtatcagc atctgcaatc catggagtct tgttatgatg cttttattgt gtatgacact    2700
aaaaactcag ctgtgacaga atgggttttg caggagctgg tggcaaaatt ggaagatcca    2760
agagaaaaac acttcaattt gtgtctagaa gaaagagact ggctaccagg acagccagtt    2820
ctagaaaacc tttcccagag catacagctc agcaaaaaga cagtgtttgt gatgacacag    2880 aaaatatgcta agactgagag ttttaagatg gcatttatt tgtctcatca gaggctcctg    2940
gatgaaaaag tggatgtgat tatcttgata ttccttggaaa agcctcttca gaagtctaag    3000
tttcttcagc tcaggaagag actctgcagg agctctgtcc ttgagtggcc tgcaaatcca    3060
caggctcacc catacttctg gcagtgcctg aaaaatgccc tgaccacaga caatcatgtg    3120
gcttatagtc aaatgttcaa ggaaacagtc                                     3150
```

<210> SEQ ID NO 175
<211> LENGTH: 1050
<212> TYPE: PRT
<213> ORGANISM: Mus musculus

<400> SEQUENCE: 175

```
Met Val Phe Ser Met Trp Thr Arg Lys Arg Gln Ile Leu Ile Phe Leu
 1               5                  10                  15

Asn Met Leu Leu Val Ser Arg Val Phe Gly Phe Arg Trp Phe Pro Lys
            20                  25                  30

Thr Leu Pro Cys Glu Val Lys Val Asn Ile Pro Glu Ala His Val Ile
        35                  40                  45

Val Asp Cys Thr Asp Lys His Leu Thr Glu Ile Pro Glu Gly Ile Pro
    50                  55                  60

Thr Asn Thr Thr Asn Leu Thr Leu Thr Ile Asn His Ile Pro Ser Ile
65                  70                  75                  80

Ser Pro Asp Ser Phe Arg Arg Leu Asn His Leu Glu Glu Ile Asp Leu
                85                  90                  95

Arg Cys Asn Cys Val Pro Val Leu Leu Gly Ser Lys Ala Asn Val Cys
            100                 105                 110

Thr Lys Arg Leu Gln Ile Arg Pro Gly Ser Phe Ser Gly Leu Ser Asp
        115                 120                 125

Leu Lys Ala Leu Tyr Leu Asp Gly Asn Gln Leu Leu Glu Ile Pro Gln
    130                 135                 140
```

```
Asp Leu Pro Ser Ser Leu His Leu Leu Ser Leu Glu Ala Asn Asn Ile
145                 150                 155                 160

Phe Ser Ile Thr Lys Glu Asn Leu Thr Glu Leu Val Asn Ile Glu Thr
            165                 170                 175

Leu Tyr Leu Gly Gln Asn Cys Tyr Tyr Arg Asn Pro Cys Asn Val Ser
        180                 185                 190

Tyr Ser Ile Glu Lys Asp Ala Phe Leu Val Met Arg Asn Leu Lys Val
        195                 200                 205

Leu Ser Leu Lys Asp Asn Asn Val Thr Ala Val Pro Thr Thr Leu Pro
    210                 215                 220

Pro Asn Leu Leu Glu Leu Tyr Leu Tyr Asn Asn Ile Ile Lys Lys Ile
225                 230                 235                 240

Gln Glu Asn Asp Phe Asn Asn Leu Asn Glu Leu Gln Val Leu Asp Leu
                245                 250                 255

Ser Gly Asn Cys Pro Arg Cys Tyr Asn Val Pro Tyr Pro Cys Thr Pro
            260                 265                 270

Cys Glu Asn Asn Ser Pro Leu Gln Ile His Asp Asn Ala Phe Asn Ser
    275                 280                 285

Leu Thr Glu Leu Lys Val Leu Arg Leu His Ser Asn Ser Leu Gln His
    290                 295                 300

Val Pro Pro Thr Trp Phe Lys Asn Met Arg Asn Leu Gln Glu Leu Asp
305                 310                 315                 320

Leu Ser Gln Asn Tyr Leu Ala Arg Glu Ile Glu Glu Ala Lys Phe Leu
                325                 330                 335

His Phe Leu Pro Asn Leu Val Glu Leu Asp Phe Ser Phe Asn Tyr Glu
            340                 345                 350

Leu Gln Val Tyr His Ala Ser Ile Thr Leu Pro His Ser Leu Ser Ser
        355                 360                 365

Leu Glu Asn Leu Lys Ile Leu Arg Val Lys Gly Tyr Val Phe Lys Glu
    370                 375                 380

Leu Lys Asn Ser Ser Leu Ser Val Leu His Lys Leu Pro Arg Leu Glu
385                 390                 395                 400

Val Leu Asp Leu Gly Thr Asn Phe Ile Lys Ile Ala Asp Leu Asn Ile
                405                 410                 415

Phe Lys His Phe Glu Asn Leu Lys Leu Ile Asp Leu Ser Val Asn Lys
            420                 425                 430

Ile Ser Pro Ser Glu Glu Ser Arg Glu Val Gly Phe Cys Pro Asn Ala
        435                 440                 445

Gln Thr Ser Val Asp Arg His Gly Pro Gln Val Leu Glu Ala Leu His
    450                 455                 460

Tyr Phe Arg Tyr Asp Glu Tyr Ala Arg Ser Cys Arg Phe Lys Asn Lys
465                 470                 475                 480

Glu Pro Pro Ser Phe Leu Pro Leu Asn Ala Asp Cys His Ile Tyr Gly
                485                 490                 495

Gln Thr Leu Asp Leu Ser Arg Asn Asn Ile Phe Phe Ile Lys Pro Ser
            500                 505                 510

Asp Phe Gln His Leu Ser Phe Leu Lys Cys Leu Asn Leu Ser Gly Asn
        515                 520                 525

Thr Ile Gly Gln Thr Leu Asn Gly Ser Glu Leu Trp Pro Leu Arg Glu
    530                 535                 540

Leu Arg Tyr Leu Asp Phe Ser Asn Asn Arg Leu Asp Leu Leu Tyr Ser
545                 550                 555                 560
```

```
Thr Ala Phe Glu Glu Leu Gln Ser Leu Glu Val Leu Asp Leu Ser Ser
                565                 570                 575

Asn Ser His Tyr Phe Gln Ala Glu Gly Ile Thr His Met Leu Asn Phe
            580                 585                 590

Thr Lys Lys Leu Arg Leu Leu Asp Lys Leu Met Met Asn Asp Asn Asp
        595                 600                 605

Ile Ser Thr Ser Ala Ser Arg Thr Met Glu Ser Asp Ser Leu Arg Ile
    610                 615                 620

Leu Glu Phe Arg Gly Asn His Leu Asp Val Leu Trp Arg Ala Gly Asp
625                 630                 635                 640

Asn Arg Tyr Leu Asp Phe Phe Lys Asn Leu Phe Asn Leu Glu Val Leu
                645                 650                 655

Asp Ile Ser Arg Asn Ser Leu Asn Ser Leu Pro Pro Glu Val Phe Glu
            660                 665                 670

Gly Met Pro Pro Asn Leu Lys Asn Leu Ser Leu Ala Lys Asn Gly Leu
        675                 680                 685

Lys Ser Phe Phe Trp Asp Arg Leu Gln Leu Leu Lys His Leu Glu Ile
    690                 695                 700

Leu Asp Leu Ser His Asn Gln Leu Thr Lys Val Pro Glu Arg Leu Ala
705                 710                 715                 720

Asn Cys Ser Lys Ser Leu Thr Thr Leu Ile Leu Lys His Asn Gln Ile
                725                 730                 735

Arg Gln Leu Thr Lys Tyr Phe Leu Glu Asp Ala Leu Gln Leu Arg Tyr
            740                 745                 750

Leu Asp Ile Ser Ser Asn Lys Ile Gln Val Ile Gln Lys Thr Ser Phe
        755                 760                 765

Pro Glu Asn Val Leu Asn Asn Leu Glu Met Leu Val Leu His His Asn
    770                 775                 780

Arg Phe Leu Cys Asn Cys Asp Ala Val Trp Phe Val Trp Trp Val Asn
785                 790                 795                 800

His Thr Asp Val Thr Ile Pro Tyr Leu Ala Thr Asp Val Thr Cys Val
                805                 810                 815

Gly Pro Gly Ala His Lys Gly Gln Ser Val Ile Ser Leu Asp Leu Tyr
            820                 825                 830

Thr Cys Glu Leu Asp Leu Thr Asn Leu Ile Leu Phe Ser Val Ser Ile
        835                 840                 845

Ser Ser Val Leu Phe Leu Met Val Val Met Thr Thr Ser His Leu Phe
    850                 855                 860

Phe Trp Asp Met Trp Tyr Ile Tyr Tyr Phe Trp Lys Ala Lys Ile Lys
865                 870                 875                 880

Gly Tyr Gln His Leu Gln Ser Met Glu Ser Cys Tyr Asp Ala Phe Ile
                885                 890                 895

Val Tyr Asp Thr Lys Asn Ser Ala Val Thr Glu Trp Val Leu Gln Glu
            900                 905                 910

Leu Val Ala Lys Leu Glu Asp Pro Arg Glu Lys His Phe Asn Leu Cys
        915                 920                 925

Leu Glu Glu Arg Asp Trp Leu Pro Gly Gln Pro Val Leu Glu Asn Leu
    930                 935                 940

Ser Gln Ser Ile Gln Leu Ser Lys Lys Thr Val Phe Val Met Thr Gln
945                 950                 955                 960

Lys Tyr Ala Lys Thr Glu Ser Phe Lys Met Ala Phe Tyr Leu Ser His
                965                 970                 975

Gln Arg Leu Leu Asp Glu Lys Val Asp Val Ile Ile Leu Ile Phe Leu
```

```
                      980              985              990
Glu Lys Pro Leu Gln Lys Ser Lys Phe Leu Gln Leu Arg Lys Arg Leu
            995                 1000                1005

Cys Arg Ser Ser Val Leu Glu Trp Pro Ala Asn Pro Gln Ala His Pro
        1010                1015                1020

Tyr Phe Trp Gln Cys Leu Lys Asn Ala Leu Thr Thr Asp Asn His Val
1025                1030                1035                1040

Ala Tyr Ser Gln Met Phe Lys Glu Thr Val
                1045                1050

<210> SEQ ID NO 176
<211> LENGTH: 66
<212> TYPE: PRT
<213> ORGANISM: Mus musculus

<400> SEQUENCE: 176

Val Asp Val Ile Ile Leu Ile Phe Leu Val Lys Pro Phe Gln Lys Phe
1               5                   10                  15

Asn Phe Leu Leu Arg Lys Arg Ile Ser Arg Ser Ser Val Leu Glu Cys
                20                  25                  30

Pro Pro Asn Pro Gln Ala His Pro Tyr Phe Cys Gln Cys Leu Lys Asn
            35                  40                  45

Ala Leu Thr Thr Asp Asn His Val Ala Tyr Ser Gln Met Phe Lys Glu
        50                  55                  60

Thr Val
65

<210> SEQ ID NO 177
<211> LENGTH: 54
<212> TYPE: PRT
<213> ORGANISM: Mus musculus

<400> SEQUENCE: 177

Gln Lys Ser Lys Phe Leu Gln Leu Arg Lys Arg Leu Cys Arg Ser Ser
1               5                   10                  15

Val Leu Glu Trp Pro Ala Asn Pro Gln Ala His Pro Tyr Phe Trp Gln
                20                  25                  30

Cys Leu Lys Asn Ala Leu Thr Thr Asp Asn His Val Ala Tyr Ser Gln
            35                  40                  45

Met Phe Lys Glu Thr Val
        50

<210> SEQ ID NO 178
<211> LENGTH: 59
<212> TYPE: PRT
<213> ORGANISM: Mus musculus

<400> SEQUENCE: 178

Leu Gly Lys Pro Leu Gln Lys Ser Lys Phe Leu Gln Leu Arg Lys Arg
1               5                   10                  15

Leu Cys Arg Ser Ser Val Leu Glu Trp Pro Ala Asn Pro Gln Ala His
                20                  25                  30

Pro Tyr Phe Trp Gln Cys Leu Lys Asn Ala Leu Thr Thr Asp Asn His
            35                  40                  45

Val Ala Tyr Ser Gln Met Phe Lys Glu Thr Val
        50                  55

<210> SEQ ID NO 179
```

<211> LENGTH: 84
<212> TYPE: PRT
<213> ORGANISM: Mus musculus

<400> SEQUENCE: 179

Ile Glu Thr Phe Gln Met Pro Ser Phe Leu Ser Ile Gln Arg Leu Leu
1               5                   10                  15

Asp Asp Lys Val Asp Val Ile Ile Leu Ile Phe Leu Glu Pro Leu Lys
            20                  25                  30

Ser Lys Phe Leu Gln Leu Arg Lys Arg Phe Cys Arg Ser Ser Val Leu
        35                  40                  45

Glu Trp Pro Ala Asn Pro Gln Ala His Pro Tyr Phe Trp Gln Cys Leu
50                  55                  60

Lys Asn Ala Leu Thr Thr Asp Asn His Val Ala Tyr Ser Gln Met Phe
65                  70                  75                  80

Lys Glu Thr Val

<210> SEQ ID NO 180
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 180
ctgcgctgct gcaagttacg gaatg                                         25

<210> SEQ ID NO 181
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 181
gcgcgaaatc atgacttaac gtcag                                         25

<210> SEQ ID NO 182
<211> LENGTH: 3310
<212> TYPE: DNA
<213> ORGANISM: Homo sapiens
<220> FEATURE:
<221> NAME/KEY: misc_feature
<222> LOCATION: (0)...(0)
<223> OTHER INFORMATION: Human TLR8 cDNA

<400> SEQUENCE: 182
gctcccggcc gccatggcgg ccgcgggaat tcgattctgc gctgctgcaa gttacggaat      60
gaaaaattag aacaacagaa acatggaaaa catgttcctt cagtcgtcaa tgctgacctg     120
cattttcctg ctaatatctg gttcctgtga gttatgcgcc gaagaaaatt tttctagaag     180
ctatccttgt gatgagaaaa agcaaaatga ctcagttatt gcagagtgca gcaatcgtcg     240
actacaggaa gttccccaaa cggtgggcaa atatgtgaca gaactagacc tgtctgataa     300
tttcatcaca cacataacga atgaatcatt tcaagggctg caaaatctca ctaaaataaa     360
tctaaaccac aaccccaatg tacagcacca gaacggaaat cccggtatac aatcaaatgg     420
cttgaatatc acagacgggg cattcctcaa cctaaaaaac taagggagt tactgcttga      480 agacaaccag ttaccccaaa taccctctgg ttgccagag tctttgacag aacttagtct      540
aattcaaaac aatatataca acataactaa agagggcatt tcaagactta aaacttgaa      600

```
aaatctctat ttggcctgga actgctatttt taacaaagtt tgcgagaaaa ctaacataga    660
agatggagta tttgaaacgc tgacaaattt ggagttgcta tcactatctt tcaattctct    720
ttcacacgtg ccacccaaac tgccaagctc cctacgcaaa cttttctga gcaacaccca    780 gatcaaatac attagtgaag aagatttcaa gggattgata aatttaacat tactagattt    840
aagcgggaac tgtccgaggt gcttcaatgc cccatttcca tgcgtgcctt gtgatggtgg    900
tgcttcaatt aatatagatc gttttgcttt tcaaaacttg acccaacttc gatacctaaa    960
cctctctagc acttccctca ggaagattaa tgctgcctgg tttaaaaata tgcctcatct   1020
gaaggtgctg gatcttgaat tcaactattt agtgggagaa atagcctctg ggcatttttt   1080
aacgatgctg ccccgcttag aaatacttga cttgtctttt aactatataa aggggagtta   1140
tccacagcat attaatattt ccagaaactt ctctaaactt ttgtctctac gggcattgca   1200
tttaagaggt tatgtgttcc aggaactcag agaagatgat ttccagcccc tgatgcagct   1260
tccaaactta tcgactatca acttgggtat taatttatt aagcaaatcg atttcaaact   1320
tttccaaaat ttctccaatc tggaaattat ttacttgtca gaaaacagaa tatcaccgtt   1380
ggtaaaagat acccggcaga gttatgcaaa tagttcctct tttcaacgtc atatccggaa   1440
acgacgctca acagattttg agtttgaccc acattcgaac ttttatcatt tcacccgtcc   1500
tttaataaag ccacaatgtg ctgcttatgg aaaagcctta gatttaagcc tcaacagtat   1560
tttcttcatt gggccaaacc aatttgaaaa tcttcctgac attgcctgtt taaatctgtc   1620
tgcaaatagc aatgctcaag tgttaagtgg aactgaattt tcagccattc ctcatgtcaa   1680
atatttggat ttgacaaaca atagactaga ctttgataat gctagtgctc ttactgaatt   1740
gtccgacttg gaagttctag atctcagcta taattcacac tatttcagaa tagcaggcgt   1800
aacacatcat ctagaattta ttcaaaattt cacaaatcta aaagttttaa acttgagcca   1860
caacaacatt tatactttaa cagataagta taacctggaa agcaagtccc tggtagaatt   1920
agttttcagt ggcaatcgcc ttgacatttt gtggaatgat gatgacaaca ggtatatctc   1980 catttttcaaa ggtctcaaga atctgacacg tctggattta tcccttaata ggctgaagca   2040
catcccaaat gaagcattcc ttaatttgcc agcgagtctc actgaactac atataaatga   2100
taatatgtta aagttttta actggacatt actccagcag tttcctcgtc tcgagttgct   2160
tgacttacgt ggaaacaaac tactcttttt aactgatagc ctatctgact ttacatcttc   2220
ccttcggaca ctgctgctga gtcataacag gatttcccac ctaccctctg gctttctttc   2280
tgaagtcagt agtctgaagc acctcgattt aagttccaat ctgctaaaaa caatcaacaa   2340
atccgcactt gaaactaaga ccaccaccaa attatctatg ttggaactac acggaaaccc   2400
ctttgaatgc acctgtgaca ttggagattt ccgaagatgg atggatgaac atctgaatgt   2460
caaaattccc agactggtag atgtcatttg tgccagtcct ggggatcaaa gagggaagag   2520
tattgtgagt ctggagctaa caacttgtgt ttcagatgtc actgcagtga tattattttt   2580
cttcacgttc tttatcacca ccatggttat gttggctgcc ctggctcacc atttgtttta   2640
ctgggatgtt tggtttatat ataatgtgtg tttagctaag gtaaaaggct acaggtctct   2700
ttccacatcc caaactttct atgatgctta catttcttat gacaccaaag acgcctctgt   2760
tactgactgg gtgataaatg agctgcgcta ccaccttgaa gagagccgag acaaaaacgt   2820
tctcctttgt ctagaggaga gggattggga cccgggattg gccatcatcg acaacctcat   2880
gcagagcatc aaccaaagca agaaaacagt atttgtttta accaaaaaat atgcaaaaag   2940
ctggaacttt aaaacagctt tttacttggc tttgcagagg ctaatggatg agaacatgga   3000
```

| | |
|---|---:|
| tgtgattata tttatcctgc tggagccagt gttacagcat tctcagtatt tgaggctacg | 3060 |
| gcagcggatc tgtaagagct ccatcctcca gtggcctgac aacccgaagg cagaaggctt | 3120 |
| gttttggcaa actctgagaa atgtggtctt gactgaaaat gattcacggt ataacaatat | 3180 |
| gtatgtcgat tccattaagc aatactaact gacgttaagt catgatttcg cgcaatcact | 3240 |
| agtgaattcg cggccgcctg caggtcgacc atatgggaga gctcccaacg cgttggatgc | 3300 |
| atagcttgag | 3310 |

```
<210> SEQ ID NO 183
<211> LENGTH: 3123
<212> TYPE: DNA
<213> ORGANISM: Homo sapiens
<220> FEATURE:
<221> NAME/KEY: misc_feature
<222> LOCATION: (0)...(0)
<223> OTHER INFORMATION: Human TLR8 ORF
```

<400> SEQUENCE: 183

| | |
|---|---:|
| atggaaaaca tgttccttca gtcgtcaatg ctgacctgca ttttcctgct aatatctggt | 60 |
| tcctgtgagt tatgcgccga agaaaatttt tctagaagct atccttgtga tgagaaaaag | 120 |
| caaaatgact cagttattgc agagtgcagc aatcgtcgac tacaggaagt tccccaaacg | 180 |
| gtgggcaaat atgtgacaga actagacctg tctgataatt tcatcacaca cataacgaat | 240 |
| gaatcatttc aagggctgca aaatctcact aaaataaatc taaaccacaa ccccaatgta | 300 |
| cagcaccaga acggaaatcc cggtatacaa tcaaatggct tgaatatcac agacggggca | 360 |
| ttcctcaacc taaaaaacct aagggagtta ctgcttgaag acaaccagtt accccaaata | 420 |
| ccctctggtt tgccagagtc tttgacagaa cttagtctaa ttcaaaacaa tatatacaac | 480 |
| ataactaaag agggcatttc aagacttata aacttgaaaa atctctattt ggcctggaac | 540 |
| tgctatttta caaagtttgc gagaaaact aacatagaag atggagtatt tgaaacgctg | 600 |
| acaaatttgg agttgctatc actatctttc aattctcttt cacacgtgcc acccaaactg | 660 |
| ccaagctccc tacgcaaact ttttctgagc aacacccaga tcaaatacat tagtgaagaa | 720 |
| gatttcaagg gattgataaa tttaacatta ctagatttaa gcgggaactg tccgaggtgc | 780 |
| ttcaatgccc catttccatg cgtgccttgt gatggtggtg cttcaattaa tatagatcgt | 840 |
| tttgcttttc aaaacttgac ccaacttcga tacctaaacc tctctagcac ttccctcagg | 900 |
| aagattaatg ctgcctggtt taaaaatatg cctcatctga aggtgctgga tcttgaattc | 960 |
| aactatttag tgggagaaat agcctctggg gcatttttaa cgatgctgcc ccgcttagaa | 1020 |
| atacttgact tgtctttaa ctatataaag gggagttatc cacagcatat taatatttcc | 1080 |
| agaaacttct ctaaactttt gtctctacgg gcattgcatt taagaggtta tgtgttccag | 1140 |
| gaactcagag aagatgattt ccagcccctg atgcagcttc caaacttatc gactatcaac | 1200 |
| ttgggtatta attttattaa gcaaatcgat ttcaaacttt tccaaaattt ctccaatctg | 1260 |
| gaaattattt acttgtcaga aaacagaata tcaccgttgg taaaagatac ccggcagagt | 1320 |
| tatgcaaata gttcctcttt tcaacgtcat atccggaaac gacgctcaac agatttgag | 1380 |
| tttgacccac attcgaactt ttatcatttc acccgtcctt aataaagcc acaatgtgct | 1440 |
| gcttatggaa aagccttaga tttaagcctc aacagtattt tcttcattgg gccaaaccaa | 1500 |
| tttgaaaatc ttcctgacat tgcctgttta aatctgtctg caaatagcaa tgctcaagtg | 1560 |
| ttaagtggaa ctgaattttc agccattcct catgtcaaat atttggattt gacaaacaat | 1620 |

-continued

```
agactagact tgataatgc tagtgctctt actgaattgt ccgacttgga agttctagat    1680
ctcagctata attcacacta tttcagaata gcaggcgtaa cacatcatct agaatttatt    1740
caaaatttca caaatctaaa agttttaaac ttgagccaca acaacattta tactttaaca    1800
gataagtata acctggaaag caagtccctg gtagaattag ttttcagtgg caatcgcctt    1860
gacattttgt ggaatgatga tgacaacagg tatatctcca ttttcaaagg tctcaagaat    1920
ctgacacgtc tggatttatc ccttaatagg ctgaagcaca tcccaaatga agcattcctt    1980
aatttgccag cgagtctcac tgaactacat ataaatgata atatgttaaa gttttttaac    2040
tggacattac tccagcagtt tcctcgtctc gagttgcttg acttacgtgg aaacaaacta    2100
ctcttttaa ctgatagcct atctgacttt acatcttccc ttcggacact gctgctgagt     2160
cataacagga tttcccacct accctctggc tttctttctg aagtcagtag tctgaagcac    2220
ctcgatttaa gttccaatct gctaaaaaca atcaacaaat ccgcacttga aactaagacc    2280
accaccaaat tatctatgtt ggaactacac ggaaacccct ttgaatgcac ctgtgacatt    2340
ggagatttcc gaagatggat ggatgaacat ctgaatgtca aaattcccag actggtagat    2400
gtcatttgtg ccagtcctgg ggatcaaaga gggaagagta ttgtgagtct ggagctaaca    2460
acttgtgttt cagatgtcac tgcagtgata ttattttct tcacgttctt tatcaccacc     2520
atggttatgt tggctgccct ggctcaccat ttgttttact gggatgtttg gtttatatat    2580
aatgtgtgtt tagctaaggt aaaaggctac aggtctcttt ccacatccca aactttctat    2640
gatgcttaca tttcttatga caccaaagac gcctctgtta ctgactgggt gataaatgag    2700
ctgcgctacc accttgaaga gagccgagac aaaaacgttc tcctttgtct agaggagagg    2760
gattgggacc cgggattggc catcatcgac aacctcatgc agagcatcaa ccaaaagcaag   2820
aaaacagtat ttgtttaac caaaaaatat gcaaaaagct ggaactttaa aacagctttt    2880
tacttggctt tgcagaggct aatggatgag aacatggatg tgattatatt tatcctgctg    2940
gagccagtgt tacagcattc tcagtatttg aggctacggc agcggatctg taagagctcc    3000
atcctccagt ggcctgacaa cccgaaggca gaaggcttgt tttggcaaac tctgagaaat    3060
gtggtcttga ctgaaaatga ttcacggtat aacaatatgt atgtcgattc cattaagcaa    3120
tac                                                                 3123
```

<210> SEQ ID NO 184
<211> LENGTH: 1041
<212> TYPE: PRT
<213> ORGANISM: Homo sapiens

<400> SEQUENCE: 184

```
Met Glu Asn Met Phe Leu Gln Ser Ser Met Leu Thr Cys Ile Phe Leu
 1               5                  10                  15
Leu Ile Ser Gly Ser Cys Glu Leu Cys Ala Glu Glu Asn Phe Ser Arg
            20                  25                  30
Ser Tyr Pro Cys Asp Glu Lys Lys Gln Asn Asp Ser Val Ile Ala Glu
        35                  40                  45
Cys Ser Asn Arg Arg Leu Gln Glu Val Pro Gln Thr Val Gly Lys Tyr
    50                  55                  60
Val Thr Glu Leu Asp Leu Ser Asp Asn Phe Ile Thr His Ile Thr Asn
65                  70                  75                  80
Glu Ser Phe Gln Gly Leu Gln Asn Leu Thr Lys Ile Asn Leu Asn His
                85                  90                  95
Asn Pro Asn Val Gln His Gln Asn Gly Asn Pro Gly Ile Gln Ser Asn
```

-continued

```
              100                 105                 110
Gly Leu Asn Ile Thr Asp Gly Ala Phe Leu Asn Leu Lys Asn Leu Arg
            115                 120                 125
Glu Leu Leu Leu Glu Asp Asn Gln Leu Pro Gln Ile Pro Ser Gly Leu
        130                 135                 140
Pro Glu Ser Leu Thr Glu Leu Ser Leu Ile Gln Asn Asn Ile Tyr Asn
145                 150                 155                 160
Ile Thr Lys Glu Gly Ile Ser Arg Leu Ile Asn Leu Lys Asn Leu Tyr
                165                 170                 175
Leu Ala Trp Asn Cys Tyr Phe Asn Lys Val Cys Glu Lys Thr Asn Ile
            180                 185                 190
Glu Asp Gly Val Phe Glu Thr Leu Thr Asn Leu Glu Leu Leu Ser Leu
        195                 200                 205
Ser Phe Asn Ser Leu Ser His Val Pro Pro Lys Leu Pro Ser Ser Leu
210                 215                 220
Arg Lys Leu Phe Leu Ser Asn Thr Gln Ile Lys Tyr Ile Ser Glu Glu
225                 230                 235                 240
Asp Phe Lys Gly Leu Ile Asn Leu Thr Leu Leu Asp Leu Ser Gly Asn
                245                 250                 255
Cys Pro Arg Cys Phe Asn Ala Pro Phe Pro Cys Val Pro Cys Asp Gly
            260                 265                 270
Gly Ala Ser Ile Asn Ile Asp Arg Phe Ala Phe Gln Asn Leu Thr Gln
        275                 280                 285
Leu Arg Tyr Leu Asn Leu Ser Ser Thr Ser Leu Arg Lys Ile Asn Ala
    290                 295                 300
Ala Trp Phe Lys Asn Met Pro His Leu Lys Val Leu Asp Leu Glu Phe
305                 310                 315                 320
Asn Tyr Leu Val Gly Glu Ile Ala Ser Gly Ala Phe Leu Thr Met Leu
                325                 330                 335
Pro Arg Leu Glu Ile Leu Asp Leu Ser Phe Asn Tyr Ile Lys Gly Ser
            340                 345                 350
Tyr Pro Gln His Ile Asn Ile Ser Arg Asn Phe Ser Lys Leu Leu Ser
        355                 360                 365
Leu Arg Ala Leu His Leu Arg Gly Tyr Val Phe Gln Glu Leu Arg Glu
    370                 375                 380
Asp Asp Phe Gln Pro Leu Met Gln Leu Pro Asn Leu Ser Thr Ile Asn
385                 390                 395                 400
Leu Gly Ile Asn Phe Ile Lys Gln Ile Asp Phe Lys Leu Phe Gln Asn
                405                 410                 415
Phe Ser Asn Leu Glu Ile Ile Tyr Leu Ser Glu Asn Arg Ile Ser Pro
            420                 425                 430
Leu Val Lys Asp Thr Arg Gln Ser Tyr Ala Asn Ser Ser Ser Phe Gln
        435                 440                 445
Arg His Ile Arg Lys Arg Ser Thr Asp Phe Glu Phe Asp Pro His
    450                 455                 460
Ser Asn Phe Tyr His Phe Thr Arg Pro Leu Ile Lys Pro Gln Cys Ala
465                 470                 475                 480
Ala Tyr Gly Lys Ala Leu Asp Leu Ser Leu Asn Ser Ile Phe Phe Ile
                485                 490                 495
Gly Pro Asn Gln Phe Glu Asn Leu Pro Asp Ile Ala Cys Leu Asn Leu
            500                 505                 510
Ser Ala Asn Ser Asn Ala Gln Val Leu Ser Gly Thr Glu Phe Ser Ala
        515                 520                 525
```

```
Ile Pro His Val Lys Tyr Leu Asp Leu Thr Asn Asn Arg Leu Asp Phe
        530                 535                 540

Asp Asn Ala Ser Ala Leu Thr Glu Leu Ser Asp Leu Glu Val Leu Asp
545                 550                 555                 560

Leu Ser Tyr Asn Ser His Tyr Phe Arg Ile Ala Gly Val Thr His His
                565                 570                 575

Leu Glu Phe Ile Gln Asn Phe Thr Asn Leu Lys Val Leu Asn Leu Ser
            580                 585                 590

His Asn Asn Ile Tyr Thr Leu Thr Asp Lys Tyr Asn Leu Glu Ser Lys
                595                 600                 605

Ser Leu Val Glu Leu Val Phe Ser Gly Asn Arg Leu Asp Ile Leu Trp
        610                 615                 620

Asn Asp Asp Asn Arg Tyr Ile Ser Ile Phe Lys Gly Leu Lys Asn
625                 630                 635                 640

Leu Thr Arg Leu Asp Leu Ser Leu Asn Arg Leu Lys His Ile Pro Asn
                645                 650                 655

Glu Ala Phe Leu Asn Leu Pro Ala Ser Leu Thr Glu Leu His Ile Asn
            660                 665                 670

Asp Asn Met Leu Lys Phe Phe Asn Trp Thr Leu Leu Gln Gln Phe Pro
        675                 680                 685

Arg Leu Glu Leu Leu Asp Leu Arg Gly Asn Lys Leu Leu Phe Leu Thr
    690                 695                 700

Asp Ser Leu Ser Asp Phe Thr Ser Ser Leu Arg Thr Leu Leu Leu Ser
705                 710                 715                 720

His Asn Arg Ile Ser His Leu Pro Ser Gly Phe Leu Ser Glu Val Ser
                725                 730                 735

Ser Leu Lys His Leu Asp Leu Ser Ser Asn Leu Leu Lys Thr Ile Asn
            740                 745                 750

Lys Ser Ala Leu Glu Thr Lys Thr Thr Thr Lys Leu Ser Met Leu Glu
        755                 760                 765

Leu His Gly Asn Pro Phe Glu Cys Thr Cys Asp Ile Gly Asp Phe Arg
    770                 775                 780

Arg Trp Met Asp Glu His Leu Asn Val Lys Ile Pro Arg Leu Val Asp
785                 790                 795                 800

Val Ile Cys Ala Ser Pro Gly Asp Gln Arg Gly Lys Ser Ile Val Ser
                805                 810                 815

Leu Glu Leu Thr Thr Cys Val Ser Asp Val Thr Ala Val Ile Leu Phe
            820                 825                 830

Phe Phe Thr Phe Phe Ile Thr Thr Met Val Met Leu Ala Ala Leu Ala
        835                 840                 845

His His Leu Phe Tyr Trp Asp Val Trp Phe Ile Tyr Asn Val Cys Leu
    850                 855                 860

Ala Lys Val Lys Gly Tyr Arg Ser Leu Ser Thr Ser Gln Thr Phe Tyr
865                 870                 875                 880

Asp Ala Tyr Ile Ser Tyr Asp Thr Lys Asp Ala Ser Val Thr Asp Trp
                885                 890                 895

Val Ile Asn Glu Leu Arg Tyr His Leu Glu Glu Ser Arg Asp Lys Asn
            900                 905                 910

Val Leu Leu Cys Leu Glu Glu Arg Asp Trp Asp Pro Gly Leu Ala Ile
        915                 920                 925

Ile Asp Asn Leu Met Gln Ser Ile Asn Gln Ser Lys Lys Thr Val Phe
    930                 935                 940
```

```
Val Leu Thr Lys Lys Tyr Ala Lys Ser Trp Asn Phe Lys Thr Ala Phe
945                 950                 955                 960

Tyr Leu Ala Leu Gln Arg Leu Met Asp Glu Asn Met Asp Val Ile Ile
                965                 970                 975

Phe Ile Leu Leu Glu Pro Val Leu Gln His Ser Gln Tyr Leu Arg Leu
            980                 985                 990

Arg Gln Arg Ile Cys Lys Ser Ser Ile Leu Gln Trp Pro Asp Asn Pro
        995                 1000                1005

Lys Ala Glu Gly Leu Phe Trp Gln Thr Leu Arg Asn Val Val Leu Thr
    1010                1015                1020

Glu Asn Asp Ser Arg Tyr Asn Asn Met Tyr Val Asp Ser Ile Lys Gln
1025                1030                1035                1040

Tyr

<210> SEQ ID NO 185
<211> LENGTH: 19
<212> TYPE: PRT
<213> ORGANISM: Homo sapiens

<400> SEQUENCE: 185

Met Lys Glu Ser Ser Leu Gln Asn Ser Ser Cys Ser Leu Gly Lys Glu
 1               5                   10                  15

Thr Lys Lys

<210> SEQ ID NO 186
<211> LENGTH: 1041
<212> TYPE: PRT
<213> ORGANISM: Homo sapiens

<400> SEQUENCE: 186

Met Glu Asn Met Phe Leu Gln Ser Ser Met Leu Thr Cys Ile Phe Leu
 1               5                   10                  15

Leu Ile Ser Gly Ser Cys Glu Leu Cys Ala Glu Gly Asn Phe Ser Arg
                20                  25                  30

Ser Tyr Pro Cys Asp Glu Lys Lys Gln Asn Asp Ser Val Ile Ala Glu
            35                  40                  45

Cys Ser Asn Arg Arg Leu Gln Glu Val Pro Gln Thr Val Gly Lys Tyr
        50                  55                  60

Val Thr Glu Leu Asp Leu Ser Asp Asn Phe Ile Thr His Ile Thr Asn
65                  70                  75                  80

Glu Ser Phe Gln Gly Leu Gln Asn Leu Thr Lys Ile Asn Leu Asn His
                85                  90                  95

Asn Pro Asn Val Gln His Gln Asn Gly Asn Pro Gly Ile Gln Ser Asn
            100                 105                 110

Gly Leu Asn Ile Thr Asp Gly Ala Phe Leu Asn Leu Lys Asn Leu Arg
        115                 120                 125

Glu Leu Leu Leu Glu Asp Asn Gln Leu Pro Gln Ile Pro Ser Gly Leu
    130                 135                 140

Pro Glu Ser Leu Thr Glu Leu Ser Leu Ile Gln Asn Asn Ile Tyr Asn
145                 150                 155                 160

Ile Thr Lys Glu Gly Ile Ser Arg Leu Ile Asn Leu Lys Asn Leu Tyr
                165                 170                 175

Leu Ala Trp Asn Cys Tyr Phe Asn Lys Val Cys Glu Lys Thr Asn Ile
            180                 185                 190

Glu Asp Gly Val Phe Glu Thr Leu Thr Asn Leu Glu Leu Leu Ser Leu
        195                 200                 205
```

```
Ser Phe Asn Ser Leu Ser His Val Pro Pro Lys Leu Pro Ser Ser Leu
    210                 215                 220
Arg Lys Leu Phe Leu Ser Asn Thr Gln Ile Lys Tyr Ile Ser Glu Glu
225                 230                 235                 240
Asp Phe Lys Gly Leu Ile Asn Leu Thr Leu Leu Asp Leu Ser Gly Asn
                245                 250                 255
Cys Pro Arg Cys Phe Asn Ala Pro Phe Pro Cys Val Pro Cys Asp Gly
            260                 265                 270
Gly Ala Ser Ile Asn Ile Asp Arg Phe Ala Phe Gln Asn Leu Thr Gln
                275                 280                 285
Leu Arg Tyr Leu Asn Leu Ser Ser Thr Ser Leu Arg Lys Ile Asn Ala
    290                 295                 300
Ala Trp Phe Lys Asn Met Pro His Leu Lys Val Leu Asp Leu Glu Phe
305                 310                 315                 320
Asn Tyr Leu Val Gly Glu Ile Ala Ser Gly Ala Phe Leu Thr Met Leu
                325                 330                 335
Pro Arg Leu Glu Ile Leu Asp Leu Ser Phe Asn Tyr Ile Lys Gly Ser
            340                 345                 350
Tyr Pro Gln His Ile Asn Ile Ser Arg Asn Phe Ser Lys Leu Leu Ser
                355                 360                 365
Leu Arg Ala Leu His Leu Arg Gly Tyr Val Phe Gln Glu Leu Arg Glu
    370                 375                 380
Asp Asp Phe Gln Pro Leu Met Gln Leu Pro Asn Leu Ser Thr Ile Asn
385                 390                 395                 400
Leu Gly Ile Asn Phe Ile Lys Gln Ile Asp Phe Lys Leu Phe Gln Asn
                405                 410                 415
Phe Ser Asn Leu Glu Ile Ile Tyr Leu Ser Glu Asn Arg Ile Ser Pro
            420                 425                 430
Leu Val Lys Asp Thr Arg Gln Ser Tyr Ala Asn Ser Ser Ser Phe Gln
                435                 440                 445
Arg His Ile Arg Lys Arg Arg Ser Thr Asp Phe Glu Phe Asp Pro His
    450                 455                 460
Ser Asn Phe Tyr His Phe Thr Arg Pro Leu Ile Lys Pro Gln Cys Ala
465                 470                 475                 480
Ala Tyr Gly Lys Ala Leu Asp Leu Ser Leu Asn Ser Ile Phe Phe Ile
                485                 490                 495
Gly Pro Asn Gln Phe Glu Asn Leu Pro Asp Ile Ala Cys Leu Asn Leu
            500                 505                 510
Ser Ala Asn Ser Asn Ala Gln Val Leu Ser Gly Thr Glu Phe Ser Ala
                515                 520                 525
Ile Pro His Val Lys Tyr Leu Asp Leu Thr Asn Asn Arg Leu Asp Phe
    530                 535                 540
Asp Asn Ala Ser Ala Leu Thr Glu Leu Ser Asp Leu Glu Val Leu Asp
545                 550                 555                 560
Leu Ser Tyr Asn Ser His Tyr Phe Arg Ile Ala Gly Val Thr His His
                565                 570                 575
Leu Glu Phe Ile Gln Asn Phe Thr Asn Leu Lys Val Leu Asn Leu Ser
            580                 585                 590
His Asn Asn Ile Tyr Thr Leu Thr Asp Lys Tyr Asn Leu Glu Ser Lys
                595                 600                 605
Ser Leu Val Glu Leu Val Phe Ser Gly Asn Arg Leu Asp Ile Leu Trp
    610                 615                 620
```

-continued

```
Asn Asp Asp Asp Asn Arg Tyr Ile Ser Ile Phe Lys Gly Leu Lys Asn
625                 630                 635                 640

Leu Thr Arg Leu Asp Leu Ser Leu Asn Arg Leu Lys His Ile Pro Asn
            645                 650                 655

Glu Ala Phe Leu Asn Leu Pro Ala Ser Leu Thr Glu Leu His Ile Asn
                660                 665                 670

Asp Asn Met Leu Lys Phe Phe Asn Trp Thr Leu Leu Gln Gln Phe Pro
            675                 680                 685

Arg Leu Glu Leu Leu Asp Leu Arg Gly Asn Lys Leu Leu Phe Leu Thr
690                 695                 700

Asp Ser Leu Ser Asp Phe Thr Ser Ser Leu Arg Thr Leu Leu Leu Ser
705                 710                 715                 720

His Asn Arg Ile Ser His Leu Pro Ser Gly Phe Leu Ser Glu Val Ser
                725                 730                 735

Ser Leu Lys His Leu Asp Leu Ser Ser Asn Leu Leu Lys Thr Ile Asn
            740                 745                 750

Lys Ser Ala Leu Glu Thr Lys Thr Thr Thr Lys Leu Ser Met Leu Glu
        755                 760                 765

Leu His Gly Asn Pro Phe Glu Cys Thr Cys Asp Ile Gly Asp Phe Arg
770                 775                 780

Arg Trp Met Asp Glu His Leu Asn Val Lys Ile Pro Arg Leu Val Asp
785                 790                 795                 800

Val Ile Cys Ala Ser Pro Gly Asp Gln Arg Gly Lys Ser Ile Val Ser
                805                 810                 815

Leu Glu Leu Thr Thr Cys Val Ser Asp Val Thr Ala Val Ile Leu Phe
            820                 825                 830

Phe Phe Thr Phe Phe Ile Thr Thr Met Val Met Leu Ala Ala Leu Ala
        835                 840                 845

His His Leu Phe Tyr Trp Asp Val Trp Phe Ile Tyr Asn Val Cys Leu
850                 855                 860

Ala Lys Val Lys Gly Tyr Arg Ser Leu Ser Thr Ser Gln Thr Phe Tyr
865                 870                 875                 880

Asp Ala Tyr Ile Ser Tyr Asp Thr Lys Asp Ala Ser Val Thr Asp Trp
                885                 890                 895

Val Ile Asn Glu Leu Arg Tyr His Leu Glu Glu Ser Arg Asp Lys Asn
            900                 905                 910

Val Leu Leu Cys Leu Glu Glu Arg Asp Trp Asp Pro Gly Leu Ala Ile
        915                 920                 925

Ile Asp Asn Leu Met Gln Ser Ile Asn Gln Ser Lys Lys Thr Val Phe
930                 935                 940

Val Leu Thr Lys Lys Tyr Ala Lys Ser Trp Asn Phe Lys Thr Ala Phe
945                 950                 955                 960

Tyr Leu Ala Leu Gln Arg Leu Met Asp Glu Asn Met Asp Val Ile Ile
                965                 970                 975

Phe Ile Leu Leu Glu Pro Val Leu Gln His Ser Gln Tyr Leu Arg Leu
            980                 985                 990

Arg Gln Arg Ile Cys Lys Ser Ser Ile Leu Gln Trp Pro Asp Asn Pro
        995                 1000                1005

Lys Ala Glu Gly Leu Phe Trp Gln Thr Leu Arg Asn Val Val Leu Thr
        1010                1015                1020

Glu Asn Asp Ser Arg Tyr Asn Asn Met Tyr Val Asp Ser Ile Lys Gln
1025                1030                1035                1040

Tyr
```

<210> SEQ ID NO 187
<211> LENGTH: 1059
<212> TYPE: PRT
<213> ORGANISM: Homo sapiens

<400> SEQUENCE: 187

```
Met Lys Glu Ser Ser Leu Gln Asn Ser Cys Ser Leu Gly Lys Glu
 1               5                  10                  15

Thr Lys Lys Glu Asn Met Phe Leu Gln Ser Ser Met Leu Thr Cys Ile
                20                  25                  30

Phe Leu Leu Ile Ser Gly Ser Cys Glu Leu Cys Ala Glu Asn Phe
            35                  40                  45

Ser Arg Ser Tyr Pro Cys Asp Glu Lys Lys Gln Asn Asp Ser Val Ile
    50                  55                  60

Ala Glu Cys Ser Asn Arg Arg Leu Gln Glu Val Pro Gln Thr Val Gly
65                  70                  75                  80

Lys Tyr Val Thr Glu Leu Asp Leu Ser Asp Asn Phe Ile Thr His Ile
                85                  90                  95

Thr Asn Glu Ser Phe Gln Gly Leu Gln Asn Leu Thr Lys Ile Asn Leu
            100                 105                 110

Asn His Asn Pro Asn Val Gln His Gln Asn Gly Asn Pro Gly Ile Gln
        115                 120                 125

Ser Asn Gly Leu Asn Ile Thr Asp Gly Ala Phe Leu Asn Leu Lys Asn
    130                 135                 140

Leu Arg Glu Leu Leu Leu Glu Asp Asn Gln Leu Pro Gln Ile Pro Ser
145                 150                 155                 160

Gly Leu Pro Glu Ser Leu Thr Glu Leu Ser Leu Ile Gln Asn Asn Ile
                165                 170                 175

Tyr Asn Ile Thr Lys Glu Gly Ile Ser Arg Leu Ile Asn Leu Lys Asn
            180                 185                 190

Leu Tyr Leu Ala Trp Asn Cys Tyr Phe Asn Lys Val Cys Glu Lys Thr
        195                 200                 205

Asn Ile Glu Asp Gly Val Phe Glu Thr Leu Thr Asn Leu Glu Leu Leu
    210                 215                 220

Ser Leu Ser Phe Asn Ser Leu Ser His Val Ser Pro Lys Leu Pro Ser
225                 230                 235                 240

Ser Leu Arg Lys Leu Phe Leu Ser Asn Thr Gln Ile Lys Tyr Ile Ser
                245                 250                 255

Glu Glu Asp Phe Lys Gly Leu Ile Asn Leu Thr Leu Leu Asp Leu Ser
            260                 265                 270

Gly Asn Cys Pro Arg Cys Phe Asn Ala Pro Phe Pro Cys Val Pro Cys
        275                 280                 285

Asp Gly Gly Ala Ser Ile Asn Ile Asp Arg Phe Ala Phe Gln Asn Leu
    290                 295                 300

Thr Gln Leu Arg Tyr Leu Asn Leu Ser Ser Thr Ser Leu Arg Lys Ile
305                 310                 315                 320

Asn Ala Ala Trp Phe Lys Asn Met Pro His Leu Lys Val Leu Asp Leu
                325                 330                 335

Glu Phe Asn Tyr Leu Val Gly Glu Ile Ala Ser Gly Ala Phe Leu Thr
            340                 345                 350

Met Leu Pro Arg Leu Glu Ile Leu Asp Leu Ser Phe Asn Tyr Ile Lys
        355                 360                 365

Gly Ser Tyr Pro Gln His Ile Asn Ile Ser Arg Asn Phe Ser Lys Pro
```

```
            370                 375                 380
Leu Ser Leu Arg Ala Leu His Leu Arg Gly Tyr Val Phe Gln Glu Leu
385                 390                 395                 400

Arg Glu Asp Asp Phe Gln Pro Leu Met Gln Leu Pro Asn Leu Ser Thr
                    405                 410                 415

Ile Asn Leu Gly Ile Asn Phe Ile Lys Gln Ile Asp Phe Lys Leu Phe
                420                 425                 430

Gln Asn Phe Ser Asn Leu Glu Ile Ile Tyr Leu Ser Glu Asn Arg Ile
            435                 440                 445

Ser Pro Leu Val Lys Asp Thr Arg Gln Ser Tyr Ala Asn Ser Ser Ser
450                 455                 460

Phe Gln Arg His Ile Arg Lys Arg Arg Ser Thr Asp Phe Glu Phe Asp
465                 470                 475                 480

Pro His Ser Asn Phe Tyr His Phe Thr Arg Pro Leu Ile Lys Pro Gln
                485                 490                 495

Cys Ala Ala Tyr Gly Lys Ala Leu Asp Leu Ser Leu Asn Ser Ile Phe
                500                 505                 510

Phe Ile Gly Pro Asn Gln Phe Glu Asn Leu Pro Asp Ile Ala Cys Leu
            515                 520                 525

Asn Leu Ser Ala Asn Ser Asn Ala Gln Val Leu Ser Gly Thr Glu Phe
530                 535                 540

Ser Ala Ile Pro His Val Lys Tyr Leu Asp Leu Thr Asn Asn Arg Leu
545                 550                 555                 560

Asp Phe Asp Asn Ala Ser Ala Leu Thr Glu Leu Ser Asp Leu Glu Val
                565                 570                 575

Leu Asp Leu Ser Tyr Asn Ser His Tyr Phe Arg Ile Ala Gly Val Thr
                580                 585                 590

His His Leu Glu Phe Ile Gln Asn Phe Thr Asn Leu Lys Val Leu Asn
            595                 600                 605

Leu Ser His Asn Asn Ile Tyr Thr Leu Thr Asp Lys Tyr Asn Leu Glu
            610                 615                 620

Ser Lys Ser Leu Val Glu Leu Val Phe Ser Gly Asn Arg Leu Asp Ile
625                 630                 635                 640

Leu Trp Asn Asp Asp Asp Asn Arg Tyr Ile Ser Ile Phe Lys Gly Leu
                645                 650                 655

Lys Asn Leu Thr Arg Leu Asp Leu Ser Leu Asn Arg Leu Lys His Ile
            660                 665                 670

Pro Asn Glu Ala Phe Leu Asn Leu Pro Ala Ser Leu Thr Glu Leu His
            675                 680                 685

Ile Asn Asp Asn Met Leu Lys Phe Phe Asn Trp Thr Leu Leu Gln Gln
690                 695                 700

Phe Pro Arg Leu Glu Leu Leu Asp Leu Arg Gly Asn Lys Leu Leu Phe
705                 710                 715                 720

Leu Thr Asp Ser Leu Ser Asp Phe Thr Ser Ser Leu Arg Thr Leu Leu
                725                 730                 735

Leu Ser His Asn Arg Ile Ser His Leu Pro Ser Gly Phe Leu Ser Glu
            740                 745                 750

Val Ser Ser Leu Lys His Leu Asp Leu Ser Ser Asn Leu Leu Lys Thr
            755                 760                 765

Ile Asn Lys Ser Ala Leu Glu Thr Lys Thr Thr Lys Leu Ser Met
            770                 775                 780

Leu Glu Leu His Gly Asn Pro Phe Glu Cys Thr Cys Asp Ile Gly Asp
785                 790                 795                 800
```

-continued

Phe Arg Arg Trp Met Asp Glu His Leu Asn Val Lys Ile Pro Arg Leu
                805                 810                 815

Val Asp Val Ile Cys Ala Ser Pro Gly Asp Gln Arg Gly Lys Ser Ile
            820                 825                 830

Val Ser Leu Glu Leu Thr Thr Cys Val Ser Asp Val Thr Ala Val Ile
        835                 840                 845

Leu Phe Phe Thr Phe Phe Ile Thr Thr Met Val Met Leu Ala Ala
    850                 855                 860

Leu Ala His His Leu Phe Tyr Trp Asp Val Trp Phe Ile Tyr Asn Val
865                 870                 875                 880

Cys Leu Ala Lys Ile Lys Gly Tyr Arg Ser Leu Ser Thr Ser Gln Thr
                885                 890                 895

Phe Tyr Asp Ala Tyr Ile Ser Tyr Asp Thr Lys Asp Ala Ser Val Thr
            900                 905                 910

Asp Trp Val Ile Asn Glu Leu Arg Tyr His Leu Glu Glu Ser Arg Asp
        915                 920                 925

Lys Asn Val Leu Leu Cys Leu Glu Glu Arg Asp Trp Asp Pro Gly Leu
    930                 935                 940

Ala Ile Ile Asp Asn Leu Met Gln Ser Ile Asn Gln Ser Lys Lys Thr
945                 950                 955                 960

Val Phe Val Leu Thr Lys Lys Tyr Ala Lys Ser Trp Asn Phe Lys Thr
                965                 970                 975

Ala Phe Tyr Leu Ala Leu Gln Arg Leu Met Asp Glu Asn Met Asp Val
            980                 985                 990

Ile Ile Phe Ile Leu Leu Glu Pro Val Leu Gln His Ser Gln Tyr Leu
        995                 1000                1005

Arg Leu Arg Gln Arg Ile Cys Lys Ser Ser Ile Leu Gln Trp Pro Asp
    1010                1015                1020

Asn Pro Lys Ala Glu Gly Leu Phe Trp Gln Thr Leu Arg Asn Val Val
1025                1030                1035                1040

Leu Thr Glu Asn Asp Ser Arg Tyr Asn Asn Met Tyr Val Asp Ser Ile
                1045                1050                1055

Lys Gln Tyr

<210> SEQ ID NO 188
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 188
gagagaaaca aacgttttac cttc                                          24

<210> SEQ ID NO 189
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 189
gatggcagag tcgtgacttc cc                                            22

<210> SEQ ID NO 190
<211> LENGTH: 3220
<212> TYPE: DNA

<213> ORGANISM: Mus musculus
<220> FEATURE:
<221> NAME/KEY: misc_feature
<222> LOCATION: (0)...(0)
<223> OTHER INFORMATION: Murine TLR8 cDNA

<400> SEQUENCE: 190

```
attcagagtt ggatgttaag agagaaacaa acgttttacc ttcctttgtc tatagaacat      60
ggaaaacatg cccctcagt catggattct gacgtgcttt tgtctgctgt cctctggaac     120
cagtgccatc ttccataaag cgaactattc cagaagctat ccttgtgacg agataaggca     180
caactccctt gtgattgcag aatgcaacca tcgtcaactg catgaagttc cccaaactat     240
aggcaagtat gtgacaaaca tagacttgtc agacaatgcc attacacata taacgaaaga     300
gtcctttcaa aagctgcaaa acctcactaa aatcgatctg aaccacaatg ccaaacaaca     360
gcacccaaat gaaaataaaa atggtatgaa tattacagaa ggggcacttc tcagcctaag     420
aaatctaaca gttttactgc tggaagacaa ccagttatat actatacctg ctgggttgcc     480
tgagtctttg aaagaactta gcctaattca aaacaatata tttcaggtaa ctaaaaacaa     540
cactttggg cttaggaact tggaaagact ctatttgggc tggaactgct atttttaaatg     600
taatcaaacc tttaaggtag aagatggggc atttaaaaat cttatacact tgaaggtact     660
ctcattatct ttcaataacc ttttctatgt gcccccaaa ctaccaagtt ctctaaggaa     720
acttttctg agtaatgcca aaatcatgaa catcactcag gaagacttca aaggactgga     780
aaatttaaca ttactagatc tgagtggaaa ctgtccaagg tgttacaatg ctccatttcc     840
ttgcacacct tgcaaggaaa actcatccat ccacatacat cctctggctt ttcaaagtct     900
cacccaactt ctctatctaa acctttccag cacttccctc aggacgattc cttctacctg     960
gtttgaaaat ctgtcaaatc tgaaggaact ccatcttgaa ttcaactatt tagttcaaga    1020
aattgcctcg ggggcatttt taacaaaact acccagttta caaatccttg atttgtcctt    1080
caactttcaa tataaggaat atttacaatt tattaatatt tcctcaaatt tctctaagct    1140
tcgttctctc aagaagttgc acttaagagg ctatgtgttc cgagaactta aaaagaagca    1200
tttcgagcat ctccagagtc ttccaaactt ggcaaccatc aacttgggca ttaactttat    1260
tgagaaaatt gatttcaaag cttttccagaa tttttccaaa ctcgacgtta tctatttatc    1320
aggaaatcgc atagcatctg tattagatgg tacagattat tcctcttggc gaaatcgtct    1380
tcggaaacct ctctcaacag acgatgatga gtttgatcca cacgtgaatt tttaccatag    1440
caccaaacct ttaataaagc cacagtgtac tgcttatggc aaggccttgg atttaagttt    1500
gaacaatatt ttcattattg ggaaaagcca atttgaaggt tttcaggata tcgcctgctt    1560
aaatctgtcc ttcaatgcca atactcaagt gtttaatggc acagaattct cctccatgcc    1620
ccacattaaa tatttggatt taaccaacaa cagactagac tttgatgata acaatgcttt    1680
cagtgatctt cacgatctag aagtgctgga cctgagccac aatgcacact atttcagtat    1740
agcaggggta acgcaccgtc taggatttat ccagaactta ataaacctca gggtgttaaa    1800
cctgagccac aatggcattt acaccctcac agaggaaagt gagctgaaaa gcatctcact    1860
gaaagaattg gttttcagtg gaaatcgtct tgaccatttg tggaatgcaa atgatggcaa    1920
atactggtcc attttaaaa gtctccagaa tttgatacgc ctggacttat catacaataa    1980
ccttcaacaa atcccaaatg gagcattcct caatttgcct cagagcctcc aagagttact    2040
tatcagtggt aacaaattac gtttctttaa ttggacatta ctccagtatt ttcctcacct    2100
tcacttgctg gatttatcga gaaatgagct gtattttcta cccaattgcc tatctaagtt    2160
```

| | | |
|---|---|---|
| tgcacattcc ctggagacac tgctactgag ccataatcat ttctctcacc taccctctgg | 2220 |
| cttcctctcc gaagccagga atctggtgca cctggatcta agtttcaaca caataaagat | 2280 |
| gatcaataaa tcctccctgc aaaccaagat gaaaacgaac ttgtctattc tggagctaca | 2340 |
| tgggaactat tttgactgca cgtgtgacat aagtgatttt cgaagctggc tagatgaaaa | 2400 |
| tctgaatatc acaattccta aattggtaaa tgttatatgt tccaatcctg gggatcaaaa | 2460 |
| atcaaagagt atcatgagcc tagatctcac gacttgtgta tcggatacca ctgcagctgt | 2520 |
| cctgtttttc ctcacattcc ttaccacctc catggttatg ttggctgctc tggttcacca | 2580 |
| cctgttttac tgggatgttt ggtttatcta tcacatgtgc tctgctaagt taaaaggcta | 2640 |
| caggacttca tccacatccc aaactttcta tgatgcttat atttcttatg acaccaaaga | 2700 |
| tgcatctgtt actgactggg taatcaatga actgcgctac caccttgaag agagtgaaga | 2760 |
| caaaagtgtc ctcctttgtt tagaggagag ggattgggat ccaggattac ccatcattga | 2820 |
| taacctcatg cagagcataa accagagcaa gaaaacaatc tttgttttaa ccaagaaata | 2880 |
| tgccaagagc tggaacttta aaacagcttt ctacttggcc ttgcagaggc taatggatga | 2940 |
| gaacatggat gtgattattt tcatcctcct ggaaccagtg ttacagtact cacagtacct | 3000 |
| gaggcttcgg cagaggatct gtaagagctc catcctccag tggcccaaca atcccaaagc | 3060 |
| agaaaacttg ttttggcaaa gtctgaaaaa tgtggtcttg actgaaaatg attcacggta | 3120 |
| tgacgatttg tacattgatt ccattaggca atactagtga tgggaagtca cgactctgcc | 3180 |
| atcataaaaa cacacagctt ctccttacaa tgaaccgaat | 3220 |

<210> SEQ ID NO 191
<211> LENGTH: 3096
<212> TYPE: DNA
<213> ORGANISM: Mus musculus
<220> FEATURE:
<221> NAME/KEY: misc_feature
<222> LOCATION: (0)...(0)
<223> OTHER INFORMATION: Murine TLR8 ORF

<400> SEQUENCE: 191

| | | |
|---|---|---|
| atggaaaaca tgcccctca gtcatggatt ctgacgtgct tttgtctgct gtcctctgga | 60 |
| accagtgcca tcttccataa agcgaactat tccagaagct atccttgtga cgagataagg | 120 |
| cacaactccc ttgtgattgc agaatgcaac catcgtcaac tgcatgaagt tccccaaact | 180 |
| ataggcaagt atgtgacaaa catagacttg tcagacaatg ccattacaca tataacgaaa | 240 |
| gagtcctttc aaaagctgca aaacctcact aaaatcgatc tgaaccacaa tgccaaacaa | 300 |
| cagcacccaa atgaaaataa aatggtatg aatattacag aaggggcact ctcagccta | 360 |
| agaaatctaa cagttttact gctggaagac aaccagttat atactatacc tgctggggttg | 420 |
| cctgagtctt tgaaagaact tagcctaatt caaaacaata tatttcaggt aactaaaaac | 480 |
| aacactttg ggcttaggaa cttggaaaga ctctatttgg gctggaactg ctatttaaa | 540 |
| tgtaatcaaa cctttaaggt agaagatggg gcatttaaaa atcttataca cttgaaggta | 600 |
| ctctcattat ctttcaataa ccttttctat gtgcccccca aactaccaag ttctctaagg | 660 |
| aaacttttc tgagtaatgc caaaatcatg aacatcactc aggaagactt caaaggactg | 720 |
| gaaaatttaa cattactaga tctgagtgga aactgtccaa ggtgttacaa tgctccattt | 780 |
| ccttgcacac cttgcaagga aaactcatcc atccacatac atcctctggc ttttcaaagt | 840 |
| ctcacccaac ttctctatct aaaccttttcc agcacttccc tcaggacgat tccttctacc | 900 |

-continued

```
tggtttgaaa atctgtcaaa tctgaaggaa ctccatcttg aattcaacta tttagttcaa      960
gaaattgcct cgggggcatt tttaacaaaa ctacccagtt tacaaatcct tgatttgtcc     1020
ttcaactttc aatataagga atatttacaa tttattaata tttcctcaaa tttctctaag     1080
cttcgttctc tcaagaagtt gcacttaaga ggctatgtgt tccgagaact taaaaagaag     1140
catttcgagc atctccagag tcttccaaac ttggcaacca tcaacttggg cattaacttt     1200
attgagaaaa ttgatttcaa agcttttcag aattttttcca aactcgacgt tatctatttta    1260 tcaggaaatc gcatagcatc tgtattagat ggtacagatt attcctcttg gcgaaatcgt     1320
cttcggaaac ctctctcaac agacgatgat gagtttgatc cacacgtgaa tttttaccat     1380
agcaccaaac ctttaataaa gccacagtgt actgcttatg gcaaggcctt ggatttaagt     1440
ttgaacaata ttttcattat tgggaaaagc caatttgaag gttttcagga tatcgcctgc     1500
ttaaatctgt ccttcaatgc caatactcaa gtgtttaatg gcacagaatt ctcctccatg     1560
ccccacatta aatatttgga tttaaccaac aacagactag actttgatga taacaatgct     1620
ttcagtgatc ttcacgatct agaagtgctg gacctgagcc acaatgcaca ctatttcagt     1680
atagcagggg taacgcaccg tctaggattt atccagaact taataaacct cagggtgtta     1740
aacctgagcc acaatggcat ttacaccctc acagaggaaa gtgagctgaa aagcatctca     1800
ctgaaagaat tggttttcag tgaaatcgt cttgaccatt tgtggaatgc aaatgatggc     1860
aaatactggt ccattttaa aagtctccag aatttgatac gcctggactt atcatacaat      1920
aaccttcaac aaatcccaaa tggagcattc ctcaatttgc ctcagagcct ccaagagtta     1980
cttatcagtg gtaacaaatt acgtttcttt aattggacat tactccagta ttttcctcac     2040
cttcacttgc tggattatc gagaaatgag ctgtattttc tacccaattg cctatctaag      2100
tttgcacatt ccctggagac actgctactg agccataatc atttctctca cctaccctct     2160
ggcttcctct ccgaagccag gaatctggtg cacctggatc taagtttcaa cacaataaag     2220
atgatcaata atcctccct gcaaaccaag atgaaaacga acttgtctat tctggagcta      2280
catgggaact attttgactg cacgtgtgac ataagtgatt ttcgaagctg gctagatgaa     2340
aatctgaata tcacaattcc taaattggta aatgttatat gttccaatcc tggggatcaa     2400
aaatcaaaga gtatcatgag cctagatctc acgacttgtg tatcggatac cactgcagct     2460
gtcctgtttt tcctcacatt ccttaccacc tccatggtta tgttggctgc tctggttcac     2520
cacctgtttt actgggatgt ttggtttatc tatcacatgt gctctgctaa gttaaaaggc     2580
tacaggactt catccacatc ccaaactttc tatgatgctt atatttctta tgacaccaaa     2640
gatgcatctg ttactgactg ggtaatcaat gaactgcgct accaccttga agagagtgaa     2700
gacaaaagtg tcctccttttg tttagaggag agggattggg atccaggatt acccatcatt     2760
gataacctca tgcagagcat aaaccagagc aagaaaacaa tctttgtttt aaccaagaaa     2820
tatgccaaga gctggaactt taaaacagct ttctacttgg ccttgcagag gctaatggat     2880
gagaacatgg atgtgattat tttcatcctc ctggaaccag tgttacagta ctcacagtac     2940
ctgaggcttc ggcagaggat ctgtaagagc tccatcctcc agtggcccaa caatcccaaa     3000
gcagaaaact tgttttggca aagtctgaaa aatgtggtct tgactgaaaa tgattcacgg     3060
tatgacgatt tgtacattga ttccattagg caatac                                3096
```

<210> SEQ ID NO 192
<211> LENGTH: 1032
<212> TYPE: PRT
<213> ORGANISM: Mus musculus

<400> SEQUENCE: 192

```
Met Glu Asn Met Pro Pro Gln Ser Trp Ile Leu Thr Cys Phe Cys Leu
 1               5                  10                  15
Leu Ser Ser Gly Thr Ser Ala Ile Phe His Lys Ala Asn Tyr Ser Arg
            20                  25                  30
Ser Tyr Pro Cys Asp Glu Ile Arg His Asn Ser Leu Val Ile Ala Glu
        35                  40                  45
Cys Asn His Arg Gln Leu His Glu Val Pro Gln Thr Ile Gly Lys Tyr
    50                  55                  60
Val Thr Asn Ile Asp Leu Ser Asp Asn Ala Ile Thr His Ile Thr Lys
65                  70                  75                  80
Glu Ser Phe Gln Lys Leu Gln Asn Leu Thr Lys Ile Asp Leu Asn His
                85                  90                  95
Asn Ala Lys Gln Gln His Pro Asn Glu Asn Lys Asn Gly Met Asn Ile
            100                 105                 110
Thr Glu Gly Ala Leu Leu Ser Leu Arg Asn Leu Thr Val Leu Leu Leu
        115                 120                 125
Glu Asp Asn Gln Leu Tyr Thr Ile Pro Ala Gly Leu Pro Glu Ser Leu
    130                 135                 140
Lys Glu Leu Ser Leu Ile Gln Asn Asn Ile Phe Gln Val Thr Lys Asn
145                 150                 155                 160
Asn Thr Phe Gly Leu Arg Asn Leu Glu Arg Leu Tyr Leu Gly Trp Asn
                165                 170                 175
Cys Tyr Phe Lys Cys Asn Gln Thr Phe Lys Val Glu Asp Gly Ala Phe
            180                 185                 190
Lys Asn Leu Ile His Leu Lys Val Leu Ser Leu Ser Phe Asn Asn Leu
        195                 200                 205
Phe Tyr Val Pro Pro Lys Leu Pro Ser Ser Leu Arg Lys Leu Phe Leu
    210                 215                 220
Ser Asn Ala Lys Ile Met Asn Ile Thr Gln Glu Asp Phe Lys Gly Leu
225                 230                 235                 240
Glu Asn Leu Thr Leu Leu Asp Leu Ser Gly Asn Cys Pro Arg Cys Tyr
                245                 250                 255
Asn Ala Pro Phe Pro Cys Thr Pro Cys Lys Glu Asn Ser Ser Ile His
            260                 265                 270
Ile His Pro Leu Ala Phe Gln Ser Leu Thr Gln Leu Leu Tyr Leu Asn
        275                 280                 285
Leu Ser Ser Thr Ser Leu Arg Thr Ile Pro Ser Thr Trp Phe Glu Asn
    290                 295                 300
Leu Ser Asn Leu Lys Glu Leu His Leu Glu Phe Asn Tyr Leu Val Gln
305                 310                 315                 320
Glu Ile Ala Ser Gly Ala Phe Leu Thr Lys Leu Pro Ser Leu Gln Ile
                325                 330                 335
Leu Asp Leu Ser Phe Asn Phe Gln Tyr Lys Glu Tyr Leu Gln Phe Ile
            340                 345                 350
Asn Ile Ser Ser Asn Phe Ser Lys Leu Arg Ser Leu Lys Leu His
        355                 360                 365
Leu Arg Gly Tyr Val Phe Arg Glu Leu Lys Lys His Phe Glu His
    370                 375                 380
Leu Gln Ser Leu Pro Asn Leu Ala Thr Ile Asn Leu Gly Ile Asn Phe
385                 390                 395                 400
Ile Glu Lys Ile Asp Phe Lys Ala Phe Gln Asn Phe Ser Lys Leu Asp
```

-continued

```
            405                 410                 415
Val Ile Tyr Leu Ser Gly Asn Arg Ile Ala Ser Val Leu Asp Gly Thr
            420                 425                 430

Asp Tyr Ser Ser Trp Arg Asn Arg Leu Arg Lys Pro Leu Ser Thr Asp
            435                 440                 445

Asp Asp Glu Phe Asp Pro His Val Asn Phe Tyr His Ser Thr Lys Pro
450                 455                 460

Leu Ile Lys Pro Gln Cys Thr Ala Tyr Gly Lys Ala Leu Asp Leu Ser
465                 470                 475                 480

Leu Asn Asn Ile Phe Ile Ile Gly Lys Ser Gln Phe Glu Gly Phe Gln
                    485                 490                 495

Asp Ile Ala Cys Leu Asn Leu Ser Phe Asn Ala Asn Thr Gln Val Phe
                    500                 505                 510

Asn Gly Thr Glu Phe Ser Ser Met Pro His Ile Lys Tyr Leu Asp Leu
            515                 520                 525

Thr Asn Asn Arg Leu Asp Phe Asp Asp Asn Asn Ala Phe Ser Asp Leu
            530                 535                 540

His Asp Leu Glu Val Leu Asp Leu Ser His Asn Ala His Tyr Phe Ser
545                 550                 555                 560

Ile Ala Gly Val Thr His Arg Leu Gly Phe Ile Gln Asn Leu Ile Asn
                    565                 570                 575

Leu Arg Val Leu Asn Leu Ser His Asn Gly Ile Tyr Thr Leu Thr Glu
            580                 585                 590

Glu Ser Glu Leu Lys Ser Ile Ser Leu Lys Glu Leu Val Phe Ser Gly
            595                 600                 605

Asn Arg Leu Asp His Leu Trp Asn Ala Asn Asp Gly Lys Tyr Trp Ser
            610                 615                 620

Ile Phe Lys Ser Leu Gln Asn Leu Ile Arg Leu Asp Leu Ser Tyr Asn
625                 630                 635                 640

Asn Leu Gln Gln Ile Pro Asn Gly Ala Phe Leu Asn Leu Pro Gln Ser
                    645                 650                 655

Leu Gln Glu Leu Leu Ile Ser Gly Asn Lys Leu Arg Phe Phe Asn Trp
            660                 665                 670

Thr Leu Leu Gln Tyr Phe Pro His Leu His Leu Leu Asp Leu Ser Arg
            675                 680                 685

Asn Glu Leu Tyr Phe Leu Pro Asn Cys Leu Ser Lys Phe Ala His Ser
            690                 695                 700

Leu Glu Thr Leu Leu Leu Ser His Asn His Phe Ser His Leu Pro Ser
705                 710                 715                 720

Gly Phe Leu Ser Glu Ala Arg Asn Leu Val His Leu Asp Leu Ser Phe
                    725                 730                 735

Asn Thr Ile Lys Met Ile Asn Lys Ser Ser Leu Gln Thr Lys Met Lys
            740                 745                 750

Thr Asn Leu Ser Ile Leu Glu Leu His Gly Asn Tyr Phe Asp Cys Thr
            755                 760                 765

Cys Asp Ile Ser Asp Phe Arg Ser Trp Leu Asp Glu Asn Leu Asn Ile
770                 775                 780

Thr Ile Pro Lys Leu Val Asn Val Ile Cys Ser Asn Pro Gly Asp Gln
785                 790                 795                 800

Lys Ser Lys Ser Ile Met Ser Leu Asp Leu Thr Thr Cys Val Ser Asp
                    805                 810                 815

Thr Thr Ala Ala Val Leu Phe Phe Leu Thr Phe Leu Thr Thr Ser Met
            820                 825                 830
```

```
Val Met Leu Ala Ala Leu Val His His Leu Phe Tyr Trp Asp Val Trp
            835                 840                 845

Phe Ile Tyr His Met Cys Ser Ala Lys Leu Lys Gly Tyr Arg Thr Ser
            850                 855                 860

Ser Thr Ser Gln Thr Phe Tyr Asp Ala Tyr Ile Ser Tyr Asp Thr Lys
865                 870                 875                 880

Asp Ala Ser Val Thr Asp Trp Val Ile Asn Glu Leu Arg Tyr His Leu
                885                 890                 895

Glu Glu Ser Glu Asp Lys Ser Val Leu Leu Cys Leu Glu Glu Arg Asp
            900                 905                 910

Trp Asp Pro Gly Leu Pro Ile Ile Asp Asn Leu Met Gln Ser Ile Asn
            915                 920                 925

Gln Ser Lys Lys Thr Ile Phe Val Leu Thr Lys Lys Tyr Ala Lys Ser
            930                 935                 940

Trp Asn Phe Lys Thr Ala Phe Tyr Leu Ala Leu Gln Arg Leu Met Asp
945                 950                 955                 960

Glu Asn Met Asp Val Ile Ile Phe Ile Leu Leu Glu Pro Val Leu Gln
                965                 970                 975

Tyr Ser Gln Tyr Leu Arg Leu Arg Gln Arg Ile Cys Lys Ser Ser Ile
            980                 985                 990

Leu Gln Trp Pro Asn Asn Pro Lys Ala Glu Asn Leu Phe Trp Gln Ser
            995                 1000                1005

Leu Lys Asn Val Val Leu Thr Glu Asn Asp Ser Arg Tyr Asp Asp Leu
            1010                1015                1020

Tyr Ile Asp Ser Ile Arg Gln Tyr
1025                1030

<210> SEQ ID NO 193
<211> LENGTH: 185
<212> TYPE: PRT
<213> ORGANISM: Mus musculus

<400> SEQUENCE: 193

Asn His Phe Ser His Leu Pro Ser Gly Phe Leu Ser Glu Ala Arg Asn
  1               5                  10                  15

Leu Val His Leu Asp Leu Ser Phe Asn Thr Ile Lys Met Ile Asn Lys
             20                  25                  30

Ser Ser Leu Gln Thr Lys Met Lys Thr Asn Leu Ser Ile Leu Glu Leu
         35                  40                  45

His Gly Asn Tyr Phe Asp Cys Thr Cys Asp Ile Ser Asp Phe Arg Ser
     50                  55                  60

Trp Leu Asp Glu Asn Leu Asn Ile Thr Ile Pro Lys Leu Val Asn Val
 65                  70                  75                  80

Ile Cys Ser Asn Pro Gly Asp Gln Lys Ser Lys Ser Ile Met Ser Leu
                 85                  90                  95

Asp Leu Thr Thr Cys Val Ser Asp Thr Thr Ala Ala Val Leu Phe Phe
            100                 105                 110

Leu Thr Phe Leu Thr Thr Ser Met Val Met Leu Ala Ala Leu Val His
            115                 120                 125

His Leu Phe Tyr Trp Asp Val Trp Phe Ile Tyr His Met Cys Ser Ala
            130                 135                 140

Lys Leu Lys Gly Tyr Arg Thr Ser Ser Thr Ser Gln Thr Phe Tyr Asp
145                 150                 155                 160

Ala Tyr Ile Ser Tyr Asp Thr Lys Asp Ala Ser Val Thr Asp Trp Val
```

```
                165                 170                 175
Ile Asn Glu Leu Arg Tyr His Leu Glu
        180                 185
```

<210> SEQ ID NO 194
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 194
atagaattca ataatgggtt tctgccgcag cgccct                               36

<210> SEQ ID NO 195
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 195
atatctagat ccaggcagag gcgcaggtc                                       29

<210> SEQ ID NO 196
<211> LENGTH: 16
<212> TYPE: PRT
<213> ORGANISM: Unknown
<220> FEATURE:
<221> NAME/KEY: misc_feature
<222> LOCATION: (4)...(5)
<223> OTHER INFORMATION: unknown
<220> FEATURE:
<221> NAME/KEY: misc_feature
<222> LOCATION: (7)...(12)
<223> OTHER INFORMATION: unknown
<220> FEATURE:
<221> NAME/KEY: misc_feature
<222> LOCATION: (14)...(15)
<223> OTHER INFORMATION: unknown

<400> SEQUENCE: 196

```
Gly Asn Cys Xaa Xaa Cys Xaa Xaa Xaa Xaa Xaa Xaa Cys Xaa Xaa Cys
1               5                   10                  15
```

<210> SEQ ID NO 197
<211> LENGTH: 16
<212> TYPE: PRT
<213> ORGANISM: Homo sapiens

<400> SEQUENCE: 197

```
Gly Asn Cys Arg Arg Cys Asp His Ala Pro Asn Pro Cys Met Glu Cys
1               5                   10                  15
```

<210> SEQ ID NO 198
<211> LENGTH: 16
<212> TYPE: PRT
<213> ORGANISM: Mus musculus

<400> SEQUENCE: 198

```
Gly Asn Cys Arg Arg Cys Asp His Ala Pro Asn Pro Cys Met Ile Cys
1               5                   10                  15
```

<210> SEQ ID NO 199
<211> LENGTH: 16
<212> TYPE: PRT
<213> ORGANISM: Homo sapiens

<400> SEQUENCE: 199

Gly Asn Cys Pro Arg Cys Tyr Asn Ala Pro Phe Pro Cys Ala Pro Cys
1               5                   10                  15

<210> SEQ ID NO 200
<211> LENGTH: 16
<212> TYPE: PRT
<213> ORGANISM: Mus musculus

<400> SEQUENCE: 200

Gly Asn Cys Pro Arg Cys Tyr Asn Val Pro Tyr Pro Cys Thr Pro Cys
1               5                   10                  15

<210> SEQ ID NO 201
<211> LENGTH: 16
<212> TYPE: PRT
<213> ORGANISM: Homo sapiens

<400> SEQUENCE: 201

Gly Asn Cys Pro Arg Cys Phe Asn Ala Pro Phe Pro Cys Val Pro Cys
1               5                   10                  15

<210> SEQ ID NO 202
<211> LENGTH: 16
<212> TYPE: PRT
<213> ORGANISM: Mus musculus

<400> SEQUENCE: 202

Gly Asn Cys Pro Arg Cys Tyr Asn Ala Pro Phe Pro Cys Thr Pro Cys
1               5                   10                  15

<210> SEQ ID NO 203
<211> LENGTH: 31
<212> TYPE: PRT
<213> ORGANISM: Homo sapiens
<220> FEATURE:
<221> NAME/KEY: misc_feature
<222> LOCATION: (2)...(8)
<223> OTHER INFORMATION: unknown
<220> FEATURE:
<221> NAME/KEY: misc_feature
<222> LOCATION: (10)...(10)
<223> OTHER INFORMATION: unknown
<220> FEATURE:
<221> NAME/KEY: misc_feature
<222> LOCATION: (12)...(12)
<223> OTHER INFORMATION: unknown
<220> FEATURE:
<221> NAME/KEY: misc_feature
<222> LOCATION: (14)...(22)
<223> OTHER INFORMATION: unknown
<220> FEATURE:
<221> NAME/KEY: misc_feature
<222> LOCATION: (25)...(30)
<223> OTHER INFORMATION: unknown

<400> SEQUENCE: 203

Arg Xaa Xaa Xaa Xaa Xaa Xaa Arg Xaa Asp Xaa Leu Xaa Xaa Xaa
1               5                   10                  15

Xaa Xaa Xaa Xaa Xaa Xaa Lys Leu Xaa Xaa Xaa Xaa Xaa Xaa Ser
                20                  25                  30

<210> SEQ ID NO 204
<211> LENGTH: 31
<212> TYPE: PRT
<213> ORGANISM: Mus musculus
<220> FEATURE:

```
<221> NAME/KEY: misc_feature
<222> LOCATION: (2)...(8)
<223> OTHER INFORMATION: unknown
<220> FEATURE:
<221> NAME/KEY: misc_feature
<222> LOCATION: (10)...(10)
<223> OTHER INFORMATION: unknown
<220> FEATURE:
<221> NAME/KEY: misc_feature
<222> LOCATION: (12)...(12)
<223> OTHER INFORMATION: unknown
<220> FEATURE:
<221> NAME/KEY: misc_feature
<222> LOCATION: (14)...(22)
<223> OTHER INFORMATION: unknown
<220> FEATURE:
<221> NAME/KEY: misc_feature
<222> LOCATION: (25)...(30)
<223> OTHER INFORMATION: unknown

<400> SEQUENCE: 204

Arg Xaa Xaa Xaa Xaa Xaa Xaa Arg Xaa Asp Xaa Leu Xaa Xaa Xaa
 1               5                  10                  15

Xaa Xaa Xaa Xaa Xaa Xaa Ser Leu Xaa Xaa Xaa Xaa Xaa Xaa Ser
            20                  25                  30

<210> SEQ ID NO 205
<211> LENGTH: 31
<212> TYPE: PRT
<213> ORGANISM: Homo sapiens
<220> FEATURE:
<221> NAME/KEY: misc_feature
<222> LOCATION: (2)...(8)
<223> OTHER INFORMATION: unknown
<220> FEATURE:
<221> NAME/KEY: misc_feature
<222> LOCATION: (10)...(10)
<223> OTHER INFORMATION: unknown
<220> FEATURE:
<221> NAME/KEY: misc_feature
<222> LOCATION: (12)...(12)
<223> OTHER INFORMATION: unknown
<220> FEATURE:
<221> NAME/KEY: misc_feature
<222> LOCATION: (14)...(22)
<223> OTHER INFORMATION: unknown
<220> FEATURE:
<221> NAME/KEY: misc_feature
<222> LOCATION: (25)...(30)
<223> OTHER INFORMATION: unknown

<400> SEQUENCE: 205

Lys Xaa Xaa Xaa Xaa Xaa Xaa Xaa Arg Xaa Asp Xaa Asp Xaa Xaa Xaa
 1               5                  10                  15

Xaa Xaa Xaa Xaa Xaa Xaa Asp Leu Xaa Xaa Xaa Xaa Xaa Xaa Tyr
            20                  25                  30

<210> SEQ ID NO 206
<211> LENGTH: 31
<212> TYPE: PRT
<213> ORGANISM: Mus musculus
<220> FEATURE:
<221> NAME/KEY: misc_feature
<222> LOCATION: (2)...(8)
<223> OTHER INFORMATION: unknown
<220> FEATURE:
<221> NAME/KEY: misc_feature
<222> LOCATION: (10)...(10)
<223> OTHER INFORMATION: unknown
<220> FEATURE:
<221> NAME/KEY: misc_feature
<222> LOCATION: (12)...(12)
<223> OTHER INFORMATION: unknown
```

-continued

```
<220> FEATURE:
<221> NAME/KEY: misc_feature
<222> LOCATION: (14)...(22)
<223> OTHER INFORMATION: unknown
<220> FEATURE:
<221> NAME/KEY: misc_feature
<222> LOCATION: (25)...(30)
<223> OTHER INFORMATION: unknown

<400> SEQUENCE: 206

Lys Xaa Xaa Xaa Xaa Xaa Xaa Xaa Arg Xaa Asp Xaa Asp Xaa Xaa Xaa
 1               5                  10                  15

Xaa Xaa Xaa Xaa Xaa Xaa Asp Leu Xaa Xaa Xaa Xaa Xaa Xaa His
             20                  25                  30

<210> SEQ ID NO 207
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (8)...(8)
<223> OTHER INFORMATION: m5c

<400> SEQUENCE: 207
tccatgacgt tcctgatgct                                              20

<210> SEQ ID NO 208
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 208
ctcctccacc agacctcttg attcc                                        25

<210> SEQ ID NO 209
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 209
caaggcatgt cctaggtggt gacattc                                      27

<210> SEQ ID NO 210
<211> LENGTH: 31
<212> TYPE: PRT
<213> ORGANISM: Homo sapiens

<400> SEQUENCE: 210

Gln Val Leu Asp Leu Ser Arg Asn Lys Leu Asp Leu Tyr His Glu His
 1               5                  10                  15

Ser Phe Thr Glu Leu Pro Arg Leu Glu Ala Leu Asp Leu Ser Tyr
             20                  25                  30

<210> SEQ ID NO 211
<211> LENGTH: 31
<212> TYPE: PRT
<213> ORGANISM: Mus musculus

<400> SEQUENCE: 211
```

```
Gln Val Leu Asp Leu Ser His Asn Lys Leu Asp Leu Tyr His Trp Lys
1               5                   10                  15

Ser Phe Ser Glu Leu Pro Gln Leu Gln Ala Leu Asp Leu Ser Tyr
            20                  25                  30
```

<210> SEQ ID NO 212
<211> LENGTH: 31
<212> TYPE: PRT
<213> ORGANISM: Homo sapiens

<400> SEQUENCE: 212

```
Arg Tyr Leu Asp Phe Ser Asn Asn Arg Leu Asp Leu Leu His Ser Thr
1               5                   10                  15

Ala Phe Glu Glu Leu His Lys Leu Glu Val Leu Asp Ile Ser Ser
            20                  25                  30
```

<210> SEQ ID NO 213
<211> LENGTH: 31
<212> TYPE: PRT
<213> ORGANISM: Mus musculus

<400> SEQUENCE: 213

```
Arg Tyr Leu Asp Phe Ser Asn Asn Arg Leu Asp Leu Leu Tyr Ser Thr
1               5                   10                  15

Ala Phe Glu Glu Leu Gln Ser Leu Glu Val Leu Asp Leu Ser Ser
            20                  25                  30
```

<210> SEQ ID NO 214
<211> LENGTH: 31
<212> TYPE: PRT
<213> ORGANISM: Homo sapiens

<400> SEQUENCE: 214

```
Lys Tyr Leu Asp Leu Thr Asn Asn Arg Leu Asp Phe Asp Asn Ala Ser
1               5                   10                  15

Ala Leu Thr Glu Leu Ser Asp Leu Glu Val Leu Asp Leu Ser Tyr
            20                  25                  30
```

<210> SEQ ID NO 215
<211> LENGTH: 31
<212> TYPE: PRT
<213> ORGANISM: Mus musculus

<400> SEQUENCE: 215

```
Lys Tyr Leu Asp Leu Thr Asn Asn Arg Leu Asp Phe Asp Asn Asn
1               5                   10                  15

Ala Phe Ser Asp Leu His Asp Leu Glu Val Leu Asp Leu Ser His
            20                  25                  30
```

<210> SEQ ID NO 216
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 216
tatggatcct cttgtgacaa aactcacaca tgc        33

<210> SEQ ID NO 217
<211> LENGTH: 33
<212> TYPE: DNA
<213> ORGANISM: Artificial Sequence

```
<220> FEATURE:
<223> OTHER INFORMATION: Synthetic oligonucleotide

<400> SEQUENCE: 217
ataaagcttt catttacccg gagacaggga gag                               33

<210> SEQ ID NO 218
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 218
tatgaattcc caccatgggt ttctgccgca g                                 31

<210> SEQ ID NO 219
<211> LENGTH: 59
<212> TYPE: DNA
<213> ORGANISM: Artificial Sequence
<220> FEATURE:
<223> OTHER INFORMATION: Synthetic oligonucleotide

<400> SEQUENCE: 219
ataggatccc cggggcacca ggccgccgcc gcggccgccg gagagggcct catccaggc   59

<210> SEQ ID NO 220
<211> LENGTH: 17
<212> TYPE: PRT
<213> ORGANISM: Artificial Sequence
<220> FEATURE:
<223> OTHER INFORMATION: Synthetic oligopeptide

<400> SEQUENCE: 220

Asp Glu Ala Leu Ser Gly Gly Arg Gly Gly Leu Val Pro Arg Gly
 1               5                  10                  15

Ser

<210> SEQ ID NO 221
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 221
tatatgcggc cgcccaccat ggttctccgt cgaag                             35

<210> SEQ ID NO 222
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 222
tatatgcggc cgccagagag gacctcatcc aggc                              34

<210> SEQ ID NO 223
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 223
```
tatatgcggc cgcccaccat ggtgttttcg atgtggacac g    41

<210> SEQ ID NO 224
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 224
tatatgcggc cgccatctaa ctcacacgta tacagatc    38

<210> SEQ ID NO 225
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 225
tatatgcggc cgcccaccat ggtgtttcca atgtggacac tg    42

<210> SEQ ID NO 226
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 226
tatatgcggc cgccatctaa ctcacaggtg tacagatc    38

<210> SEQ ID NO 227
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 227
tatatgcggc cgcccaccat ggaaaacatg ccccctcag    39

<210> SEQ ID NO 228
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 228
tatatgcggc cgccatccga tacacaagtc gtgagatc    38

<210> SEQ ID NO 229
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 229
tatatgcggc cgcccaccat ggaaaacatg ttccttcagt c    41

<210> SEQ ID NO 230
<211> LENGTH: 38
<212> TYPE: DNA

```
<213> ORGANISM: Artificial Sequence
<220> FEATURE:
<223> OTHER INFORMATION: Synthetic oligonucleotide

<400> SEQUENCE: 230
tatatgcggc cgccatctga aacacaagtt gttagctc                            38
```